United States Patent
Stadheim et al.

(10) Patent No.: US 11,541,076 B2
(45) Date of Patent: Jan. 3, 2023

(54) CHIMERIC ANTIGEN RECEPTORS TARGETING TIM-1

(71) Applicants: CELDARA MEDICAL, LLC, Lebanon, NH (US); CELLDEX THERAPEUTICS, INC., Hampton, NJ (US)

(72) Inventors: Terrance A. Stadheim, Lyme, NH (US); Joana M. Murad, Hanover, NH (US); Jake Reder, Hanover, NH (US); Henry C. Marsh, Jr., Reading, MA (US); Li-Zhen He, Allentown, PA (US); Tibor Keler, Pipersville, PA (US)

(73) Assignees: CELDARA MEDICAL, LLC, Lebanon, NH (US); CELLDEX THERAPEUTICS, INC., Hampton, NJ (US)

( * ) Notice: Subject to any disclaimer, the term of this patent is extended or adjusted under 35 U.S.C. 154(b) by 408 days.

(21) Appl. No.: 16/477,609

(22) PCT Filed: Jan. 12, 2018

(86) PCT No.: PCT/US2018/013551
§ 371 (c)(1),
(2) Date: Jul. 12, 2019

(87) PCT Pub. No.: WO2018/132695
PCT Pub. Date: Jul. 19, 2018

(65) Prior Publication Data
US 2019/0336534 A1 Nov. 7, 2019

Related U.S. Application Data

(60) Provisional application No. 62/445,976, filed on Jan. 13, 2017.

(51) Int. Cl.
| | | |
|---|---|---|
| *C07K 16/28* | (2006.01) | |
| *A61K 35/17* | (2015.01) | |
| *A61P 35/00* | (2006.01) | |
| *C07K 14/725* | (2006.01) | |
| *C07K 14/705* | (2006.01) | |
| *C07K 16/30* | (2006.01) | |
| *C12N 15/85* | (2006.01) | |

(52) U.S. Cl.
CPC .............. *A61K 35/17* (2013.01); *A61P 35/00* (2018.01); *C07K 14/7051* (2013.01); *C07K 14/70521* (2013.01); *C07K 16/2803* (2013.01); *C07K 16/30* (2013.01); *C12N 15/85* (2013.01)

(58) Field of Classification Search
None
See application file for complete search history.

(56) References Cited

U.S. PATENT DOCUMENTS

| 7,728,114 B2 * | 6/2010 | Mach ................. A61K 39/3955 530/388.15 |
| 2016/0130357 A1 | 5/2016 | Mukherjee et al. |

FOREIGN PATENT DOCUMENTS

| WO | 03/080856 | 10/2003 | |
| WO | 2004084823 | 10/2004 | |
| WO | 2007/059082 | 5/2007 | |
| WO | 2012/079000 | 6/2012 | |
| WO | 2014031687 | 2/2014 | |
| WO | 2015/121454 | 8/2015 | |
| WO | WO-2015142675 A2 * | 9/2015 | ..... A61K 39/001102 |
| WO | WO-2015165997 A1 * | 11/2015 | ......... A61K 39/3955 |
| WO | WO-2016062898 A1 * | 4/2016 | ......... C07K 16/2803 |
| WO | 2016/168595 | 10/2016 | |
| WO | 02/098920 | 12/2020 | |

OTHER PUBLICATIONS

Harlow et al. (Antibodies, A Laboratory Manual, Cold Spring Harbor laboratory, 1988, pp. 37-47). (Year: 1988).*
Edwards et al. (J. Mol. Biol. (2003) 334, 103-118). (Year: 2003).*
Lloyd et al., Protein Engineering, Design & Selection vol. 22 No. 3 pp. 159-168, 2009). (Year: 2009).*
Meyer et al. (British Journal of Haematology, 2018, 180, 808-820, Supp Figs S1-S4 and pp. 1-5). (Year: 2018).*
Zhao et al. (The Journal of Immunology, 2009, vol. 183, pp. 5563-5574 and Supplemental Figs. 1-5). (Year: 2009).*
Jang et al. (Biochemical and Biophysical Research Communications (1998)), vol. 242, pp. 613-620). (Year: 1998).*
Arch et al. (MCB, Jan. 1998, p. 558-565). (Year: 1998).*
Barao et al. (Front Immunol. Jan. 4, 2013;3:402). (Year: 2013).*
Esensten et al., Immunity, pp. 973-988, 2016. (Year: 2016).*
Tian et al., Proc Natl Acad Sci U S A. Mar. 31, 2015;112(13):E1594-603. (Year: 2015).*

(Continued)

*Primary Examiner* — Zachary S Skelding
(74) *Attorney, Agent, or Firm* — Robin L. Teskin; Baker, Donelson, Bearman, Caldwell & Berkowitz PC

(57) ABSTRACT

The invention provides chimeric antigen receptors (CARs) that specifically bind to the T-cell immunoglobulin and mucin domain 1 (TIM-1) protein. The invention further relates to modified immune cells, e.g., T or NK cells, comprising such CARs, CAR-encoding nucleic acids, CAR-encoding vectors, and methods of making such compositions. The invention further relates to methods for therapeutic use of these CARs and modified immune cells for the treatment of a condition, disorder, or disease associated with cells expressing TIM-1 (e.g., cancer).

Figure 1:
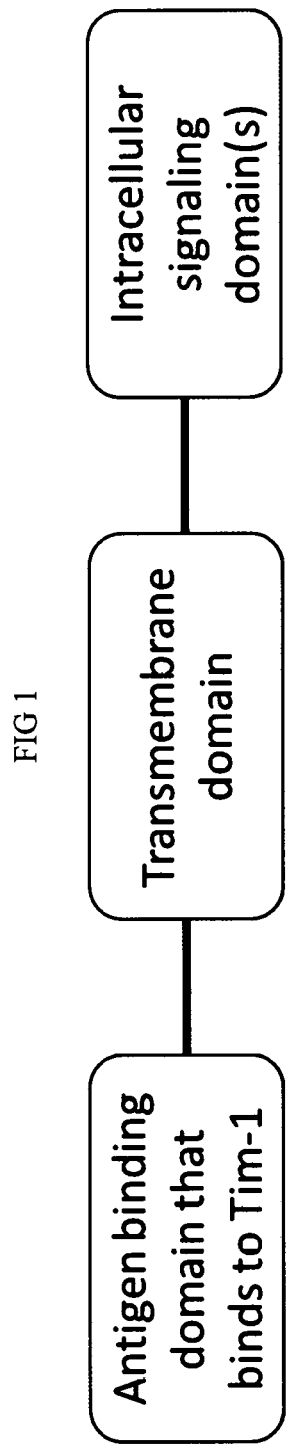

20 Claims, 28 Drawing Sheets
Specification includes a Sequence Listing.

(56) References Cited

OTHER PUBLICATIONS

Upshaw et al., Nat Immunol. May 2006;7(5):524-32 and Supplemental pp. 1-6. (Year: 2006).*
McIntire, J J et al. "Identification of Tapr (an airway hyperreactivity regulatory locus) and the linked Tim gene family." Mature immunology vol. 2,12 (2001): 1109-16. doi:10.1038/ni739.

* cited by examiner

FIG 2C

| | Signal peptide | Anti-TIM-1 2592 VH-linker-VL | CD28 Hinge/TM | CD28 Co-simulation | CD3ζ stimulation | T2A | tCD19 |
|---|---|---|---|---|---|---|---|
| 1) | Signal peptide | Anti-TIM-1 2592 VH-linker-VL | CD28 Hinge/TM | CD28 Co-simulation | CD3ζ stimulation | T2A | tCD19 |
| 2) | Signal peptide | Anti-TIM-1 2592 VH-linker-VL | CD28 Hinge/TM | 4-1BB Co-simulation | CD3ζ stimulation | T2A | tCD19 |
| 3) | Signal peptide | Anti-TIM-1 2592 VH-linker-VL | CD28 Hinge/TM | DAP10 Co-simulation | CD3ζ stimulation | T2A | tCD19 |
| 4) | Signal peptide | Anti-TIM-1 272 VH-linker-VL | CD28 Hinge/TM | CD28 Co-simulation | CD3ζ stimulation | T2A | tCD19 |
| 5) | Signal peptide | Anti-TIM-1 272 VH-linker-VL | CD28 Hinge/TM | 4-1BB Co-simulation | CD3ζ stimulation | T2A | tCD19 |
| 6) | Signal peptide | Anti-TIM-1 272 VH-linker-VL | CD28 Hinge/TM | DAP10 Co-simulation | CD3ζ stimulation | T2A | tCD19 |

FIG 4

| | Donor | Expt # | Live | CD3 | % Expression by flow | | | |
| --- | --- | --- | --- | --- | --- | --- | --- | --- |
| | | | | | CD4 [CD3] | CD8 [CD3] | TIM-1 CAR (TIM1-Fc) | CD19 [CD3] |
| pFB | 218 | CXTM15 | 86.5 | 97.1 | 19.2 | 76 | 4.8 | 0.1 |
| pFB.CX272H | 218 | CXTM15 | 77.5 | 92.5 | 25.4 | 66.9 | 22.3 | 0.2 |
| pFB.CX272H_tCD19 | 218 | CXTM15 | 79 | 91 | 21.5 | 71.1 | 16.8 | 10.4 |
| Mock | 223 | CXTM23 | 75.1 | 97.9 | 32 | 50.5 | 7.22 | 1.03 |
| SFG.2592H | 223 | CXTM23 | 71.6 | 91.4 | 40.5 | 40.8 | 12.9 | 1.29 |
| SFG.2592H_tCD19 | 223 | CXTM23 | 71.5 | 99.3 | 36.2 | 44 | 35.6 | 39 |
| SFG.2592L | 223 | CXTM23 | 80.7 | 99.3 | 38.4 | 45.7 | 17.4 | 1.23 |
| SFG.2592L_tCD19 | 223 | CXTM23 | 72.5 | 99.3 | 36.2 | 44.8 | 26 | 37.2 |

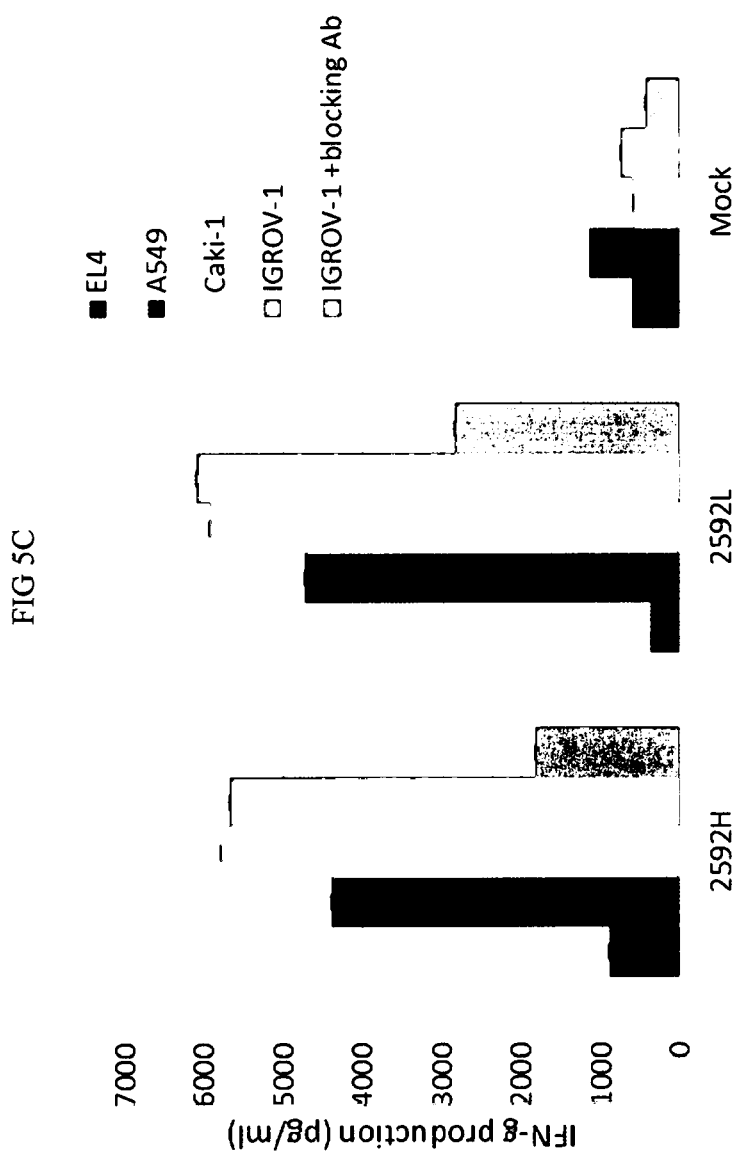

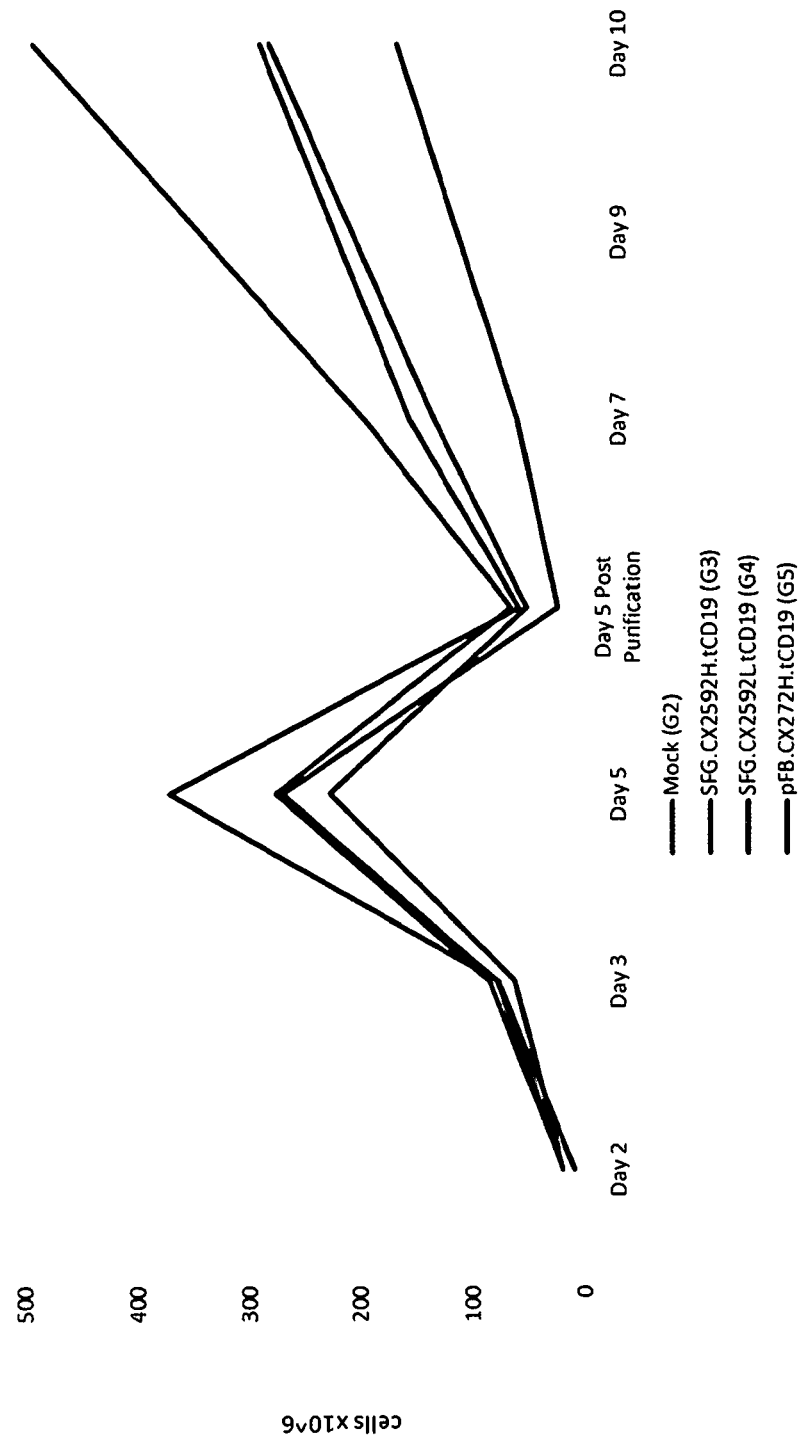

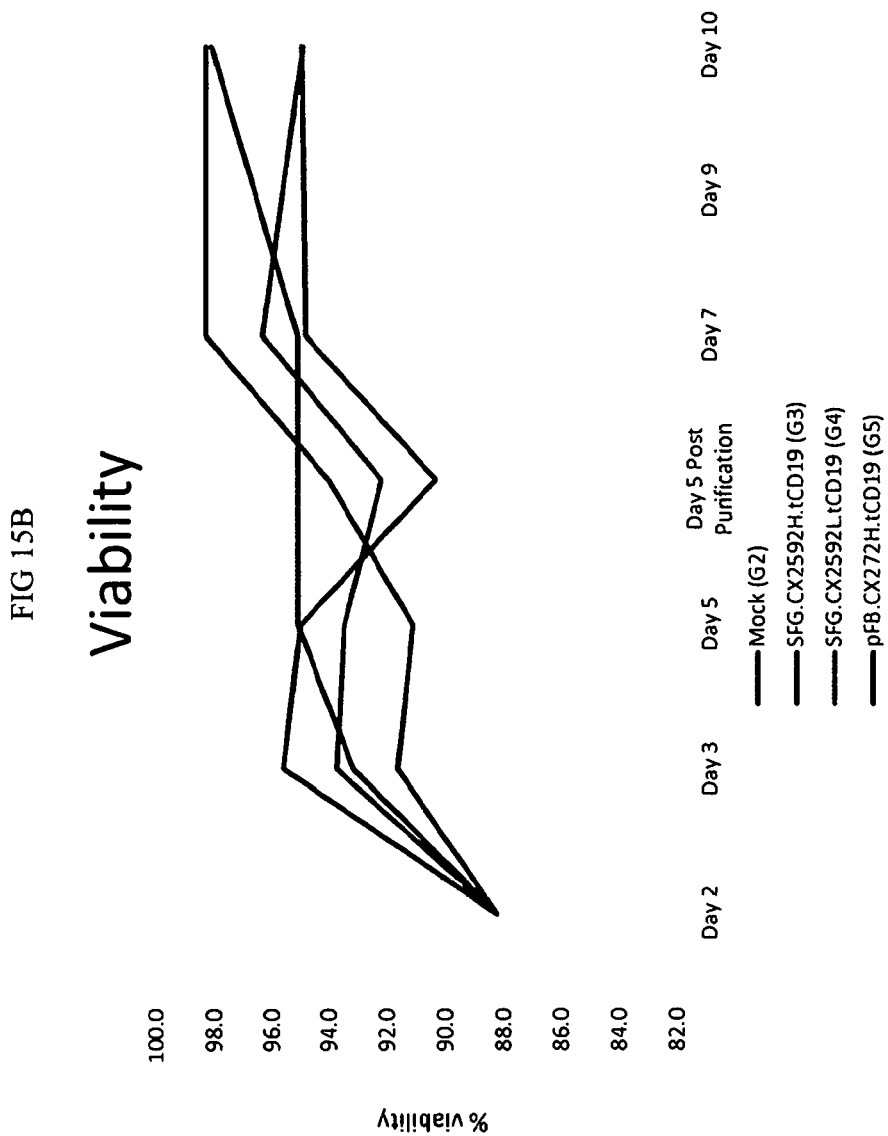

FIG 16

|     | FITC   | PE    | APC  | APCH7 | Violet |
|-----|--------|-------|------|-------|--------|
| AB1 | CD3    | CD8   | CD19 | CD4   | LD     |
| AB2 | CD45RA | CCR7  | CD3  | CD4   | LD     |
| AB3 | CD27   | CD62L | CD19 | CD4   | LD     |

FIG 17

| | % CD3+ | % CD3+ CD19+ | % CD4+ | % CD4+ CD19 | % CD8+ | % CD8+ CD19+ |
|---|---|---|---|---|---|---|
| Group 2: Mock | 99.46 | 2.82 | 24.86 | 1.11 | 67.81 | 1.68 |
| Group 3: SFG.2592H.tCD19 | 98.87 | 92.2 | 23.64 | 92.56 | 67.82 | 92.37 |
| Group 4: SFG.2592L.tCD19 | 99.08 | 94.03 | 23.31 | 95 | 67.84 | 93.98 |
| Group 5: pFB.272H.tCD19 | 98.2 | 56.59 | 30.09 | 63.96 | 61.27 | 53.4 |

FIG 19

| Group 1: CX2592H_tC D19 | Group 2: CX2592L_tC D19 | Group 3: CX2702H_tC D19 | Group 4: Mock CAR-T | Group 5: saline |
|---|---|---|---|---|
| sb-118 | sb-128 | sb-138 | sb-148 | sb-158 |
| sb-119 | sb-129 | sb-139 | sb-149 | sb-159 |
| sb-120 | sb-130 | sb-140 | sb-150 | sb-160 |
| sb-121 | sb-131 | sb-141 | sb-151 | sb-161 |
| sb-122 | sb-132 | sb-142 | sb-152 | sb-162 |
| sb-123 | sb-133 | sb-143 | sb-153 | |
| sb-124 | sb-134 | sb-144 | sb-154 | |
| sb-125 | sb-135 | sb-145 | sb-155 | |
| sb-126 | sb-136 | sb-146 | sb-156 | |
| sb-127 | sb-137 | sb-147 | sb-157 | |

SEQUENCE LISTING

<160> NUMBER OF SEQ ID NOS: 316

<210> SEQ ID NO 1

<400> SEQUENCE: 1

000

<210> SEQ ID NO 2

<400> SEQUENCE: 2

000

<210> SEQ ID NO 3
<400> SEQUENCE: 3
000

<210> SEQ ID NO 4
<400> SEQUENCE: 4
000

<210> SEQ ID NO 5
<400> SEQUENCE: 5
000

<210> SEQ ID NO 6
<400> SEQUENCE: 6
000

<210> SEQ ID NO 7
<400> SEQUENCE: 7
000

<210> SEQ ID NO 8
<400> SEQUENCE: 8
000

<210> SEQ ID NO 9
<400> SEQUENCE: 9
000

<210> SEQ ID NO 10
<400> SEQUENCE: 10
000

<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

```
<210> SEQ ID NO 25
<400> SEQUENCE: 25
000

<210> SEQ ID NO 26
<400> SEQUENCE: 26
000

<210> SEQ ID NO 27
<400> SEQUENCE: 27
000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
```

```
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
<400> SEQUENCE: 46
000

<210> SEQ ID NO 47
<400> SEQUENCE: 47
```

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

-continued

<210> SEQ ID NO 59
<400> SEQUENCE: 59
000

<210> SEQ ID NO 60
<400> SEQUENCE: 60
000

<210> SEQ ID NO 61
<400> SEQUENCE: 61
000

<210> SEQ ID NO 62
<400> SEQUENCE: 62
000

<210> SEQ ID NO 63
<400> SEQUENCE: 63
000

<210> SEQ ID NO 64
<400> SEQUENCE: 64
000

<210> SEQ ID NO 65
<400> SEQUENCE: 65
000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70

-continued

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97
<211> LENGTH: 6
<212> TYPE: PRT
<213> ORGANISM: Artificial Sequence
<220> FEATURE:
<223> OTHER INFORMATION: 2592 minimal binding epitope

<400> SEQUENCE: 97

Leu Pro Arg Gln Asn His
1               5

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
000

<210> SEQ ID NO 124
<400> SEQUENCE: 124
000

<210> SEQ ID NO 125
<400> SEQUENCE: 125
000

```
<210> SEQ ID NO 126
<400> SEQUENCE: 126
000

<210> SEQ ID NO 127
<400> SEQUENCE: 127
000

<210> SEQ ID NO 128
<400> SEQUENCE: 128
000

<210> SEQ ID NO 129
<400> SEQUENCE: 129
000

<210> SEQ ID NO 130
<400> SEQUENCE: 130
000

<210> SEQ ID NO 131
<400> SEQUENCE: 131
000

<210> SEQ ID NO 132
<400> SEQUENCE: 132
000

<210> SEQ ID NO 133
<400> SEQUENCE: 133
000

<210> SEQ ID NO 134
<400> SEQUENCE: 134
000

<210> SEQ ID NO 135
<400> SEQUENCE: 135
000

<210> SEQ ID NO 136
<400> SEQUENCE: 136
000
```

```
<210> SEQ ID NO 137
<400> SEQUENCE: 137
000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
<400> SEQUENCE: 141
000

<210> SEQ ID NO 142
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000

<210> SEQ ID NO 146
<400> SEQUENCE: 146
000

<210> SEQ ID NO 147
<400> SEQUENCE: 147
000

<210> SEQ ID NO 148
```

```
<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159
```

000

<210> SEQ ID NO 160
<400> SEQUENCE: 160
000

<210> SEQ ID NO 161
<400> SEQUENCE: 161
000

<210> SEQ ID NO 162
<400> SEQUENCE: 162
000

<210> SEQ ID NO 163
<400> SEQUENCE: 163
000

<210> SEQ ID NO 164
<400> SEQUENCE: 164
000

<210> SEQ ID NO 165
<400> SEQUENCE: 165
000

<210> SEQ ID NO 166
<400> SEQUENCE: 166
000

<210> SEQ ID NO 167
<400> SEQUENCE: 167
000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

-continued

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200
<211> LENGTH: 5
<212> TYPE: PRT
<213> ORGANISM: Artificial Sequence
<220> FEATURE:
<223> OTHER INFORMATION: Linker region subunit

<400> SEQUENCE: 200

Gly Gly Gly Gly Ser
1               5

<210> SEQ ID NO 201
<211> LENGTH: 15
<212> TYPE: PRT
<213> ORGANISM: Artificial Sequence
<220> FEATURE:
<223> OTHER INFORMATION: Linker region

<400> SEQUENCE: 201

Gly Gly Gly Gly Ser Gly Gly Gly Gly Ser Gly Gly Gly Gly Ser
1               5                   10                  15

<210> SEQ ID NO 202
<211> LENGTH: 120
<212> TYPE: PRT
<213> ORGANISM: Artificial Sequence
<220> FEATURE:
<223> OTHER INFORMATION: Ab 129 VH -continued

<400> SEQUENCE: 202

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Phe Ile Tyr Tyr Thr Gly Ser Thr Asn Tyr Asn Pro Ser
    50                  55                  60

Leu Lys Ser Arg Val Ser Ile Ser Val Asp Thr Ser Lys Asn Gln Phe
65                  70                  75                  80

Ser Leu Lys Leu Ser Ser Val Thr Ala Ala Asp Ala Ala Val Tyr Tyr
                85                  90                  95

Cys Ala Arg Asp Tyr Asp Trp Ser Phe His Phe Asp Tyr Trp Gly Gln
            100                 105                 110

Gly Thr Leu Val Thr Val Ser Ser
        115                 120

<210> SEQ ID NO 203
<211> LENGTH: 107
<212> TYPE: PRT
<213> ORGANISM: Artificial Sequence
<220> FEATURE:
<223> OTHER INFORMATION: Ab 129 VL

<400> SEQUENCE: 203

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 204
<211> LENGTH: 123
<212> TYPE: PRT
<213> ORGANISM: Artificial Sequence
<220> FEATURE:
<223> OTHER INFORMATION: Ab 272 VH

<400> SEQUENCE: 204

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Arg Tyr
            20                  25                  30

Gly Met His Trp Val Arg Gln Ala Pro Gly Lys Gly Leu Lys Trp Val
        35                  40                  45

Ala Val Ile Trp Tyr Asp Gly Ser Asn Lys Leu Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Asp Asn Ser Arg His His Trp Gly Phe Asp Tyr
            100                 105                 110

Trp Gly Gln Gly Thr Leu Val Thr Val Ser Ser
            115                 120
```

<210> SEQ ID NO 205
<211> LENGTH: 113
<212> TYPE: PRT
<213> ORGANISM: Artificial Sequence
<220> FEATURE:
<223> OTHER INFORMATION: Ab 272 VL

<400> SEQUENCE: 205

```
Asp Ile Val Met Thr Gln Thr Pro Leu Ser Leu Pro Val Thr Pro Gly
 1               5                  10                  15

Glu Pro Ala Ser Ile Ser Cys Arg Ser Ser Arg Ser Leu Leu Asp Ser
                 20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Val Glu Phe Pro Ile Thr Phe Gly Gln Gly Thr Arg Leu Glu Ile
            100                 105                 110

Lys
```

<210> SEQ ID NO 206
<211> LENGTH: 124
<212> TYPE: PRT
<213> ORGANISM: Artificial Sequence
<220> FEATURE:
<223> OTHER INFORMATION: Ab 2592 VH

<400> SEQUENCE: 206

```
Gln Val Gln Leu Gln Glu Ser Gly Pro Arg Leu Val Lys Pro Ser Gln
 1               5                  10                  15

Thr Leu Ser Leu Thr Cys Thr Val Ser Gly Gly Ser Ile Ser Ser Asp
                 20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Phe Tyr Asn Pro Ser
 50                  55                  60

Leu Lys Ser Arg Val Ala Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Ser Pro His Ser Ser Asn Trp Tyr Ser Gly Phe Asp
            100                 105                 110

Cys Trp Gly Gln Gly Thr Leu Val Thr Val Ser Ser
            115                 120
```

<210> SEQ ID NO 207
<211> LENGTH: 107
<212> TYPE: PRT
<213> ORGANISM: Artificial Sequence
<220> FEATURE:
<223> OTHER INFORMATION: Ab 2592 VL

<400> SEQUENCE: 207

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Arg
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Asn Leu Pro Phe
                85                  90                  95

Thr Phe Gly Pro Gly Thr Lys Val Asp Ile Lys
            100                 105
```

<210> SEQ ID NO 208
<211> LENGTH: 242
<212> TYPE: PRT
<213> ORGANISM: Artificial Sequence
<220> FEATURE:
<223> OTHER INFORMATION: 129 hv-linker-lv

<400> SEQUENCE: 208

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Phe Ile Tyr Tyr Thr Gly Ser Thr Asn Tyr Asn Pro Ser
    50                  55                  60

Leu Lys Ser Arg Val Ser Ile Ser Val Asp Thr Ser Lys Asn Gln Phe
65                  70                  75                  80

Ser Leu Lys Leu Ser Ser Val Thr Ala Ala Asp Ala Val Tyr Tyr
                85                  90                  95

Cys Ala Arg Asp Tyr Asp Trp Ser Phe His Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Ile Gly Asp Arg Val Thr Ile Thr Cys Arg Ala
145                 150                 155                 160

Ser Gln Gly Ile Arg Asn Asp Leu Gly Trp Tyr Gln Gln Lys Pro Gly
                165                 170                 175

Lys Ala Pro Lys Arg Leu Ile Tyr Ala Ala Ser Ser Leu Gln Ser Gly
            180                 185                 190

Val Pro Ser Arg Phe Ser Gly Ser Gly Ser Gly Thr Glu Phe Thr Leu
        195                 200                 205
```

Thr Ile Ser Ser Leu Gln Pro Glu Asp Phe Ala Thr Tyr Tyr Cys Leu
        210                 215                 220

Gln His Asn Ser Tyr Pro Leu Thr Phe Gly Gly Gly Thr Lys Val Glu
225                 230                 235                 240

Ile Lys

<210> SEQ ID NO 209
<211> LENGTH: 242
<212> TYPE: PRT
<213> ORGANISM: Artificial Sequence
<220> FEATURE:
<223> OTHER INFORMATION: 129 lv-linker-hv

<400> SEQUENCE: 209

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
130                 135                 140

Thr Val Ser Gly Gly Ser Val Ser Ser Gly Gly Tyr Tyr Trp Ser Trp
145                 150                 155                 160

Ile Arg Gln Pro Pro Gly Lys Gly Leu Glu Trp Ile Gly Phe Ile Tyr
                165                 170                 175

Tyr Thr Gly Ser Thr Asn Tyr Asn Pro Ser Leu Lys Ser Arg Val Ser
            180                 185                 190

Ile Ser Val Asp Thr Ser Lys Asn Gln Phe Ser Leu Lys Leu Ser Ser
        195                 200                 205

Val Thr Ala Ala Asp Ala Ala Val Tyr Tyr Cys Ala Arg Asp Tyr Asp
    210                 215                 220

Trp Ser Phe His Phe Asp Tyr Trp Gly Gln Gly Thr Leu Val Thr Val
225                 230                 235                 240

Ser Ser

<210> SEQ ID NO 210
<211> LENGTH: 251
<212> TYPE: PRT
<213> ORGANISM: Artificial Sequence
<220> FEATURE:
<223> OTHER INFORMATION: 272 hv-linker-lv

<400> SEQUENCE: 210

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Arg Tyr
            20                  25                  30

Gly Met His Trp Val Arg Gln Ala Pro Gly Lys Gly Leu Lys Trp Val
        35                  40                  45

Ala Val Ile Trp Tyr Asp Gly Ser Asn Lys Leu Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Asp Asn Ser Arg His His Trp Gly Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Asp Ile Val Met Thr Gln
    130                 135                 140

Thr Pro Leu Ser Leu Pro Val Thr Pro Gly Glu Pro Ala Ser Ile Ser
145                 150                 155                 160

Cys Arg Ser Ser Arg Ser Leu Leu Asp Ser Asp Gly Asn Thr Tyr
            165                 170                 175

Leu Asp Trp Tyr Leu Gln Lys Pro Gly Gln Ser Pro Gln Leu Leu Ile
            180                 185                 190

Tyr Thr Leu Ser Tyr Arg Ala Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Met Gln Arg Val Glu Phe Pro Ile
225                 230                 235                 240

Thr Phe Gly Gln Gly Thr Arg Leu Glu Ile Lys
            245                 250

<210> SEQ ID NO 211
<211> LENGTH: 251
<212> TYPE: PRT
<213> ORGANISM: Artificial Sequence
<220> FEATURE:
<223> OTHER INFORMATION: 272 lv-linker-hv

<400> SEQUENCE: 211

Asp Ile Val Met Thr Gln Thr Pro Leu Ser Leu Pro Val Thr Pro Gly
1               5                   10                  15

Glu Pro Ala Ser Ile Ser Cys Arg Ser Ser Arg Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Val Glu Phe Pro Ile Thr Phe Gly Gln Gly Thr Arg Leu Glu Ile
            100                 105                 110

Lys Gly Gly Gly Gly Ser Gly Gly Gly Gly Ser Gly Gly Gly Gly Ser
        115                 120                 125

```
Gln Val Gln Leu Val Glu Ser Gly Gly Val Gln Pro Gly Arg
130                 135                 140

Ser Leu Arg Leu Ser Cys Ala Ala Ser Gly Phe Ile Phe Ser Arg Tyr
145                 150                 155                 160

Gly Met His Trp Val Arg Gln Ala Pro Gly Lys Gly Leu Lys Trp Val
                165                 170                 175

Ala Val Ile Trp Tyr Asp Gly Ser Asn Lys Leu Tyr Ala Asp Ser Val
                180                 185                 190

Lys Gly Arg Phe Thr Ile Ser Arg Asp Asn Ser Lys Asn Thr Leu Tyr
                195                 200                 205

Leu Gln Met Asn Ser Leu Arg Ala Glu Asp Thr Ala Val Tyr Tyr Cys
210                 215                 220

Ala Arg Asp Tyr Tyr Asp Asn Ser Arg His His Trp Gly Phe Asp Tyr
225                 230                 235                 240

Trp Gly Gln Gly Thr Leu Val Thr Val Ser Ser
                245                 250

<210> SEQ ID NO 212
<211> LENGTH: 246
<212> TYPE: PRT
<213> ORGANISM: Artificial Sequence
<220> FEATURE:
<223> OTHER INFORMATION: 2592 hv-linker-lv

<400> SEQUENCE: 212

Gln Val Gln Leu Gln Glu Ser Gly Pro Arg Leu Val Lys Pro Ser Gln
1               5                   10                  15

Thr Leu Ser Leu Thr Cys Thr Val Ser Gly Gly Ser Ile Ser Ser Asp
                20                  25                  30

Gly Tyr Tyr Trp Ser Trp Ile Arg Gln His Pro Gly Lys Gly Leu Glu
                35                  40                  45

Trp Ile Gly Tyr Ile Tyr Tyr Ser Gly Ser Thr Phe Tyr Asn Pro Ser
            50                  55                  60

Leu Lys Ser Arg Val Ala Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Pro His Ser Ser Asn Trp Tyr Ser Gly Phe Asp
            100                 105                 110

Cys Trp Gly Gln Gly Thr Leu Val Thr Val Ser Ser Gly Gly Gly Gly
            115                 120                 125

Ser Gly Gly Gly Gly Ser Gly Gly Gly Gly Ser Glu Ile Val Leu Thr
130                 135                 140

Gln Ser Pro Asp Phe Gln Ser Val Thr Pro Lys Glu Lys Val Thr Ile
145                 150                 155                 160

Thr Cys Arg Ala Ser Gln Ser Ile Gly Ser Arg Leu His Trp Tyr Gln
                165                 170                 175

Gln Lys Pro Asp Gln Ser Pro Lys Leu Leu Ile Lys Tyr Ala Ser Gln
                180                 185                 190

Ser Phe Ser Gly Val Pro Ser Arg Phe Ser Gly Ser Gly Ser Gly Thr
                195                 200                 205

Asp Phe Thr Leu Thr Ile Asn Ser Leu Glu Ala Glu Asp Ala Ala Thr
                210                 215                 220

Tyr Tyr Cys His Gln Ser Ser Asn Leu Pro Phe Thr Phe Gly Pro Gly
225                 230                 235                 240
```

```
Thr Lys Val Asp Ile Lys
                245

<210> SEQ ID NO 213
<211> LENGTH: 246
<212> TYPE: PRT
<213> ORGANISM: Artificial Sequence
<220> FEATURE:
<223> OTHER INFORMATION: 2592 lv-linker-hv

<400> SEQUENCE: 213

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Arg
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Asn Leu Pro Phe
                85                  90                  95

Thr Phe Gly Pro Gly Thr Lys Val Asp Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Arg Leu Val Lys Pro Ser Gln Thr Leu Ser Leu Thr Cys
    130                 135                 140

Thr Val Ser Gly Gly Ser Ile Ser Ser Asp Gly Tyr Tyr Trp Ser Trp
145                 150                 155                 160

Ile Arg Gln His Pro Gly Lys Gly Leu Glu Trp Ile Gly Tyr Ile Tyr
                165                 170                 175

Tyr Ser Gly Ser Thr Phe Tyr Asn Pro Ser Leu Lys Ser Arg Val Ala
            180                 185                 190

Ile Ser Val Asp Thr Ser Lys Asn Gln Phe Ser Leu Lys Leu Ser Ser
        195                 200                 205

Val Thr Ala Ala Asp Thr Ala Val Tyr Tyr Cys Ala Arg Glu Ser Pro
    210                 215                 220

His Ser Ser Asn Trp Tyr Ser Gly Phe Asp Cys Trp Gly Gln Gly Thr
225                 230                 235                 240

Leu Val Thr Val Ser Ser
                245

<210> SEQ ID NO 214
<211> LENGTH: 18
<212> TYPE: PRT
<213> ORGANISM: Artificial Sequence
<220> FEATURE:
<223> OTHER INFORMATION: CD28 hinge domain

<400> SEQUENCE: 214

Val Lys Gly Lys His Leu Cys Pro Ser Pro Leu Phe Pro Gly Pro Ser
1               5                   10                  15

Lys Pro

<210> SEQ ID NO 215
<211> LENGTH: 27
```

```
<212> TYPE: PRT
<213> ORGANISM: Artificial Sequence
<220> FEATURE:
<223> OTHER INFORMATION: CD28 transmembrane domain

<400> SEQUENCE: 215

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 216
<211> LENGTH: 42
<212> TYPE: PRT
<213> ORGANISM: Artificial Sequence
<220> FEATURE:
<223> OTHER INFORMATION: 4-1BB costim domain

<400> SEQUENCE: 216

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 217
<211> LENGTH: 40
<212> TYPE: PRT
<213> ORGANISM: Artificial Sequence
<220> FEATURE:
<223> OTHER INFORMATION: CD28 costim domain

<400> SEQUENCE: 217

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 218
<211> LENGTH: 24
<212> TYPE: PRT
<213> ORGANISM: Artificial Sequence
<220> FEATURE:
<223> OTHER INFORMATION: DAP10 costim domain

<400> SEQUENCE: 218

Leu Cys Ala Arg Pro Arg Arg Ser Pro Ala Gln Glu Asp Gly Lys Val
1               5                   10                  15

Tyr Ile Asn Met Pro Gly Arg Gly
            20

<210> SEQ ID NO 219
<211> LENGTH: 114
<212> TYPE: PRT
<213> ORGANISM: Artificial Sequence
<220> FEATURE:
<223> OTHER INFORMATION: CD3zeta intracellular domain

<400> SEQUENCE: 219

Leu Arg Val Lys Phe Ser Arg Ser Ala Asp Ala Pro Ala Tyr Gln Gln
1               5                   10                  15
```

-continued

```
Gly Gln Asn Gln Leu Tyr Asn Glu Leu Asn Leu Gly Arg Arg Glu Glu
             20                  25                  30

Tyr Asp Val Leu Asp Lys Arg Arg Gly Arg Asp Pro Glu Met Gly Gly
         35                  40                  45

Lys Pro Gln Arg Arg Lys Asn Pro Gln Glu Gly Leu Tyr Asn Glu Leu
     50                  55                  60

Gln Lys Asp Lys Met Ala Glu Ala Tyr Ser Glu Ile Gly Met Lys Gly
 65                  70                  75                  80

Glu Arg Arg Arg Gly Lys Gly His Asp Gly Leu Tyr Gln Gly Leu Ser
                 85                  90                  95

Thr Ala Thr Lys Asp Thr Tyr Asp Ala Leu His Met Gln Ala Leu Pro
            100                 105                 110

Pro Arg

<210> SEQ ID NO 220
<211> LENGTH: 465
<212> TYPE: PRT
<213> ORGANISM: Artificial Sequence
<220> FEATURE:
<223> OTHER INFORMATION: 129H-CD28H-CD28TM-CD28CYP-CD3zetaCYP CAR
      (includes leader)

<400> SEQUENCE: 220

Met Glu Thr Pro Ala Gln Leu Leu Phe Leu Leu Leu Leu Trp Leu Pro
  1               5                  10                  15

Asp Thr Thr Gly Gln Val Gln Leu Gln Glu Ser Gly Pro Gly Leu Val
             20                  25                  30

Lys Pro Ser Glu Thr Leu Ser Leu Thr Cys Thr Val Ser Gly Gly Ser
         35                  40                  45

Val Ser Ser Gly Gly Tyr Tyr Trp Ser Trp Ile Arg Gln Pro Pro Gly
     50                  55                  60

Lys Gly Leu Glu Trp Ile Gly Phe Ile Tyr Tyr Thr Gly Ser Thr Asn
 65                  70                  75                  80

Tyr Asn Pro Ser Leu Lys Ser Arg Val Ser Ile Ser Val Asp Thr Ser
                 85                  90                  95

Lys Asn Gln Phe Ser Leu Lys Leu Ser Ser Val Thr Ala Ala Asp Ala
            100                 105                 110

Ala Val Tyr Tyr Cys Ala Arg Asp Tyr Asp Trp Ser Phe His Phe Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Asp Ile Gln Met Thr
145                 150                 155                 160

Gln Ser Pro Ser Ser Leu Ser Ala Ser Ile Gly Asp Arg Val Thr Ile
                165                 170                 175

Thr Cys Arg Ala Ser Gln Gly Ile Arg Asn Asp Leu Gly Trp Tyr Gln
            180                 185                 190

Gln Lys Pro Gly Lys Ala Pro Lys Arg Leu Ile Tyr Ala Ala Ser Ser
        195                 200                 205

Leu Gln Ser Gly Val Pro Ser Arg Phe Ser Gly Ser Gly Ser Gly Thr
    210                 215                 220

Glu Phe Thr Leu Thr Ile Ser Ser Leu Gln Pro Glu Asp Phe Ala Thr
225                 230                 235                 240

Tyr Tyr Cys Leu Gln His Asn Ser Tyr Pro Leu Thr Phe Gly Gly Gly
                245                 250                 255
```

```
Thr Lys Val Glu Ile Lys Ala Ser Val Lys Gly Lys His Leu Cys Pro
                260                 265                 270

Ser Pro Leu Phe Pro Gly Pro Ser Lys Pro Phe Trp Val Leu Val Val
            275                 280                 285

Val Gly Gly Val Leu Ala Cys Tyr Ser Leu Leu Val Thr Val Ala Phe
290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Lys Leu
            340                 345                 350

Arg Val Lys Phe Ser Arg Ser Ala Asp Ala Pro Ala Tyr Gln Gln Gly
            355                 360                 365

Gln Asn Gln Leu Tyr Asn Glu Leu Asn Leu Gly Arg Arg Glu Glu Tyr
370                 375                 380

Asp Val Leu Asp Lys Arg Arg Gly Arg Asp Pro Glu Met Gly Gly Lys
385                 390                 395                 400

Pro Gln Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
            435                 440                 445

Ala Thr Lys Asp Thr Tyr Asp Ala Leu His Met Gln Ala Leu Pro Pro
450                 455                 460

Arg
465

<210> SEQ ID NO 221
<211> LENGTH: 465
<212> TYPE: PRT
<213> ORGANISM: Artificial Sequence
<220> FEATURE:
<223> OTHER INFORMATION: 129L-CD28H-CD28TM-CD28CYP-CD3zetaCYP CAR
      (includes leader)

<400> SEQUENCE: 221

Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Ile Gly Asp Arg Val Thr Ile Thr Cys Arg Ala Ser Gln Gly
        35                  40                  45

Ile Arg Asn Asp Leu Gly Trp Tyr Gln Gln Lys Pro Gly Lys Ala Pro
    50                  55                  60

Lys Arg Leu Ile Tyr Ala Ala Ser Ser Leu Gln Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Tyr Cys Leu Gln His Asn
            100                 105                 110

Ser Tyr Pro Leu Thr Phe Gly Gly Gly Thr Lys Val Glu Ile Lys Gly
        115                 120                 125

Gly Gly Gly Ser Gly Gly Gly Gly Ser Gly Gly Gly Gly Ser Gln Val
```

```
                130                 135                 140
Gln Leu Gln Glu Ser Gly Pro Gly Leu Val Lys Pro Ser Glu Thr Leu
145                 150                 155                 160

Ser Leu Thr Cys Thr Val Ser Gly Gly Ser Val Ser Ser Gly Gly Tyr
                165                 170                 175

Tyr Trp Ser Trp Ile Arg Gln Pro Pro Gly Lys Gly Leu Glu Trp Ile
            180                 185                 190

Gly Phe Ile Tyr Tyr Thr Gly Ser Thr Asn Tyr Asn Pro Ser Leu Lys
        195                 200                 205

Ser Arg Val Ser Ile Ser Val Asp Thr Ser Lys Asn Gln Phe Ser Leu
    210                 215                 220

Lys Leu Ser Ser Val Thr Ala Ala Asp Ala Ala Val Tyr Tyr Cys Ala
225                 230                 235                 240

Arg Asp Tyr Asp Trp Ser Phe His Phe Asp Tyr Trp Gly Gln Gly Thr
                245                 250                 255

Leu Val Thr Val Ser Ser Ala Ser Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
    290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Lys Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Gln Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465

<210> SEQ ID NO 222
<211> LENGTH: 475
<212> TYPE: PRT
<213> ORGANISM: Artificial Sequence
<220> FEATURE:
<223> OTHER INFORMATION: 272H-CD28H-CD28TM-BBCYP-CD3zetaCYP CAR
      (includes leader)

<400> SEQUENCE: 222

Met Glu Thr Pro Ala Gln Leu Leu Phe Leu Leu Leu Leu Trp Leu Pro
1               5                   10                  15
```

```
Asp Thr Thr Gly Gln Val Gln Leu Val Glu Ser Gly Gly Val Val
            20                  25                  30

Gln Pro Gly Arg Ser Leu Arg Leu Ser Cys Ala Ala Ser Gly Phe Ile
        35                  40                  45

Phe Ser Arg Tyr Gly Met His Trp Val Arg Gln Ala Pro Gly Lys Gly
    50                  55                  60

Leu Lys Trp Val Ala Val Ile Trp Tyr Asp Gly Ser Asn Lys Leu Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Tyr Tyr Asp Asn Ser Arg His His Trp
        115                 120                 125

Gly Phe Asp Tyr Trp Gly Gln Gly Thr Leu Val Thr Val Ser Ser Gly
    130                 135                 140

Gly Gly Gly Ser Gly Gly Gly Ser Gly Gly Gly Ser Asp Ile
145                 150                 155                 160

Val Met Thr Gln Thr Pro Leu Ser Leu Pro Val Thr Pro Gly Glu Pro
                165                 170                 175

Ala Ser Ile Ser Cys Arg Ser Ser Arg Ser Leu Leu Asp Ser Asp Asp
            180                 185                 190

Gly Asn Thr Tyr Leu Asp Trp Tyr Leu Gln Lys Pro Gly Gln Ser Pro
        195                 200                 205

Gln Leu Leu Ile Tyr Thr Leu Ser Tyr Arg Ala Ser Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Val Gly Val Tyr Tyr Cys Met Gln Arg Val
                245                 250                 255

Glu Phe Pro Ile Thr Phe Gly Gln Gly Thr Arg Leu Glu Ile Lys Leu
            260                 265                 270

Glu Val Lys Gly Lys His Leu Cys Pro Ser Pro Leu Phe Pro Gly Pro
        275                 280                 285

Ser Lys Pro Phe Trp Val Leu Val Val Gly Gly Val Leu Ala Cys
    290                 295                 300

Tyr Ser Leu Leu Val Thr Val Ala Phe Ile Ile Phe Trp Val Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Lys Leu Arg Val Lys Phe Ser Arg
        355                 360                 365

Ser Ala Asp Ala Pro Ala Tyr Gln Gln Gly Gln Asn Gln Leu Tyr Asn
    370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Gln Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
```

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475

<210> SEQ ID NO 223
<211> LENGTH: 474
<212> TYPE: PRT
<213> ORGANISM: Artificial Sequence
<220> FEATURE:
<223> OTHER INFORMATION: 272H-CD28H-CD28TM-CD28CYP-CD3zetaCYP CAR
      (includes leader)

<400> SEQUENCE: 223

Met Glu Thr Pro Ala Gln Leu Leu Phe Leu Leu Leu Leu Trp Leu Pro
1               5                   10                  15

Asp Thr Thr Gly Gln Val Gln Leu Val Glu Ser Gly Gly Gly Val Val
                20                  25                  30

Gln Pro Gly Arg Ser Leu Arg Leu Ser Cys Ala Ala Ser Gly Phe Ile
            35                  40                  45

Phe Ser Arg Tyr Gly Met His Trp Val Arg Gln Ala Pro Gly Lys Gly
        50                  55                  60

Leu Lys Trp Val Ala Val Ile Trp Tyr Asp Gly Ser Asn Lys Leu Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Tyr Tyr Asp Asn Ser Arg His His Trp
        115                 120                 125

Gly Phe Asp Tyr Trp Gly Gln Gly Thr Leu Val Thr Val Ser Ser Gly
130                 135                 140

Gly Gly Gly Ser Gly Gly Gly Ser Gly Gly Gly Ser Asp Ile
145                 150                 155                 160

Val Met Thr Gln Thr Pro Leu Ser Leu Pro Val Thr Pro Gly Glu Pro
                165                 170                 175

Ala Ser Ile Ser Cys Arg Ser Ser Arg Ser Leu Leu Asp Ser Asp Asp
            180                 185                 190

Gly Asn Thr Tyr Leu Asp Trp Tyr Leu Gln Lys Pro Gly Gln Ser Pro
        195                 200                 205

Gln Leu Leu Ile Tyr Thr Leu Ser Tyr Arg Ala Ser Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Val Gly Val Tyr Tyr Cys Met Gln Arg Val
                245                 250                 255

Glu Phe Pro Ile Thr Phe Gly Gln Gly Thr Arg Leu Glu Ile Lys Leu
            260                 265                 270

Glu Val Lys Gly Lys His Leu Cys Pro Ser Pro Leu Phe Pro Gly Pro
        275                 280                 285

Ser Lys Pro Phe Trp Val Leu Val Val Val Gly Gly Val Leu Ala Cys
    290                 295                 300

Tyr Ser Leu Leu Val Thr Val Ala Phe Ile Ile Phe Trp Val Arg Ser
305                 310                 315                 320

```
Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
            340                 345                 350

Asp Phe Ala Ala Tyr Arg Ser Lys Leu Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Gln Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
        435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470

<210> SEQ ID NO 224
<211> LENGTH: 457
<212> TYPE: PRT
<213> ORGANISM: Artificial Sequence
<220> FEATURE:
<223> OTHER INFORMATION: 272H-CD28H-CD28TM-DAP10CYP-CD3zetaCYP CAR
      (includes leader)

<400> SEQUENCE: 224

Met Glu Thr Pro Ala Gln Leu Leu Phe Leu Leu Leu Leu Trp Leu Pro
1               5                   10                  15

Asp Thr Thr Gly Gln Val Gln Leu Val Glu Ser Gly Gly Gly Val Val
            20                  25                  30

Gln Pro Gly Arg Ser Leu Arg Leu Ser Cys Ala Ala Ser Gly Phe Ile
        35                  40                  45

Phe Ser Arg Tyr Gly Met His Trp Val Arg Gln Ala Pro Gly Lys Gly
    50                  55                  60

Leu Lys Trp Val Ala Val Ile Trp Tyr Asp Gly Ser Asn Lys Leu Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Tyr Tyr Asp Asn Ser Arg His His Trp
        115                 120                 125

Gly Phe Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Thr Pro Leu Ser Leu Pro Val Thr Pro Gly Glu Pro
                165                 170                 175

Ala Ser Ile Ser Cys Arg Ser Ser Arg Ser Leu Leu Asp Ser Asp Asp
            180                 185                 190

Gly Asn Thr Tyr Leu Asp Trp Tyr Leu Gln Lys Pro Gly Gln Ser Pro
        195                 200                 205
```

```
Gln Leu Leu Ile Tyr Thr Leu Ser Tyr Arg Ala Ser Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Val Gly Val Tyr Tyr Cys Met Gln Arg Val
            245                 250                 255

Glu Phe Pro Ile Thr Phe Gly Gln Gly Thr Arg Leu Glu Ile Lys Leu
        260                 265                 270

Glu Val Lys Gly Lys His Leu Cys Pro Ser Pro Leu Phe Pro Gly Pro
    275                 280                 285

Ser Lys Pro Phe Trp Val Leu Val Val Val Gly Gly Val Leu Ala Cys
    290                 295                 300

Tyr Ser Leu Leu Val Thr Val Ala Phe Ile Ile Phe Trp Val Leu Cys
305                 310                 315                 320

Ala Arg Pro Arg Arg Ser Pro Ala Gln Glu Asp Gly Lys Val Tyr Ile
            325                 330                 335

Asn Met Pro Gly Arg Gly Lys Leu Arg Val Lys Phe Ser Arg Ser Ala
        340                 345                 350

Asp Ala Pro Ala Tyr Gln Gln Gly Gln Asn Gln Leu Tyr Asn Glu Leu
    355                 360                 365

Asn Leu Gly Arg Arg Glu Glu Tyr Asp Val Leu Asp Lys Arg Arg Gly
370                 375                 380

Arg Asp Pro Glu Met Gly Gly Lys Pro Gln Arg Arg Lys Asn Pro Gln
385                 390                 395                 400

Glu Gly Leu Tyr Asn Glu Leu Gln Lys Asp Lys Met Ala Glu Ala Tyr
            405                 410                 415

Ser Glu Ile Gly Met Lys Gly Glu Arg Arg Arg Gly Lys Gly His Asp
        420                 425                 430

Gly Leu Tyr Gln Gly Leu Ser Thr Ala Thr Lys Asp Thr Tyr Asp Ala
    435                 440                 445

Leu His Met Gln Ala Leu Pro Pro Arg
    450                 455

<210> SEQ ID NO 225
<211> LENGTH: 474
<212> TYPE: PRT
<213> ORGANISM: Artificial Sequence
<220> FEATURE:
<223> OTHER INFORMATION: 272L-CD28H-CD28TM-CD28CYP-CD3zetaCYP CAR
      (includes leader)

<400> SEQUENCE: 225

Met Glu Thr Pro Ala Gln Leu Leu Phe Leu Leu Leu Trp Leu Pro
1               5                   10                  15

Asp Thr Thr Gly Asp Ile Val Met Thr Gln Thr Pro Leu Ser Leu Pro
            20                  25                  30

Val Thr Pro Gly Glu Pro Ala Ser Ile Ser Cys Arg Ser Ser Arg Ser
        35                  40                  45

Leu Leu Asp Ser Asp Asp Gly Asn Thr Tyr Leu Asp Trp Tyr Leu Gln
    50                  55                  60

Lys Pro Gly Gln Ser Pro Gln Leu Leu Ile Tyr Thr Leu Ser Tyr Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
```

```
            100                 105                 110
Tyr Cys Met Gln Arg Val Glu Phe Pro Ile Thr Phe Gly Gln Gly Thr
            115                 120                 125

Arg Leu Glu Ile Lys Gly Gly Gly Ser Gly Gly Gly Gly Ser Gly
130                 135                 140

Gly Gly Gly Ser Gln Val Gln Leu Val Glu Ser Gly Gly Val Val
145                 150                 155                 160

Gln Pro Gly Arg Ser Leu Arg Leu Ser Cys Ala Ala Ser Gly Phe Ile
                165                 170                 175

Phe Ser Arg Tyr Gly Met His Trp Val Arg Gln Ala Pro Gly Lys Gly
                180                 185                 190

Leu Lys Trp Val Ala Val Ile Trp Tyr Asp Gly Ser Asn Lys Leu Tyr
            195                 200                 205

Ala Asp Ser Val Lys Gly Arg Phe Thr Ile Ser Arg Asp Asn Ser Lys
210                 215                 220

Asn Thr Leu Tyr Leu Gln Met Asn Ser Leu Arg Ala Glu Asp Thr Ala
225                 230                 235                 240

Val Tyr Tyr Cys Ala Arg Asp Tyr Tyr Asp Asn Ser Arg His His Trp
                245                 250                 255

Gly Phe Asp Tyr Trp Gly Gln Gly Thr Leu Val Thr Val Ser Ser Leu
                260                 265                 270

Glu Val Lys Gly Lys His Leu Cys Pro Ser Pro Leu Phe Pro Gly Pro
            275                 280                 285

Ser Lys Pro Phe Trp Val Leu Val Val Val Gly Gly Val Leu Ala Cys
290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
                340                 345                 350

Asp Phe Ala Ala Tyr Arg Ser Lys Leu Arg Val Lys Phe Ser Arg Ser
                355                 360                 365

Ala Asp Ala Pro Ala Tyr Gln Gln Gly Gln Asn Gln Leu Tyr Asn Glu
370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Gln Arg Arg Lys Asn Pro
                405                 410                 415

Gln Glu Gly Leu Tyr Asn Glu Leu Gln Lys Asp Lys Met Ala Glu Ala
                420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
            450                 455                 460

Ala Leu His Met Gln Ala Leu Pro Pro Arg
465                 470

<210> SEQ ID NO 226
<211> LENGTH: 470
<212> TYPE: PRT
<213> ORGANISM: Artificial Sequence
<220> FEATURE:
<223> OTHER INFORMATION: 2592H-CD28H-CD28TM-BBCYP-CD3zetaCYP CAR
      (includes leader)
```

<400> SEQUENCE: 226

```
Met Glu Thr Pro Ala Gln Leu Leu Phe Leu Leu Leu Leu Trp Leu Pro
1               5                   10                  15

Asp Thr Thr Gly Gln Val Gln Leu Gln Glu Ser Gly Pro Arg Leu Val
            20                  25                  30

Lys Pro Ser Gln Thr Leu Ser Leu Thr Cys Thr Val Ser Gly Gly Ser
        35                  40                  45

Ile Ser Ser Asp Gly Tyr Tyr Trp Ser Trp Ile Arg Gln His Pro Gly
50                  55                  60

Lys Gly Leu Glu Trp Ile Gly Tyr Ile Tyr Tyr Ser Gly Ser Thr Phe
65                  70                  75                  80

Tyr Asn Pro Ser Leu Lys Ser Arg Val Ala Ile Ser Val Asp Thr Ser
            85                  90                  95

Lys Asn Gln Phe Ser Leu Lys Leu Ser Ser Val Thr Ala Ala Asp Thr
        100                 105                 110

Ala Val Tyr Tyr Cys Ala Arg Glu Ser Pro His Ser Ser Asn Trp Tyr
    115                 120                 125

Ser Gly Phe Asp Cys Trp Gly Gln Gly Thr Leu Val Thr Val Ser Ser
130                 135                 140

Gly Gly Gly Gly Ser Gly Gly Gly Ser Gly Gly Gly Gly Ser Glu
145                 150                 155                 160

Ile Val Leu Thr Gln Ser Pro Asp Phe Gln Ser Val Thr Pro Lys Glu
            165                 170                 175

Lys Val Thr Ile Thr Cys Arg Ala Ser Gln Ser Ile Gly Ser Arg Leu
        180                 185                 190

His Trp Tyr Gln Gln Lys Pro Asp Gln Ser Pro Lys Leu Leu Ile Lys
    195                 200                 205

Tyr Ala Ser Gln Ser Phe Ser Gly Val Pro Ser Arg Phe Ser Gly Ser
210                 215                 220

Gly Ser Gly Thr Asp Phe Thr Leu Thr Ile Asn Ser Leu Glu Ala Glu
225                 230                 235                 240

Asp Ala Ala Thr Tyr Tyr Cys His Gln Ser Ser Asn Leu Pro Phe Thr
            245                 250                 255

Phe Gly Pro Gly Thr Lys Val Asp Ile Lys Ala Ser Val Lys Gly Lys
        260                 265                 270

His Leu Cys Pro Ser Pro Leu Phe Pro Gly Pro Ser Lys Pro Phe Trp
    275                 280                 285

Val Leu Val Val Val Gly Gly Val Leu Ala Cys Tyr Ser Leu Leu Val
290                 295                 300

Thr Val Ala Phe Ile Ile Phe Trp Val Lys Arg Gly Arg Lys Lys Leu
305                 310                 315                 320

Leu Tyr Ile Phe Lys Gln Pro Phe Met Arg Pro Val Gln Thr Thr Gln
            325                 330                 335

Glu Glu Asp Gly Cys Ser Cys Arg Phe Pro Glu Glu Glu Glu Gly Gly
        340                 345                 350

Cys Glu Leu Lys Leu Arg Val Lys Phe Ser Arg Ser Ala Asp Ala Pro
    355                 360                 365

Ala Tyr Gln Gln Gly Gln Asn Gln Leu Tyr Asn Glu Leu Asn Leu Gly
370                 375                 380

Arg Arg Glu Glu Tyr Asp Val Leu Asp Lys Arg Arg Gly Arg Asp Pro
385                 390                 395                 400

Glu Met Gly Gly Lys Pro Gln Arg Arg Lys Asn Pro Gln Glu Gly Leu
```

```
                    405                 410                 415
Tyr Asn Glu Leu Gln Lys Asp Lys Met Ala Glu Ala Tyr Ser Glu Ile
                420                 425                 430

Gly Met Lys Gly Glu Arg Arg Arg Gly Lys Gly His Asp Gly Leu Tyr
            435                 440                 445

Gln Gly Leu Ser Thr Ala Thr Lys Asp Thr Tyr Asp Ala Leu His Met
        450                 455                 460

Gln Ala Leu Pro Pro Arg
465                 470

<210> SEQ ID NO 227
<211> LENGTH: 469
<212> TYPE: PRT
<213> ORGANISM: Artificial Sequence
<220> FEATURE:
<223> OTHER INFORMATION: 2592H-CD28H-CD28TM-CD28CYP-CD3zetaCYP CAR
      (includes leader)

<400> SEQUENCE: 227

Met Glu Thr Pro Ala Gln Leu Leu Phe Leu Leu Leu Leu Trp Leu Pro
1               5                   10                  15

Asp Thr Thr Gly Gln Val Gln Leu Gln Glu Ser Gly Pro Arg Leu Val
            20                  25                  30

Lys Pro Ser Gln Thr Leu Ser Leu Thr Cys Thr Val Ser Gly Gly Ser
        35                  40                  45

Ile Ser Ser Asp Gly Tyr Tyr Trp Ser Trp Ile Arg Gln His Pro Gly
    50                  55                  60

Lys Gly Leu Glu Trp Ile Gly Tyr Ile Tyr Tyr Ser Gly Ser Thr Phe
65                  70                  75                  80

Tyr Asn Pro Ser Leu Lys Ser Arg Val Ala Ile Ser Val Asp Thr Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Glu Ser Pro His Ser Ser Asn Trp Tyr
        115                 120                 125

Ser Gly Phe Asp Cys Trp Gly Gln Gly Thr Leu Val Thr Val Ser Ser
    130                 135                 140

Gly Gly Gly Gly Ser Gly Gly Gly Ser Gly Gly Gly Gly Ser Glu
145                 150                 155                 160

Ile Val Leu Thr Gln Ser Pro Asp Phe Gln Ser Val Thr Pro Lys Glu
                165                 170                 175

Lys Val Thr Ile Thr Cys Arg Ala Ser Gln Ser Ile Gly Ser Arg Leu
            180                 185                 190

His Trp Tyr Gln Gln Lys Pro Asp Gln Ser Pro Lys Leu Leu Ile Lys
        195                 200                 205

Tyr Ala Ser Gln Ser Phe Ser Gly Val Pro Ser Arg Phe Ser Gly Ser
    210                 215                 220

Gly Ser Gly Thr Asp Phe Thr Leu Thr Ile Asn Ser Leu Glu Ala Glu
225                 230                 235                 240

Asp Ala Ala Thr Tyr Tyr Cys His Gln Ser Ser Asn Leu Pro Phe Thr
                245                 250                 255

Phe Gly Pro Gly Thr Lys Val Asp Ile Lys Ala Ser Val Lys Gly Lys
            260                 265                 270

His Leu Cys Pro Ser Pro Leu Phe Pro Gly Pro Ser Lys Pro Phe Trp
        275                 280                 285
```

```
Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Lys Leu Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
450                 455                 460

Ala Leu Pro Pro Arg
465

<210> SEQ ID NO 228
<211> LENGTH: 452
<212> TYPE: PRT
<213> ORGANISM: Artificial Sequence
<220> FEATURE:
<223> OTHER INFORMATION: 2592H-CD28H-CD28TM-DAP10CYP-CD3zetaCYP CAR
      (includes leader)

<400> SEQUENCE: 228

Met Glu Thr Pro Ala Gln Leu Leu Phe Leu Leu Leu Leu Trp Leu Pro
1               5                   10                  15

Asp Thr Thr Gly Gln Val Gln Leu Gln Glu Ser Gly Pro Arg Leu Val
            20                  25                  30

Lys Pro Ser Gln Thr Leu Ser Leu Thr Cys Thr Val Ser Gly Gly Ser
        35                  40                  45

Ile Ser Ser Asp Gly Tyr Tyr Trp Ser Trp Ile Arg Gln His Pro Gly
    50                  55                  60

Lys Gly Leu Glu Trp Ile Gly Tyr Ile Tyr Tyr Ser Gly Ser Thr Phe
65                  70                  75                  80

Tyr Asn Pro Ser Leu Lys Ser Arg Val Ala Ile Ser Val Asp Thr Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Glu Ser Pro His Ser Ser Asn Trp Tyr
        115                 120                 125

Ser Gly Phe Asp Cys Trp Gly Gln Gly Thr Leu Val Thr Val Ser Ser
    130                 135                 140

Gly Gly Gly Gly Ser Gly Gly Gly Ser Gly Gly Gly Gly Ser Glu
145                 150                 155                 160

Ile Val Leu Thr Gln Ser Pro Asp Phe Gln Ser Val Thr Pro Lys Glu
                165                 170                 175
```

Lys Val Thr Ile Thr Cys Arg Ala Ser Gln Ser Ile Gly Ser Arg Leu
                180                 185                 190

His Trp Tyr Gln Gln Lys Pro Asp Gln Ser Pro Lys Leu Leu Ile Lys
            195                 200                 205

Tyr Ala Ser Gln Ser Phe Ser Gly Val Pro Ser Arg Phe Ser Gly Ser
        210                 215                 220

Gly Ser Gly Thr Asp Phe Thr Leu Thr Ile Asn Ser Leu Glu Ala Glu
225                 230                 235                 240

Asp Ala Ala Thr Tyr Tyr Cys His Gln Ser Ser Asn Leu Pro Phe Thr
                245                 250                 255

Phe Gly Pro Gly Thr Lys Val Asp Ile Lys Ala Ser Val Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
290                 295                 300

Thr Val Ala Phe Ile Ile Phe Trp Val Leu Cys Ala Arg Pro Arg Arg
305                 310                 315                 320

Ser Pro Ala Gln Glu Asp Gly Lys Val Tyr Ile Asn Met Pro Gly Arg
                325                 330                 335

Gly Lys Leu Arg Val Lys Phe Ser Arg Ser Ala Asp Ala Pro Ala Tyr
            340                 345                 350

Gln Gln Gly Gln Asn Gln Leu Tyr Asn Glu Leu Asn Leu Gly Arg Arg
        355                 360                 365

Glu Glu Tyr Asp Val Leu Asp Lys Arg Arg Gly Arg Asp Pro Glu Met
370                 375                 380

Gly Gly Lys Pro Gln Arg Arg Lys Asn Pro Gln Glu Gly Leu Tyr Asn
385                 390                 395                 400

Glu Leu Gln Lys Asp Lys Met Ala Glu Ala Tyr Ser Glu Ile Gly Met
                405                 410                 415

Lys Gly Glu Arg Arg Arg Gly Lys Gly His Asp Gly Leu Tyr Gln Gly
            420                 425                 430

Leu Ser Thr Ala Thr Lys Asp Thr Tyr Asp Ala Leu His Met Gln Ala
        435                 440                 445

Leu Pro Pro Arg
    450

<210> SEQ ID NO 229
<211> LENGTH: 469
<212> TYPE: PRT
<213> ORGANISM: Artificial Sequence
<220> FEATURE:
<223> OTHER INFORMATION: 2592L-CD28H-CD28TM-CD28CYP-CD3ZCYP CAR
      (includes leader)

<400> SEQUENCE: 229

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Asp Phe Gln Ser
            20                  25                  30

Val Thr Pro Lys Glu Lys Val Thr Ile Thr Cys Arg Ala Ser Gln Ser
        35                  40                  45

Ile Gly Ser Arg Leu His Trp Tyr Gln Gln Lys Pro Asp Gln Ser Pro
    50                  55                  60

Lys Leu Leu Ile Lys Tyr Ala Ser Gln Ser Phe Ser Gly Val Pro Ser

```
            65                  70                  75                  80
        Arg Phe Ser Gly Ser Gly Ser Gly Thr Asp Phe Thr Leu Thr Ile Asn
                        85                  90                  95

Ser Leu Glu Ala Glu Asp Ala Ala Thr Tyr Tyr Cys His Gln Ser Ser
                        100                 105                 110

Asn Leu Pro Phe Thr Phe Gly Pro Gly Thr Lys Val Asp Ile Lys Gly
                        115                 120                 125

Gly Gly Gly Ser Gly Gly Gly Gly Ser Gly Gly Gly Ser Gln Val
        130                 135                 140

Gln Leu Gln Glu Ser Gly Pro Arg Leu Val Lys Pro Ser Gln Thr Leu
        145                 150                 155                 160

Ser Leu Thr Cys Thr Val Ser Gly Gly Ser Ile Ser Ser Asp Gly Tyr
                        165                 170                 175

Tyr Trp Ser Trp Ile Arg Gln His Pro Gly Lys Gly Leu Glu Trp Ile
                        180                 185                 190

Gly Tyr Ile Tyr Tyr Ser Gly Ser Thr Phe Tyr Asn Pro Ser Leu Lys
                        195                 200                 205

Ser Arg Val Ala Ile Ser Val Asp Thr Ser Lys Asn Gln Phe Ser Leu
                        210                 215                 220

Lys Leu Ser Ser Val Thr Ala Ala Asp Thr Ala Val Tyr Tyr Cys Ala
        225                 230                 235                 240

Arg Glu Ser Pro His Ser Ser Asn Trp Tyr Ser Gly Phe Asp Cys Trp
                        245                 250                 255

Gly Gln Gly Thr Leu Val Thr Val Ser Ser Ala Ser Val Lys Gly Lys
                        260                 265                 270

His Leu Cys Pro Ser Pro Leu Phe Pro Gly Pro Ser Lys Pro Phe Trp
                        275                 280                 285

Val Leu Val Val Val Gly Gly Val Leu Ala Cys Tyr Ser Leu Leu Val
                        290                 295                 300

Thr Val Ala Phe Ile Ile Phe Trp Val Arg Ser Lys Arg Ser Arg Leu
        305                 310                 315                 320

Leu His Ser Asp Tyr Met Asn Met Thr Pro Arg Arg Pro Gly Pro Thr
                        325                 330                 335

Arg Lys His Tyr Gln Pro Tyr Ala Pro Pro Arg Asp Phe Ala Ala Tyr
                        340                 345                 350

Arg Ser Lys Leu Arg Val Lys Phe Ser Arg Ser Ala Asp Ala Pro Ala
                        355                 360                 365

Tyr Gln Gln Gly Gln Asn Gln Leu Tyr Asn Glu Leu Asn Leu Gly Arg
                        370                 375                 380

Arg Glu Glu Tyr Asp Val Leu Asp Lys Arg Arg Gly Arg Asp Pro Glu
        385                 390                 395                 400

Met Gly Gly Lys Pro Gln Arg Arg Lys Asn Pro Gln Glu Gly Leu Tyr
                        405                 410                 415

Asn Glu Leu Gln Lys Asp Lys Met Ala Glu Ala Tyr Ser Glu Ile Gly
                        420                 425                 430

Met Lys Gly Glu Arg Arg Arg Gly Lys Gly His Asp Gly Leu Tyr Gln
                        435                 440                 445

Gly Leu Ser Thr Ala Thr Lys Asp Thr Tyr Asp Ala Leu His Met Gln
                        450                 455                 460

Ala Leu Pro Pro Arg
        465

<210> SEQ ID NO 230
```

<211> LENGTH: 20
<212> TYPE: PRT
<213> ORGANISM: Artificial Sequence
<220> FEATURE:
<223> OTHER INFORMATION: signal peptide

<400> SEQUENCE: 230

Met Glu Thr Pro Ala Gln Leu Leu Phe Leu Leu Leu Trp Leu Pro
1               5                   10                  15

Asp Thr Thr Gly
            20

<210> SEQ ID NO 231
<211> LENGTH: 21
<212> TYPE: PRT
<213> ORGANISM: Artificial Sequence
<220> FEATURE:
<223> OTHER INFORMATION: T2A ribosomal skip sequence

<400> SEQUENCE: 231

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 232
<211> LENGTH: 327
<212> TYPE: PRT
<213> ORGANISM: Artificial Sequence
<220> FEATURE:
<223> OTHER INFORMATION: Truncated CD19

<400> SEQUENCE: 232

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

```
Arg Gly Pro Leu Ser Trp Thr His Val His Pro Lys Gly Pro Lys Ser
    210                 215                 220
Leu Leu Ser Leu Glu Leu Lys Asp Asp Arg Pro Ala Arg Asp Met Trp
225                 230                 235                 240
Val Met Glu Thr Gly Leu Leu Leu Pro Arg Ala Thr Ala Gln Asp Ala
                245                 250                 255
Gly Lys Tyr Tyr Cys His Arg Gly Asn Leu Thr Met Ser Phe His Leu
                260                 265                 270
Glu Ile Thr Ala Arg Pro Val Leu Trp His Trp Leu Leu Arg Thr Gly
                275                 280                 285
Gly Trp Lys Val Ser Ala Val Thr Leu Ala Tyr Leu Ile Phe Cys Leu
290                 295                 300
Cys Ser Leu Val Gly Ile Leu His Leu Gln Arg Ala Leu Val Leu Arg
305                 310                 315                 320
Arg Lys Arg Lys Arg Met Thr
                325
```

<210> SEQ ID NO 233
<211> LENGTH: 10
<212> TYPE: PRT
<213> ORGANISM: Artificial Sequence
<220> FEATURE:
<223> OTHER INFORMATION: Ab 129 CDR H1

<400> SEQUENCE: 233

```
Gly Gly Ser Val Ser Ser Gly Gly Tyr Tyr
1               5                   10
```

<210> SEQ ID NO 234
<211> LENGTH: 7
<212> TYPE: PRT
<213> ORGANISM: Artificial Sequence
<220> FEATURE:
<223> OTHER INFORMATION: Ab 129 CDR H2

<400> SEQUENCE: 234

```
Ile Tyr Tyr Thr Gly Ser Thr
1               5
```

<210> SEQ ID NO 235
<211> LENGTH: 10
<212> TYPE: PRT
<213> ORGANISM: Artificial Sequence
<220> FEATURE:
<223> OTHER INFORMATION: Ab 129 CDR H3

<400> SEQUENCE: 235

```
Asp Tyr Asp Trp Ser Phe His Phe Asp Tyr
1               5                   10
```

<210> SEQ ID NO 236
<211> LENGTH: 6
<212> TYPE: PRT
<213> ORGANISM: Artificial Sequence
<220> FEATURE:
<223> OTHER INFORMATION: Ab 129 CDR L1

<400> SEQUENCE: 236

```
Gln Gly Ile Arg Asn Asp
1               5
```

<210> SEQ ID NO 237
<211> LENGTH: 3

```
<212> TYPE: PRT
<213> ORGANISM: Artificial Sequence
<220> FEATURE:
<223> OTHER INFORMATION: Ab 129 CDR L2

<400> SEQUENCE: 237

Ala Ala Ser
1

<210> SEQ ID NO 238
<211> LENGTH: 7
<212> TYPE: PRT
<213> ORGANISM: Artificial Sequence
<220> FEATURE:
<223> OTHER INFORMATION: Ab 129 CDR L3

<400> SEQUENCE: 238

Leu Gln His Asn Ser Tyr Pro
1               5

<210> SEQ ID NO 239
<211> LENGTH: 8
<212> TYPE: PRT
<213> ORGANISM: Artificial Sequence
<220> FEATURE:
<223> OTHER INFORMATION: Ab 272 CDR H1

<400> SEQUENCE: 239

Gly Phe Ile Phe Ser Arg Tyr Gly
1               5

<210> SEQ ID NO 240
<211> LENGTH: 8
<212> TYPE: PRT
<213> ORGANISM: Artificial Sequence
<220> FEATURE:
<223> OTHER INFORMATION: Ab 272 CDR H2

<400> SEQUENCE: 240

Ile Trp Tyr Asp Gly Ser Asn Lys
1               5

<210> SEQ ID NO 241
<211> LENGTH: 14
<212> TYPE: PRT
<213> ORGANISM: Artificial Sequence
<220> FEATURE:
<223> OTHER INFORMATION: Ab 272 CDR H3

<400> SEQUENCE: 241

Asp Tyr Tyr Asp Asn Ser Arg His His Trp Gly Phe Asp Tyr
1               5                   10

<210> SEQ ID NO 242
<211> LENGTH: 17
<212> TYPE: PRT
<213> ORGANISM: Artificial Sequence
<220> FEATURE:
<223> OTHER INFORMATION: Ab 272 CDR L1

<400> SEQUENCE: 242

Arg Ser Ser Arg Ser Leu Leu Asp Ser Asp Asp Gly Asn Thr Tyr Leu
1               5                   10                  15

Asp

<210> SEQ ID NO 243
```

```
<211> LENGTH: 7
<212> TYPE: PRT
<213> ORGANISM: Artificial Sequence
<220> FEATURE:
<223> OTHER INFORMATION: Ab 272 CDR L2

<400> SEQUENCE: 243

Thr Leu Ser Tyr Arg Ala Ser
1               5

<210> SEQ ID NO 244
<211> LENGTH: 9
<212> TYPE: PRT
<213> ORGANISM: Artificial Sequence
<220> FEATURE:
<223> OTHER INFORMATION: Ab 272 CDR L3

<400> SEQUENCE: 244

Met Gln Arg Val Glu Phe Pro Ile Thr
1               5

<210> SEQ ID NO 245
<211> LENGTH: 9
<212> TYPE: PRT
<213> ORGANISM: Artificial Sequence
<220> FEATURE:
<223> OTHER INFORMATION: Ab 2592 CDR H1

<400> SEQUENCE: 245

Gly Gly Ser Ile Ser Ser Asp Gly Tyr
1               5

<210> SEQ ID NO 246
<211> LENGTH: 7
<212> TYPE: PRT
<213> ORGANISM: Artificial Sequence
<220> FEATURE:
<223> OTHER INFORMATION: Ab 2592 CDR H2

<400> SEQUENCE: 246

Ile Tyr Tyr Ser Gly Ser Thr
1               5

<210> SEQ ID NO 247
<211> LENGTH: 14
<212> TYPE: PRT
<213> ORGANISM: Artificial Sequence
<220> FEATURE:
<223> OTHER INFORMATION: Ab 2592 CDR H3

<400> SEQUENCE: 247

Glu Ser Pro His Ser Ser Asn Trp Tyr Ser Gly Phe Asp Cys
1               5                   10

<210> SEQ ID NO 248
<211> LENGTH: 6
<212> TYPE: PRT
<213> ORGANISM: Artificial Sequence
<220> FEATURE:
<223> OTHER INFORMATION: Ab 2592 CDR L1

<400> SEQUENCE: 248

Gln Ser Ile Gly Ser Arg
1               5

<210> SEQ ID NO 249
<211> LENGTH: 3
```

```
<212> TYPE: PRT
<213> ORGANISM: Artificial Sequence
<220> FEATURE:
<223> OTHER INFORMATION: Ab 2592 CDR L2

<400> SEQUENCE: 249

Tyr Ala Ser
1

<210> SEQ ID NO 250
<211> LENGTH: 9
<212> TYPE: PRT
<213> ORGANISM: Artificial Sequence
<220> FEATURE:
<223> OTHER INFORMATION: Ab 2592 CDR L3

<400> SEQUENCE: 250

His Gln Ser Ser Asn Leu Pro Phe Thr
1               5

<210> SEQ ID NO 251
<211> LENGTH: 45
<212> TYPE: DNA
<213> ORGANISM: Artificial Sequence
<220> FEATURE:
<223> OTHER INFORMATION: Linker region

<400> SEQUENCE: 251
ggtggtggtg gttctggcgg cggcggctcc ggtggtggtg gttcc            45

<210> SEQ ID NO 252
<211> LENGTH: 360
<212> TYPE: DNA
<213> ORGANISM: Artificial Sequence
<220> FEATURE:
<223> OTHER INFORMATION: Ab 129 VH

<400> SEQUENCE: 252
caggtgcagc tgcaggagtc gggcccagga ctggtgaagc cttcggagac cctgtccctc      60
acctgcactg tctctggtgg ctccgtcagc agtggtggtt actactggag ctggatccgg     120
cagcccccag ggaagggact ggagtggatt gggtttatct attacactgg gagcaccaac     180
tacaacccct ccctcaagag tcgagtctcc atatcagtag acacgtccaa gaaccagttc     240
tccctgaagc tgagctctgt gaccgctgcg gacgcggccg tgtattactg cgcgagagat     300
tatgactgga gcttccactt tgactactgg ggccagggaa ccctggtcac cgtctcctca     360

<210> SEQ ID NO 253
<211> LENGTH: 321
<212> TYPE: DNA
<213> ORGANISM: Artificial Sequence
<220> FEATURE:
<223> OTHER INFORMATION: Ab 129 VL

<400> SEQUENCE: 253
gacatccaga tgacccagtc tccatcctcc ctgtctgcat ctataggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt accctctcac tttcggcgga     300
gggaccaagg tggagatcaa a                                               321
```

<210> SEQ ID NO 254
<211> LENGTH: 369
<212> TYPE: DNA
<213> ORGANISM: Artificial Sequence
<220> FEATURE:
<223> OTHER INFORMATION: Ab 272 VH

<400> SEQUENCE: 254

```
caggtgcagc tggtggagtc tgggggaggc gtggtccagc ctgggaggtc cctgagactc      60
tcctgtgcag cgtctggatt catcttcagt cgctatggca tgcactgggt ccgccaggct     120
ccaggcaagg ggctgaaatg ggtggcagtt atatggtatg atggaagtaa taaactctat     180
gcagactccg tgaagggccg attcaccatc tccagagaca attccaagaa cacgctgtat     240
ctgcaaatga acagcctgag agccgaggac acggctgtgt attactgtgc gagagattac     300
tatgataata gtagacatca ctgggggttt gactactggg gccagggaac cctggtcacc     360
gtctcctca                                                              369
```

<210> SEQ ID NO 255
<211> LENGTH: 339
<212> TYPE: DNA
<213> ORGANISM: Artificial Sequence
<220> FEATURE:
<223> OTHER INFORMATION: Ab 272 VL

<400> SEQUENCE: 255

```
gatattgtga tgacccagac tccactctcc ctgcccgtca cccctggaga gccggcctcc      60
atctcctgca ggtctagtcg gagcctcttg gatagtgatg atggaaacac ctatttggac     120
tggtacctgc agaagccagg gcagtctcca cagctcctga tctacacgct ttcctatcgg     180
gcctctggag tcccagacag gttcagtggc agtgggtcag gcactgattt cacactgaaa     240
atcagcaggg tggaggctga ggatgttgga gtttattact gcatgcaacg tgtagagttt     300
cctatcacct tcggccaagg gacacgactg gagattaaa                             339
```

<210> SEQ ID NO 256
<211> LENGTH: 372
<212> TYPE: DNA
<213> ORGANISM: Artificial Sequence
<220> FEATURE:
<223> OTHER INFORMATION: Ab 2592 VH

<400> SEQUENCE: 256

```
caggtgcagc tgcaggagtc gggcccaaga ctggtgaagc cttcacagac cctgtccctc      60
acctgcactg tctctggtgg ctccatcagt agtgatggtt actactggag ctggatccgc     120
cagcacccag ggaagggcct ggagtggatt gggtacatct attacagtgg gagcaccttc     180
tacaacccgt ccctcaagag tcgagttgcc atatcagtgg acacgtctaa gaaccagttc     240
tccctgaagc tgagctctgt gactgccgcg gacacggccg tgtattactg tgcgagagaa     300
tccccctcata gcagcaactg gtactcgggc tttgactgct ggggccaggg aaccctggtc     360
accgtctcct ca                                                          372
```

<210> SEQ ID NO 257
<211> LENGTH: 321
<212> TYPE: DNA
<213> ORGANISM: Artificial Sequence
<220> FEATURE:
<223> OTHER INFORMATION: Ab 2592 VL

<400> SEQUENCE: 257

```
gaaattgtgc tgactcagtc tccagacttt cagtctgtga ctccaaagga gaaagtcacc    60
atcacctgcc gggccagtca gagcattggt agtaggttac actggtacca gcagaaacca   120
gatcagtctc caaagctcct catcaagtat gcttcccagt ccttctcagg ggtcccctcg   180
aggttcagtg gcagtggatc tgggacagat ttcaccctca ccatcaatag cctggaagct   240
gaagatgctg caacgtatta ctgtcatcag agtagtaatt taccattcac tttcggccct   300
gggaccaaag tggatatcaa a                                             321

<210> SEQ ID NO 258
<211> LENGTH: 726
<212> TYPE: DNA
<213> ORGANISM: Artificial Sequence
<220> FEATURE:
<223> OTHER INFORMATION: 129 hv-linker-lv

<400> SEQUENCE: 258
caggtgcagc tgcaggagtc gggcccagga ctggtgaagc cttcggagac cctgtccctc    60
acctgcactg tctctggtgg ctccgtcagc agtggtggtt actactggag ctggatccgg   120
cagcccccag ggaagggact ggagtggatt gggtttatct attacactgg gagcaccaac   180
tacaacccct ccctcaagag tcgagtctcc atatcagtag acacgtccaa gaaccagttc   240
tccctgaagc tgagctctgt gaccgctgcg gacgcggccg tgtattactg tgcgagagat   300
tatgactgga gcttccactt tgactactgg ggccagggaa ccctggtcac cgtctcctca   360
ggtggtggtg gttctggcgg cggcggctcc ggtggtggtg gttccgacat ccagatgacc   420
cagtctccat cctccctgtc tgcatctata ggagacagag tcaccatcac ttgccgggca   480
agtcagggca ttagaaatga tttaggctgg tatcagcaga aaccagggaa agcccctaag   540
cgcctgatct atgctgcatc cagtttgcaa agtggggtcc catcaaggtt cagcggcagt   600
ggatctggga cagaattcac tctcacaatc agcagcctgc agcctgaaga ttttgcaact   660
tattactgtc tacagcataa tagttaccct ctcacttttcg gcggagggac caaggtggag   720
atcaaa                                                             726

<210> SEQ ID NO 259
<211> LENGTH: 726
<212> TYPE: DNA
<213> ORGANISM: Artificial Sequence
<220> FEATURE:
<223> OTHER INFORMATION: 129 lv-linker-hv

<400> SEQUENCE: 259
gacatccaga tgacccagtc tccatcctcc ctgtctgcat ctataggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctctcac ttttcggcgga   300 gggaccaagg tggagatcaa aggtggtggt ggttctggcg gcggcggctc cggtggtggt   360
ggttcccagg tgcagctgca ggagtcgggc ccaggactgg tgaagccttc ggagaccctg   420
tccctcacct gcactgtctc tggtggctcc gtcagcagtg gtggttacta ctggagctgg   480
atccggcagc ccccagggaa gggactggag tggattgggt ttatctatta cactgggagc   540
accaactaca acccctccct caagagtcga gtctccatat cagtagacac gtccaagaac   600
```

```
cagttctccc tgaagctgag ctctgtgacc gctgcggacg cggccgtgta ttactgtgcg    660
agagattatg actggagctt ccactttgac tactggggcc agggaaccct ggtcaccgtc    720
tcctca                                                                726
```

<210> SEQ ID NO 260
<211> LENGTH: 753
<212> TYPE: DNA
<213> ORGANISM: Artificial Sequence
<220> FEATURE:
<223> OTHER INFORMATION: 272 hv-linker-lv

<400> SEQUENCE: 260

```
caggtgcagc tggtggagtc tgggggaggc gtggtccagc ctgggaggtc cctgagactc     60
tcctgtgcag cgtctggatt catcttcagt cgctatggca tgcactgggt ccgccaggct    120
ccaggcaagg ggctgaaatg ggtggcagtt atatggtatg atggaagtaa taaactctat    180
gcagactccg tgaagggccg attcaccatc tccagagaca attccaagaa cacgctgtat    240
ctgcaaatga acagcctgag agccgaggac acggctgtgt attactgtgc gagagattac    300
tatgataata gtagacatca ctggggggttt gactactggg gccagggaac cctggtcacc    360
gtctcctcag gtggtggtgg ttctggcggc ggcggctccg gtggtggtgg ttccgatatt    420
gtgatgaccc agactccact ctccctgccc gtcacccctg gagagccggc ctccatctcc    480
tgcaggtcta gtcggagcct cttggatagt gatgatggaa acacctattt ggactggtac    540
ctgcagaagc cagggcagtc tccacagctc ctgatctaca cgctttccta tcgggcctct    600
ggagtcccag acaggttcag tggcagtggg tcaggcactg atttcacact gaaaatcagc    660
agggtggagg ctgaggatgt tggagtttat tactgcatgc aacgtgtaga gtttcctatc    720
accttcggcc aagggacacg actggagatt aaa                                 753
```

<210> SEQ ID NO 261
<211> LENGTH: 753
<212> TYPE: DNA
<213> ORGANISM: Artificial Sequence
<220> FEATURE:
<223> OTHER INFORMATION: 272 lv-linker-hv

<400> SEQUENCE: 261

```
gatattgtga tgacccagac tccactctcc ctgcccgtca cccctggaga gccggcctcc     60
atctcctgca ggtctagtcg gagcctcttg atagtgatg atggaaacac ctatttggac    120
tggtacctgc agaagccagg gcagtctcca cagctcctga tctacacgct ttcctatcgg    180
gcctctggag tcccagacag gttcagtggc agtgggtcag gcactgattt cacactgaaa    240
atcagcaggg tggaggctga ggatgttgga gtttattact gcatgcaacg tgtagagttt    300
cctatcacct tcggccaagg gacacgactg gagattaaag gtggtggtgg ttctggcggc    360
ggcggctccg gtggtggtgg ttcccaggtg cagctggtgg agtctggggg aggcgtggtc    420
cagcctggga ggtccctgag actctcctgt gcagcgtctg gattcatctt cagtcgctat    480
ggcatgcact gggtccgcca ggctccaggc aaggggctga atgggtggc agttatatgg    540 tatgatggaa gtaataaact ctatgcagac tccgtgaagg gccgattcac catctccaga    600
gacaattcca agaacacgct gtatctgcaa atgaacagcc tgagagccga ggacacggct    660
gtgtattact gtgcgagaga ttactatgat aatagtagac atcactgggg gtttgactac    720
tggggccagg gaaccctggt caccgtctcc tca                                 753
```

<210> SEQ ID NO 262
<211> LENGTH: 738
<212> TYPE: DNA
<213> ORGANISM: Artificial Sequence
<220> FEATURE:
<223> OTHER INFORMATION: 2592 hv-linker-lv

<400> SEQUENCE: 262

```
caggtgcagc tgcaggagtc gggcccaaga ctggtgaagc cttcacagac cctgtccctc      60
acctgcactg tctctggtgg ctccatcagt agtgatggtt actactggag ctggatccgc     120
cagcacccag ggaagggcct ggagtggatt gggtacatct attacagtgg gagcaccttc     180
tacaacccgt ccctcaagag tcgagttgcc atatcagtgg acacgtctaa gaaccagttc     240
tccctgaagc tgagctctgt gactgccgcg gacacggccg tgtattactg tgcgagagaa     300
tcccctcata gcagcaactg gtactcgggc tttgactgct ggggccaggg aaccctggtc     360
accgtctcct caggtggtgg tggttctggc ggcggcggct ccggtggtgg tggttccgaa     420
attgtgctga ctcagtctcc agactttcag tctgtgactc caaaggagaa agtcaccatc     480
acctgccggg ccagtcagag cattggtagt aggttacact ggtaccagca gaaaccagat     540
cagtctccaa agctcctcat caagtatgct tcccagtcct ctcagggggt ccctcgagg     600
ttcagtggca gtggatctgg gacagatttc accctcacca tcaatagcct ggaagctgaa     660
gatgctgcaa cgtattactg tcatcagagt agtaatttac cattcacttt cggccctggg     720
accaaagtgg atatcaaa                                                    738
```

<210> SEQ ID NO 263
<211> LENGTH: 738
<212> TYPE: DNA
<213> ORGANISM: Artificial Sequence
<220> FEATURE:
<223> OTHER INFORMATION: 2592 lv-linker-hv

<400> SEQUENCE: 263

```
gaaattgtgc tgactcagtc tccagacttt cagtctgtga ctccaaagga gaaagtcacc      60
atcacctgcc gggccagtca gagcattggt agtaggttac actggtacca gcagaaacca     120
gatcagtctc caaagctcct catcaagtat gcttcccagt ccttctcagg ggtcccctcg     180
aggttcagtg gcagtggatc tgggacagat ttcaccctca ccatcaatag cctggaagct     240
gaagatgctg caacgtatta ctgtcatcag agtagtaatt taccattcac tttcggccct     300
gggaccaaag tggatatcaa aggtggtggt ggttctggcg gcggcggctc cggtggtggt     360
ggttcccagg tgcagctgca ggagtcgggc ccaagactgg tgaagccttc acagaccctg     420
tccctcacct gcactgtctc tggtggctcc atcagtagtg atggttacta ctggagctgg     480
atccgccagc acccagggaa gggcctggag tggattgggt acatctatta cagtgggagc     540
accttctaca acccgtccct caagagtcga gttgccatat cagtggacac gtctaagaac     600
cagttctccc tgaagctgag ctctgtgact gccgcggaca cggccgtgta ttactgtgcg     660
agagaatccc ctcatagcag caactggtac tcgggctttg actgctgggg ccagggaacc     720
ctggtcaccg tctcctca                                                    738
```

<210> SEQ ID NO 264
<211> LENGTH: 54
<212> TYPE: DNA
<213> ORGANISM: Artificial Sequence
<220> FEATURE:
<223> OTHER INFORMATION: CD28 hinge domain

```
<400> SEQUENCE: 264
gtgaaaggga acacctttg tccaagtccc ctatttcccg gaccttctaa gccc          54

<210> SEQ ID NO 265
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 265
ttttgggtgc tggtggtggt tgtggagtc ctggcttgct atagcttgct agtaacagtg    60
gcctttatta ttttctgggt g                                             81

<210> SEQ ID NO 266
<211> LENGTH: 126
<212> TYPE: DNA
<213> ORGANISM: Artificial Sequence
<220> FEATURE:
<223> OTHER INFORMATION: 4-1BB costim domain

<400> SEQUENCE: 266
aaacggggca gaaagaaact cctgtatata ttcaaacaac catttatgag accagtacaa   60
actactcaag aggaagatgg ctgtagctgc cgatttccag aagaagaaga aggaggatgt  120
gaactg                                                             126

<210> SEQ ID NO 267
<211> LENGTH: 123
<212> TYPE: DNA
<213> ORGANISM: Artificial Sequence
<220> FEATURE:
<223> OTHER INFORMATION: CD28 costim domain

<400> SEQUENCE: 267
aggagtaaga ggagcaggct cctgcacagt gactacatga acatgactcc ccgccgcccc   60
gggcccaccc gcaagcatta ccagccctat gccccaccac gcgacttcgc agcctatcgc  120
tcc                                                                123

<210> SEQ ID NO 268
<211> LENGTH: 72
<212> TYPE: DNA
<213> ORGANISM: Artificial Sequence
<220> FEATURE:
<223> OTHER INFORMATION: DAP10 costim domain

<400> SEQUENCE: 268
ctgtgcgcac gcccacgccg cagccccgcc caagaagatg gcaaagtcta catcaacatg   60
ccaggcaggg gc                                                       72

<210> SEQ ID NO 269
<211> LENGTH: 342
<212> TYPE: DNA
<213> ORGANISM: Artificial Sequence
<220> FEATURE:
<223> OTHER INFORMATION: CD3zeta intracellular domain

<400> SEQUENCE: 269
cttagagtga agttcagcag gagcgcagac gccccgcgt accagcaggg ccagaaccag    60
ctctataacg agctcaatct aggacgaaga gaggagtacg atgttttgga caagagacgt  120
ggccgggacc ctgagatggg gggaaagccg cagagaagga gaaccctca ggaaggcctg   180
```

```
tacaatgaac tgcagaaaga taagatggcg gaggcctaca gtgagattgg gatgaaaggc      240
gagcgccgga ggggcaaggg gcacgatggc ctttaccagg gtctcagtac agccaccaag      300
gacacctacg acgcccttca catgcaggcc ctgccccctc gc                        342
```

<210> SEQ ID NO 270
<211> LENGTH: 1398
<212> TYPE: DNA
<213> ORGANISM: Artificial Sequence
<220> FEATURE:
<223> OTHER INFORMATION: 129H-CD28H-CD28TM-CD28CYP-CD3ZCYP CAR (includes
      leader)

<400> SEQUENCE: 270

```
atggaaaccc cagcgcagct tctcttcctc ctgctactct ggctcccaga taccaccgga      60
caggtgcagc tgcaggagtc gggcccagga ctggtgaagc cttcggagac cctgtccctc     120
acctgcactg tctctggtgg ctccgtcagc agtggtggtt actactggag ctggatccgg     180
cagcccccag ggaagggact ggagtggatt gggtttatct attacactgg gagcaccaac     240 tacaaccccl ccctcaagag tcgagtctcc atatcagtag acacgtccaa gaaccagttc     300
tccctgaagc tgagctctgt gaccgctgcg gacgcggccg tgtattactg tgcgagagat     360
tatgactgga gcttccactt tgactactgg ggccagggaa ccctggtcac cgtctcctca     420
ggtggtggtg gttctggcgg cggcggctcc ggtggtggtg gttccgacat ccagatgacc     480
cagtctccat cctccctgtc tgcatctata ggagacagag tcaccatcac ttgccgggca     540
agtcagggca ttagaaatga tttaggctgg tatcagcaga aaccagggaa agcccctaag     600
cgcctgatct atgctgcatc cagtttgcaa agtggggtcc catcaaggtt cagcggcagt     660
ggatctggga cagaattcac tctcacaatc agcagcctgc agcctgaaga ttttgcaact     720
tattactgtc tacagcataa tagttaccct ctcactttcg gcggagggac caaggtggag     780
atcaaagcta gcgtgaaagg aaacaccttt gtccaagtc ccctatttcc cggaccttct     840
aagccctttt gggtgctggt ggtggttggt ggagtcctgg cttgctatag cttgctagta     900
acagtggcct ttattatttt ctgggtgagg agtaagagga gcaggctcct gcacagtgac     960
tacatgaaca tgactccccg ccgccccggg cccacccgca agcattacca gccctatgcc    1020
ccaccacgcg acttcgcagc ctatcgctcc aagcttagag tgaagttcag caggagcgca    1080
gacgcccccg cgtaccagca gggccagaac cagctctata acgagctcaa tctaggacga    1140
agagaggagt acgatgtttt ggacaagaga cgtggccggg accctgagat ggggggaaag    1200
ccgcagagaa ggaagaaccc tcaggaaggc ctgtacaatg aactgcagaa agataagatg    1260
gcggaggcct acagtgagat tgggatgaaa ggcgagcgcc ggaggggcaa ggggcacgat    1320
ggcctttacc agggtctcag tacagccacc aaggacacct acgacgccct tcacatgcag    1380
gccctgcccc ctcgctaa                                                  1398
```

<210> SEQ ID NO 271
<211> LENGTH: 1398
<212> TYPE: DNA
<213> ORGANISM: Artificial Sequence
<220> FEATURE:
<223> OTHER INFORMATION: 129L-CD28H-CD28TM-CD28CYP-CD3ZCYP CAR (includes
      leader)

<400> SEQUENCE: 271

```
atggaaaccc cagcgcagct tctcttcctc ctgctactct ggctcccaga taccaccgga      60
```

```
gacatccaga tgacccagtc tccatcctcc ctgtctgcat ctataggaga cagagtcacc      120
atcacttgcc gggcaagtca gggcattaga aatgatttag ctggtatca gcagaaacca      180
gggaaagccc ctaagcgcct gatctatgct gcatccagtt tgcaaagtgg ggtcccatca     240
aggttcagcg gcagtggatc tgggacagaa ttcactctca caatcagcag cctgcagcct    300
gaagattttg caacttatta ctgtctacag cataatagtt accctctcac tttcggcgga    360
gggaccaagg tggagatcaa aggtggtggt ggttctggcg gcggcggctc cggtggtggt    420
ggttcccagg tgcagctgca ggagtcgggc ccaggactgg tgaagccttc ggagaccctg    480
tccctcacct gcactgtctc tggtggctcc gtcagcagtg gtggttacta ctggagctgg    540
atccggcagc ccccagggaa gggactggag tggattgggt ttatctatta cactgggagc    600
accaactaca acccctccct caagagtcga gtctccatat cagtagacac gtccaagaac    660
cagttctccc tgaagctgag ctctgtgacc gctgcggacg cggccgtgta ttactgtgcg    720
agagattatg actggagctt ccactttgac tactgggggcc agggaaccct ggtcaccgtc    780
tcctcagcta gcgtgaaagg gaaacacctt tgtccaagtc ccctatttcc cggaccttct    840
aagcccttt gggtgctggt ggtgttggt ggagtcctgg cttgctatag cttgctagta     900
acagtggcct ttattatttt ctgggtgagg agtaagagga gcaggctcct gcacagtgac    960
tacatgaaca tgactccccg ccgccccggg cccacccgca agcattacca gccctatgcc   1020
ccaccacgcg acttcgcagc ctatcgctcc aagcttagag tgaagttcag caggagcgca   1080
gacgcccccg cgtaccagca gggccagaac cagctctata cgagctcaa tctaggacga    1140
agagaggagt acgatgtttt ggacaagaga cgtggccggg accctgagat ggggggaaag    1200
ccgcagagaa ggaagaaccc tcaggaaggc ctgtacaatg aactgcagaa agataagatg   1260
gcggaggcct acagtgagat tgggatgaaa ggcgagcgcc ggaggggcaa ggggcacgat   1320
ggcctttacc agggtctcag tacagccacc aaggacacct acgacgccct tcacatgcag   1380
gccctgcccc ctcgctaa                                                  1398

<210> SEQ ID NO 272
<211> LENGTH: 1425
<212> TYPE: DNA
<213> ORGANISM: Artificial Sequence
<220> FEATURE:
<223> OTHER INFORMATION: 272H-CD28H-CD28TM-BBCYP-CD3ZCYP CAR (includes
      leader)

<400> SEQUENCE: 272
atggaaaccc cagcgcagct tctcttcctc ctgctactct ggctcccaga taccaccgga     60
caggtgcagc tggtggagtc tgggggaggc gtggtccagc ctgggaggtc cctgagactc    120
tcctgtgcag cgtctggatt catcttcagt cgctatggca tgcactgggt ccgccaggct   180
ccaggcaagg ggctgaaatg ggtggcagtt atatggtatg atggaagtaa taaactctat    240
gcagactccg tgaagggccg attcaccatc tccagagaca attccaagaa cacgctgtat    300
ctgcaaatga acagcctgag agccgaggac acggctgtgt attactgtgc gagagattac    360
tatgataata gtagacatca ctgggggttt gactactggg gccagggaac cctggtcacc    420
gtctcctcag gtggtggtgg ttctggcggc ggcggctccg gtggtggtgg ttccgatatt   480
gtgatgaccc agactccact ctccctgccc gtcacccctg gagagccggc ctccatctcc    540
tgcaggtcta gtcggagcct cttggatagt gatgatggaa acacctattt ggactggtac    600
ctgcagaagc cagggcagtc tccacagctc ctgatctaca cgctttccta tcgggcctct    660
```

-continued

| | |
|---|---|
| ggagtcccag acaggttcag tggcagtggg tcaggcactg atttcacact gaaaatcagc | 720 |
| agggtggagg ctgaggatgt tggagtttat tactgcatgc aacgtgtaga gtttcctatc | 780 |
| accttcggcc aagggacacg actggagatt aaactcgagg tgaagggaaa cacctttgt | 840 |
| ccaagtcccc tatttcccgg accttctaag ccctttgggg tgctggtggt ggttggtgga | 900 |
| gtcctggctt gctatagctt gctagtaaca gtggccttta ttattttctg ggtgaaacgg | 960 |
| ggcagaaaga aactcctgta tatattcaaa caaccattta tgagaccagt acaaactact | 1020 |
| caagaggaag atggctgtag ctgccgattt ccagaagaag aagaaggagg atgtgaactg | 1080 |
| aagcttagag tgaagttcag caggagcgca gacgcccccg cgtaccagca gggccagaac | 1140 |
| cagctctata cgagctcaa tctaggacga agagaggagt acgatgtttt ggacaagaga | 1200 |
| cgtggccggg accctgagat ggggggaaag ccgcagagaa ggaagaaccc tcaggaaggc | 1260 |
| ctgtacaatg aactgcagaa agataagatg gcggaggcct acagtgagat tgggatgaaa | 1320 |
| ggcgagcgcc ggaggggcaa ggggcacgat ggcctttacc agggtctcag tacagccacc | 1380 |
| aaggacacct acgacgccct tcacatgcag gccctgcccc ctcgc | 1425 |

<210> SEQ ID NO 273
<211> LENGTH: 1422
<212> TYPE: DNA
<213> ORGANISM: Artificial Sequence
<220> FEATURE:
<223> OTHER INFORMATION: 272H-CD28H-CD28TM-CD28CYP-CD3ZCYP CAR (includes leader)

<400> SEQUENCE: 273

| | |
|---|---|
| atggaaaccc cagcgcagct tctcttcctc ctgctactct ggctcccaga taccaccgga | 60 |
| caggtgcagc tggtggagtc tggggggaggc gtggtccagc ctgggaggtc cctgagactc | 120 |
| tcctgtgcag cgtctggatt catcttcagt cgctatggca tgcactgggt ccgccaggct | 180 |
| ccaggcaagg ggctgaaatg ggtggcagtt atatggtatg atggaagtaa taaactctat | 240 |
| gcagactccg tgaagggccg attcaccatc tccagagaca attccaagaa cacgctgtat | 300 |
| ctgcaaatga acagcctgag agccgaggac acggctgtgt attactgtgc gagagattac | 360 |
| tatgataata gtagacatca ctgggggttt gactactggg gccagggaac cctggtcacc | 420 |
| gtctcctcag gtggtggtgg ttctggcggc ggcggctccg gtggtggtgg ttccgatatt | 480 |
| gtgatgaccc agactccact ctccctgccc gtcacccctg gagagccggc ctccatctcc | 540 |
| tgcaggtcta gtcggagcct cttggatagt gatgatggaa acacctattt ggactggtac | 600 |
| ctgcagaagc cagggcagtc tccacagctc ctgatctaca cgctttccta tcgggcctct | 660 |
| ggagtcccag acaggttcag tggcagtggg tcaggcactg atttcacact gaaaatcagc | 720 |
| agggtggagg ctgaggatgt tggagtttat tactgcatgc aacgtgtaga gtttcctatc | 780 |
| accttcggcc aagggacacg actggagatt aaactcgagg tgaagggaaa cacctttgt | 840 |
| ccaagtcccc tatttcccgg accttctaag ccctttgggg tgctggtggt ggttggtgga | 900 |
| gtcctggctt gctatagctt gctagtaaca gtggccttta ttattttctg ggtgaggagt | 960 |
| aagaggagca gctcctgca cagtgactac atgaacatga ctccccgccg cccggggccc | 1020 |
| acccgcaagc attaccagcc ctatgcccca ccacgcgact cgcagcctta cgctccaag | 1080 |
| cttagagtga agttcagcag gagcgcagac gccccgcgt accagcaggg ccagaaccag | 1140 |
| ctctataacg agctcaatct aggacgaaga gaggagtacg atgttttgga caagagacgt | 1200 |
| ggccgggacc ctgagatggg gggaaagccg cagagaagga gaaccctca ggaaggcctg | 1260 |

```
tacaatgaac tgcagaaaga taagatggcg gaggcctaca gtgagattgg gatgaaaggc    1320
gagcgccgga ggggcaaggg gcacgatggc ctttaccagg gtctcagtac agccaccaag    1380
gacacctacg acgcccttca catgcaggcc ctgccccctc gc                      1422
```

<210> SEQ ID NO 274
<211> LENGTH: 1371
<212> TYPE: DNA
<213> ORGANISM: Artificial Sequence
<220> FEATURE:
<223> OTHER INFORMATION: 272H-CD28H-CD28TM-DAP10CYP-CD3ZCYP CAR
      (includes leader)

<400> SEQUENCE: 274

```
atggaaaccc cagcgcagct tctcttcctc ctgctactct ggctcccaga taccaccgga     60
caggtgcagc tggtggagtc tgggggaggc gtggtccagc ctgggaggtc cctgagactc    120
tcctgtgcag cgtctggatt catcttcagt cgctatggca tgcactgggt ccgccaggct    180
ccaggcaagg ggctgaaatg ggtggcagtt atatggtatg atggaagtaa taaactctat    240
gcagactccg tgaagggccg attcaccatc tccagagaca attccaagaa cacgctgtat    300
ctgcaaatga acagcctgag agccgaggac acggctgtgt attactgtgc gagagattac    360
tatgataata gtagacatca ctgggggttt gactactggg gccagggaac cctggtcacc    420
gtctcctcag gtggtggtgg ttctggcggc ggcggctccg gtggtggtgg ttccgatatt    480
gtgatgaccc agactccact ctccctgccc gtcacccctg gagagccggc ctccatctcc    540
tgcaggtcta gtcggagcct cttggatagt gatgatggaa acacctattt ggactggtac    600
ctgcagaagc cagggcagtc tccacagctc ctgatctaca cgctttccta tcgggcctct    660
ggagtcccag acaggttcag tggcagtggg tcaggcactg atttcacact gaaaatcagc    720
agggtggagg ctgaggatgt tggagtttat tactgcatgc aacgtgtaga gtttcctatc    780
accttcggcc aagggacacg actggagatt aaactcgagg tgaaagggaa aacactttgt    840
ccaagtcccc tatttcccgg accttctaag ccctttttgg gtgctggtgg ggttggtgga    900
gtcctggctt gctatagctt gctagtaaca gtggccttta ttattttctg ggtgctgtgc    960
gcacgcccac gccgcagccc cgcccaagaa gatggcaaag tctacatcaa catgccaggc    1020 agggcaagc ttagagtgaa gttcagcagg agcgcagacg cccccgcgta ccagcagggc    1080
cagaaccagc tctataacga gctcaatcta ggacgaagag gagtacga tgttttggac    1140 aagagacgtg gccgggaccc tgagatgggg ggaaagccgc agagaaggaa gaaccctcag    1200
gaaggcctgt acaatgaact gcagaaagat aagatggcgg aggcctacag tgagattggg    1260
atgaaaggcg agcgccggag gggcaagggg cacgatggcc tttaccaggg tctcagtaca    1320
gccaccaagg acacctacga cgcccttcac atgcaggccc tgccccctcg c             1371
```

<210> SEQ ID NO 275
<211> LENGTH: 1422
<212> TYPE: DNA
<213> ORGANISM: Artificial Sequence
<220> FEATURE:
<223> OTHER INFORMATION: 272L-CD28H-CD28TM-CD28CYP-CD3ZCYP CAR (includes
      leader)

<400> SEQUENCE: 275

```
atggaaaccc cagcgcagct tctcttcctc ctgctactct ggctcccaga taccaccgga     60
gatattgtga tgacccagac tccactctcc ctgcccgtca cccctggaga gccggcctcc    120
atctcctgca ggtctagtcg gagcctcttg gatagtgatg atggaaacac ctatttggac    180
```

```
tggtacctgc agaagccagg gcagtctcca cagctcctga tctacacgct ttcctatcgg    240
gcctctggag tcccagacag gttcagtggc agtgggtcag gcactgattt cacactgaaa    300
atcagcaggg tggaggctga ggatgttgga gtttattact gcatgcaacg tgtagagttt    360
cctatcacct tcggccaagg gacacgactg gagattaaag gtggtggtgg ttctggcggc    420
ggcggctccg gtggtggtgg ttcccaggtg cagctggtgg agtctggggg aggcgtggtc    480
cagcctggga ggtccctgag actctcctgt gcagcgtctg gattcatctt cagtcgctat    540
ggcatgcact gggtccgcca ggctccaggc aaggggctga atgggtggc agttatatgg     600 tatgatggaa gtaataaact ctatgcagac tccgtgaagg gccgattcac catctccaga    660
gacaattcca agaacacgct gtatctgcaa atgaacagcc tgagagccga ggacacggct    720
gtgtattact gtgcgagaga ttactatgat aatagtagac atcactgggg gtttgactac    780
tggggccagg gaaccctggt caccgtctcc tcactcgagg tgaaagggaa cacctttgt     840 ccaagtcccc tatttcccgg accttctaag ccctttggg tgctggtggt ggttggtgga     900
gtcctggctt gctatagctt gctagtaaca gtggccttta ttattttctg ggtgaggagt    960
aagaggagca ggctcctgca cagtgactac atgaacatga ctccccgccg ccccgggccc   1020
acccgcaagc attaccagcc ctatgcccca ccacgcgact cgcagcctac tcgctccaag   1080
cttagagtga agttcagcag gagcgcagac gcccccgcgt accagcaggg ccagaaccag   1140
ctctataacg agctcaatct aggacgaaga gaggagtacg atgttttgga caagagacgt   1200
ggccgggacc ctgagatggg gggaaagccg cagagaagga gaaccctca ggaaggcctg    1260 tacaatgaac tgcagaaaga taagatggcg gaggcctaca gtgagattgg gatgaaaggc   1320
gagcgccgga ggggcaaggg gcacgatggc ctttaccagg gtctcagtac agccaccaag   1380
gacacctacg acgccttca catgcaggcc ctgccccctc gc                        1422

<210> SEQ ID NO 276
<211> LENGTH: 1410
<212> TYPE: DNA
<213> ORGANISM: Artificial Sequence
<220> FEATURE:
<223> OTHER INFORMATION: 2592H-CD28H-CD28TM-BBCYP-CD3ZCYP CAR (includes
      leader)

<400> SEQUENCE: 276
atggaaaccc cagcgcagct tctcttcctc ctgctactct ggctcccaga taccaccgga     60
caggtgcagc tgcaggagtc gggcccaaga ctggtgaagc cttcacagac cctgtccctc    120
acctgcactg tctctggtgg ctccatcagt agtgatggtt actactggag ctggatccgc    180
cagcacccag ggaagggcct ggagtggatt gggtacatct attacagtgg gagcaccttc    240
tacaacccgt ccctcaagag tcgagttgcc atatcagtgg acacgtctaa gaaccagttc    300
tccctgaagc tgagctctgt gactgccgcg gacacggccg tgtattactg tgcgagagaa    360
tcccctcata gcagcaactg gtactcgggc tttgactgct ggggcaggg aaccctggtc      420 accgtctcct caggtggtgg tggttctggc ggcggcggct ccgtggtgg tggttccgaa     480 attgtgctga ctcagtctcc agactttcag tctgtgactc caaggagaa agtcaccatc     540 acctgccggg ccagtcagag cattggtagt aggttacact ggtaccagca gaaaccagat    600
cagtctccaa agctcctcat caagtatgct cccagtcct tctcagggt ccctcgagg       660 ttcagtggca gtggatctgg gacagatttc accctcacca tcaatagcct ggaagctgaa    720
gatgctgcaa cgtattactg tcatcagagt agtaatttac cattcacttt cggccctggg    780
```

```
accaaagtgg atatcaaagc tagcgtgaaa gggaaacacc tttgtccaag tcccctattt      840
cccggacctt ctaagccctt tgggtgctg gtggtggttg gtggagtcct ggcttgctat       900
agcttgctag taacagtggc ctttattatt ttctgggtga acgggggcag aaagaaactc      960
ctgtatatat tcaaacaacc atttatgaga ccagtacaaa ctactcaaga ggaagatggc     1020
tgtagctgcc gatttccaga agaagaagaa ggaggatgtg aactgaagct tagagtgaag     1080
ttcagcagga gcgcagacgc ccccgcgtac cagcagggcc agaaccagct ctataacgag     1140
ctcaatctag gacgaagaga ggagtacgat gttttggaca agagacgtgg ccgggaccct     1200
gagatggggg gaaagccgca gagaaggaag aaccctcagg aaggcctgta caatgaactg     1260
cagaaagata gatggcggag gcctacagt gagattggga tgaaaggcga gcgccggagg      1320
ggcaaggggc acgatggcct ttaccagggt ctcagtacag ccaccaagga cacctacgac     1380
gcccttcaca tgcaggccct gccccctcgc                                      1410
```

<210> SEQ ID NO 277
<211> LENGTH: 1407
<212> TYPE: DNA
<213> ORGANISM: Artificial Sequence
<220> FEATURE:
<223> OTHER INFORMATION: 2592H-CD28H-CD28TM-CD28CYP-CD3zetaCYP CAR
      (includes leader)

<400> SEQUENCE: 277

```
atggaaaccc cagcgcagct tctcttcctc ctgctactct ggctcccaga taccaccgga      60
caggtgcagc tgcaggagtc gggcccaaga ctggtgaagc cttcacagac cctgtccctc     120
acctgcactg tctctggtgg ctccatcagt agtgatggtt actactggag ctggatccgc     180
cagcacccag ggaagggcct ggagtggatt gggtacatct attacagtgg gagcaccttc     240
tacaacccgt ccctcaagag tcgagttgcc atatcagtgg acacgtctaa gaaccagttc     300
tccctgaagc tgagctctgt gactgccgcg gacacggccg tgtattactg tgcgagagaa     360
tcccctcata gcagcaactg gtactcgggc tttgactgct ggggccaggg aaccctggtc     420
accgtctcct caggtggtgg tggttctggc ggcggcggct ccgtggtgg tggttccgaa     480 attgtgctga ctcagtctcc agactttcag tctgtgactc caaggagaa agtcaccatc      540 acctgccggg ccagtcagag cattggtagt aggttacact ggtaccagca gaaaccagat     600
cagtctccaa agctcctcat caagtatgct tcccagtcct tctcagggt ccctcgagg      660 ttcagtggca gtggatctgg gacagatttc accctcacca tcaatagcct ggaagctgaa     720
gatgctgcaa cgtattactg tcatcagagt agtaatttac cattcacttt cggccctggg     780
accaaagtgg atatcaaagc tagcgtgaaa gggaaacacc tttgtccaag tcccctattt     840
cccggacctt ctaagccctt tgggtgctg gtggtggttg gtggagtcct ggcttgctat      900
agcttgctag taacagtggc ctttattatt ttctgggtga ggagtaagag gagcaggctc     960
ctgcacagtg actacatgaa catgactccc cgccgccccg ggcccacccg caagcattac    1020
cagccctatg ccccaccacg cgacttcgca gcctatcgct ccaagcttag agtgaagttc    1080
agcaggagcg cagacgcccc cgcgtaccag cagggccaga accagctcta taacgagctc    1140
aatctaggac gaagagagga gtacgatgtt ttggacaaga cgtggccg ggaccctgag      1200 atggggggaa agccgcagag aaggaagaac cctcaggaag gcctgtacaa tgaactgcag    1260
aaagataaga tggcggaggc ctacagtgag attgggatga aaggcgagcg ccggaggggc    1320
aaggggcacg atggccttta ccagggtctc agtacagcca ccaaggacac ctacgacgcc    1380
```
cttcacatgc aggccctgcc ccctcgc                                    1407

<210> SEQ ID NO 278
<211> LENGTH: 1356
<212> TYPE: DNA
<213> ORGANISM: Artificial Sequence
<220> FEATURE:
<223> OTHER INFORMATION: 2592H-CD28H-CD28TM-DAP10CYP-CD3ZCYP CAR
      (includes leader)

<400> SEQUENCE: 278
atggaaaccc cagcgcagct tctcttcctc ctgctactct ggctcccaga taccaccgga     60
caggtgcagc tgcaggagtc gggcccaaga ctggtgaagc cttcacagac cctgtccctc    120
acctgcactg tctctggtgg ctccatcagt agtgatggtt actactggag ctggatccgc    180
cagcacccag ggaagggcct ggagtggatt gggtacatct attacagtgg gagcaccttc    240
tacaacccgt ccctcaagag tcgagttgcc atatcagtgg acacgtctaa gaaccagttc    300
tccctgaagc tgagctctgt gactgccgcg gacacggccg tgtattactg tgcgagagaa    360 tccctcata gcagcaactg gtactcgggc tttgactgct ggggccaggg aaccctggtc     420
accgtctcct caggtggtgg tggttctggc ggcggcggct ccggtggtgg tggttccgaa    480
attgtgctga ctcagtctcc agactttcag tctgtgactc aaaggagaa agtcaccatc     540 acctgccggg ccagtcagag cattggtagt aggttacact ggtaccagca gaaaccagat    600
cagtctccaa agctcctcat caagtatgct tcccagtcct ctcagggggt ccctcgagg    660 ttcagtggca gtggatctgg gacagatttc accctcacca tcaatagcct ggaagctgaa    720
gatgctgcaa cgtattactg tcatcagagt agtaatttac cattcacttt cggccctggg    780
accaaagtgg atatcaaagc tagcgtgaaa gggaaacacc tttgtccaag tcccctatt    840 cccggacctt ctaagccctt tggtgctg gtggtggttg gtggagtcct ggcttgctat      900
agcttgctag taacagtggc ctttattatt ttctgggtgc tgtgcgcacg cccacgccgc    960
agccccgccc aagaagatgg caaagtctac atcaacatgc aggcagggg caagcttaga    1020 gtgaagttca gcaggagcgc agacgccccc cgcgtaccag cgggccagaa ccagctctat    1080
aacgagctca atctaggacg aagagaggag tacgatgttt tggacaagag acgtggccgg    1140
gaccctgaga tgggggggaaa gccgcagaga aggaagaacc ctcaggaagg cctgtacaat    1200
gaactgcaga aagataagat ggcggaggcc tacagtgaga ttgggatgaa aggcgagcgc    1260
cggaggggca aggggcacga tggcctttac cagggtctca gtacagccac caaggacacc    1320
tacgacgccc ttcacatgca ggccctgccc cctcgc                              1356

<210> SEQ ID NO 279
<211> LENGTH: 1407
<212> TYPE: DNA
<213> ORGANISM: Artificial Sequence
<220> FEATURE:
<223> OTHER INFORMATION: 2592L-CD28H-CD28TM-CD28CYP-CD3ZCYP CAR
      (includes leader)

<400> SEQUENCE: 279
atggaaaccc cagcgcagct tctcttcctc ctgctactct ggctcccaga taccaccgga     60
gaaattgtgc tgactcagtc tccagacttt cagtctgtga ctccaaagga aaagtcacc     120 atcacctgcc gggccagtca gagcattggt agtaggttac actggtacca gcagaaacca    180
gatcagtctc caaagctcct catcaagtat gcttcccagt ccttctcagg ggtcccctcg    240

```
aggttcagtg gcagtggatc tgggacagat ttcaccctca ccatcaatag cctggaagct      300
gaagatgctg caacgtatta ctgtcatcag agtagtaatt taccattcac tttcggccct      360
gggaccaaag tggatatcaa aggtggtggt ggttctggcg gcggcggctc cggtggtggt      420
ggttcccagg tgcagctgca ggagtcgggc ccaagactgg tgaagccttc acagaccctg      480
tccctcacct gcactgtctc tggtggctcc atcagtagtg atggttacta ctggagctgg      540
atccgccagc acccagggaa gggcctgagt ggattgggt acatctatta cagtgggagc       600
accttctaca acccgtccct caagagtcga gttgccatat cagtggacac gtctaagaac      660
cagttctccc tgaagctgag ctctgtgact gccgcggaca cggccgtgta ttactgtgcg      720
agagaatccc ctcatagcag caactggtac tcgggctttg actgctgggg ccagggaacc      780
ctggtcaccg tctcctcagc tagcgtgaaa gggaaacacc tttgtccaag tcccctattt      840
cccggacctt ctaagccctt tgggtgctg tggtggttg tggagtcct ggcttgctat         900 agcttgctag taacagtggc ctttattatt ttctgggtga ggagtaagag gagcaggctc      960
ctgcacagtg actacatgaa catgactccc cgccgccccg ggcccacccg caagcattac     1020
cagccctatg ccccaccacg cgacttcgca gcctatcgct ccaagcttag agtgaagttc     1080
agcaggagcg cagacgcccc cgcgtaccag cagggccaga accagctcta taacgagctc     1140
aatctaggac gaagagagga gtacgatgtt ttggacaaga cgtggccg ggaccctgag       1200 atggggggaa agccgcagag aaggaagaac cctcaggaag cctgtacaa tgaactgcag      1260 aaagataaga tggcggaggc ctacagtgag attgggatga aggcgagcg ccggagggc       1320 aaggggcacg atggccttta ccagggtctc agtacagcca ccaaggacac ctacgacgcc     1380
cttcacatgc aggccctgcc ccctcgc                                         1407

<210> SEQ ID NO 280
<211> LENGTH: 60
<212> TYPE: DNA
<213> ORGANISM: Artificial Sequence
<220> FEATURE:
<223> OTHER INFORMATION: signal peptide

<400> SEQUENCE: 280
atggaaaccc cagcgcagct tctcttcctc ctgctactct ggctcccaga taccaccgga       60

<210> SEQ ID NO 281
<211> LENGTH: 63
<212> TYPE: DNA
<213> ORGANISM: Artificial Sequence
<220> FEATURE:
<223> OTHER INFORMATION: T2A ribosomal skip sequence

<400> SEQUENCE: 281
ggctccggtg agggcagagg aagtcttcta acatgcggtg acgtggagga gaatcccggc       60
cct                                                                    63

<210> SEQ ID NO 282
<211> LENGTH: 984
<212> TYPE: DNA
<213> ORGANISM: Artificial Sequence
<220> FEATURE:
<223> OTHER INFORMATION: Truncated CD19

<400> SEQUENCE: 282
atgccacctc ctcgcctcct cttcttcctc ctcttcctca ccccccatgga agtcaggccc       60 gaggaacctc tagtggtgaa ggtggaagag ggagataacg ctgtgctgca gtgcctcaag      120
```

```
gggacctcag atggccccac tcagcagctg acctggtctc gggagtcccc gcttaaaccc      180
ttcttaaaac tcagcctggg gctgccaggc ctgggaatcc acatgaggcc cctggccatc      240
tggcttttca tcttcaacgt ctctcaacag atggggggct tctacctgtg ccagccgggg      300
cccccctctg agaaggcctg gcagcctggc tggacagtca atgtggaggg cagcggggag      360
ctgttccggt ggaatgtttc ggacctaggt ggcctgggct gtggcctgaa gaacaggtcc      420
tcagagggcc ccagctcccc ttccgggaag ctcatgagcc ccaagctgta tgtgtgggcc      480
aaagaccgcc ctgagatctg ggagggagag cctccgtgtc tcccaccgag ggacagcctg      540
aaccagagcc tcagccagga cctcaccatg gcccctggct ccacactctg gctgtcctgt      600
ggggtacccc ctgactctgt gtccagggac ccctctcct ggacccatgt gcaccccaag      660
gggcctaagt cattgctgag cctagagctg aaggacgatc gcccggccag agatatgtgg      720
gtaatggaga cgggtctgtt gttgccccgg gccacagctc aagacgctgg aaagtattat      780
tgtcaccgtg caacctgac catgtcattc cacctggaga tcactgctcg gccagtacta      840
tggcactggc tgctgaggac tggtggctgg aaggtctcag ctgtgacttt ggcttatctg      900
atcttctgcc tgtgttccct tgtgggcatt cttcatcttc aaagagccct ggtcctgagg      960
aggaaaagaa agcgaatgac ttaa                                              984
```

<210> SEQ ID NO 283
<211> LENGTH: 30
<212> TYPE: DNA
<213> ORGANISM: Artificial Sequence
<220> FEATURE:
<223> OTHER INFORMATION: Ab 129 CDR H1

<400> SEQUENCE: 283

```
ggtggctccg tcagcagtgg tggttactac                                         30
```

<210> SEQ ID NO 284
<211> LENGTH: 21
<212> TYPE: DNA
<213> ORGANISM: Artificial Sequence
<220> FEATURE:
<223> OTHER INFORMATION: Ab 129 CDR H2

<400> SEQUENCE: 284

```
atctattaca ctgggagcac c                                                  21
```

<210> SEQ ID NO 285
<211> LENGTH: 30
<212> TYPE: DNA
<213> ORGANISM: Artificial Sequence
<220> FEATURE:
<223> OTHER INFORMATION: Ab 129 CDR H3

<400> SEQUENCE: 285

```
gattatgact ggagcttcca ctttgactac                                         30
```

<210> SEQ ID NO 286
<211> LENGTH: 18
<212> TYPE: DNA
<213> ORGANISM: Artificial Sequence
<220> FEATURE:
<223> OTHER INFORMATION: Ab 129 CDR L1

<400> SEQUENCE: 286

```
cagggcatta gaaatgat                                                      18
```

<210> SEQ ID NO 287
<211> LENGTH: 9
<212> TYPE: DNA
<213> ORGANISM: Artificial Sequence
<220> FEATURE:
<223> OTHER INFORMATION: Ab 129 CDR L2

<400> SEQUENCE: 287 gctgcatcc                                                                9

<210> SEQ ID NO 288
<211> LENGTH: 21
<212> TYPE: DNA
<213> ORGANISM: Artificial Sequence
<220> FEATURE:
<223> OTHER INFORMATION: Ab 129 CDR L3

<400> SEQUENCE: 288
ctacagcata atagttaccc t                                                 21

<210> SEQ ID NO 289
<211> LENGTH: 24
<212> TYPE: DNA
<213> ORGANISM: Artificial Sequence
<220> FEATURE:
<223> OTHER INFORMATION: Ab 272 CDR H1

<400> SEQUENCE: 289
ggattcatct tcagtcgcta tggc                                              24

<210> SEQ ID NO 290
<211> LENGTH: 24
<212> TYPE: DNA
<213> ORGANISM: Artificial Sequence
<220> FEATURE:
<223> OTHER INFORMATION: Ab 272 CDR H2

<400> SEQUENCE: 290
atatggtatg atggaagtaa taaa                                              24

<210> SEQ ID NO 291
<211> LENGTH: 42
<212> TYPE: DNA
<213> ORGANISM: Artificial Sequence
<220> FEATURE:
<223> OTHER INFORMATION: Ab 272 CDR H3

<400> SEQUENCE: 291
gattactatg ataatagtag acatcactgg gggtttgact ac                          42

<210> SEQ ID NO 292
<211> LENGTH: 51
<212> TYPE: DNA
<213> ORGANISM: Artificial Sequence
<220> FEATURE:
<223> OTHER INFORMATION: Ab 272 CDR L1

<400> SEQUENCE: 292
aggtctagtc ggagcctctt ggatagtgat gatggaaaca cctatttgga c                51

<210> SEQ ID NO 293
<211> LENGTH: 21
<212> TYPE: DNA
<213> ORGANISM: Artificial Sequence
<220> FEATURE:
<223> OTHER INFORMATION: Ab 272 CDR L2

```
<400> SEQUENCE: 293
acgctttcct atcgggcctc t                                              21

<210> SEQ ID NO 294
<211> LENGTH: 27
<212> TYPE: DNA
<213> ORGANISM: Artificial Sequence
<220> FEATURE:
<223> OTHER INFORMATION: Ab 272 CDR L3

<400> SEQUENCE: 294
atgcaacgtg tagagtttcc tatcacc                                        27

<210> SEQ ID NO 295
<211> LENGTH: 27
<212> TYPE: DNA
<213> ORGANISM: Artificial Sequence
<220> FEATURE:
<223> OTHER INFORMATION: Ab 2592 CDR H1

<400> SEQUENCE: 295
ggtggctcca tcagtagtga tggttac                                        27

<210> SEQ ID NO 296
<211> LENGTH: 21
<212> TYPE: DNA
<213> ORGANISM: Artificial Sequence
<220> FEATURE:
<223> OTHER INFORMATION: Ab 2592 CDR H2

<400> SEQUENCE: 296
atctattaca gtgggagcac c                                              21

<210> SEQ ID NO 297
<211> LENGTH: 42
<212> TYPE: DNA
<213> ORGANISM: Artificial Sequence
<220> FEATURE:
<223> OTHER INFORMATION: Ab 2592 CDR H3

<400> SEQUENCE: 297
gaatcccctc atagcagcaa ctggtactcg ggctttgact gc                       42

<210> SEQ ID NO 298
<211> LENGTH: 18
<212> TYPE: DNA
<213> ORGANISM: Artificial Sequence
<220> FEATURE:
<223> OTHER INFORMATION: Ab 2592 CDR L1

<400> SEQUENCE: 298
cagagcattg gtagtagg                                                  18

<210> SEQ ID NO 299
<211> LENGTH: 9
<212> TYPE: DNA
<213> ORGANISM: Artificial Sequence
<220> FEATURE:
<223> OTHER INFORMATION: Ab 2592 CDR L2

<400> SEQUENCE: 299 tatgcttcc                                                             9

<210> SEQ ID NO 300
```

<211> LENGTH: 27
<212> TYPE: DNA
<213> ORGANISM: Artificial Sequence
<220> FEATURE:
<223> OTHER INFORMATION: Ab 2592 CDR L3

<400> SEQUENCE: 300
catcagagta gtaatttacc attcact        27

<210> SEQ ID NO 301
<211> LENGTH: 829
<212> TYPE: PRT
<213> ORGANISM: Artificial Sequence
<220> FEATURE:
<223> OTHER INFORMATION: leader_272H-CD28H-CD28TM-BBCYP-CD3ZCYP_T2A-
      tCD19

<400> SEQUENCE: 301

Met Glu Thr Pro Ala Gln Leu Leu Phe Leu Leu Leu Leu Trp Leu Pro
1               5                   10                  15

Asp Thr Thr Gly Gln Val Gln Leu Val Glu Ser Gly Gly Gly Val Val
                20                  25                  30

Gln Pro Gly Arg Ser Leu Arg Leu Ser Cys Ala Ala Ser Gly Phe Ile
            35                  40                  45

Phe Ser Arg Tyr Gly Met His Trp Val Arg Gln Ala Pro Gly Lys Gly
        50                  55                  60

Leu Lys Trp Val Ala Val Ile Trp Tyr Asp Gly Ser Asn Lys Leu Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Tyr Tyr Asp Asn Ser Arg His His Trp
        115                 120                 125

Gly Phe Asp Tyr Trp Gly Gln Gly Thr Leu Val Thr Val Ser Ser Gly
    130                 135                 140

Gly Gly Ser Gly Gly Gly Gly Ser Gly Gly Gly Gly Ser Asp Ile
145                 150                 155                 160

Val Met Thr Gln Thr Pro Leu Ser Leu Pro Val Thr Pro Gly Glu Pro
                165                 170                 175

Ala Ser Ile Ser Cys Arg Ser Ser Arg Ser Leu Leu Asp Ser Asp Asp
            180                 185                 190

Gly Asn Thr Tyr Leu Asp Trp Tyr Leu Gln Lys Pro Gly Gln Ser Pro
        195                 200                 205

Gln Leu Leu Ile Tyr Thr Leu Ser Tyr Arg Ala Ser Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Val Gly Val Tyr Tyr Cys Met Gln Arg Val
                245                 250                 255

Glu Phe Pro Ile Thr Phe Gly Gln Gly Thr Arg Leu Glu Ile Lys Leu
            260                 265                 270

Glu Val Lys Gly Lys His Leu Cys Pro Ser Pro Leu Phe Pro Gly Pro
        275                 280                 285

Ser Lys Pro Phe Trp Val Leu Val Val Gly Gly Val Leu Ala Cys
    290                 295                 300

Tyr Ser Leu Leu Val Thr Val Ala Phe Ile Ile Phe Trp Val Lys Arg

-continued

```
            305                 310                 315                 320
Gly Arg Lys Lys Leu Leu Tyr Ile Phe Lys Gln Pro Phe Met Arg Pro
                    325                 330                 335

Val Gln Thr Thr Gln Glu Asp Gly Cys Ser Cys Arg Phe Pro Glu
            340                 345                 350

Glu Glu Glu Gly Gly Cys Glu Leu Lys Leu Arg Val Lys Phe Ser Arg
                    355                 360                 365

Ser Ala Asp Ala Pro Ala Tyr Gln Gln Gly Gln Asn Gln Leu Tyr Asn
            370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Gln Arg Arg Lys Asn
                    405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
                    435                 440                 445

His Asp Gly Leu Tyr Gln Gly Leu Ser Thr Ala Thr Lys Asp Thr Tyr
            450                 455                 460

Asp Ala Leu His Met Gln Ala Leu Pro Pro Arg Ala Gly Ala Lys Arg
465                 470                 475                 480

Ser Gly Ser Gly Glu Gly Arg Gly Ser Leu Leu Thr Cys Gly Asp Val
                    485                 490                 495

Glu Glu Asn Pro Gly Pro Met Pro Pro Arg Leu Leu Phe Phe Leu
            500                 505                 510

Leu Phe Leu Thr Pro Met Glu Val Arg Pro Glu Glu Pro Leu Val Val
            515                 520                 525

Lys Val Glu Glu Gly Asp Asn Ala Val Leu Gln Cys Leu Lys Gly Thr
            530                 535                 540

Ser Asp Gly Pro Thr Gln Gln Leu Thr Trp Ser Arg Glu Ser Pro Leu
545                 550                 555                 560

Lys Pro Phe Leu Lys Leu Ser Leu Gly Leu Pro Gly Leu Gly Ile His
                    565                 570                 575

Met Arg Pro Leu Ala Ile Trp Leu Phe Ile Phe Asn Val Ser Gln Gln
            580                 585                 590

Met Gly Gly Phe Tyr Leu Cys Gln Pro Gly Pro Pro Ser Glu Lys Ala
                    595                 600                 605

Trp Gln Pro Gly Trp Thr Val Asn Val Glu Gly Ser Gly Glu Leu Phe
            610                 615                 620

Arg Trp Asn Val Ser Asp Leu Gly Gly Leu Gly Cys Gly Leu Lys Asn
625                 630                 635                 640

Arg Ser Ser Glu Gly Pro Ser Ser Pro Ser Gly Lys Leu Met Ser Pro
                    645                 650                 655

Lys Leu Tyr Val Trp Ala Lys Asp Arg Pro Glu Ile Trp Glu Gly Glu
                    660                 665                 670

Pro Pro Cys Leu Pro Pro Arg Asp Ser Leu Asn Gln Ser Leu Ser Gln
            675                 680                 685

Asp Leu Thr Met Ala Pro Gly Ser Thr Leu Trp Leu Ser Cys Gly Val
            690                 695                 700

Pro Pro Asp Ser Val Ser Arg Gly Pro Leu Ser Trp Thr His Val His
705                 710                 715                 720

Pro Lys Gly Pro Lys Ser Leu Leu Ser Leu Glu Leu Lys Asp Asp Arg
                    725                 730                 735
```

```
            Pro Ala Arg Asp Met Trp Val Met Glu Thr Gly Leu Leu Leu Pro Arg
                        740                 745                 750

Ala Thr Ala Gln Asp Ala Gly Lys Tyr Tyr Cys His Arg Gly Asn Leu
                        755                 760                 765

Thr Met Ser Phe His Leu Glu Ile Thr Ala Arg Pro Val Leu Trp His
                        770                 775                 780

Trp Leu Leu Arg Thr Gly Gly Trp Lys Val Ser Ala Val Thr Leu Ala
            785                 790                 795                 800

Tyr Leu Ile Phe Cys Leu Cys Ser Leu Val Gly Ile Leu His Leu Gln
                        805                 810                 815

Arg Ala Leu Val Leu Arg Arg Lys Arg Lys Arg Met Thr
                        820                 825

<210> SEQ ID NO 302
<211> LENGTH: 2490
<212> TYPE: DNA
<213> ORGANISM: Artificial Sequence
<220> FEATURE:
<223> OTHER INFORMATION: leader_272H-CD28H-CD28TM-BBCYP-CD3ZCYP_T2A-
      tCD19

<400> SEQUENCE: 302
atggaaaccc cagcgcagct tctcttcctc ctgctactct ggctcccaga taccaccgga      60
caggtgcagc tggtggagtc tgggggaggc gtggtccagc ctgggaggtc cctgagactc     120
tcctgtgcag cgtctggatt catcttcagt cgctatggca tgcactgggt ccgccaggct     180
ccaggcaagg gactgaaatg ggtggcagtt atatggtatg atggaagtaa taaactctat     240
gcagactccg tgaagggccg attcaccatc tccagagaca attccaagaa cacgctgtat     300
ctgcaaatga acagcctgag agccgaggac acggctgtgt attactgtgc gagagattac     360
tatgataata gtagacatca ctggggggttt gactactggg gccagggaac cctggtcacc     420
gtctcctcag gtggtggtgg ttctggcggc ggcggctccg gtggtggtgg ttccgatatt     480
gtgatgaccc agactccact ctccctgccc gtcacccctg gagagccggc ctccatctcc     540
tgcaggtcta gtcggagcct cttggatagt gatgatggaa acacctattt ggactggtac     600
ctgcagaagc cagggcagtc tccacagctc ctgatctaca cgctttccta tcgggcctct     660
ggagtcccag acaggttcag tggcagtggg tcaggcactg atttcacact gaaaatcagc     720
agggtggagg ctgaggatgt tggagtttat tactgcatgc aacgtgtaga gtttcctatc     780
accttcggcc aagggacacg actggagatt aaactcgagg tgaaagggaa acacctttgt     840
ccaagtcccc tatttcccgg accttctaag ccccttttggg tgctggtggt ggttggtgga     900
gtcctggctt gctatagctt gctagtaaca gtggccttta ttattttctg ggtgaaacgg     960
ggcagaaaga aactcctgta tatattcaaa caaccattta tgagaccagt acaaactact    1020
caagaggaag atggctgtag ctgccgattt ccagaagaag aagaaggagg atgtgaactg    1080
aagcttagag tgaagttcag caggagcgca gacgcccccg cgtaccagca gggccagaac    1140
cagctctata acgagctcaa tctaggacga agagaggagt acgatgtttt ggacaagaga    1200
cgtggccggg accctgagat ggggggaaag ccgcagagaa ggaagaaccc tcaggaaggc    1260
ctgtacaatg aactgcagaa agataagatg gcggaggcct acagtgagat tgggatgaaa    1320
ggcgagcgcc ggaggggcaa ggggcacgat ggcctttacc agggtctcag tacagccacc    1380
aaggacacct acgacgccct tcacatgcag gccctgcccc ctcgcgccgg cgccaaaagg    1440
tctggctccg gtgagggcag aggaagtctt ctaacatgcg gtgacgtgga ggagaatccc    1500
```

-continued

```
ggccctatgc cacctcctcg cctcctcttc ttcctcctct tcctcacccc catggaagtc   1560
aggcccgagg aacctctagt ggtgaaggtg aagagggag ataacgctgt gctgcagtgc    1620
ctcaagggga cctcagatgg ccccactcag cagctgacct ggtctcggga gtccccgctt   1680
aaacccttct taaaactcag cctggggctg ccaggcctgg gaatccacat gaggcccctg   1740
gccatctggc ttttcatctt caacgtctct caacagatgg ggggcttcta cctgtgccag   1800
ccggggcccc cctctgagaa ggcctggcag cctggctgga cagtcaatgt ggagggcagc   1860
ggggagctgt tccggtggaa tgtttcggac ctaggtggcc tgggctgtgg cctgaagaac   1920
aggtcctcag agggccccag ctccccttcc gggaagctca tgagcccaa gctgtatgtg    1980 tgggccaaag accgccctga gatctgggag ggagagcctc cgtgtctccc accgagggac   2040
agcctgaacc agagcctcag ccaggacctc accatggccc ctggctccac actctggctg   2100
tcctgtgggg taccccctga ctctgtgtcc aggggccccc tcctctggac ccatgtgcac   2160 cccaagggc ctaagtcatt gctgagccta gagctgaagg acgatcgccc ggccagagat    2220
atgtgggtaa tggagacggg tctgttgttg ccccggggcca cagctcaaga cgctggaaag   2280
tattattgtc accgtggcaa cctgaccatg tcattccacc tggagatcac tgctcggcca   2340
gtactatggc actggctgct gaggactggt ggctggaagg tctcagctgt gactttggct   2400
tatctgatct tctgcctgtg ttccttgtg ggcattcttc atcttcaaag agccctggtc    2460
ctgaggagga aagaaagcg aatgacttaa                                     2490
```

<210> SEQ ID NO 303
<211> LENGTH: 829
<212> TYPE: PRT
<213> ORGANISM: Artificial Sequence
<220> FEATURE:
<223> OTHER INFORMATION: leader_272H-CD28H-CD28TM-CD28CYP-CD3ZCYP_T2A-tCD19

<400> SEQUENCE: 303

```
Met Glu Thr Pro Ala Gln Leu Leu Phe Leu Leu Leu Leu Trp Leu Pro
1               5                   10                  15

Asp Thr Thr Gly Gln Val Gln Leu Val Glu Ser Gly Gly Gly Val Val
                20                  25                  30

Gln Pro Gly Arg Ser Leu Arg Leu Ser Cys Ala Ala Ser Gly Phe Ile
            35                  40                  45

Phe Ser Arg Tyr Gly Met His Trp Val Arg Gln Ala Pro Gly Lys Gly
        50                  55                  60

Leu Lys Trp Val Ala Val Ile Trp Tyr Asp Gly Ser Asn Lys Leu Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Tyr Tyr Asp Asn Ser Arg His His Trp
        115                 120                 125

Gly Phe Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Thr Pro Leu Ser Leu Pro Val Thr Pro Gly Glu Pro
                165                 170                 175
```

```
Ala Ser Ile Ser Cys Arg Ser Arg Ser Leu Leu Asp Ser Asp Asp
            180                 185                 190

Gly Asn Thr Tyr Leu Asp Trp Tyr Leu Gln Lys Pro Gly Gln Ser Pro
        195                 200                 205

Gln Leu Leu Ile Tyr Thr Leu Ser Tyr Arg Ala Ser Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Val Gly Val Tyr Tyr Cys Met Gln Arg Val
                245                 250                 255

Glu Phe Pro Ile Thr Phe Gly Gln Gly Thr Arg Leu Glu Ile Lys Leu
            260                 265                 270

Glu Val Lys Gly Lys His Leu Cys Pro Ser Pro Leu Phe Pro Gly Pro
        275                 280                 285

Ser Lys Pro Phe Trp Val Leu Val Val Val Gly Gly Val Leu Ala Cys
    290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
            340                 345                 350

Asp Phe Ala Ala Tyr Arg Ser Lys Leu Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Gln Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
        435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg Ala Gly Ala Lys Arg Ser
465                 470                 475                 480

Gly Ser Gly Glu Gly Arg Gly Ser Leu Leu Thr Cys Gly Asp Val Glu
                485                 490                 495

Glu Asn Pro Gly Pro Arg Met Pro Pro Arg Leu Leu Phe Phe Leu
            500                 505                 510

Leu Phe Leu Thr Pro Met Glu Val Arg Pro Glu Glu Pro Leu Val Val
        515                 520                 525

Lys Val Glu Glu Gly Asp Asn Ala Val Leu Gln Cys Leu Lys Gly Thr
    530                 535                 540

Ser Asp Gly Pro Thr Gln Gln Leu Thr Trp Ser Arg Glu Ser Pro Leu
545                 550                 555                 560

Lys Pro Phe Leu Lys Leu Ser Leu Gly Leu Pro Gly Leu Gly Ile His
                565                 570                 575

Met Arg Pro Leu Ala Ile Trp Leu Phe Ile Phe Asn Val Ser Gln Gln
            580                 585                 590

Met Gly Gly Phe Tyr Leu Cys Gln Pro Gly Pro Pro Ser Glu Lys Ala
```

```
            595                 600                 605
Trp Gln Pro Gly Trp Thr Val Asn Val Glu Gly Ser Gly Glu Leu Phe
    610                 615                 620

Arg Trp Asn Val Ser Asp Leu Gly Gly Leu Gly Cys Gly Leu Lys Asn
625                 630                 635                 640

Arg Ser Ser Glu Gly Pro Ser Ser Pro Ser Gly Lys Leu Met Ser Pro
                645                 650                 655

Lys Leu Tyr Val Trp Ala Lys Asp Arg Pro Glu Ile Trp Glu Gly Glu
            660                 665                 670

Pro Pro Cys Leu Pro Pro Arg Asp Ser Leu Asn Gln Ser Leu Ser Gln
        675                 680                 685

Asp Leu Thr Met Ala Pro Gly Ser Thr Leu Trp Leu Ser Cys Gly Val
    690                 695                 700

Pro Pro Asp Ser Val Ser Arg Gly Pro Leu Ser Trp Thr His Val His
705                 710                 715                 720

Pro Lys Gly Pro Lys Ser Leu Leu Ser Leu Glu Leu Lys Asp Asp Arg
                725                 730                 735

Pro Ala Arg Asp Met Trp Val Met Glu Thr Gly Leu Leu Leu Pro Arg
            740                 745                 750

Ala Thr Ala Gln Asp Ala Gly Lys Tyr Tyr Cys His Arg Gly Asn Leu
        755                 760                 765

Thr Met Ser Phe His Leu Glu Ile Thr Ala Arg Pro Val Leu Trp His
    770                 775                 780

Trp Leu Leu Arg Thr Gly Gly Trp Lys Val Ser Ala Val Thr Leu Ala
785                 790                 795                 800

Tyr Leu Ile Phe Cys Leu Cys Ser Leu Val Gly Ile Leu His Leu Gln
                805                 810                 815

Arg Ala Leu Val Leu Arg Arg Lys Arg Lys Arg Met Thr
            820                 825

<210> SEQ ID NO 304
<211> LENGTH: 2490
<212> TYPE: DNA
<213> ORGANISM: Artificial Sequence
<220> FEATURE:
<223> OTHER INFORMATION: leader_272H-CD28H-CD28TM-CD28CYP-CD3ZCYP_T2A-
      tCD19

<400> SEQUENCE: 304
atggaaaccc cagcgcagct tctcttcctc ctgctactct ggctcccaga taccaccgga      60
caggtgcagc tggtggagtc tgggggaggc gtggtccagc ctgggaggtc cctgagactc     120
tcctgtgcag cgtctggatt catcttcagt cgctatggca tgcactgggt ccgccaggct     180
ccaggcaagg ggctgaaatg ggtggcagtt atatggtatg atggaagtaa taaactctat     240
gcagactccg tgaagggccg attcaccatc tccagagaca attccaagaa cacgctgtat     300
ctgcaaatga acagcctgag agccgaggac acggctgtgt attactgtgc gagagattac     360
tatgataata gtagacatca ctgggggttt gactactggg gccagggaac cctggtcacc     420
gtctcctcag gtggtggtgg ttctggcggc ggcggctccg gtggtggtgg ttccgatatt     480
gtgatgaccc agactccact ctccctgccc gtcacccctg gagagccggc ctccatctcc     540
tgcaggtcta gtcggagcct cttggatagt gatgatggaa acacctattt ggactggtac     600
ctgcagaagc cagggcagtc tccacagctc ctgatctaca cgctttccta tcgggcctct     660
ggagtcccag acaggttcag tggcagtggg tcaggcactg atttcacact gaaaatcagc     720
```

```
agggtggagg ctgaggatgt tggagtttat tactgcatgc aacgtgtaga gtttcctatc    780
accttcggcc aagggacacg actggagatt aaactcgagg tgaaagggaa acacctttgt    840
ccaagtcccc tatttcccgg accttctaag ccctttgggg tgctggtggt ggttggtgga    900
gtcctggctt gctatagctt gctagtaaca gtggccttta ttattttctg ggtgaggagt    960
aagaggagca ggctcctgca cagtgactac atgaacatga ctccccgccg ccccgggccc   1020
acccgcaagc attaccagcc ctatgcccca ccacgcgact cgcagcccta tcgctccaag   1080
cttagagtga agttcagcag gagcgcagac gcccccgcgt accagcaggg ccagaaccag   1140
ctctataacg agctcaatct aggacgaaga gaggagtacg atgttttgga caagagacgt   1200
ggccgggacc ctgagatggg gggaaagccg cagagaagga gaaccctcag gaaggcctg    1260
tacaatgaac tgcagaaaga taagatggcg gaggcctaca gtgagattgg gatgaaaggc   1320
gagcgccgga ggggcaaggg gcacgatggc ctttaccagg gtctcagtac agccaccaag   1380
gacacctacg acgcccttca catgcaggcc ctgccccctc gcgccggcgc caaaaggtct   1440
ggctccggtg agggcagagg aagtcttcta acatgcggtg acgtggagga gaatcccggc   1500
cctagaatgc cacctcctcg cctcctcttc ttcctcctct tcctcacccc catggaagtc   1560
aggcccgagg aacctctagt ggtgaaggtg aagagggag ataacgctgt gctgcagtgc   1620
ctcaagggga cctcagatgg cccccactcag cagctgacct ggtctcggga gtccccgctt   1680
aaacccttct taaaactcag cctggggctg ccaggcctgg gaatccacat gaggcccctg   1740
gccatctggc ttttcatctt caacgtctct caacagatgg ggggcttcta cctgtgccag   1800
ccgggggccc cctctgagaa ggcctggcag cctggctgga cagtcaatgt ggagggcagc   1860
ggggagctgt tccggtggaa tgtttcggac ctaggtggcc tgggctgtgg cctgaagaac   1920
aggtcctcag agggccccag ctcccttcc gggaagctca tgagcccaa gctgtatgtg   1980
tgggccaaag accgccctga gatctgggag ggagagcctc cgtgtctccc accgagggac   2040
agcctgaacc agagcctcag ccaggacctc accatggccc ctggctccac actctggctg   2100
tcctgtgggg tacccctga ctctgtgtcc agggggcccc tctcctggac ccatgtgcac   2160
cccaaggggc taagtcatt gctgagccta gagctgaagg acgatcgccc ggccagagat   2220
atgtgggtaa tggagacggg tctgttgttg ccccggggcca cagctcaaga cgctggaaag   2280
tattattgtc accgtggcaa cctgaccatg tcattccacc tggagatcac tgctcggcca   2340
gtactatggc actggctgct gaggactggt ggctggaagg tctcagctgt gactttggct   2400
tatctgatct tctgcctgtg ttcccttgtg ggcattcttc atcttcaaag agccctggtc   2460
ctgaggagga aagaaagcg aatgacttaa                                    2490
```

<210> SEQ ID NO 305
<211> LENGTH: 811
<212> TYPE: PRT
<213> ORGANISM: Artificial Sequence
<220> FEATURE:
<223> OTHER INFORMATION: leader_272H-CD28H-CD28TM-DAP10CYP-CD3ZCYP_T2A-tCD19

<400> SEQUENCE: 305

Met Glu Thr Pro Ala Gln Leu Leu Phe Leu Leu Leu Leu Trp Leu Pro
1               5                   10                  15

Asp Thr Thr Gly Gln Val Gln Leu Val Glu Ser Gly Gly Gly Val Val
                20                  25                  30

Gln Pro Gly Arg Ser Leu Arg Leu Ser Cys Ala Ala Ser Gly Phe Ile
            35                  40                  45

```
Phe Ser Arg Tyr Gly Met His Trp Val Arg Gln Ala Pro Gly Lys Gly
 50                  55                  60

Leu Lys Trp Val Ala Val Ile Trp Tyr Asp Gly Ser Asn Lys Leu Tyr
 65                      70                  75                  80

Ala Asp Ser Val Lys Gly Arg Phe Thr Ile Ser Arg Asp Asn Ser Lys
                 85                  90                  95

Asn Thr Leu Tyr Leu Gln Met Asn Ser Leu Arg Ala Glu Asp Thr Ala
                100                 105                 110

Val Tyr Tyr Cys Ala Arg Asp Tyr Tyr Asp Asn Ser Arg His His Trp
            115                 120                 125

Gly Phe Asp Tyr Trp Gly Gln Gly Thr Leu Val Thr Val Ser Ser Gly
        130                 135                 140

Gly Gly Gly Ser Gly Gly Gly Ser Gly Gly Gly Ser Asp Ile
145                 150                 155                 160

Val Met Thr Gln Thr Pro Leu Ser Leu Pro Val Thr Pro Gly Glu Pro
                165                 170                 175

Ala Ser Ile Ser Cys Arg Ser Ser Arg Ser Leu Leu Asp Ser Asp Asp
            180                 185                 190

Gly Asn Thr Tyr Leu Asp Trp Tyr Leu Gln Lys Pro Gly Gln Ser Pro
        195                 200                 205

Gln Leu Leu Ile Tyr Thr Leu Ser Tyr Arg Ala Ser Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Val Gly Val Tyr Tyr Cys Met Gln Arg Val
                245                 250                 255

Glu Phe Pro Ile Thr Phe Gly Gln Gly Thr Arg Leu Glu Ile Lys Leu
            260                 265                 270

Glu Val Lys Gly Lys His Leu Cys Pro Ser Pro Leu Phe Pro Gly Pro
        275                 280                 285

Ser Lys Pro Phe Trp Val Leu Val Val Val Gly Gly Val Leu Ala Cys
    290                 295                 300

Tyr Ser Leu Leu Val Thr Val Ala Phe Ile Ile Phe Trp Val Leu Cys
305                 310                 315                 320

Ala Arg Pro Arg Arg Ser Pro Ala Gln Glu Asp Gly Lys Val Tyr Ile
                325                 330                 335

Asn Met Pro Gly Arg Gly Lys Leu Arg Val Lys Phe Ser Arg Ser Ala
            340                 345                 350

Asp Ala Pro Ala Tyr Gln Gln Gly Gln Asn Gln Leu Tyr Asn Glu Leu
        355                 360                 365

Asn Leu Gly Arg Arg Glu Glu Tyr Asp Val Leu Asp Lys Arg Arg Gly
    370                 375                 380

Arg Asp Pro Glu Met Gly Gly Lys Pro Gln Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
            420                 425                 430

Gly Leu Tyr Gln Gly Leu Ser Thr Ala Thr Lys Asp Thr Tyr Asp Ala
        435                 440                 445

Leu His Met Gln Ala Leu Pro Pro Arg Ala Gly Ala Lys Arg Ser Gly
    450                 455                 460
```

Ser Gly Glu Gly Arg Gly Ser Leu Leu Thr Cys Gly Asp Val Glu
465                 470                 475                 480

Asn Pro Gly Pro Met Pro Pro Arg Leu Leu Phe Phe Leu Leu Phe
            485                 490                 495

Leu Thr Pro Met Glu Val Arg Pro Glu Glu Pro Leu Val Val Lys Val
            500                 505                 510

Glu Glu Gly Asp Asn Ala Val Leu Gln Cys Leu Lys Gly Thr Ser Asp
        515                 520                 525

Gly Pro Thr Gln Gln Leu Thr Trp Ser Arg Glu Ser Pro Leu Lys Pro
        530                 535                 540

Phe Leu Lys Leu Ser Leu Gly Leu Pro Gly Leu Gly Ile His Met Arg
545                 550                 555                 560

Pro Leu Ala Ile Trp Leu Phe Ile Phe Asn Val Ser Gln Gln Met Gly
                565                 570                 575

Gly Phe Tyr Leu Cys Gln Pro Gly Pro Pro Ser Glu Lys Ala Trp Gln
            580                 585                 590

Pro Gly Trp Thr Val Asn Val Glu Gly Ser Gly Glu Leu Phe Arg Trp
        595                 600                 605

Asn Val Ser Asp Leu Gly Gly Leu Gly Cys Gly Leu Lys Asn Arg Ser
610                 615                 620

Ser Glu Gly Pro Ser Ser Pro Ser Gly Lys Leu Met Ser Pro Lys Leu
625                 630                 635                 640

Tyr Val Trp Ala Lys Asp Arg Pro Glu Ile Trp Glu Gly Glu Pro Pro
                645                 650                 655

Cys Leu Pro Pro Arg Asp Ser Leu Asn Gln Ser Leu Ser Gln Asp Leu
            660                 665                 670

Thr Met Ala Pro Gly Ser Thr Leu Trp Leu Ser Cys Gly Val Pro Pro
        675                 680                 685

Asp Ser Val Ser Arg Gly Pro Leu Ser Trp Thr His Val His Pro Lys
690                 695                 700

Gly Pro Lys Ser Leu Leu Ser Leu Glu Leu Lys Asp Asp Arg Pro Ala
705                 710                 715                 720

Arg Asp Met Trp Val Met Glu Thr Gly Leu Leu Leu Pro Arg Ala Thr
                725                 730                 735

Ala Gln Asp Ala Gly Lys Tyr Tyr Cys His Arg Gly Asn Leu Thr Met
            740                 745                 750

Ser Phe His Leu Glu Ile Thr Ala Arg Pro Val Leu Trp His Trp Leu
        755                 760                 765

Leu Arg Thr Gly Gly Trp Lys Val Ser Ala Val Thr Leu Ala Tyr Leu
770                 775                 780

Ile Phe Cys Leu Cys Ser Leu Val Gly Ile Leu His Leu Gln Arg Ala
785                 790                 795                 800

Leu Val Leu Arg Arg Lys Arg Lys Arg Met Thr
                805                 810

<210> SEQ ID NO 306
<211> LENGTH: 2436
<212> TYPE: DNA
<213> ORGANISM: Artificial Sequence
<220> FEATURE:
<223> OTHER INFORMATION: leader_272H-CD28H-CD28TM-DAP10CYP-CD3ZCYP_T2A-
      tCD19

<400> SEQUENCE: 306
atggaaaccc cagcgcagct tctcttcctc ctgctactct ggctcccaga taccaccgga        60

```
caggtgcagc tggtggagtc tggggggaggc gtggtccagc ctgggaggtc cctgagactc    120
tcctgtgcag cgtctggatt catcttcagt cgctatggca tgcactgggt ccgccaggct    180
ccaggcaagg ggctgaaatg ggtggcagtt atatggtatg atggaagtaa taaactctat    240
gcagactccg tgaagggccg attcaccatc tccagagaca attccaagaa cacgctgtat    300
ctgcaaatga acagcctgag agccgaggac acggctgtgt attactgtgc gagagattac    360
tatgataata gtagacatca ctgggggttt gactactggg gccagggaac cctggtcacc    420
gtctcctcag gtggtggtgg ttctggcggc ggcggctccg gtggtggtgg ttccgatatt    480
gtgatgaccc agactccact ctccctgccc gtcaccctg gagagccggc ctccatctcc    540
tgcaggtcta gtcggagcct cttggatagt gatgatggaa acacctattt ggactggtac    600
ctgcagaagc cagggcagtc tccacagctc ctgatctaca cgctttccta tcgggcctct    660
ggagtcccag acaggttcag tggcagtggg tcaggcactg atttcacact gaaaatcagc    720
agggtggagg ctgaggatgt tggagtttat tactgcatgc aacgtgtaga gtttcctatc    780
accttcggcc aagggacacg actggagatt aaactcgagg tgaaagggaa acactttgt    840
ccaagtcccc tatttcccgg accttctaag ccctttgg tgctggtggt ggttggtgga    900
gtcctggctt gctatagctt gctagtaaca gtggcctta ttattttctg ggtgctgtgc    960
gcacgcccac gccgcagccc cgcccaagaa gatggcaaag tctacatcaa catgccaggc   1020
aggggcaagc ttagagtgaa gttcagcagg agcgcagacg cccccgcgta ccagcagggc   1080
cagaaccagc tctataacga gctcaatcta ggacgaagag aggagtacga tgttttggac   1140
aagagacgtg gccgggaccc tgagatgggg ggaaagccgc agagaaggaa gaaccctcag   1200
gaaggcctgt acaatgaact gcagaaagat aagatggcgg aggcctacag tgagattggg   1260
atgaaaggcg agcgccggag gggcaagggg cacgatggcc tttaccaggg tctcagtaca   1320
gccaccaagg acacctacga cgcccttcac atgcaggccc tgccccctcg cgccggcgcc   1380
aaaaggtctg gctccggtga gggcagagga agtcttctaa catgcggtga cgtggaggag   1440
aatcccggcc ctatgccacc tcctcgcctc ctcttcttcc tcctcttcct caccccatg   1500
gaagtcaggc ccgaggaacc tctagtggtg aaggtggaag agggagataa cgctgtgctg   1560
cagtgcctca aggggaccctc agatggcccc actcagcagc tgacctggtc tcgggagtcc   1620
ccgcttaaac ccttcttaaa actcagcctg ggctgccag gctgggaat ccacatgagg    1680
cccctggcca tctggctttt catcttcaac gtctctcaac agatggggg cttctacctg    1740
tgccagccgg ggcccccctc tgagaaggcc tggcagcctg gctggacagt caatgtggag    1800
ggcagcgggg agctgttccg gtggaatgtt tcggacctag gtggcctggg ctgtggcctg    1860
aagaacaggt cctcagaggg ccccagctcc ccttccggga agctcatgag ccccaagctg   1920
tatgtgtggg ccaaagaccg ccctgagatc tgggaggag agcctccgtg tctcccaccg    1980
agggacagcc tgaaccagag cctcagccag gacctcacca tggcccctgg ctccacactc   2040
tggctgtcct gtgggtacc ccctgactct gtgtccaggg gcccctctc ctggacccat    2100
gtgcacccca aggggcctaa gtcattgctg agcctagagc tgaaggacga tcgcccggcc   2160
agagatatgt gggtaatgga gacgggtctg ttgttgcccc gggccacagc tcaagacgct   2220
ggaaagtatt attgtcaccg tggcaacctg accatgtcat tccacctgga gatcactgct   2280
cggccagtac tatggcactg gctgctgagg actggtggct ggaaggtctc agctgtgact   2340
ttggcttatc tgatcttctg cctgtgttcc cttgtgggca ttcttcatct tcaaagagcc   2400
ctggtcctga ggaggaaaag aaagcgaatg acttaa                             2436
```

<210> SEQ ID NO 307
<211> LENGTH: 824
<212> TYPE: PRT
<213> ORGANISM: Artificial Sequence
<220> FEATURE:
<223> OTHER INFORMATION: leader_2592H-CD28H-CD28TM-BBCYP-CD3ZCYP_T2A-tCD19

<400> SEQUENCE: 307

```
Met Glu Thr Pro Ala Gln Leu Leu Phe Leu Leu Leu Leu Trp Leu Pro
1               5                   10                  15

Asp Thr Thr Gly Gln Val Gln Leu Gln Glu Ser Gly Pro Arg Leu Val
            20                  25                  30

Lys Pro Ser Gln Thr Leu Ser Leu Thr Cys Thr Val Ser Gly Gly Ser
        35                  40                  45

Ile Ser Ser Asp Gly Tyr Tyr Trp Ser Trp Ile Arg Gln His Pro Gly
    50                  55                  60

Lys Gly Leu Glu Trp Ile Gly Tyr Ile Tyr Tyr Ser Gly Ser Thr Phe
65                  70                  75                  80

Tyr Asn Pro Ser Leu Lys Ser Arg Val Ala Ile Ser Val Asp Thr Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Glu Ser Pro His Ser Ser Asn Trp Tyr
        115                 120                 125

Ser Gly Phe Asp Cys Trp Gly Gln Gly Thr Leu Val Thr Val Ser Ser
    130                 135                 140

Gly Gly Gly Gly Ser Gly Gly Gly Ser Gly Gly Gly Gly Ser Glu
145                 150                 155                 160

Ile Val Leu Thr Gln Ser Pro Asp Phe Gln Ser Val Thr Pro Lys Glu
                165                 170                 175

Lys Val Thr Ile Thr Cys Arg Ala Ser Gln Ser Ile Gly Ser Arg Leu
            180                 185                 190

His Trp Tyr Gln Gln Lys Pro Asp Gln Ser Pro Lys Leu Leu Ile Lys
        195                 200                 205

Tyr Ala Ser Gln Ser Phe Ser Gly Val Pro Ser Arg Phe Ser Gly Ser
    210                 215                 220

Gly Ser Gly Thr Asp Phe Thr Leu Thr Ile Asn Ser Leu Glu Ala Glu
225                 230                 235                 240

Asp Ala Ala Thr Tyr Tyr Cys His Gln Ser Ser Asn Leu Pro Phe Thr
                245                 250                 255

Phe Gly Pro Gly Thr Lys Val Asp Ile Lys Ala Ser Val Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Lys Leu Arg Val Lys Phe Ser Arg Ser Ala Asp Ala Pro
```

```
                    355                 360                 365
Ala Tyr Gln Gln Gly Gln Asn Gln Leu Tyr Asn Glu Leu Asn Leu Gly
370                 375                 380

Arg Arg Glu Glu Tyr Asp Val Leu Asp Lys Arg Arg Gly Arg Asp Pro
385                 390                 395                 400

Glu Met Gly Gly Lys Pro Gln Arg Arg Lys Asn Pro Gln Glu Gly Leu
                405                 410                 415

Tyr Asn Glu Leu Gln Lys Asp Lys Met Ala Glu Ala Tyr Ser Glu Ile
                420                 425                 430

Gly Met Lys Gly Glu Arg Arg Arg Gly Lys Gly His Asp Gly Leu Tyr
                435                 440                 445

Gln Gly Leu Ser Thr Ala Thr Lys Asp Thr Tyr Asp Ala Leu His Met
                450                 455                 460

Gln Ala Leu Pro Pro Arg Ala Gly Ala Lys Arg Ser Gly Ser Gly Glu
465                 470                 475                 480

Gly Arg Gly Ser Leu Leu Thr Cys Gly Asp Val Glu Glu Asn Pro Gly
                485                 490                 495

Pro Met Pro Pro Pro Arg Leu Leu Phe Phe Leu Leu Phe Leu Thr Pro
                500                 505                 510

Met Glu Val Arg Pro Glu Glu Pro Leu Val Val Lys Val Glu Glu Gly
                515                 520                 525

Asp Asn Ala Val Leu Gln Cys Leu Lys Gly Thr Ser Asp Gly Pro Thr
530                 535                 540

Gln Gln Leu Thr Trp Ser Arg Glu Ser Pro Leu Lys Pro Phe Leu Lys
545                 550                 555                 560

Leu Ser Leu Gly Leu Pro Gly Leu Gly Ile His Met Arg Pro Leu Ala
                565                 570                 575

Ile Trp Leu Phe Ile Phe Asn Val Ser Gln Gln Met Gly Gly Phe Tyr
                580                 585                 590

Leu Cys Gln Pro Gly Pro Pro Ser Glu Lys Ala Trp Gln Pro Gly Trp
                595                 600                 605

Thr Val Asn Val Glu Gly Ser Gly Glu Leu Phe Arg Trp Asn Val Ser
                610                 615                 620

Asp Leu Gly Gly Leu Gly Cys Gly Leu Lys Asn Arg Ser Ser Glu Gly
625                 630                 635                 640

Pro Ser Ser Pro Ser Gly Lys Leu Met Ser Pro Lys Leu Tyr Val Trp
                645                 650                 655

Ala Lys Asp Arg Pro Glu Ile Trp Glu Gly Glu Pro Pro Cys Leu Pro
                660                 665                 670

Pro Arg Asp Ser Leu Asn Gln Ser Leu Ser Gln Asp Leu Thr Met Ala
                675                 680                 685

Pro Gly Ser Thr Leu Trp Leu Ser Cys Gly Val Pro Pro Asp Ser Val
                690                 695                 700

Ser Arg Gly Pro Leu Ser Trp Thr His Val His Pro Lys Gly Pro Lys
705                 710                 715                 720

Ser Leu Leu Ser Leu Glu Leu Lys Asp Asp Arg Pro Ala Arg Asp Met
                725                 730                 735

Trp Val Met Glu Thr Gly Leu Leu Leu Pro Arg Ala Thr Ala Gln Asp
                740                 745                 750

Ala Gly Lys Tyr Tyr Cys His Arg Gly Asn Leu Thr Met Ser Phe His
                755                 760                 765

Leu Glu Ile Thr Ala Arg Pro Val Leu Trp His Trp Leu Leu Arg Thr
770                 775                 780
```

Gly Gly Trp Lys Val Ser Ala Val Thr Leu Ala Tyr Leu Ile Phe Cys
785                 790                 795                 800

Leu Cys Ser Leu Val Gly Ile Leu His Leu Gln Arg Ala Leu Val Leu
            805                 810                 815

Arg Arg Lys Arg Lys Arg Met Thr
            820

<210> SEQ ID NO 308
<211> LENGTH: 2475
<212> TYPE: DNA
<213> ORGANISM: Artificial Sequence
<220> FEATURE:
<223> OTHER INFORMATION: leader_2592H-CD28H-CD28TM-BBCYP-CD3ZCYP_T2A-
      tCD19

<400> SEQUENCE: 308

```
atggaaaccc cagcgcagct tctcttcctc ctgctactct ggctcccaga taccaccgga      60
caggtgcagc tgcaggagtc gggcccaaga ctggtgaagc cttcacagac cctgtccctc     120
acctgcactg tctctggtgg ctccatcagt agtgatggtt actactggag ctggatccgc     180
cagcacccag gaagggcct ggagtggatt gggtacatct attacagtgg gagcaccttc     240
tacaacccgt ccctcaagag tcgagttgcc atatcagtgg acacgtctaa gaaccagttc     300
tccctgaagc tgagctctgt gactgccgcg gacacggccg tgtattactg tgcgagagaa     360
tcccctcata gcagcaactg gtactcgggc tttgactgct ggggccaggg aaccctggtc     420
accgtctcct caggtggtgg tggttctggc ggcggcggct ccggtggtgg tggttccgaa     480
attgtgctga ctcagtctcc agactttcag tctgtgactc caaggagaa agtcaccatc     540 acctgccggg ccagtcagag cattggtagt aggttacact ggtaccagca gaaaccagat     600
cagtctccaa agctcctcat caagtatgct tcccagtcct ctcagggggt ccctcgagg     660 ttcagtggca gtggatctgg gacagatttc accctcacca tcaatagcct ggaagctgaa     720
gatgctgcaa cgtattactg tcatcagagt agtaatttac cattcacttt cggccctggg     780
accaaagtgg atatcaaagc tagcgtgaaa gggaaacacc tttgtccaag tcccctattt     840
cccggacctt ctaagccctt tgggtgctg tggtggttg tggagtcct ggcttgctat     900 agcttgctag taacagtggc ctttattatt ttctgggtga acggggcag aaagaaactc     960 ctgtatatat tcaaacaacc atttatgaga ccagtacaaa ctactcaaga ggaagatggc    1020
tgtagctgcc gatttccaga agaagaagaa ggaggatgtg aactgaagct tagagtgaag    1080
ttcagcagga gcgcagacgc ccccgcgtac cagcagggcc agaaccagct ctataacgag    1140
ctcaatctag gacgaagaga ggagtacgat gttttggaca gagacgtgg ccgggaccct    1200 gagatggggg gaaagccgca gagaaggaag aaccctcagg aaggcctgta caatgaactg    1260
cagaaagata gatggcgga ggcctacagt gagattggga tgaaaggcga gcgccggagg    1320
ggcaaggggc acgatggcct ttaccagggt ctcagtacag ccaccaagga cacctacgac    1380
gcccttcaca tgcaggccct gccccctcgc gccggcgcca aaaggtctgg ctccggtgag    1440
ggcagaggaa gtcttctaac atgcggtgac gtggaggaga tcccggccc tatgccacct    1500 cctcgcctcc tcttcttcct cctcttcctc acccccatgg aagtcaggcc cgaggaacct    1560
ctagtggtga aggtggaaga gggagataac gctgtgctgc agtgcctcaa ggggacctca    1620
gatgccccca tcagcagct gacctggtct cgggagtccc cgcttaaacc cttcttaaaa    1680
ctcagcctgg ggctgccagg cctgggaatc cacatgaggc ccctggccat ctggctttc    1740
```

-continued

```
atcttcaacg tctctcaaca gatgggggc ttctacctgt gccagccggg gccccctct    1800 gagaaggcct ggcagcctgg ctggacagtc aatgtggagg gcagcgggga gctgttccgg    1860
tggaatgttt cggacctagg tggcctgggc tgtggcctga agaacaggtc ctcagagggc    1920
cccagctccc cttccgggaa gctcatgagc cccaagctgt atgtgtgggc caaagaccgc    1980
cctgagatct gggagggaga gcctccgtgt ctcccaccga gggacagcct gaaccagagc    2040
ctcagccagg acctcaccat ggcccctggc tccacactct ggctgtcctg tgggggtaccc    2100 cctgactctg tgtccagggg ccccctctcc tggacccatg tgcaccccaa ggggcctaag    2160
tcattgctga gcctagagct gaaggacgat cgcccggcca gagatatgtg ggtaatggag    2220
acgggtctgt tgttgccccg ggccacagct caagacgctg gaaagtatta ttgtcaccgt    2280
ggcaacctga ccatgtcatt ccacctggag atcactgctc ggccagtact atggcactgg    2340
ctgctgagga ctggtggctg gaaggtctca gctgtgactt tggcttatct gatcttctgc    2400
ctgtgttccc ttgtgggcat tcttcatctt caaagagccc tggtcctgag gaggaaaaga    2460
aagcgaatga cttaa                                                     2475
```

<210> SEQ ID NO 309
<211> LENGTH: 823
<212> TYPE: PRT
<213> ORGANISM: Artificial Sequence
<220> FEATURE:
<223> OTHER INFORMATION: leader_2592H-CD28H-CD28TM-CD28CYP-CD3ZCYP_T2A-tCD19

<400> SEQUENCE: 309

```
Met Glu Thr Pro Ala Gln Leu Leu Phe Leu Leu Leu Leu Trp Leu Pro
 1               5                  10                  15

Asp Thr Thr Gly Gln Val Gln Leu Gln Glu Ser Gly Pro Arg Leu Val
            20                  25                  30

Lys Pro Ser Gln Thr Leu Ser Leu Thr Cys Thr Val Ser Gly Gly Ser
        35                  40                  45

Ile Ser Ser Asp Gly Tyr Tyr Trp Ser Trp Ile Arg Gln His Pro Gly
    50                  55                  60

Lys Gly Leu Glu Trp Ile Gly Tyr Ile Tyr Ser Gly Ser Thr Phe
65                  70                  75                  80

Tyr Asn Pro Ser Leu Lys Ser Arg Val Ala Ile Ser Val Asp Thr Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Glu Ser Pro His Ser Ser Asn Trp Tyr
        115                 120                 125

Ser Gly Phe Asp Cys Trp Gly Gln Gly Thr Leu Val Thr Val Ser Ser
    130                 135                 140

Gly Gly Gly Gly Ser Gly Gly Gly Gly Ser Gly Gly Gly Gly Ser Glu
145                 150                 155                 160

Ile Val Leu Thr Gln Ser Pro Asp Phe Gln Ser Val Thr Pro Lys Glu
                165                 170                 175

Lys Val Thr Ile Thr Cys Arg Ala Ser Gln Ser Ile Gly Ser Arg Leu
            180                 185                 190

His Trp Tyr Gln Gln Lys Pro Asp Gln Ser Pro Lys Leu Leu Ile Lys
        195                 200                 205

Tyr Ala Ser Gln Ser Phe Ser Gly Val Pro Ser Arg Phe Ser Gly Ser
    210                 215                 220
```

```
Gly Ser Gly Thr Asp Phe Thr Leu Thr Ile Asn Ser Leu Glu Ala Glu
225                 230                 235                 240

Asp Ala Ala Thr Tyr Tyr Cys His Gln Ser Ser Asn Leu Pro Phe Thr
                245                 250                 255

Phe Gly Pro Gly Thr Lys Val Asp Ile Lys Ala Ser Val Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
        290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Lys Leu Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
450                 455                 460

Ala Leu Pro Pro Arg Ala Gly Ala Lys Arg Ser Gly Ser Gly Glu Gly
465                 470                 475                 480

Arg Gly Ser Leu Leu Thr Cys Gly Asp Val Glu Glu Asn Pro Gly Pro
                485                 490                 495

Met Pro Pro Pro Arg Leu Leu Phe Phe Leu Leu Phe Leu Thr Pro Met
            500                 505                 510

Glu Val Arg Pro Glu Glu Pro Leu Val Val Lys Val Glu Glu Gly Asp
        515                 520                 525

Asn Ala Val Leu Gln Cys Leu Lys Gly Thr Ser Asp Gly Pro Thr Gln
530                 535                 540

Gln Leu Thr Trp Ser Arg Glu Ser Pro Leu Lys Pro Phe Leu Lys Leu
545                 550                 555                 560

Ser Leu Gly Leu Pro Gly Leu Gly Ile His Met Arg Pro Leu Ala Ile
                565                 570                 575

Trp Leu Phe Ile Phe Asn Val Ser Gln Gln Met Gly Gly Phe Tyr Leu
            580                 585                 590

Cys Gln Pro Gly Pro Pro Ser Glu Lys Ala Trp Gln Pro Gly Trp Thr
        595                 600                 605

Val Asn Val Glu Gly Ser Gly Glu Leu Phe Arg Trp Asn Val Ser Asp
        610                 615                 620

Leu Gly Gly Leu Gly Cys Gly Leu Lys Asn Arg Ser Ser Glu Gly Pro
625                 630                 635                 640

Ser Ser Pro Ser Gly Lys Leu Met Ser Pro Lys Leu Tyr Val Trp Ala
```

```
                    645                 650                 655
Lys Asp Arg Pro Glu Ile Trp Glu Gly Glu Pro Pro Cys Leu Pro Pro
            660                 665                 670

Arg Asp Ser Leu Asn Gln Ser Leu Ser Gln Asp Leu Thr Met Ala Pro
            675                 680                 685

Gly Ser Thr Leu Trp Leu Ser Cys Gly Val Pro Pro Asp Ser Val Ser
            690                 695                 700

Arg Gly Pro Leu Ser Trp Thr His Val His Pro Lys Gly Pro Lys Ser
705                 710                 715                 720

Leu Leu Ser Leu Glu Leu Lys Asp Asp Arg Pro Ala Arg Asp Met Trp
                725                 730                 735

Val Met Glu Thr Gly Leu Leu Leu Pro Arg Ala Thr Ala Gln Asp Ala
            740                 745                 750

Gly Lys Tyr Tyr Cys His Arg Gly Asn Leu Thr Met Ser Phe His Leu
            755                 760                 765

Glu Ile Thr Ala Arg Pro Val Leu Trp His Trp Leu Leu Arg Thr Gly
            770                 775                 780

Gly Trp Lys Val Ser Ala Val Thr Leu Ala Tyr Leu Ile Phe Cys Leu
785                 790                 795                 800

Cys Ser Leu Val Gly Ile Leu His Leu Gln Arg Ala Leu Val Leu Arg
                805                 810                 815

Arg Lys Arg Lys Arg Met Thr
            820
```

<210> SEQ ID NO 310
<211> LENGTH: 2472
<212> TYPE: DNA
<213> ORGANISM: Artificial Sequence
<220> FEATURE:
<223> OTHER INFORMATION: leader_2592H-CD28H-CD28TM-CD28CYP-CD3ZCYP_T2A-
    tCD19

<400> SEQUENCE: 310

```
atggaaaccc cagcgcagct tctcttcctc ctgctactct ggctcccaga taccaccgga      60
caggtgcagc tgcaggagtc gggcccaaga ctggtgaagc cttcacagac cctgtccctc     120
acctgcactg tctctggtgg ctccatcagt agtgatggtt actactggag ctggatccgc     180
cagcacccag ggaagggcct ggagtggatt gggtacatct attacagtgg gagcaccttc     240
tacaacccgt ccctcaagag tcgagttgcc atatcagtgg acacgtctaa gaaccagttc     300
tccctgaagc tgagctctgt gactgccgcg gacacggccg tgtattactg tgcgagagaa     360
tcccctcata gcagcaactg gtactcgggc tttgactgct ggggccaggg aaccctggtc     420
accgtctcct caggtggtgg tggttctggc ggcggcggct ccggtggtgg tggttccgaa     480
attgtgctga ctcagtctcc agactttcag tctgtgactc caaaggagaa agtcaccatc     540
acctgccggg ccagtcagag cattggtagt aggttacact ggtaccagca gaaaccagat     600
cagtctccaa agctcctcat caagtatgct tcccagtcct ctcagggggt ccctcgagg      660
ttcagtggca gtggatctgg gacagatttc accctcacca tcaatagcct ggaagctgaa     720
gatgctgcaa cgtattactg tcatcagagt agtaatttac cattcacttt cggccctggg     780
accaaagtgg atatcaaagc tagcgtgaaa gggaaacacc tttgtccaag tccctatttt     840
cccggacctt ctaagccctt tgggtgctg gtggtggttg gtggagtcct ggcttgctat      900
agcttgctag taacagtggc ctttattatt ttctgggtga ggagtaagag gagcaggctc     960
ctgcacagtg actacatgaa catgactccc cgccgccccg ggcccacccg caagcattac    1020
```

```
cagccctatg ccccaccacg cgacttcgca gcctatcgct ccaagcttag agtgaagttc    1080
agcaggagcg cagacgcccc cgcgtaccag cagggccaga accagctcta taacgagctc    1140
aatctaggac gaagagagga gtacgatgtt ttggacaaga gacgtggccg ggaccctgag    1200 atgggggaa  agccgcagag aaggaagaac cctcaggaag gcctgtacaa tgaactgcag    1260
aaagataaga tggcggaggc ctacagtgag attgggatga aggcgagcg  ccggagggc     1320 aagggcacg  atggccttta ccagggtctc agtacagcca ccaaggacac ctacgacgcc    1380
cttcacatgc aggccctgcc ccctcgcgcc ggcgccaaaa ggtctggctc cggtgagggc    1440
agaggaagtc ttctaacatg cggtgacgtg gaggagaatc ccggccctat gccacctcct    1500
cgcctcctct tcttcctcct cttcctcacc cccatggaag tcaggcccga ggaacctcta    1560
gtggtgaagg tggaagaggg agataacgct gtgctgcagt gcctcaaggg gacctcagat    1620
ggccccactc agcagctgac ctggtctcgg gagtccccgc ttaaacccct cttaaaactc    1680 agcctgggc  tgccaggcct gggaatccac atgaggcccc tggccatctg gctttcatc    1740 ttcaacgtct ctcaacagat gggggggcttc tacctgtgcc agccggggcc ccctctgag    1800 aaggcctggc agcctggctg gacagtcaat gtggagggca gcggggagct gttccggtgg    1860
aatgtttcgg acctaggtgg cctgggctgt ggcctgaaga caggtcctc agagggcccc    1920 agctcccctt ccgggaagct catgagcccc aagctgtatg tgtgggccaa agaccgccct    1980
gagatctggg agggagagcc tccgtgtctc ccaccgaggg acagcctgaa ccagagcctc    2040
agccaggacc tcaccatggc ccctggctcc acactctggc tgtcctgtgg ggtacccct     2100 gactctgtgt ccagggccc  cctctcctgg acccatgtgc accccaaggg gcctaagtca    2160
ttgctgagcc tagagctgaa ggacgatcgc ccggccagag atatgtgggt aatggagacg    2220
ggtctgttgt tgccccgggc cacagctcaa gacgctggaa agtattattg tcaccgtggc    2280
aacctgacca tgtcattcca cctggagatc actgctcggc cagtactatg gcactggctg    2340
ctgaggactg gtggctggaa ggtctcagct gtgactttgg cttatctgat cttctgcctg    2400
tgttcccttg tgggcattct tcatcttcaa agagccctgg tcctgaggag gaaaagaaag    2460
cgaatgactt aa                                                       2472
```

<210> SEQ ID NO 311
<211> LENGTH: 806
<212> TYPE: PRT
<213> ORGANISM: Artificial Sequence
<220> FEATURE:
<223> OTHER INFORMATION: leader_2592H-CD28H-CD28TM-DAP10CYP-CD3ZCYP_T2A-
      tCD19

<400> SEQUENCE: 311

```
Met Glu Thr Pro Ala Gln Leu Leu Phe Leu Leu Leu Leu Trp Leu Pro
1               5                   10                  15

Asp Thr Thr Gly Gln Val Gln Leu Gln Glu Ser Gly Pro Arg Leu Val
            20                  25                  30

Lys Pro Ser Gln Thr Leu Ser Leu Thr Cys Thr Val Ser Gly Gly Ser
        35                  40                  45

Ile Ser Ser Asp Gly Tyr Tyr Trp Ser Trp Ile Arg Gln His Pro Gly
    50                  55                  60

Lys Gly Leu Glu Trp Ile Gly Tyr Ile Tyr Tyr Ser Gly Ser Thr Phe
65                  70                  75                  80

Tyr Asn Pro Ser Leu Lys Ser Arg Val Ala Ile Ser Val Asp Thr Ser
                85                  90                  95
```

```
Lys Asn Gln Phe Ser Leu Lys Leu Ser Ser Val Thr Ala Ala Asp Thr
                100                 105                 110

Ala Val Tyr Tyr Cys Ala Arg Glu Ser Pro His Ser Asn Trp Tyr
            115                 120                 125

Ser Gly Phe Asp Cys Trp Gly Gln Gly Thr Leu Val Thr Val Ser Ser
        130                 135                 140

Gly Gly Gly Gly Ser Gly Gly Gly Ser Gly Gly Gly Gly Ser Glu
145                 150                 155                 160

Ile Val Leu Thr Gln Ser Pro Asp Phe Gln Ser Val Thr Pro Lys Glu
                165                 170                 175

Lys Val Thr Ile Thr Cys Arg Ala Ser Gln Ser Ile Gly Ser Arg Leu
            180                 185                 190

His Trp Tyr Gln Gln Lys Pro Asp Gln Ser Pro Lys Leu Leu Ile Lys
        195                 200                 205

Tyr Ala Ser Gln Ser Phe Ser Gly Val Pro Ser Arg Phe Ser Gly Ser
210                 215                 220

Gly Ser Gly Thr Asp Phe Thr Leu Thr Ile Asn Ser Leu Glu Ala Glu
225                 230                 235                 240

Asp Ala Ala Thr Tyr Tyr Cys His Gln Ser Ser Asn Leu Pro Phe Thr
                245                 250                 255

Phe Gly Pro Gly Thr Lys Val Asp Ile Lys Ala Ser Val Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
290                 295                 300

Thr Val Ala Phe Ile Ile Phe Trp Val Leu Cys Ala Arg Pro Arg Arg
305                 310                 315                 320

Ser Pro Ala Gln Glu Asp Gly Lys Val Tyr Ile Asn Met Pro Gly Arg
                325                 330                 335

Gly Lys Leu Arg Val Lys Phe Ser Arg Ser Ala Asp Ala Pro Ala Tyr
            340                 345                 350

Gln Gln Gly Gln Asn Gln Leu Tyr Asn Glu Leu Asn Leu Gly Arg Arg
        355                 360                 365

Glu Glu Tyr Asp Val Leu Asp Lys Arg Arg Gly Arg Asp Pro Glu Met
370                 375                 380

Gly Gly Lys Pro Gln Arg Arg Lys Asn Pro Gln Glu Gly Leu Tyr Asn
385                 390                 395                 400

Glu Leu Gln Lys Asp Lys Met Ala Glu Ala Tyr Ser Glu Ile Gly Met
                405                 410                 415

Lys Gly Glu Arg Arg Arg Gly Lys Gly His Asp Gly Leu Tyr Gln Gly
            420                 425                 430

Leu Ser Thr Ala Thr Lys Asp Thr Tyr Asp Ala Leu His Met Gln Ala
        435                 440                 445

Leu Pro Pro Arg Ala Gly Ala Lys Arg Ser Gly Ser Gly Glu Gly Arg
450                 455                 460

Gly Ser Leu Leu Thr Cys Gly Asp Val Glu Glu Asn Pro Gly Pro Met
465                 470                 475                 480

Pro Pro Pro Arg Leu Leu Phe Phe Leu Leu Phe Leu Thr Pro Met Glu
                485                 490                 495

Val Arg Pro Glu Glu Pro Leu Val Val Lys Val Glu Glu Gly Asp Asn
            500                 505                 510
```

```
Ala Val Leu Gln Cys Leu Lys Gly Thr Ser Asp Gly Pro Thr Gln Gln
            515                 520                 525

Leu Thr Trp Ser Arg Glu Ser Pro Leu Lys Pro Phe Leu Lys Leu Ser
            530                 535                 540

Leu Gly Leu Pro Gly Leu Gly Ile His Met Arg Pro Leu Ala Ile Trp
545                 550                 555                 560

Leu Phe Ile Phe Asn Val Ser Gln Gln Met Gly Phe Tyr Leu Cys
            565                 570                 575

Gln Pro Gly Pro Pro Ser Glu Lys Ala Trp Gln Pro Gly Trp Thr Val
                580                 585                 590

Asn Val Glu Gly Ser Gly Glu Leu Phe Arg Trp Asn Val Ser Asp Leu
            595                 600                 605

Gly Gly Leu Gly Cys Gly Leu Lys Asn Arg Ser Ser Glu Gly Pro Ser
610                 615                 620

Ser Pro Ser Gly Lys Leu Met Ser Pro Lys Leu Tyr Val Trp Ala Lys
625                 630                 635                 640

Asp Arg Pro Glu Ile Trp Glu Gly Glu Pro Pro Cys Leu Pro Pro Arg
                645                 650                 655

Asp Ser Leu Asn Gln Ser Leu Ser Gln Asp Leu Thr Met Ala Pro Gly
            660                 665                 670

Ser Thr Leu Trp Leu Ser Cys Gly Val Pro Pro Asp Ser Val Ser Arg
            675                 680                 685

Gly Pro Leu Ser Trp Thr His Val His Pro Lys Gly Pro Lys Ser Leu
690                 695                 700

Leu Ser Leu Glu Leu Lys Asp Asp Arg Pro Ala Arg Asp Met Trp Val
705                 710                 715                 720

Met Glu Thr Gly Leu Leu Leu Pro Arg Ala Thr Ala Gln Asp Ala Gly
                725                 730                 735

Lys Tyr Tyr Cys His Arg Gly Asn Leu Thr Met Ser Phe His Leu Glu
            740                 745                 750

Ile Thr Ala Arg Pro Val Leu Trp His Trp Leu Leu Arg Thr Gly Gly
            755                 760                 765

Trp Lys Val Ser Ala Val Thr Leu Ala Tyr Leu Ile Phe Cys Leu Cys
770                 775                 780

Ser Leu Val Gly Ile Leu His Leu Gln Arg Ala Leu Val Leu Arg Arg
785                 790                 795                 800

Lys Arg Lys Arg Met Thr
                805

<210> SEQ ID NO 312
<211> LENGTH: 2421
<212> TYPE: DNA
<213> ORGANISM: Artificial Sequence
<220> FEATURE:
<223> OTHER INFORMATION: leader_2592H-CD28H-CD28TM-DAP10CYP-CD3ZCYP_T2A-
      tCD19

<400> SEQUENCE: 312
atggaaaccc cagcgcagct tctcttcctc ctgctactct ggctcccaga taccaccgga    60
caggtgcagc tgcaggagtc gggcccaaga ctggtgaagc cttcacagac cctgtccctc   120
acctgcactg tctctggtgg ctccatcagt agtgatggtt actactggag ctggatccgc   180
cagcacccag ggaagggcct ggagtggatt gggtacatct attacagtgg gagcaccttc   240
tacaacccgt ccctcaagag tcgagttgcc atatcagtgg acacgtctaa gaaccagttc   300
tccctgaagc tgagctctgt gactgccgcg gacacggccg tgtattactg tgcgagagaa   360
```

```
tcccctcata gcagcaactg gtactcgggc tttgactgct ggggccaggg aaccctggtc    420
accgtctcct caggtggtgg tggttctggc ggcggcggcc ccggtggtgg tggttccgaa    480
attgtgctga ctcagtctcc agactttcag tctgtgactc caaaggagaa agtcaccatc    540
acctgccggg ccagtcagag cattggtagt aggttacact ggtaccagca gaaaccagat    600
cagtctccaa agctcctcat caagtatgct tcccagtcct ctcagggggt ccctcgagg    660 ttcagtggca gtggatctgg gacagatttc accctcacca tcaatagcct ggaagctgaa    720
gatgctgcaa cgtattactg tcatcagagt agtaatttac cattcacttt cggccctggg    780
accaaagtgg atatcaaagc tagcgtgaaa gggaaacacc tttgtccaag tcccctattt    840
cccggacctt ctaagccctt ttgggtgctg gtggtggttg gtggagtcct ggcttgctat    900
agcttgctag taacagtggc ctttattatt ttctgggtgc tgtgcgcacg cccacgccgc    960
agccccgccc aagaagatgg caaagtctac atcaacatgc caggcagggg caagcttaga   1020
gtgaagttca gcaggagcgc agacgccccc gcgtaccagc agggccagaa ccagctctat   1080
aacgagctca atctaggacg aagagaggag tacgatgttt tggacaagag acgtggccgg   1140
gaccctgaga tgggggggaaa gccgcagaga aggaagaacc ctcaggaagg cctgtacaat   1200
gaactgcaga agataagat ggcggaggcc tacagtgaga ttgggatgaa aggcgagcgc   1260
cggaggggca aggggcacga tggcctttac caggtctca gtacagccac caaggacacc   1320
tacgacgccc ttcacatgca ggccctgccc cctcgcgccg cgccaaaag gtctggctcc   1380 ggtgagggca gaggaagtct tctaacatgc ggtgacgtgg aggagaatcc cggccctatg   1440
ccacctcctc gcctcctctt cttcctcctc ttcctcaccc ccatggaagt caggcccgag   1500
gaacctctag tggtgaaggt ggaagaggga gataacgctg tgctgcagtg cctcaagggg   1560
acctcagatg gccccactca gcagctgacc tggtctcggg agtccccgct taaacccttc   1620
ttaaaactca gcctggggct gccaggcctg ggaatccaca tgaggcccct ggccatctgg   1680
cttttcatct tcaacgtctc tcaacagatg gggggcttct acctgtgcca gccggggccc   1740
ccctctgaga aggcctggca gcctggctgg acagtcaatg tggagggcag cggggagctg   1800
ttccggtgga atgtttcgga cctaggtggc ctggctgtg gcctgaagaa caggtcctca   1860
gagggcccca gctcccttc cgggaagctc atgagcccca gctgtatgt gtgggccaaa   1920 gaccgccctg agatctggga gggagagcct ccgtgtctcc caccgaggga cagcctgaac   1980
cagagcctca gccaggacct caccatggcc cctggctcca cactctggct gtcctgtggg   2040
gtaccccctg actctgtgtc caggggcccc ctctcctgga cccatgtgca ccccaagggg   2100
cctaagtcat tgctgagcct agagctgaag gacgatcgcc cggccagaga tatgtgggta   2160
atggagacgg gtctgttgtt gccccgggcc acagctcaag acgctggaaa gtattattgt   2220
caccgtggca acctgaccat gtcattccac ctggagatca ctgctcggcc agtactatgg   2280
cactggctgc tgaggactgg tggctggaag gtctcagctg tgactttggc ttatctgatc   2340
ttctgcctgt gttcccttgt gggcattctt catcttcaaa gagccctggt cctgaggagg   2400
aaaagaaagc gaatgactta a                                            2421
```

<210> SEQ ID NO 313
<211> LENGTH: 823
<212> TYPE: PRT
<213> ORGANISM: Artificial Sequence
<220> FEATURE:
<223> OTHER INFORMATION: leader_2592L-CD28H-CD28TM-CD28CYP-CD3ZCYP_T2A-tCD19

<400> SEQUENCE: 313

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Asp Phe Gln Ser
            20                  25                  30

Val Thr Pro Lys Glu Lys Val Thr Ile Thr Cys Arg Ala Ser Gln Ser
            35                  40                  45

Ile Gly Ser Arg Leu His Trp Tyr Gln Gln Lys Pro Asp Gln Ser Pro
        50                  55                  60

Lys Leu Leu Ile Lys Tyr Ala Ser Gln Ser Phe Ser Gly Val Pro Ser
65                  70                  75                  80

Arg Phe Ser Gly Ser Gly Ser Gly Thr Asp Phe Thr Leu Thr Ile Asn
                85                  90                  95

Ser Leu Glu Ala Glu Asp Ala Ala Thr Tyr Tyr Cys His Gln Ser Ser
            100                 105                 110

Asn Leu Pro Phe Thr Phe Gly Pro Gly Thr Lys Val Asp Ile Lys Gly
            115                 120                 125

Gly Gly Gly Ser Gly Gly Gly Ser Gly Gly Gly Ser Gln Val
            130                 135                 140

Gln Leu Gln Glu Ser Gly Pro Arg Leu Val Lys Pro Ser Gln Thr Leu
145                 150                 155                 160

Ser Leu Thr Cys Thr Val Ser Gly Gly Ser Ile Ser Ser Asp Gly Tyr
                165                 170                 175

Tyr Trp Ser Trp Ile Arg Gln His Pro Gly Lys Gly Leu Glu Trp Ile
            180                 185                 190

Gly Tyr Ile Tyr Tyr Ser Gly Ser Thr Phe Tyr Asn Pro Ser Leu Lys
            195                 200                 205

Ser Arg Val Ala Ile Ser Val Asp Thr Ser Lys Asn Gln Phe Ser Leu
            210                 215                 220

Lys Leu Ser Ser Val Thr Ala Ala Asp Thr Ala Val Tyr Tyr Cys Ala
225                 230                 235                 240

Arg Glu Ser Pro His Ser Ser Asn Trp Tyr Ser Gly Phe Asp Cys Trp
                245                 250                 255

Gly Gln Gly Thr Leu Val Thr Val Ser Ser Ala Ser Val Lys Gly Lys
            260                 265                 270

His Leu Cys Pro Ser Pro Leu Phe Pro Gly Pro Ser Lys Pro Phe Trp
            275                 280                 285

Val Leu Val Val Val Gly Gly Val Leu Ala Cys Tyr Ser Leu Leu Val
            290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Lys Leu Arg Val Lys Phe Ser Arg Ser Ala Asp Ala Pro Ala
            355                 360                 365

Tyr Gln Gln Gly Gln Asn Gln Leu Tyr Asn Glu Leu Asn Leu Gly Arg
            370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
```

-continued

```
                405                 410                 415
Asn Glu Leu Gln Lys Asp Lys Met Ala Glu Ala Tyr Ser Glu Ile Gly
                420                 425                 430

Met Lys Gly Glu Arg Arg Gly Lys Gly His Asp Gly Leu Tyr Gln
                435                 440                 445

Gly Leu Ser Thr Ala Thr Lys Asp Thr Tyr Asp Ala Leu His Met Gln
    450                 455                 460

Ala Leu Pro Pro Arg Ala Gly Ala Lys Arg Ser Gly Ser Gly Glu Gly
465                 470                 475                 480

Arg Gly Ser Leu Leu Thr Cys Gly Asp Val Glu Glu Asn Pro Gly Pro
                485                 490                 495

Met Pro Pro Pro Arg Leu Leu Phe Phe Leu Leu Phe Leu Thr Pro Met
                500                 505                 510

Glu Val Arg Pro Glu Glu Pro Leu Val Val Lys Val Glu Glu Gly Asp
                515                 520                 525

Asn Ala Val Leu Gln Cys Leu Lys Gly Thr Ser Asp Gly Pro Thr Gln
                530                 535                 540

Gln Leu Thr Trp Ser Arg Glu Ser Pro Leu Lys Pro Phe Leu Lys Leu
545                 550                 555                 560

Ser Leu Gly Leu Pro Gly Leu Gly Ile His Met Arg Pro Leu Ala Ile
                565                 570                 575

Trp Leu Phe Ile Phe Asn Val Ser Gln Gln Met Gly Gly Phe Tyr Leu
                580                 585                 590

Cys Gln Pro Gly Pro Pro Ser Glu Lys Ala Trp Gln Pro Gly Trp Thr
                595                 600                 605

Val Asn Val Glu Gly Ser Gly Glu Leu Phe Arg Trp Asn Val Ser Asp
                610                 615                 620

Leu Gly Gly Leu Gly Cys Gly Leu Lys Asn Arg Ser Ser Glu Gly Pro
625                 630                 635                 640

Ser Ser Pro Ser Gly Lys Leu Met Ser Pro Lys Leu Tyr Val Trp Ala
                645                 650                 655

Lys Asp Arg Pro Glu Ile Trp Glu Gly Glu Pro Pro Cys Leu Pro Pro
                660                 665                 670

Arg Asp Ser Leu Asn Gln Ser Leu Ser Gln Asp Leu Thr Met Ala Pro
                675                 680                 685

Gly Ser Thr Leu Trp Leu Ser Cys Gly Val Pro Pro Asp Ser Val Ser
                690                 695                 700

Arg Gly Pro Leu Ser Trp Thr His Val His Pro Lys Gly Pro Lys Ser
705                 710                 715                 720

Leu Leu Ser Leu Glu Leu Lys Asp Asp Arg Pro Ala Arg Asp Met Trp
                725                 730                 735

Val Met Glu Thr Gly Leu Leu Leu Pro Arg Ala Thr Ala Gln Asp Ala
                740                 745                 750

Gly Lys Tyr Tyr Cys His Arg Gly Asn Leu Thr Met Ser Phe His Leu
                755                 760                 765

Glu Ile Thr Ala Arg Pro Val Leu Trp His Trp Leu Leu Arg Thr Gly
                770                 775                 780

Gly Trp Lys Val Ser Ala Val Thr Leu Ala Tyr Leu Ile Phe Cys Leu
785                 790                 795                 800

Cys Ser Leu Val Gly Ile Leu His Leu Gln Arg Ala Leu Val Leu Arg
                805                 810                 815

Arg Lys Arg Lys Arg Met Thr
                820
```

<210> SEQ ID NO 314
<211> LENGTH: 2472
<212> TYPE: DNA
<213> ORGANISM: Artificial Sequence
<220> FEATURE:
<223> OTHER INFORMATION: leader_2592L-CD28H-CD28TM-CD28CYP-CD3ZCYP_T2A-tCD19

<400> SEQUENCE: 314

```
atggaaaccc cagcgcagct tctcttcctc ctgctactct ggctcccaga taccaccgga      60
gaaattgtgc tgactcagtc tccagacttt cagtctgtga ctccaaagga aaagtcacc     120
atcacctgcc gggccagtca gagcattggt agtaggttac actggtacca gcagaaacca     180
gatcagtctc caaagctcct catcaagtat gcttcccagt ccttctcagg gtcccctcg     240
aggttcagtg gcagtggatc tgggacagat ttcacccctca ccatcaatag cctggaagct     300
gaagatgctg caacgtatta ctgtcatcag agtagtaatt taccattcac tttcggccct     360
gggaccaaag tggatatcaa aggtggtggt ggttctggcg gcggcggctc cggtggtggt     420
ggttcccagg tgcagctgca ggagtcgggc ccaagactgg tgaagccttc acagaccctg     480
tccctcacct gcactgtctc tggtggctcc atcagtagtg atggttacta ctggagctgg     540
atccgccagc acccagggaa gggcctggag tggattgggt acatctatta cagtgggagc     600
accttctaca acccgtccct caagagtcga gttgccatat cagtggacac gtctaagaac     660
cagttctccc tgaagctgag ctctgtgact gccgcggaca cggccgtgta ttactgtgcg     720
agagaatccc ctcatagcag caactggtac tcgggctttg actgctgggg ccagggaacc     780
ctggtcaccg tctcctcagc tagcgtgaaa gggaaacacc tttgtccaag tcccctattt     840
cccgaccctt ctaagccctt tgggtgctg gtggtggttg gtggagtcct ggcttgctat     900
agcttgctag taacagtggc ctttattatt ttctgggtga ggagtaagag gagcaggctc     960
ctgcacagtg actacatgaa catgactccc cgccgcccg ggcccacccg caagcattac    1020
cagccctatg ccccaccacg cgacttcgca gcctatcgct ccaagcttag agtgaagttc    1080
agcaggagcg cagacgcccc cgcgtaccag cagggccaga accagctcta taacgagctc    1140
aatctaggac gaagagagga gtacgatgtt ttggacaaga cgtggccg ggaccctgag    1200
atggggggaa agccgcagag aaggaagaac cctcaggaag gcctgtacaa tgaactgcag    1260
aaagataaga tggcggaggc ctacagtgag attgggatga aggcgagcg ccggaggggc    1320
aaggggcacg atggccttta ccagggtctc agtacagcca ccaaggacac ctacgacgcc    1380
cttcacatgc aggccctgcc ccctcgcgcc ggcgccaaaa ggtctggctc cggtgagggc    1440
agaggaagtc ttctaacatg cggtgacgtg gaggagaatc ccggccctat gccacctcct    1500
cgcctcctct tcttcctcct cttcctcacc cccatgcaag tcaggcccga ggaacctcta    1560
gtggtgaagg tggaagaggg agataacgct gtgctgcagt gcctcaaggg gacctcagat    1620
ggccccactc agcagctgac ctggtctcgg gagtccccgc ttaaacccttc ttaaaactc    1680
agcctgggc tgccaggcct gggaatccac atgaggcccc tggccatctg cttttcatc    1740
ttcaacgtct ctcaacagat ggggggcttc tacctgtgcc agccggggcc ccctctgag    1800
aaggcctggc agcctggctg acagtcaat gtggagggca gcgggagct gttccggtgg    1860
aatgtttcgg acctaggtgg cctgggctgt ggcctgaaga caggtcctc agagggcccc    1920
agctccccctt ccgggaagct catgagcccc aagctgtatg tgtgggccaa agaccgccct    1980
gagatctggg agggagagcc tccgtgtctc ccaccgaggg acagcctgaa ccagagcctc    2040
```

```
agccaggacc tcaccatggc ccctggctcc acactctggc tgtcctgtgg ggtaccccct    2100
gactctgtgt ccaggggccc cctctcctgg acccatgtgc accccaaggg gcctaagtca    2160
ttgctgagcc tagagctgaa ggacgatcgc ccggccagag atatgtgggt aatggagacg    2220
ggtctgttgt tgccccgggc cacagctcaa gacgctggaa agtattattg tcaccgtggc    2280
aacctgacca tgtcattcca cctggagatc actgctcggc cagtactatg cactggctg     2340 ctgaggactg gtggctggaa ggtctcagct gtgactttgg cttatctgat cttctgcctg    2400
tgttcccttg tgggcattct tcatcttcaa agagccctgg tcctgaggag gaaaagaaag    2460
cgaatgactt aa                                                        2472
```

<210> SEQ ID NO 315
<211> LENGTH: 359
<212> TYPE: PRT
<213> ORGANISM: Homo sapiens

<400> SEQUENCE: 315

```
Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Val Pro Thr Thr Thr
145                 150                 155                 160

Val Pro Thr Thr Met Ser Ile Pro Thr Thr Thr Val Pro Thr Thr
                165                 170                 175

Met Thr Val Ser Thr Thr Thr Ser Val Pro Thr Thr Ser Ile Pro
            180                 185                 190

Thr Thr Thr Ser Val Pro Val Thr Thr Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
        275                 280                 285
```

```
Lys Gly Ile Tyr Ala Gly Val Cys Ile Ser Val Leu Val Leu Ala
    290                 295                 300

Leu Leu Gly Val Ile Ile Ala Lys Lys Tyr Phe Phe Lys Lys Glu Val
305             310                 315                 320

Gln Gln Leu Ser Val Ser Phe Ser Ser Leu Gln Ile Lys Ala Leu Gln
            325                 330                 335

Asn Ala Val Glu Lys Glu Val Gln Ala Glu Asp Asn Ile Tyr Ile Glu
            340                 345                 350

Asn Ser Leu Tyr Ala Thr Asp
        355

<210> SEQ ID NO 316
<211> LENGTH: 15
<212> TYPE: DNA
<213> ORGANISM: Artificial Sequence
<220> FEATURE:
<223> OTHER INFORMATION: Linker region subunit

<400> SEQUENCE: 316
ggtggtggtg gttct                                                    15
```

CHIMERIC ANTIGEN RECEPTORS TARGETING TIM-1

RELATED APPLICATION DISCLOSURE

This application is a U.S. National Phase Application submitted under 35 U.S.C. 371 based on International Application No. PCT/US2018/013551 filed Jan. 12, 2018 (published as WO/2018/132695 on Jul. 19, 2018), which claims the benefit of U.S. Provisional Application Ser. No. 62/445,976, filed Jan. 13, 2017, each and all of which are hereby incorporated by reference in their entirety.

SEQUENCE DISCLOSURE

This application includes as part of its disclosure a biological sequence listing in a file named "56867o01001.txt" created on Jul. 12, 2019 and having a size of 193,278 bytes, which is hereby incorporated by reference in its entirety.

FIELD OF THE INVENTION

The invention disclosed herein relates to chimeric antigen receptors (CARs) that bind to the antigen T cell immunoglobulin domain and mucin domain 1 (TIM-1) protein and uses of such CARs. In particular, there are provided chimeric antigen receptors comprising an antigen-binding domain that binds to TIM-1, a transmembrane domain, and one or more intracellular signaling domains. Nucleotide sequences encoding, and amino acid sequences comprising, anti-TIM-1 CAR constructs are included. Vectors comprising the nucleic acids encoding such constructs, cells expressing such constructs, pharmaceutical compositions, and methods of making and using such compositions are also provided.

BACKGROUND OF THE INVENTION

Ovarian cancer represents the deadliest gynecological malignancy with more than 22,000 women diagnosed and more than 14,000 killed in the United States each year (Siegel et al. *CA Cancer J Clin* 2016; 66(1):7-30). Five-year survival rates have improved little in the last 40 years, yet remain under 30% (at best) for patients with metastatic ovarian carcinoma, the stage at which most cases are diagnosed (Siegel et al. *CA Cancer J Clin* 2016; 66(1):7-30). Certain subtypes of ovarian cancer have even more dire prognoses. Ovarian clear cell carcinoma (OCCC) accounts for 5-25% of epithelial ovarian cancer cases depending on location, with Japan having a higher prevalence than the rest of the world (Okamoto et al. *Int J Gynecol Cancer* 2014 November; 24(9):S20-5.). OCCC carries a dismal prognosis in advanced stages with very low response rates to salvage therapy and a progression free survival duration of less than 6 months (Crotzer et al. *Gynecol Oncol.* 2007; 105:404-408; Mabuchi et al. *J Gynecol Oncol.* 2016; 27:e31; Takano et al. *Int J Gynecol Cancer.* 2008; 18:937-942). Therefore, in order to improve survival rates and pivot the treatment intent of this cancer towards one that is curative, orthogonal approaches to traditional ovarian cancer treatment practices are needed.

Renal Cell Carcinoma is another important malignancy, accounting for 3% of adult malignancies and 95% of renal tumors. In the European Union, approximately 85 new cases and 35 deaths per 100,000 were reported in 2012. The rates are comparable in the USA, with approximately 61,000 new cases in 2015 alone. Currently, complete surgical resection is the only curative treatment of renal cell carcinoma in patients with locally advanced RCC or limited metastatic disease. However, these patients carry a high risk of developing systemic progression, and options for fully metastatic disease are even more limited.

Chimeric antigen receptor (CAR) T cell therapy represents an emerging type of immunotherapy whereby patient lymphocytes are genetically modified to express a receptor that allows recognition of a specific antigen. Upon antigen recognition, these modified T cells are activated via signaling domains converting them into potent cell killers. While this approach has shown curative potential in many patients with chemotherapy-refractory hematological malignancies (Kalos et al. *Sci Transl Med.* 2011; 3:95ra73; Maus et al. *Cancer Immunol Res.* 2013; 1:26-31; Porter et al. *N Engl J Med.* 2011; 365:725-733), similar successes in solid tumors have not been realized. Several reasons may account for this disparity in efficacy including: the presence of an immunosuppressive tumor microenvironment; less tumor sensitivity to T-cell-mediated killing; and a lack of the tumor-selective targeting required to minimize on-target, off-tumor toxicity (Lamers et al. *J Clin Oncol* 2006; 24:e20-22).

The family of genes encoding T cell immunoglobulin domain and mucin domain (TIM) proteins (three in humans and eight in mice) has been described. Kuchroo et al., *Nat Rev Immunol* 3:454-462 (2003); McIntire et al., *Nat Immunol* 2:1109-1116 (2001). The TIM gene family members reside in chromosomal regions, 5q33.2 in human and 11B1.1 in mouse, and have been linked to allergy and autoimmune diseases. Shevach, *Nat Rev Immunol* 2:389-400 (2002); Wills-Karp et al., *Nat Immunol* 4:1050-1052 (2003).

One TIM family member, TIM-1, is also known as Hepatitis A virus cellular receptor (HAVcr-1) and was originally discovered as a receptor for Hepatitis A virus (HAV) (Kaplan et al, *EMBO J* 15(16):4282-96 (1996)). This gene was later cloned as kidney injury molecule 1 (KIM-1) (Ichimura et al., *J Biol Chem* 273:4135-4142 (1998); Han et al., *Kidney Int* 62:237-244 (2002)).

Kaplan et al. isolated the cellular receptor for hepatitis A virus from a cDNA library from a primary African Green Monkey Kidney (AGMK) cell line expressing the receptor. See U.S. Pat. No. 5,622,861. The human homolog, hHAVcr-1 (aka TIM-1), was described by Feigelstock et al., *J Virology* 72(8): 6621-6628 (1998). The same molecules were described in PCT Publication Nos: WO 97/44460 and WO 98/53071 and U.S. Pat. No. 6,664,385 as Kidney Injury-related Molecules (KIM) that were found to be upregulated in renal tissue after injury to the kidney.

TIM-1 is a type 1 membrane protein that contains a novel six-cysteine immunoglobulin-like domain and a mucin threonine/serine/proline-rich (T/S/P) domain. TIM-1 was originally identified in rat. TIM-1 has been found in mouse, African green monkey, and humans (Feigelstock et al., *J Virol* 72(8):6621-8 (1998). The African green monkey ortholog is most closely related to human TIM-1 showing 77.6% amino acid identity over 358 aligned amino acids. Rat and mouse orthologs exhibit 50% (155/310) and 45.6% (126/276) amino acid identity respectively, although over shorter segments of aligned sequence than for African green monkey. Monoclonal antibodies to the Ig-like domain of TIM-1 have been shown to be protective against Hepatitis A virus infection in vitro. Silberstein et al., *J Virol* 75(2):717-25 (2001). In addition, KIM-1 was shown to be expressed at low levels in normal kidney but its expression is increased dramatically in postischemic kidney. Ichimura et al., *J Biol Chem* 273(7):4135-42 (1998).

TIM-1 maps to a region of human chromosome 5 known as Tapr in the murine syntenic region that has been implicated in asthma. Tapr, a major T cell regulatory locus, controls the development of airway hyperreactivity. Wills-Karp, *Nature Immunology* 2:1095-1096 (2001); McIntire et al., *Nature Immunology* 2:1109-1116 (2001).

SUMMARY OF THE INVENTION

The present invention relates to chimeric antigen receptors targeting TIM-1.

In one embodiment, the invention provides a chimeric antigen receptor (CAR) comprising an antigen-binding domain that binds to TIM-1, a transmembrane domain, and at least one intracellular signaling domain.

The antigen-binding domain of the CAR may be an antibody or an antigen-binding fragment thereof that binds to TIM-1.

In some embodiments, the antibody or antigen-binding fragment thereof is selected from the group of: a monoclonal antibody; a monospecific antibody; a polyspecific antibody; a humanized antibody; a tetrameric antibody; a tetravalent antibody; a multispecific antibody; a single chain antibody; a domain-specific antibody; a single domain antibody; a domain-deleted antibody; an scFc fusion protein; a single-chain antibody; a chimeric antibody; a synthetic antibody; a recombinant antibody; a hybrid antibody, a mutated antibody; CDR-grafted antibodies; an antibody fragment comprising an Fab; an F(ab')2; an Fab' fragment; an Fv fragment; a single-chain Fv (scFv) fragment; an Fd fragment; a dAb fragment; diabodies; a nanobody; a bivalent nanobody; a shark variable IgNAR domain; a VHH antibody; a camelid antibody; and a minibody.

In some embodiments, the antibody or antigen-binding fragment thereof is a human IgG antibody or antigen-binding fragment thereof.

In a preferred embodiment, the antigen-binding domain is a Fab or an scFv.

In some aspects, the antigen-binding domain may bind to the extracellular mucin domain region of TIM-1.

In another aspect, the antigen-binding domain may bind to the amino acid sequence LPRQNH (SEQ ID NO:97) corresponding to amino acid residues at positions 192-197 of TIM-1 (SEQ ID NO:315).

In yet another aspect, the antibody or antigen-binding fragment thereof may compete for binding to TIM-1 with an antibody comprising a VL chain having at least 80%, at least 85%, at least 90%, at least 95%, at least 98%, at least 99%, or 100% identity to the amino acid sequence of the VL chain of Ab 1.29, Ab 2.70.2, or Ab 2.59.2 (SEQ ID NO: 203, 205, or 207), or having at least 80%, at least 85%, at least 90%, at least 95%, at least 98%, at least 99%, or 100% identity to the amino acid sequence encoded by SEQ ID NO: 253, 255, or 257; and comprising a VH chain having at least 80%, at least 85%, at least 90%, at least 95%, at least 98%, at least 99%, or 100% identity to the amino acid sequence of the VH chain of Ab 1.29, Ab 2.70.2, or Ab 2.59.2 (SEQ ID NO: 202, 204, or 206), or having at least 80%, at least 85%, at least 90%, at least 95%, at least 98%, at least 99%, or 100% identity to the amino acid sequence encoded by SEQ ID NO: 252, 254, or 256.

In some embodiments, the antibody or antigen-binding fragment thereof comprises a VL chain having at least 80%, at least 85%, at least 90%, at least 95%, at least 98%, at least 99%, or 100% identity to the amino acid sequence of the VL chain of Ab 1.29, Ab 2.70.2, or Ab 2.59.2 (SEQ ID NO: 203, 205, or 207), or having at least 80%, at least 85%, at least 90%, at least 95%, at least 98%, at least 99%, or 100% identity to the amino acid sequence encoded by SEQ ID NO: 253, 255, or 257; and comprises a VH chain having at least 80%, at least 85%, at least 90%, at least 95%, at least 98%, at least 99%, or 100% identity to the amino acid sequence of the VH chain of Ab 1.29, Ab 2.70.2, or Ab 2.59.2 (SEQ ID NO: 202, 204, or 206), or having at least 80%, at least 85%, at least 90%, at least 95%, at least 98%, at least 99%, or 100% identity to the amino acid sequence encoded by SEQ ID NO: 252, 254, or 256.

The VL and VH chains of the antigen-binding domain may be linked by a flexible linker. In a preferred embodiment, the flexible linker is a (G4S)3 aka (GGGGSGGGGSGGGGS) linker, optionally having at least 80%, at least 85%, at least 90%, at least 95%, at least 98%, at least 99%, or 100% identity to the amino acid sequence of SEQ ID NO: 201, or having at least 80%, at least 85%, at least 90, at least 95%, at least 98%, at least 99%, or 100% identity to the amino acid sequence encoded by SEQ ID NO: 251.

In certain embodiments, the antigen-binding domain may have at least 80%, at least 85%, at least 90%, at least 95%, at least 98%, at least 99%, or 100% identity to the amino acid sequence of the scFv 1.29H, 1.29L, 2.70.2H, 2.70.2L, 2.59.2H, or 2.59.2L (SEQ ID NO: 208, 209, 210, 211, 212, or 213), or has at least 80%, at least 85%, at least 90%, at least 95%, at least 98%, at least 99%, or 100% identity to the amino acid sequence encoded by SEQ ID NO: 258, 259, 260, 261, 262, or 263.

In one aspect, the VL chain of the antigen-binding domain is located at the N-terminus of the CAR (the VL chain is positioned N-terminal to the VH chain in the CAR).

In another aspect, the VH chain of the antigen-binding domain is located at the N-terminus of the CAR (the VH chain is positioned N-terminal to the VL chain in the CAR).

In some embodiments, the antigen-binding domain is joined to the transmembrane domain by a linker, a spacer, or a hinge, optionally derived from one or more of the group of: CD28, CD8α, an immunoglobulin constant region or variant thereof, an immunoglobulin hinge region, an IgG4 hinge region, an immunoglobulin CH1/CL region, an Fc region, an immunoglobulin CH2 domain, an immunoglobulin CH3 domain, and/or any combination thereof.

In certain embodiments, the linker, the spacer, or the hinge is derived from CD28, optionally having at least 80%, at least 85%, at least 90%, at least 95%, at least 98%, at least 99%, or 100% identity to the amino acid sequence of CD28H (SEQ ID NO: 214), or having at least 80%, at least 85%, at least 90%, at least 95%, at least 98%, at least 99%, or 100% identity to the amino acid sequence encoded by SEQ ID NO: 264.

In one aspect, the antigen-binding domain may be conjugated to a cytotoxic agent.

The transmembrane domain may comprise a transmembrane domain derived from a protein selected from the group consisting of CD28, CD3 epsilon, CD45, CD4, CD5, CDS, CD9, CD16, CD22, CD33, CD37, CD64, CD80, CD86, CD134, CD137, CD154, TCR alpha, TCR beta, or TCR zeta. In a preferred embodiment, the transmembrane domain is derived from CD28, optionally having at least 80%, at least 85%, at least 90%, at least 95%, at least 98%, at least 99%, or 100% identity to the amino acid sequence of CD28TM (SEQ ID NO: 215), or having at least 80%, at least 85%, at least 90%, at least 95%, at least 98%, at least 99%, or 100% identity to the amino acid sequence encoded by SEQ ID NO: 265.

The intracellular signaling domain may be an intracellular signaling domain of a lymphocyte receptor chain, a TCR/CD3 complex protein, an Fc receptor subunit, or an IL-2 receptor subunit. In a preferred embodiment, the intracellular signaling domain is derived from CD3ζ, optionally having at least 80%, at least 85%, at least 90%, at least 95%, at least 98%, at least 99%, or 100% identity to the amino acid sequence of CD3ζCYP (SEQ ID NO: 219), or having at least 80%, at least 85%, at least 90%, at least 95%, at least 98%, at least 99%, or 100% identity to the amino acid sequence encoded by SEQ ID NO: 269.

The CAR of the invention may further comprise one or more costimulatory domains derived from a protein selected from the group consisting of CD27, CD28, 4-1BB (CD137), OX40 (CD134), CD30, CD40, PD-1, ICOS, lymphocyte function-associated antigen-1 (LFA-1), CD2, CD5, CD7, LIGHT, NKG2C, B7-H3, DAP10, and a ligand that specifically binds with CD83.

In a preferred embodiment, the one or more costimulatory domains are derived from a protein selected from the group consisting of CD28, 4-1BB (CD137), and DAP10, optionally having at least 80%, at least 85%, at least 90%, at least 95%, at least 98%, at least 99%, or 100% identity to the amino acid sequence of CD28CYP (SEQ ID NO: 217), BBCYP (SEQ ID NO: 216), or DAP10CYP (SEQ ID NO: 218), or having at least 80%, at least 85%, at least 90%, at least 95%, at least 98%, at least 99%, or 100% identity to the amino acid sequence encoded by SEQ ID NO: 266, 267, or 268.

In one aspect, the antigen-binding domain comprises an scFv comprising the amino acid sequence of 2.70.2H (SEQ ID NO: 210); the transmembrane domain comprises a CD28 transmembrane domain comprising the amino acid sequence of CD28TM (SEQ ID NO: 215); and the intracellular signaling domain comprises a CD3 intracellular signaling domain comprising the amino acid sequence of CD3 CYP (SEQ ID NO: 219).

In another aspect, the antigen-binding domain comprises an scFv comprising the amino acid sequence of 2.59.2H (SEQ ID NO: 212) or 2592L (SEQ ID NO:213); the transmembrane domain comprises a CD28 transmembrane domain comprising the amino acid sequence of CD28TM (SEQ ID NO: 215); and the intracellular signaling domain comprises a CD3 intracellular signaling domain comprising the amino acid sequence of CD3 CYP (SEQ ID NO: 219).

The antigen-binding domain may be joined to the transmembrane domain via a CD28 hinge, optionally having at least 80%, at least 85%, at least 90%, at least 95%, at least 98%, at least 99%, or 100% identity to the amino acid sequence of CD28H (SEQ ID NO: 214), or having at least 80%, at least 85%, at least 90%, at least 95%, at least 98%, at least 99%, or 100% identity to the amino acid sequence encoded by SEQ ID NO: 264.

The CAR of the invention may further comprise one or more costimulatory domains derived from CD28, 4-1BB, or DAP10, optionally having at least 80%, at least 85%, at least 90%, at least 95%, at least 98%, at least 99%, or 100% identity to the amino acid sequence of CD28CYP (SEQ ID NO: 217), BBCYP (SEQ ID NO: 216), or DAP10CYP (SEQ ID NO: 218), or having at least 80%, at least 85%, at least 90%, at least 95%, at least 98%, at least 99%, or 100% identity to the amino acid sequence encoded by SEQ ID NO: 266, 267, or 268.

In one aspect, the CAR comprises an amino acid sequence having at least 80%, at least 85%, at least 90%, at least 95%, at least 98%, at least 99%, or 100% identity to the amino acid sequence of 2592H-BB (SEQ ID NO: 220), or having at least 80%, at least 85%, at least 90%, at least 95%, at least 98%, at least 99%, or 100% identity to the amino acid sequence encoded by SEQ ID NO: 270.

In one aspect, the CAR comprises an amino acid sequence having at least 80%, at least 85%, at least 90%, at least 95%, at least 98%, at least 99%, or 100% identity to the amino acid sequence of 2592H-BB (SEQ ID NO: 221), or having at least 80%, at least 85%, at least 90%, at least 95%, at least 98%, at least 99%, or 100% identity to the amino acid sequence encoded by SEQ ID NO: 271.

In one aspect, the CAR comprises an amino acid sequence having at least 80%, at least 85%, at least 90%, at least 95%, at least 98%, at least 99%, or 100% identity to the amino acid sequence of 2.70.2H-BB (SEQ ID NO: 222), or having at least 80%, at least 85%, at least 90%, at least 95%, at least 98%, at least 99%, or 100% identity to the amino acid sequence encoded by SEQ ID NO: 272.

In one aspect, the CAR comprises an amino acid sequence having at least 80%, at least 85%, at least 90%, at least 95%, at least 98%, at least 99%, or 100% identity to the amino acid sequence of 2.70.2H-CD28 (SEQ ID NO: 223), or having at least 80%, at least 85%, at least 90%, at least 95%, at least 98%, at least 99%, or 100% identity to the amino acid sequence encoded by SEQ ID NO: 273.

In one aspect, the CAR comprises an amino acid sequence having at least 80%, at least 85%, at least 90%, at least 95%, at least 98%, at least 99%, or 100% identity to the amino acid sequence of 2.70.2H-DAP10 (SEQ ID NO: 224), or having at least 80%, at least 85%, at least 90%, at least 95%, at least 98%, at least 99%, or 100% identity to the amino acid sequence encoded by SEQ ID NO: 274.

In one aspect, the CAR comprises an amino acid sequence having at least 80%, at least 85%, at least 90%, at least 95%, at least 98%, at least 99%, or 100% identity to the amino acid sequence of 2592H-BB (SEQ ID NO: 225), or having at least 80%, at least 85%, at least 90%, at least 95%, at least 98%, at least 99%, or 100% identity to the amino acid sequence encoded by SEQ ID NO: 275.

In one aspect, the CAR comprises an amino acid sequence having at least 80%, at least 85%, at least 90%, at least 95%, at least 98%, at least 99%, or 100% identity to the amino acid sequence of 2592H-BB (SEQ ID NO: 226), or having at least 80%, at least 85%, at least 90%, at least 95%, at least 98%, at least 99%, or 100% identity to the amino acid sequence encoded by SEQ ID NO: 276.

In one aspect, the CAR comprises an amino acid sequence having at least 80%, at least 85%, at least 90%, at least 95%, at least 98%, at least 99%, or 100% identity to the amino acid sequence of 2.59.2H-CD28 (SEQ ID NO: 227) or 2.59.2L-CD28 (SEQ ID NO: 229), or having at least 80%, at least 85%, at least 90%, at least 95%, at least 98%, at least 99%, or 100% identity to the amino acid sequence encoded by SEQ ID NO: 277 or 279.

In one aspect, the CAR comprises an amino acid sequence having at least 80%, at least 85%, at least 90%, at least 95%, at least 98%, at least 99%, or 100% identity to the amino acid sequence of 2.59.2H-DAP10 (SEQ ID NO: 228), or having at least 80%, at least 85%, at least 90%, at least 95%, at least 98%, at least 99%, or 100% identity to the amino acid sequence encoded by SEQ ID NO: 278.

In some embodiments, a cytotoxic immune cell expressing the CAR of the invention may be activated or stimulated to proliferate when said CAR binds to TIM-1.

In some embodiments, the CAR, when expressed on the surface of a cytotoxic immune cell, directs the cytotoxic immune cell to kill a cell expressing TIM-1.

In some embodiments, the cytotoxic immune cell is a T lymphocyte.

The invention also provides a recombinant or isolated cell which expresses at least one CAR according to any of the foregoing embodiments. In some embodiments, the cell may be a human or other mammalian cell. In a preferred embodiment, the cell is a primary human cell or is derived therefrom.

In some embodiments, the recombinant or isolated cell may be an immune cell. In one aspect, this immune cell is selected from T and B lymphocytes, natural killer cells, eosinophils, NK/T cells, macrophages and monocytes. In another aspect, the immune cell is a T cell or a T cell progenitor cell.

In some embodiments, the immune cell is selected from a T cell, a CD4$^+$ T cell, a CD8$^+$ T cell, a naïve T (TN) cell, an effector T (TEFF) cell, a memory T cell, a stem cell memory T (TSCM) cell, a central memory T (TCM) cell, an effector memory T (TEM) cell, a terminally differentiated effector memory T cell, a tumor-infiltrating lymphocyte (TIL), an immature T cell, a mature T cell, a helper T cell, a cytotoxic T cell, a mucosa-associated invariant T (MAIT) cell, a regulatory T (Treg) cell, a helper T cell, a TH1 cell, a TH2 cell, a TH3 cell, a TH17 cell, a TH9 cell, a TH22 cell, a follicular helper T cell, an alpha/beta T cell, a delta/gamma T cell, a Natural Killer (NK) cell, a Natural Killer T (NKT) cell, a cytokine-induced killer (CIK) cell, and a lymphokine-activated killer (LAK) cell. In one aspect, the T cell of the foregoing embodiments is modified such that its endogenous TCR is not expressed, is not functionally expressed or is expressed at reduced levels compared to a wildtype T cell.

In another aspect, the immune cell of any of the foregoing embodiments may be MHC$^+$ or MHC$^-$.

In some embodiments, the recombinant or isolated cells according to any of the foregoing may be further modified to incorporate one or more of the following modifications: to express another CAR, optionally an activating or inhibitory CAR; to comprise a suicide gene that is expressible under specific conditions; to be specific for another antigen, optionally a tumor antigen; to overexpress pro-survival signals; to reverse anti-survival signals; to overexpress Bcl-xL or BCL-2; to suppress the expression or inhibit the function of cell death genes, including, but not limited to, Bak or Bax; to overexpress hTERT; to eliminate Fas expression; to express a TGFβ dominant negative receptor; to evade immunosuppressive mediators; and/or to comprise a homing mechanism. In some embodiments, the cell is selected from a pp65CMV-specific T cell, a CMV-specific T cell, an EBV-specific T cell, a Varicella Virus-specific T cell, an Influenza Virus-specific T cell and/or an Adenovirus-specific T cell.

The invention further provides a pharmaceutical composition comprising a pharmaceutically effective amount of a cell or CAR according to any of the foregoing.

The invention also provides an isolated nucleic acid sequence encoding a chimeric antigen receptor (CAR) comprising an antigen-binding domain that binds to TIM-1, a transmembrane domain, and at least one intracellular signaling domain.

The isolated nucleic acid may encode a CAR having any of the features of previous aspects and embodiments.

In one aspect, the isolated nucleic acid sequence further comprises a T2A ribosome skip sequence, optionally having at least 80%, at least 85%, at least 90%, at least 95%, at least 98%, at least 99%, or 100% identity to the amino acid sequence of SEQ ID NO: 231, or having at least 80%, at least 85%, at least 90%, at least 95%, at least 98%, at least 99%, or 100% identity to the amino acid sequence encoded by SEQ ID NO: 281.

In some embodiments, the isolated nucleic acid sequence further comprises a sequence encoding a selectable marker. In one aspect, the selectable marker is truncated CD19 (tCD19), optionally having at least 80%, at least 85%, at least 90%, at least 95%, at least 98%, at least 99%, or 100% identity to the amino acid sequence of SEQ ID NO: 232, or having at least 80%, at least 85%, at least 90%, at least 95%, at least 98%, at least 99%, or 100% identity to the amino acid sequence encoded by SEQ ID NO: 282.

In another aspect, the isolated nucleic acid sequence further comprises a sequence encoding a suicide mechanism.

In another aspect, the isolated nucleic acid sequence further comprises one or more signaling domains of a co-inhibitory receptor, such as CTLA-4 or PD-1 ("iCAR"); and/or expresses a substrate peptide cleaved in the presence of matrix metalloproteinases enriched within the tumor microenvironment ("masked CAR").

In yet another aspect, the isolated nucleic acid sequence further comprises a signal peptide, optionally having at least 80%, at least 85%, at least 90%, at least 95%, at least 98%, at least 99%, or 100% identity to the amino acid sequence of SEQ ID NO: 230, or having at least 80%, at least 85%, at least 90%, at least 95%, at least 98%, at least 99%, or 100% identity to the amino acid sequence encoded by SEQ ID NO: 280.

The invention further provides a vector comprising a nucleic acid sequence encoding a chimeric antigen receptor (CAR) according to any one of the previous embodiments.

The vector may further comprise a T2A ribosome skip sequence, optionally having at least 80%, at least 85%, at least 90%, at least 95%, at least 98%, at least 99%, or 100% identity to the amino acid sequence of SEQ ID NO: 231, or having at least 80%, at least 85%, at least 90%, at least 95%, at least 98%, at least 99%, or 100% identity to the amino acid sequence encoded by SEQ ID NO: 281.

The vector may further comprise a nucleic acid sequence encoding a selectable marker. In some embodiments, the selectable marker may be truncated CD19 (tCD19), optionally having at least 80%, at least 85%, at least 90%, at least 95%, at least 98%, at least 99%, or 100% identity to the amino acid sequence of SEQ ID NO: 232, or having at least 80%, at least 85%, at least 90%, at least 95%, at least 98%, at least 99%, or 100% identity to the amino acid sequence encoded by SEQ ID NO: 282.

The vector may be selected from the group consisting of a DNA, a RNA, a plasmid, a lentivirus vector, adenoviral vector, or a retrovirus vector.

In one aspect, the vector further comprises a promoter.

In another aspect, the vector is an in vitro transcribed vector.

In another aspect, the vector further comprises a poly(A) tail and/or a 3'UTR.

The invention further provides an isolated cell comprising a nucleic acid sequence encoding a chimeric antigen receptor (CAR) according to any of the preceding embodiments.

In some embodiments, the cell is a cytotoxic immune cell, optionally selected from a T cell, a CD4$^+$ T cell, a CD8$^+$ T cell, a naïve T (TN) cell, an effector T (TEFF) cell, a memory T cell, a stem cell memory T (TSCM) cell, a central memory T (TCM) cell, an effector memory T (TEM) cell, a terminally differentiated effector memory T cell, a tumor-infiltrating lymphocyte (TIL), an immature T cell, a mature T cell, a helper T cell, a cytotoxic T cell, a mucosa-associated invariant T (MAIT) cell, a regulatory T (Treg) cell, a helper T cell, a TH1 cell, a TH2 cell, a TH3 cell, a TH17 cell, a TH9 cell, a TH22 cell, a follicular helper T cell, an alpha/beta T cell, a delta/gamma T cell, a Natural Killer (NK) cell, a Natural Killer T (NKT) cell, a cytokine-induced killer (CIK) cell, and a lymphokine-activated killer (LAK) cell.

In some embodiments, the cell exhibits anti-tumor cytotoxicity when the CAR binds to TIM-1.

In some embodiments, the CAR expressing cell increases production of cytokines and chemokines upon exposure to TIM-1 expressing cells. In a preferred embodiment, the cytokines and chemokines that are produced are one or more of GM-CSF, IL-6, RANTES (CCL5), TNF-α, IL-4, IL-10, IL-13, or IFN-γ.

In some embodiments, the cell exhibits cytotoxic activity upon exposure to TIM-1-expressing cells, optionally measured via lactate dehydrogenase production.

In some embodiments, the cell may be specific for another antigen, optionally a tumor antigen; may be selected from a pp65CMV-specific T cell, a CMV-specific T cell, an EBV-specific T cell, a Varicella Virus-specific T cell, an Influenza Virus-specific T cell and/or an Adenovirus-specific T cell; may be further modified to overexpress pro-survival signals, reverse anti-survival signals, overexpress Bcl-xL or BCL-2, suppress the expression or inhibit the function of cell death genes, including, but not limited to, Bak or Bax, overexpress hTERT, lack Fas, or express a TGFβ dominant negative receptor; may be further modified to evade immunosuppressive mediators; further comprises a homing mechanism; and/or may further comprise another CAR, optionally an activating or inhibiting CAR.

The invention also provides a therapeutic or pharmaceutical composition comprising a therapeutically effective amount of a CAR or isolated cell according to any of the foregoing embodiments.

The invention also encompasses a method of immune therapy comprising administering a therapeutically effective amount of a CAR or isolated cell or composition containing according to any of the foregoing embodiments. In some embodiments, this method may be used in the treatment of a condition selected from cancer, autoimmunity, infection and an inflammatory disorder.

The invention also encompasses a method for stimulating an immune cell-mediated response in a subject, the method comprising administering to a subject in need thereof an effective amount of an immune cell modified to express a CAR comprising (i) an antigen-binding domain that binds to TIM-1; (ii) a transmembrane domain; and (iii) at least one intracellular signaling domain, wherein the modified immune cell is activated or stimulated to proliferate when the CAR binds to TIM-1, thereby stimulating an immune cell-mediated response in the subject.

The invention also provides a method for treating a disease, a disorder, or a condition associated with undesired proliferation of cells expressing TIM-1 in a subject, the method comprising administering to the subject in need thereof an effective amount of an immune cell genetically modified to express a CAR comprising (i) an antigen-binding domain that binds to TIM-1; (ii) a transmembrane domain; and (iii) at least one intracellular signaling domain, wherein the modified immune cell is activated or stimulated to proliferate when the CAR binds to TIM-1 thereby treating the disease, disorder, or condition associated with undesired proliferation of cells expressing TIM-1.

The invention additionally encompasses a method for treating a cancer in a subject, the method comprising administering to the subject in need thereof an effective amount of an immune cell modified to express a CAR comprising (i) an antigen-binding domain that binds to TIM-1, (ii) a transmembrane domain, and (iii) at least one intracellular signaling domain.

In some embodiments, the immune response in the subject is measured via production of cytokines and chemokines. In a preferred embodiment, the cytokines and chemokines are GM-CSF, IL-6, RANTES (CCL5), TNF-α, IL-4, IL-10, IL-13, or IFN-γ.

In some embodiments, the modified immune cell is a T cell. The T cell may be an autologous T cell or a donor-derived T cell.

In some embodiments, the method is used to treat a cancer that is a solid tumor. The cancer may be selected from a group consisting of carcinomas, melanomas, sarcomas, gliomas, and skin cancers. In some embodiments, the tumor cells express TIM-1.

In some embodiments, the cancer is a renal cell carcinoma, an ovarian clear cell carcinoma or a lung carcinoma. In a preferred embodiment, the cancer is an ovarian clear cell carcinoma or renal cell carcinoma.

The modified immune cells of the aforementioned methods may be administered topically, enterally, or parenterally.

In some embodiments, the modified immune cells reduce tumor growth and/or tumor volume.

The subject of the method may be resistant to at least one chemotherapeutic agent.

In one aspect, the method further comprises administration of another therapy to the subject. In some embodiments, the therapy is chemotherapy, radiotherapy, toxin-based therapy, radiochemical based therapy, or surgical therapy.

For any of the foregoing methods, the modified cells may be administered in combination with another therapeutic agent. In some embodiments, the therapeutic agent increases the efficacy of a cell expressing a CAR molecule. In some embodiments, the therapeutic agent ameliorates one or more side effects associated with administration of a cell expressing a CAR molecule.

The modified immune cell of these methods may express a CAR according to any of the foregoing or a nucleic acid encoding said CAR according to any of the foregoing.

The invention also provides a method of generating a persisting population of modified immune cells in a subject, the method comprising administering to the subject an immune cell comprising a nucleic acid sequence encoding a chimeric antigen receptor (CAR) according to any of the foregoing embodiments, wherein the modified immune cells persists in the subject for at least one month after administration. The persisting population of modified immune cells may comprise at least one modified immune cell that was administered to the subject, a progeny of the modified immune cell that was administered to the subject, or a combination thereof. In some embodiments, the persisting population of modified immune cells comprises a memory T cell. In some embodiments, the persisting population of modified immune cells persists in the subject for at least three months, at least four months, at least five months, at least six months, at least seven months, at least eight months, at least nine months, at least ten months, at least eleven months, at least twelve months, at least eighteen months, at least two years, or at least three years after administration.

The invention also encompasses a method of expanding a population of modified immune cells in a subject, the method comprising administering to the subject an immune cell comprising a nucleic acid sequence encoding a chimeric antigen receptor (CAR) according to any of the foregoing embodiments, wherein the administered modified immune cell produces a population of progeny cells in the subject. In some embodiments, the population of progeny cells persists in the subject for at least three months, at least four months, at least five months, at least six months, at least seven months, at least eight months, at least nine months, at least ten months, at least eleven months, at least twelve months, at least eighteen months, at least two years, or at least three years after administration.

The invention further contemplates a pharmaceutical composition comprising an immune cell modified to express a nucleic acid sequence encoding a chimeric antigen receptor (CAR) according to any of the foregoing embodiments and a pharmaceutically acceptable carrier or excipient. The composition may further comprise one or more additional agents that specifically bind to one or more tumor associated antigens. The composition may be suitable for topical, enteral, or parenteral administration.

The invention also encompasses a method of producing a CAR-expressing immune cell comprising introducing into an immune cell a nucleic acid sequence encoding a chimeric antigen receptor (CAR) according to any of the foregoing embodiments. The invention also encompasses a method of producing a CAR-expressing immune cell comprising introducing into an immune cell a nucleic acid sequence according to any of the foregoing embodiments.

The invention also provides a method of producing a CAR-expressing immune cell comprising transducing an immune cell with a vector according to any of the foregoing embodiments.

In one aspect of the methods of producing CAR-expressing immune cells, the CAR-expressing immune cell is isolated based on expression of said CAR as determined via flow cytometry or immunofluorescence assays. In another aspect of these methods, the CAR-expressing immune cell is enriched for CD3 and tCD19 expression. In yet another aspect of these methods, the CAR-expressing immune cell is stimulated to grow via exposure to magnetic beads, soluble antibodies, and/or cytokines. In one aspect, the CAR-expressing immune cell is stimulated to grow via exposure to OKT3 and IL-2.

The invention also encompasses a method of generating a population of RNA-engineered cells comprising introducing an in vitro transcribed RNA or synthetic RNA into a cell, where the RNA comprises a nucleic acid encoding a CAR molecule according to any of the preceding claims.

DETAILED DESCRIPTION OF THE SEVERAL VIEWS OF THE DRAWINGS

FIG. 1 contains a general schematic of the TIM-1 CAR.

Figures 2A, 2B:
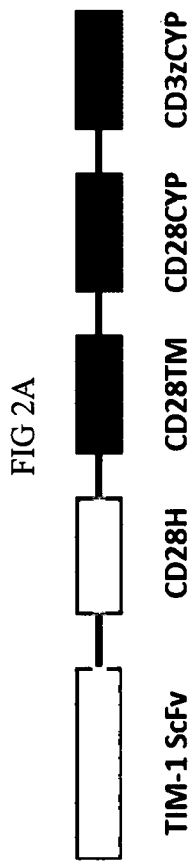

FIG. 2A-2C contain schematics illustrating various TIM-1 CARs. FIG. 2A illustrates one possible organization of the CAR: anti-TIM-1 ScFv, the CD28 hinge domain, the CD28 transmembrane domain, the CD28 cytoplasmic/costimulatory domain, and the CD3ζ cytoplasmic/intracellular signaling domain. FIG. 2B illustrates two different anti-TIM-1 ScFv configurations (VL-linker-VH and VH-linker-VL) for the VL and VH regions derived from three different antibodies: Ab 1.29, Ab 2.70.2, and Ab 2.59.2. The sequences of these six scFv's are provided in SEQ ID NO: 208, 209, 210, 211, 212, and 213. FIG. 2C illustrates six different gene constructs encoding various TIM-1 CARs. These CAR gene constructs feature a signal peptide followed, in order, by an anti-TIM-1 ScFv, the CD28 hinge and transmembrane domains, the CD28/4-1BB/DAP10 costimulatory domain, the CD3ζ intracellular signaling domain, a T2A ribosomal skip sequence, and the gene encoding truncated CD19.

Figure 3:
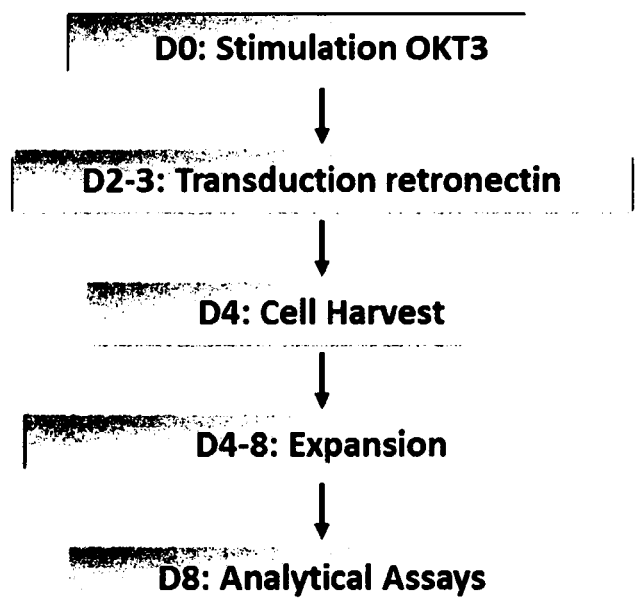

FIG. 3 contains a flow chart illustrating a potential method for manufacturing isolated CAR-expressing cells for in vitro assays.

FIG. 4 contains the tabulated results of an exemplary flow cytometry analysis of TIM-1 CAR T-cells. The analysis indicates the percentage of cells that were living ("Live"), the percentage of living cells that were CD3$^+$ ("CD3"), the percentage of CD3$^+$ cells that were CD4$^+$ ("CD4 [CD3]"), the percentage of CD3$^+$ cells that were CD8$^+$ ("CD8 [CD3]"), the percentage of live cells expressing a TIM-1 CAR ("TIM-1 CAR"), and the percentage of CD3$^+$ cells expressing truncated CD19 ("CD19 [CD3]").

Figure 5A:
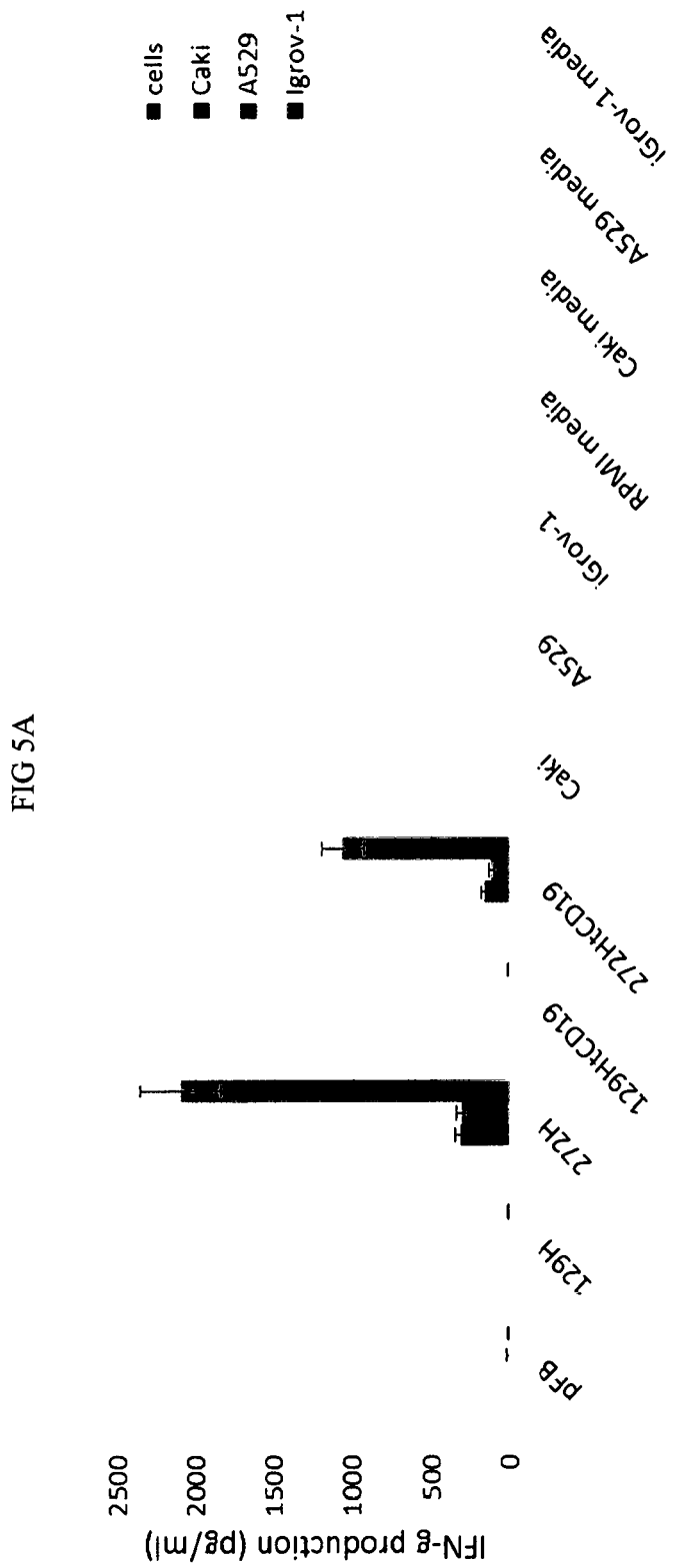
Figure 5B:
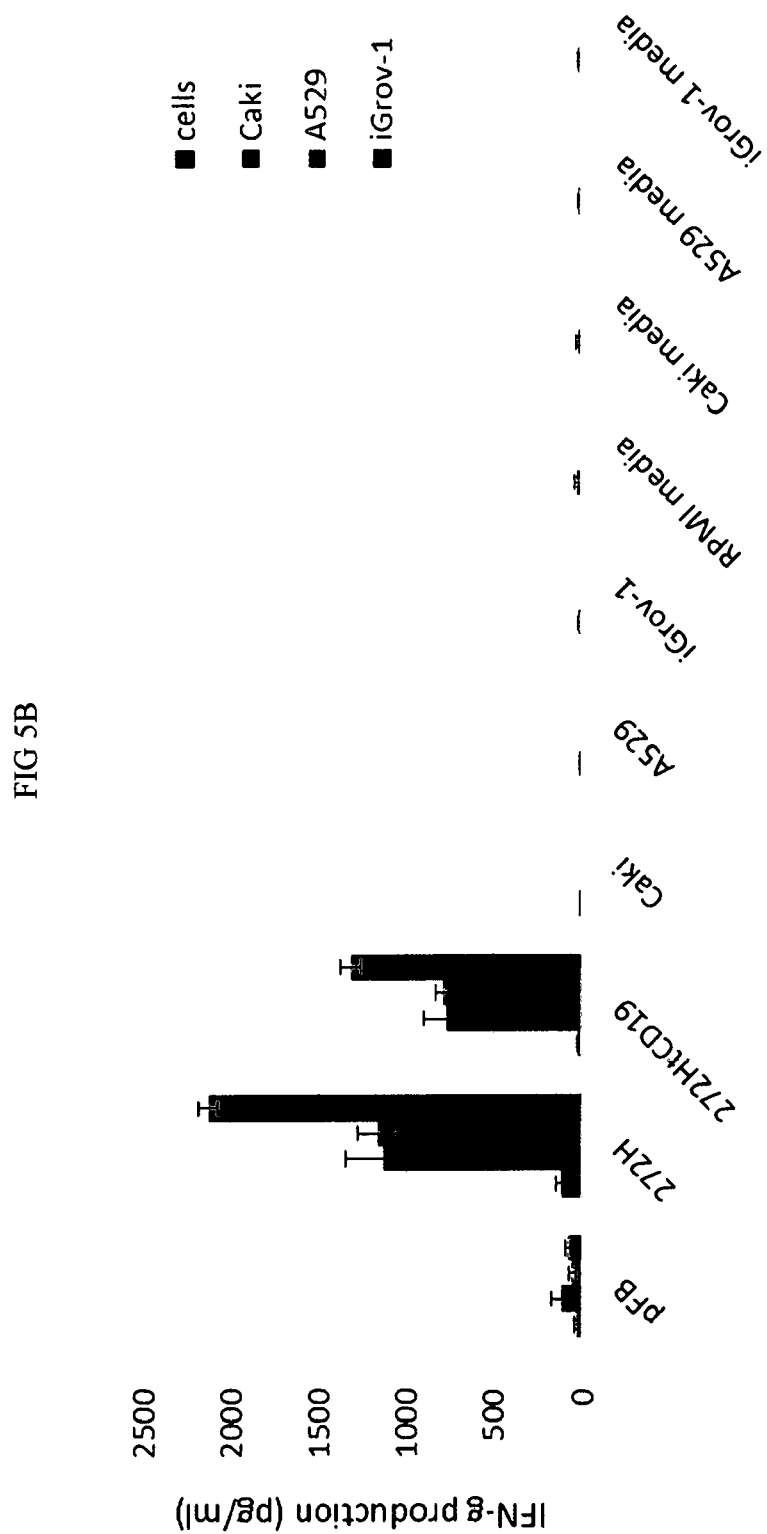
Figure 5D:
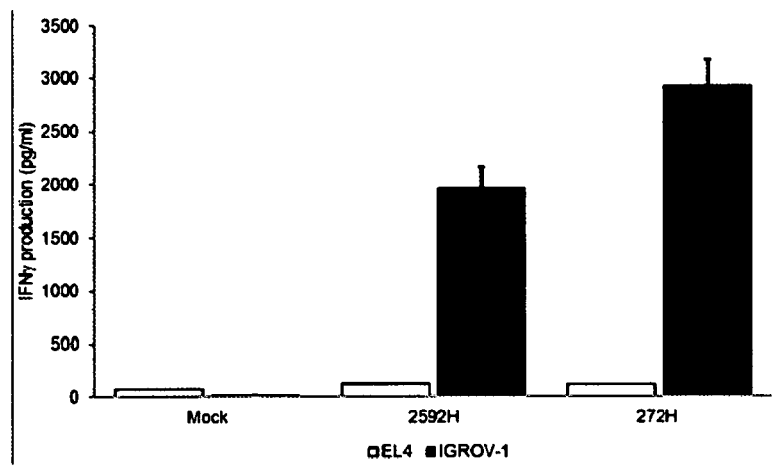
Figure 5E:
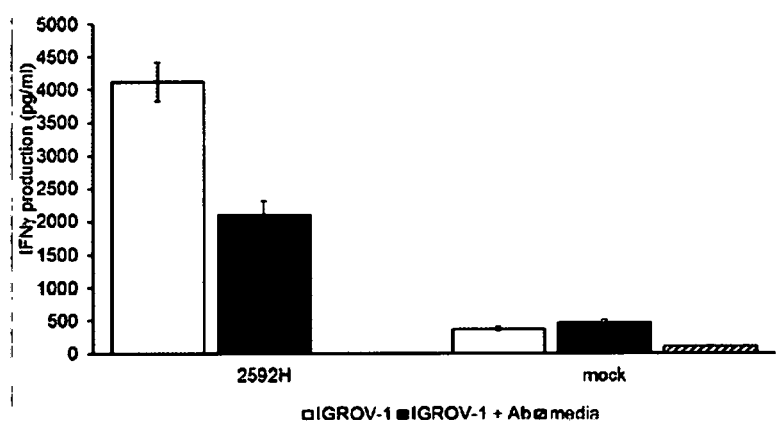

FIG. 5A-5E contain data demonstrating the IFN-γ production in pg/mL of TIM-1 CAR T-cells upon exposure to various cell types. FIG. 5A shows the IFN-γ production (from left to right) of control-vector-transduced cells, 129H (129H-CD28) CAR T-cells, 272H (272H-CD28) CAR T-cells, 129HtCD19 (129H-CD28+tCD19) CAR T-cells, 272HtCD19 (272H-CD28+tCD19) CAR T-cells, and seven other media or cell controls. FIG. 5B shows the IFN-γ production of (from left to right) control-vector-transduced cells, 272H (272H-CD28) CAR T-cells, 272HtCD19 (272H-CD28+tCD19) CAR T-cells, and seven other media or cell controls. For FIG. 5A and FIG. 5B, IFN-γ production was measured upon exposure to (from left to right) no coculture with cells, Caki-1 (renal cancer) cells, A549 (lung cancer) cells, and IGROV-1 (ovarian cancer) cells. FIG. 5C shows the IFN-γ production (from left to right) of 2592H (2592H-CD28) CAR T-cells, 2592L (2592L-CD28) CAR T-cells, and mock-transduced cells upon exposure to (from left to right) EL4 (non-TIM-1-expressing) cells, A549 cells, Caki-1 cells, IGROV-1 cells, and IGROV-1 cells in the presence of anti-TIM-1 antibodies. FIG. 5D shows the IFN-γ production (from left to right) of mock-transduced cells, 2592H (2592H-CD28) CAR T-cells, and 272H (272H-CD28) CAR T-cells upon exposure to EL4 cells (left), and IGROV-1 cells (right). FIG. 5E shows the IFN-γ production of 2592H (2592H-CD28) CAR T-cells (left), and mock-transduced cells (right) after 22 h incubation with (from left to right) IGROV-1 cells, IGROV-1 cells in the presence of anti-TIM-1 antibodies, and a media control.

Figure 6A:
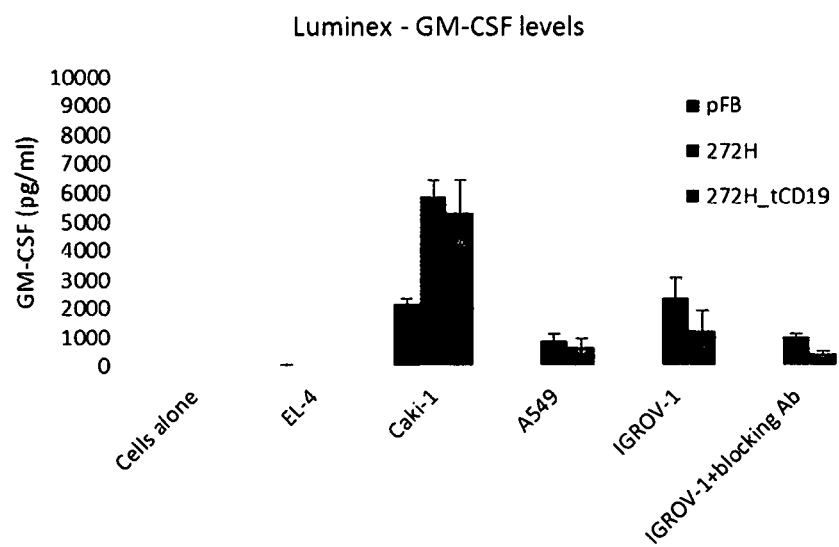
Figure 6B:
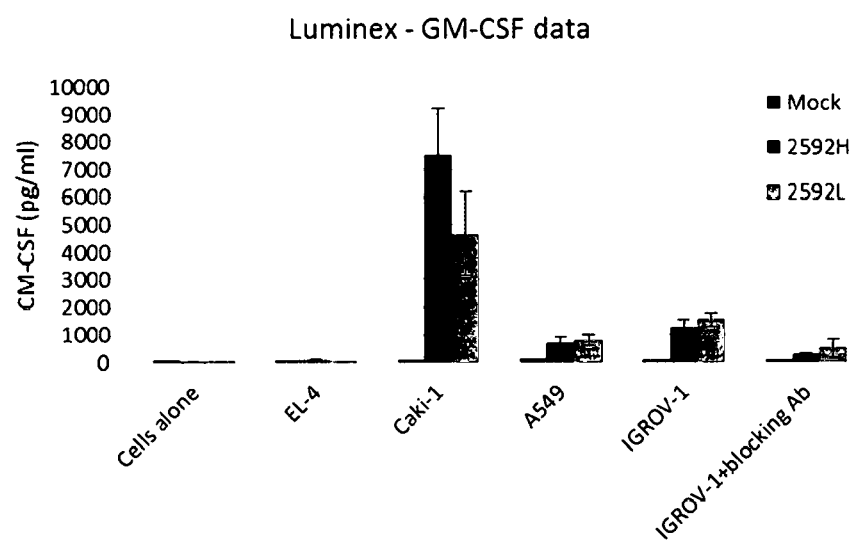

FIG. 6A-6B contain data reporting GM-CSF production upon exposure to (from left to right) media control, EL-4 cells, Caki-1 cells, A549 cells, IGROV-1 cells and IGROV-1 cells in the presence of anti-TIM-1 antibodies. These levels are reported in FIG. 6A for (from left to right) control-vector-transduced cells, 272H (272H-CD28) CAR T-cells, and 272HtCD19 (272H-CD28+tCD19) CAR T-cells; and in FIG. 6B for mock-transduced cells, 2592H (2592H-CD28) CAR T-cells, and 2592L (2592L-CD28) CAR T-cells.

Figure 7A:
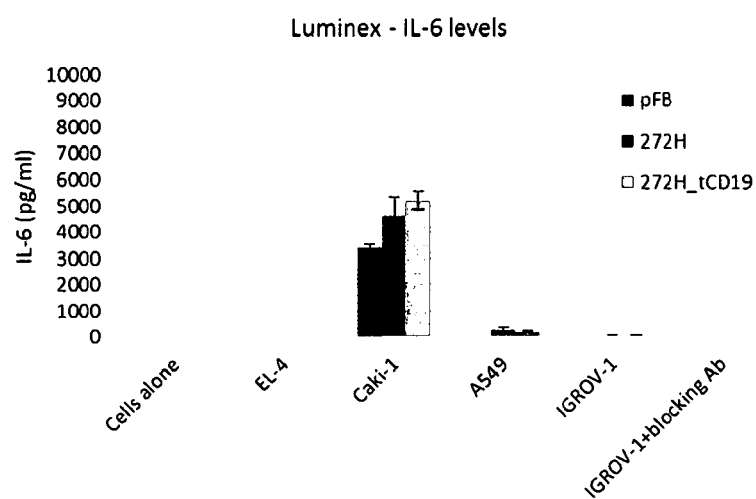
Figure 7B:
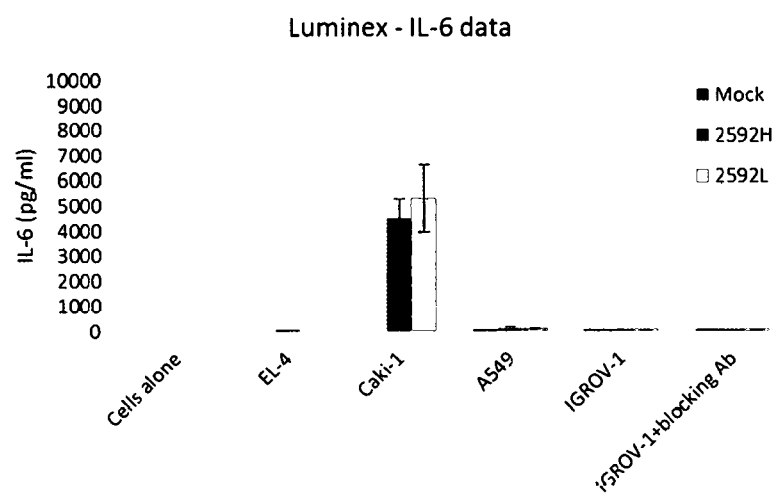

FIG. 7A-7B contain data reporting IL-6 production upon exposure to (from left to right) media control, EL-4 cells, Caki-1 cells, A549 cells, IGROV-1 cells and IGROV-1 cells in the presence of anti-TIM-1 antibodies. These levels are reported in FIG. 7A for (from left to right) control-vector-transduced cells, 272H (272H-CD28) CAR T-cells, and 272HtCD19 (272H-CD28+tCD19) CAR T-cells; and in FIG. 7B for mock-transduced cells, 2592H (2592H-CD28) CAR T-cells, and 2592L CAR T-cells.

Figure 8A:
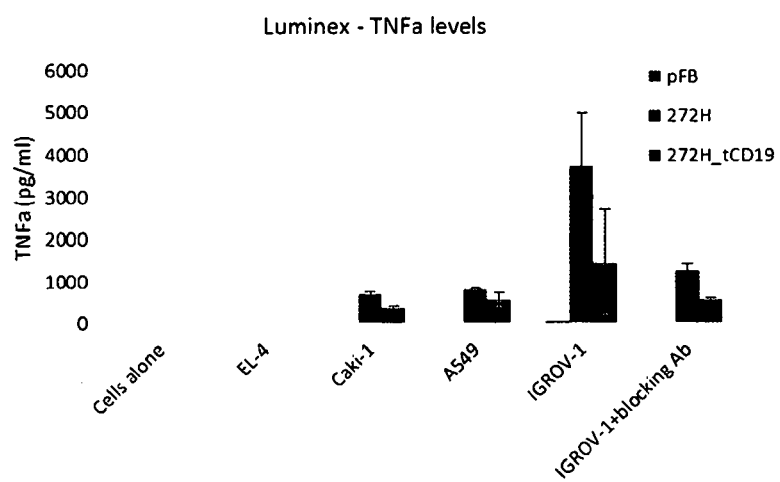
Figure 8B:
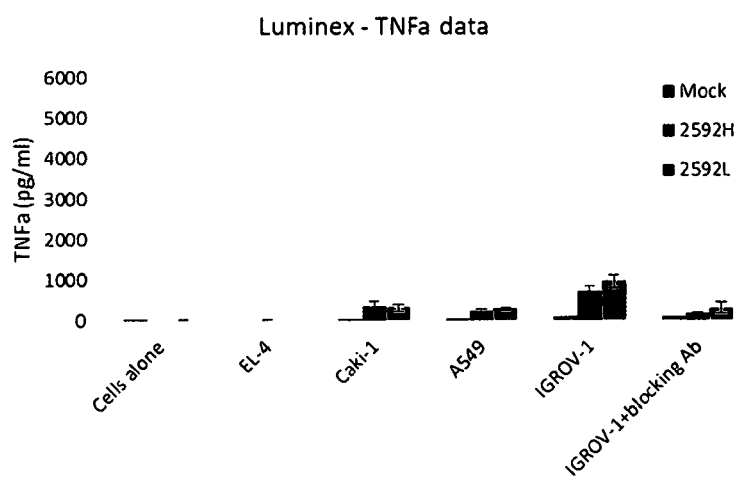

FIG. 8A-8B contain data reporting TNF-α production upon exposure to (from left to right) media control, EL-4 cells, Caki-1 cells, A549 cells, IGROV-1 cells and IGROV-1 cells in the presence of anti-TIM-1 antibodies. These levels are reported in FIG. 8A for (from left to right) controlvector-transduced cells, 272H (272H-CD28) CAR T-cells, and 272HtCD19 (272H-CD28+tCD19) CAR T-cells; and in FIG. 8B for mock-transduced cells, 2592H (2592H-CD28) CAR T-cells, and 2592L CAR T-cells.

Figure 9A:
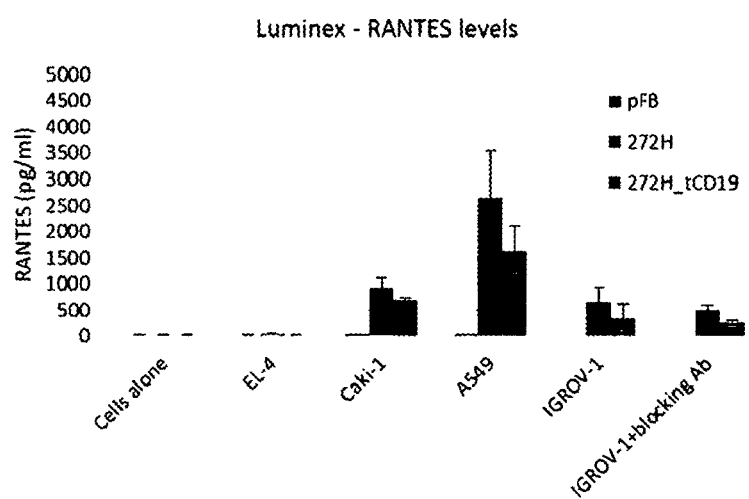
Figure 9B:
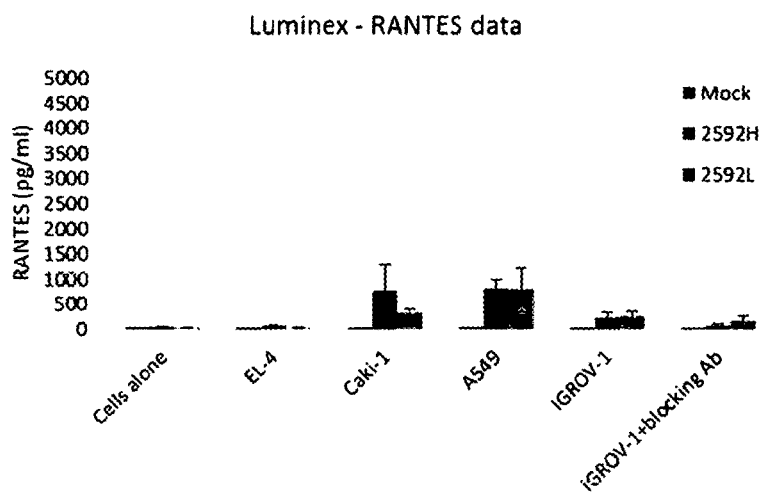

FIG. 9A-9B contain data reporting RANTES production upon exposure to (from left to right) media control, EL-4 cells, Caki-1 cells, A549 cells, IGROV-1 cells and IGROV-1 cells in the presence of anti-TIM-1 antibodies. These levels are reported in FIG. 9A for (from left to right) control-vector-transduced cells, 272H (272H-CD28) CAR T-cells, and 272HtCD19 (272H-CD28+tCD19) CAR T-cells; and in FIG. 9B for mock-transduced cells, 2592H (2592H-CD28) CAR T-cells, and 2592L CAR T-cells.

Figure 10A:
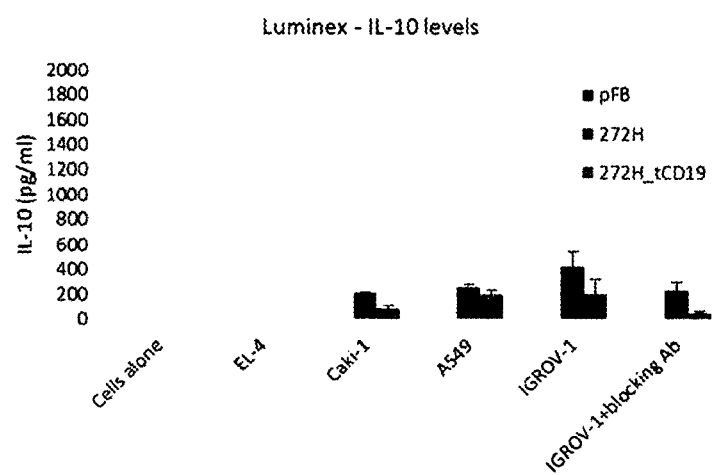
Figure 10B:
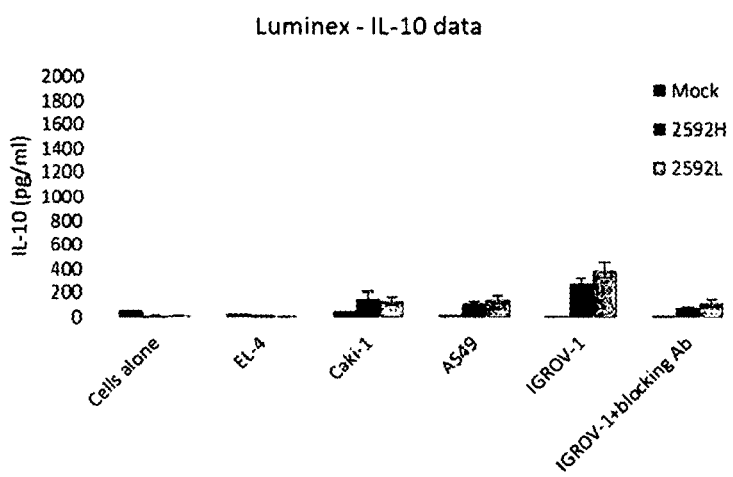

FIG. 10A-10B contain data reporting IL-10 production upon exposure to (from left to right) media control, EL-4 cells, Caki-1 cells, A549 cells, IGROV-1 cells and IGROV-1 cells in the presence of anti-TIM-1 antibodies. These levels are reported in FIG. 10A for (from left to right) control-vector-transduced cells, 272H (272H-CD28) CAR T-cells, and 272HtCD19 (272H-CD28+tCD19) CAR T-cells; and in FIG. 10B for mock-transduced cells, 2592H (2592H-CD28) CAR T-cells, and 2592L CAR T-cells.

Figure 11A:
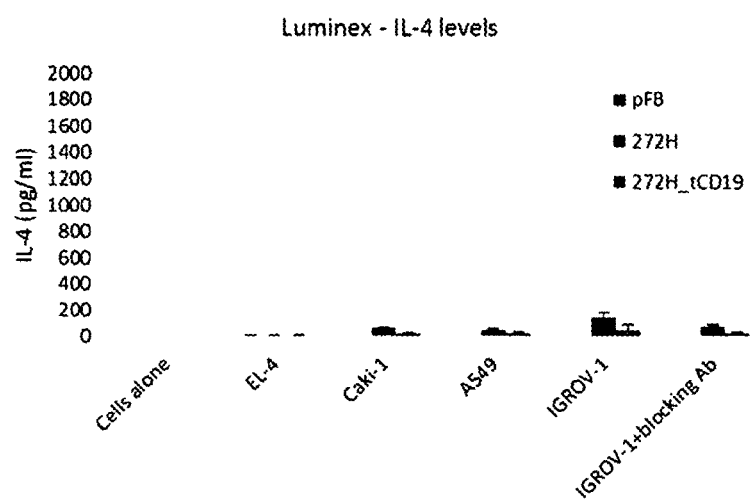
Figure 11B:
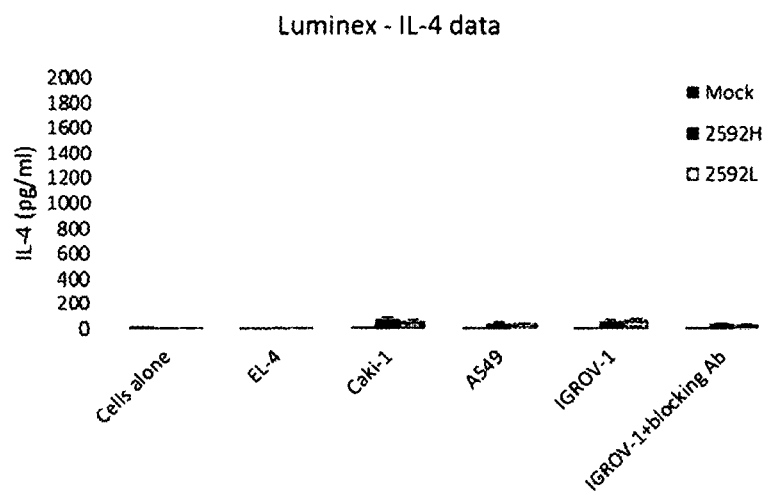

FIG. 11A-11B contain data reporting IL-4 production upon exposure to (from left to right) media control, EL-4 cells, Caki-1 cells, A549 cells, IGROV-1 cells and IGROV-1 cells in the presence of anti-TIM-1 antibodies. These levels are reported in FIG. 11A for (from left to right) control-vector-transduced cells, 272H (272H-CD28) CAR T-cells, and 272HtCD19 (272H-CD28+tCD19) CAR T-cells; and in FIG. 11B for mock-transduced cells, 2592H (2592H-CD28) CAR T-cells, and 2592L CAR T-cells.

Figure 12A:
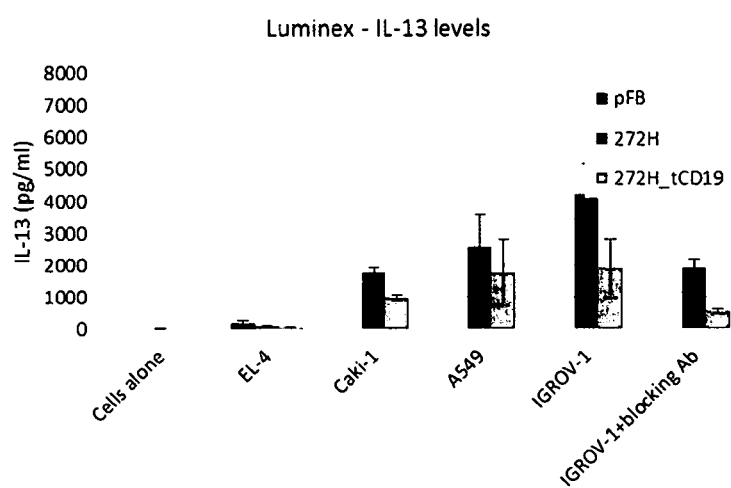
Figure 12B:
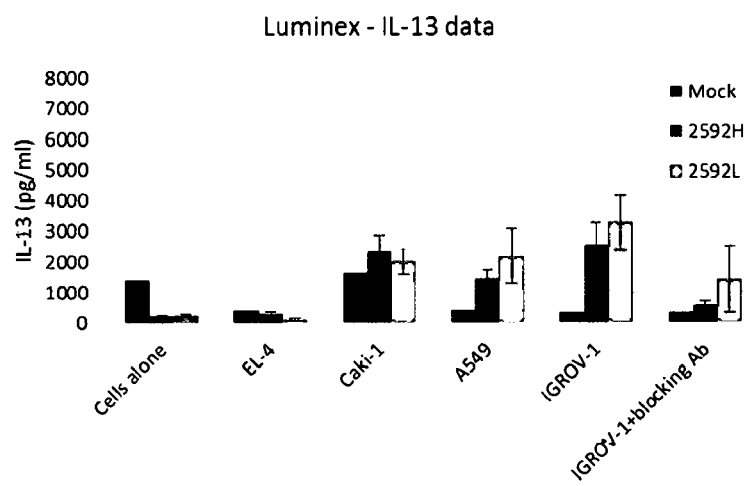

FIG. 12A-12B contain data reporting IL-13 production upon exposure to (from left to right) media control, EL-4 cells, Caki-1 cells, A549 cells, IGROV-1 cells and IGROV-1 cells in the presence of anti-TIM-1 antibodies. These levels are reported in FIG. 12A for (from left to right) control-vector-transduced cells, 272H (272H-CD28) CAR T-cells, and 272HtCD19 (272H-CD28+tCD19) CAR T-cells; and in FIG. 12B for mock-transduced cells, 2592H (2592H-CD28) CAR T-cells, and 2592L CAR T-cells.

Figure 13A:
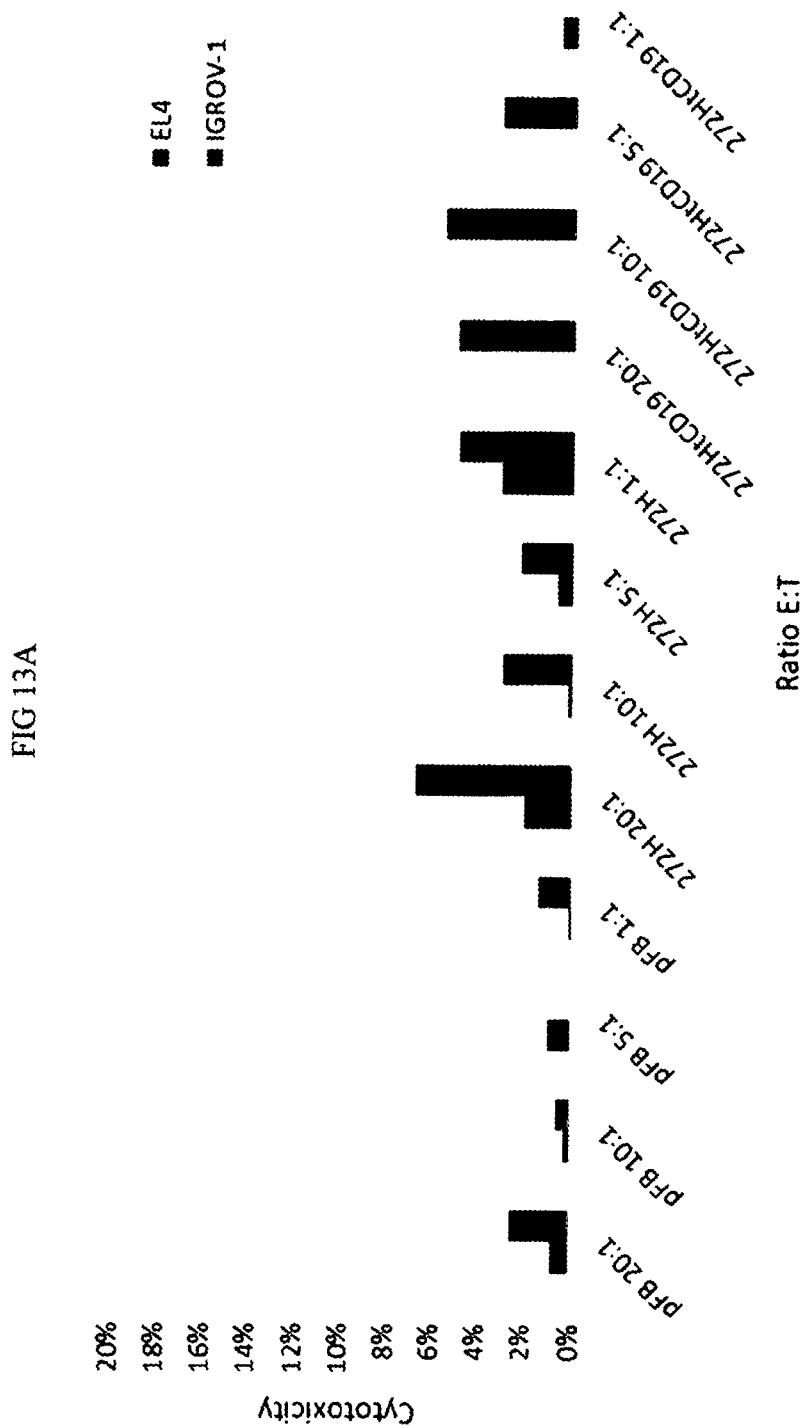
Figure 13B:
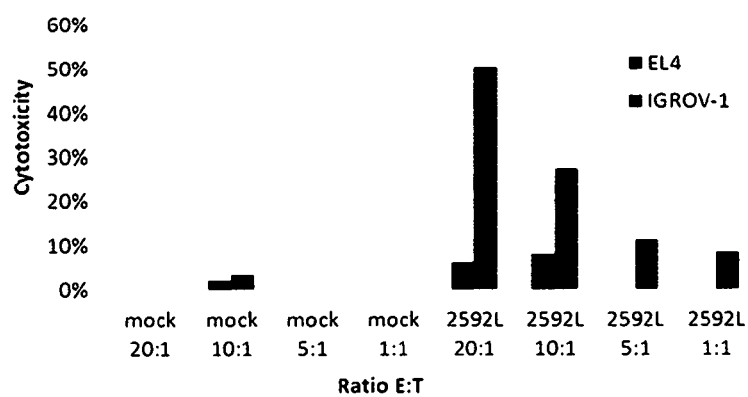
Figure 13C:
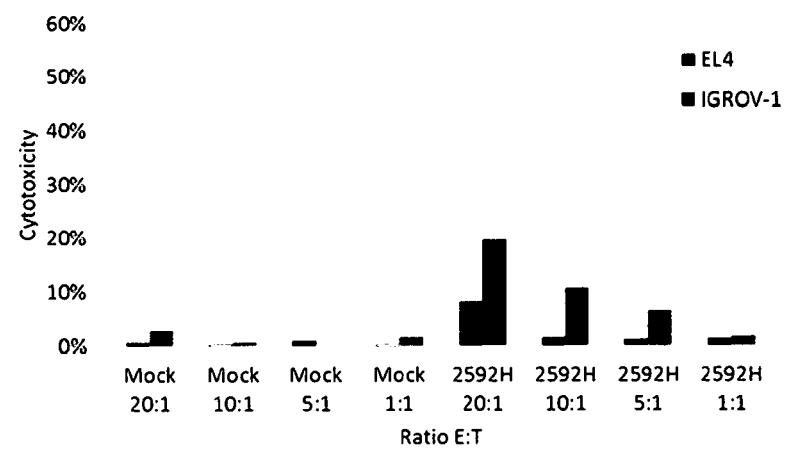

FIG. 13A-13C contain in vitro cytotoxicity data for TIM-1 CARs, as indicated via detection of lactate dehydrogenase in the media. In each grouping, the left bar reports cytotoxicity against EL4 cells and the right bar reports cytotoxicity against IGROV-1 cells. In FIG. 13A, cytotoxicity is reported for control-vector-transduced cells, 272H (272H-CD28) CAR T-cells, and 272HtCD19 (272H-CD28+tCD19) CAR T-cells at various ratios with cancer cells. In FIG. 13B, cytotoxicity is reported for mock-transduced cells and 2592L CAR T-cells. In FIG. 13C, cytotoxicity is reported for mock-transduced cells and 2592H (2592H-CD28) CAR T-cells.

Figure 14:
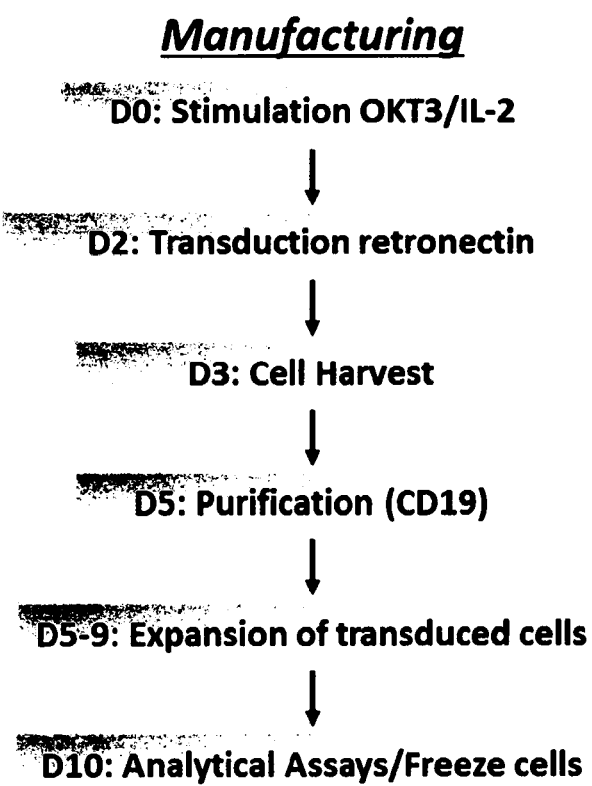

FIG. 14 contains a flow chart illustrating a potential method for manufacturing isolated CAR-expressing cells for in vivo assays.

FIG. 15A-15B contain a growth chart (FIG. 15A) and a cell viability assessment (FIG. 15B) for cells manufactured as in FIG. 14 for mock-transduced cells, and for cells transduced with the 2592HtCD19 (2592H-CD28+tCD19), 2592LtCD19, and the 272HtCD19 (272H-CD28+tCD19) constructs.

FIG. 16 contains a table indicating three antibody cocktails for flow cytometric characterization of transduced cells.

FIG. 17 contains the tabulated results of a flow cytometry analysis of transduced cells, manufactured as in FIG. 14, detected via the Ab1 configuration of FIG. 16.

Figure 18:
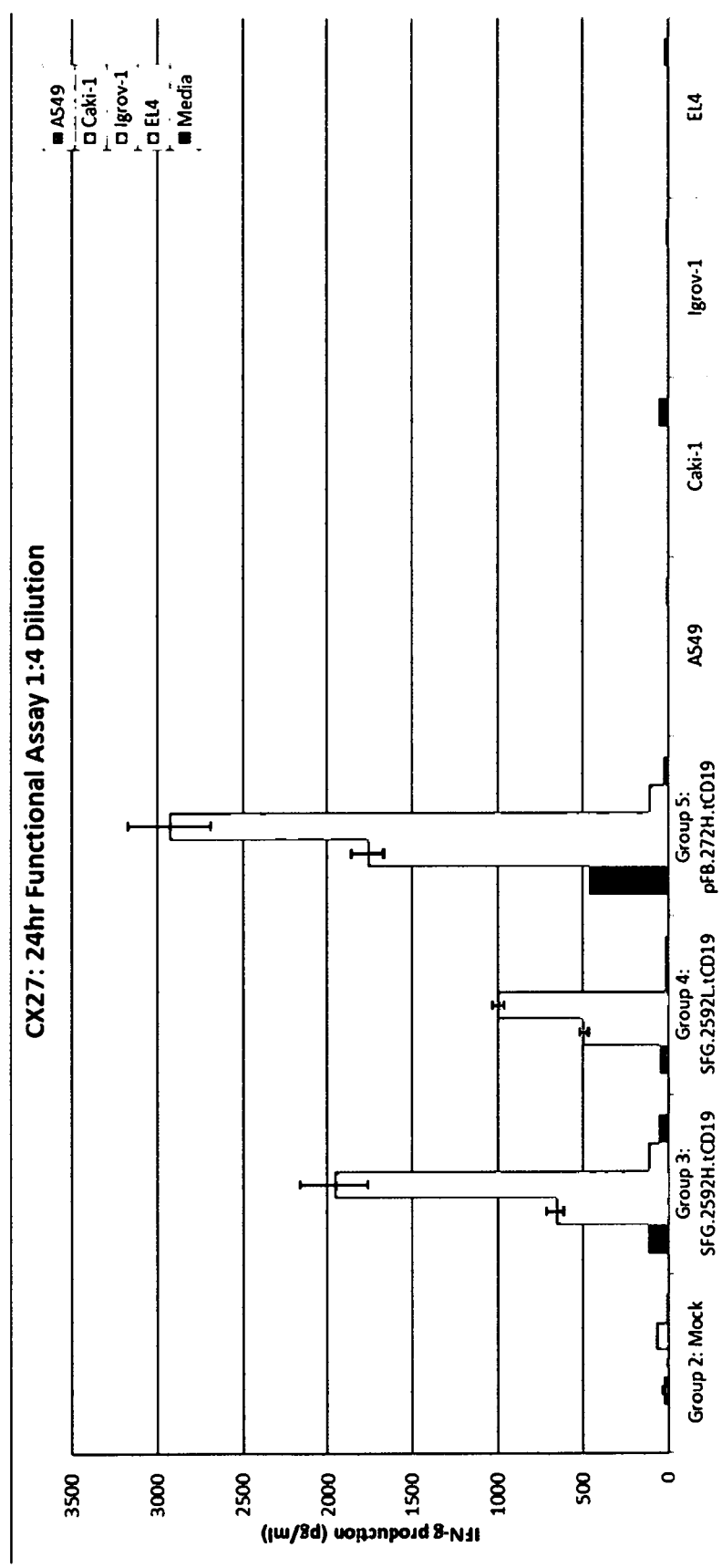

FIG. 18 contains the results of a 24 hr functional assay measuring the production of IFN-γ for a 1:1 ratio of mock-transduced cells, 2592HtCD19 (2592H-CD28+tCD19) CAR T-cells, 2592LtCD19 CAR T-cells, and 272HtCD19 (272H-CD28+tCD19) CAR T-cells exposed to A549 cells, Caki-1 cell, IGROV-1 cells, EL4 cells, and media alone. Also included are the cancer cell alone controls. In each case, the cells were diluted 1:4 in buffer for assay purposes.

FIG. 19 contains a schematic representation of treatment groups of mice for an in vivo anti-TIM-1 CAR T efficacy study.

Figure 20A:
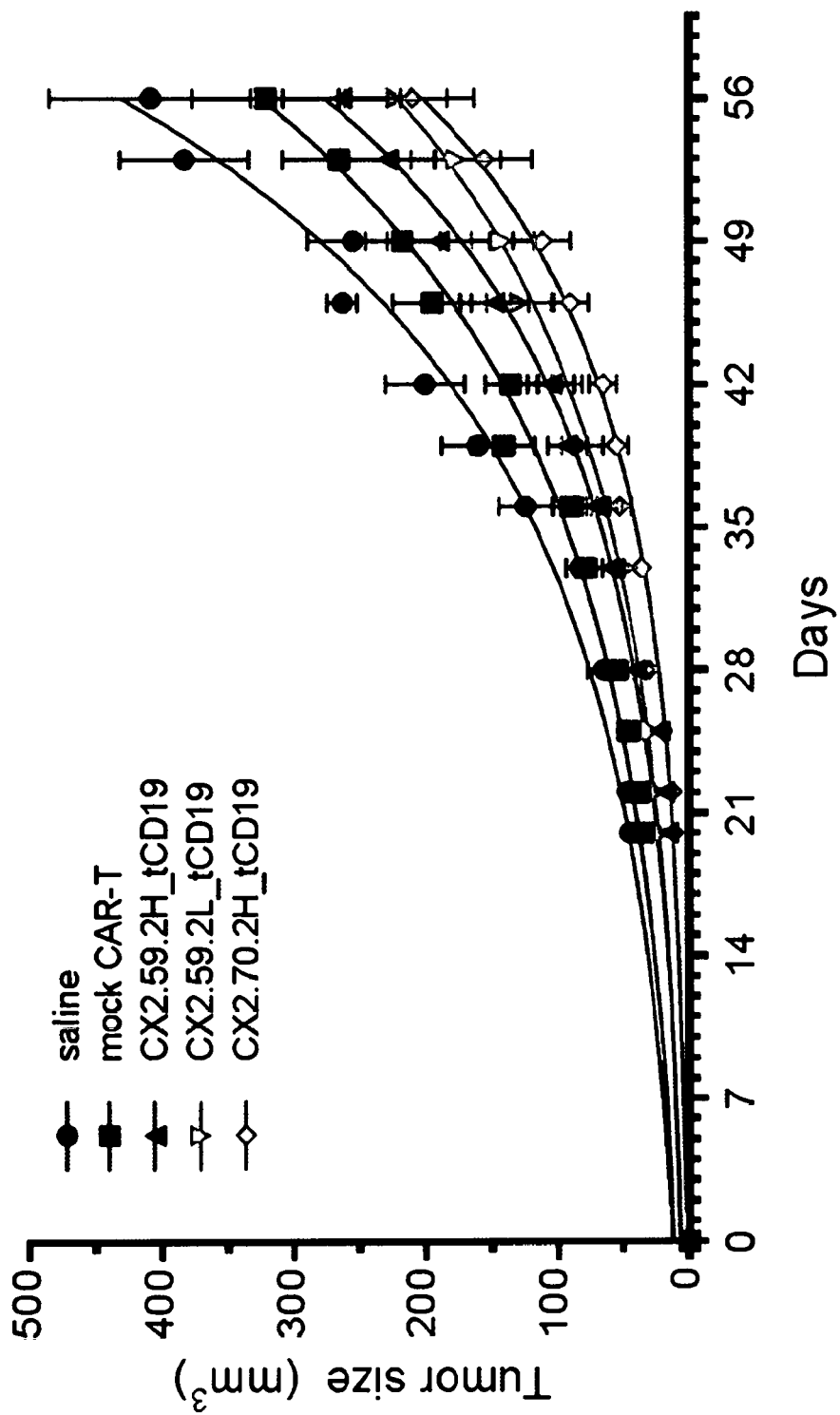
Figure 20B:
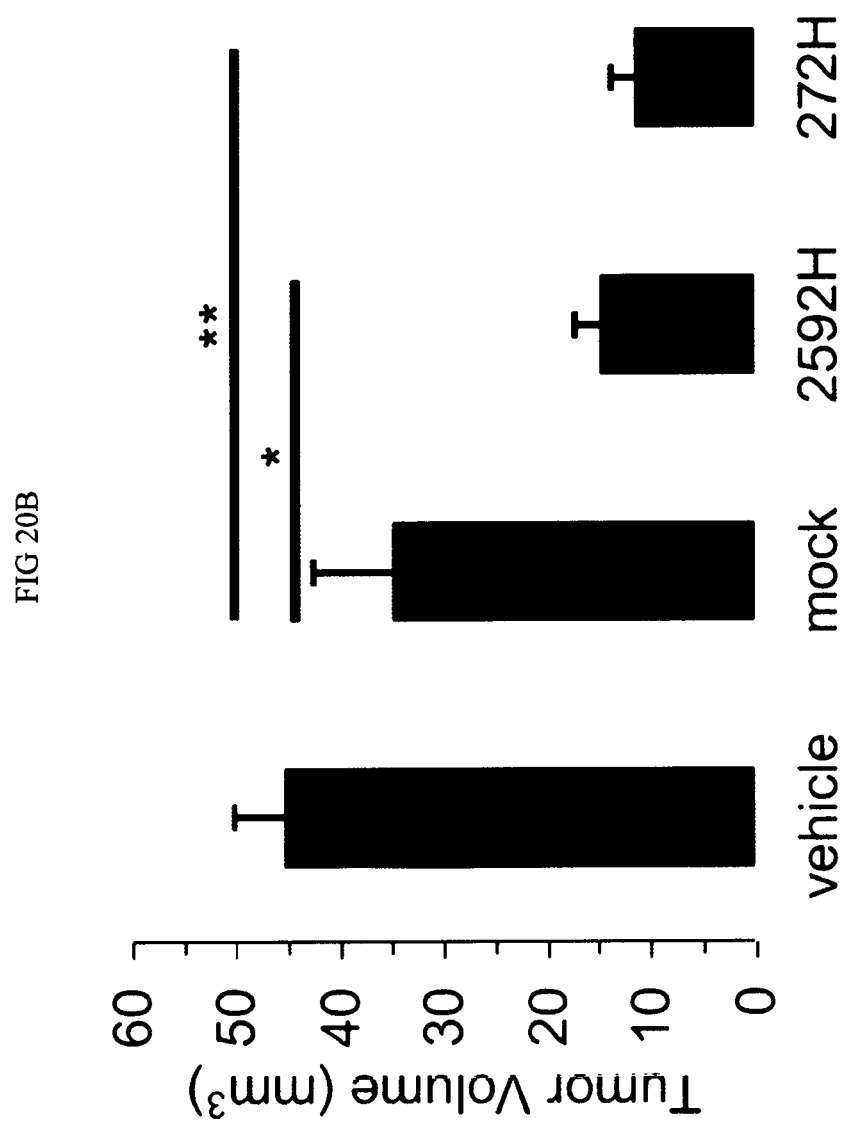

FIG. 20A-20B contain the results of an in vivo anti-TIM-1 CAR T efficacy study in SCID-beige mice. $2.5 \times 10^6$ IGROV-1 cells were delivered alone, or delivered with $7.5 \times 10^6$ mock-transduced or CAR-transduced cells. This mixture was injected into the right flank of SCID-beige mice on Day 0 via subcutaneous delivery for 10 mice per group, except for the control group which had 5 mice. FIG. 20A shows tumor size in mm$^3$, measured twice weekly. The lines (from top to bottom) correspond to no CAR T delivered (saline), mock CAR T, 2592H_tCD19 CAR T, 2592L_tCD19 CAR T, and 272H_tCD19 CAR T. FIG. 20B shows a comparison of tumor sizes measured at day 20. The data corresponds to $2.5 \times 10^6$ IGROV-1 cells mixed with (from left to right) saline only, $7.5 \times 10^6$ mock-transduced cells, $7.5 \times 10^6$ 2592H_tCD19 CAR T-cells, and $7.5 \times 10^6$ 272H_tCD19 CAR T-cells. Tumor size is reported as the average volume±SEM followed by statistical analysis using a Mann-Whitney test. CAR T cell treatments showed a significant inhibition of tumor growth (*, p=0.02; **, p=0.002).

Figure 21:
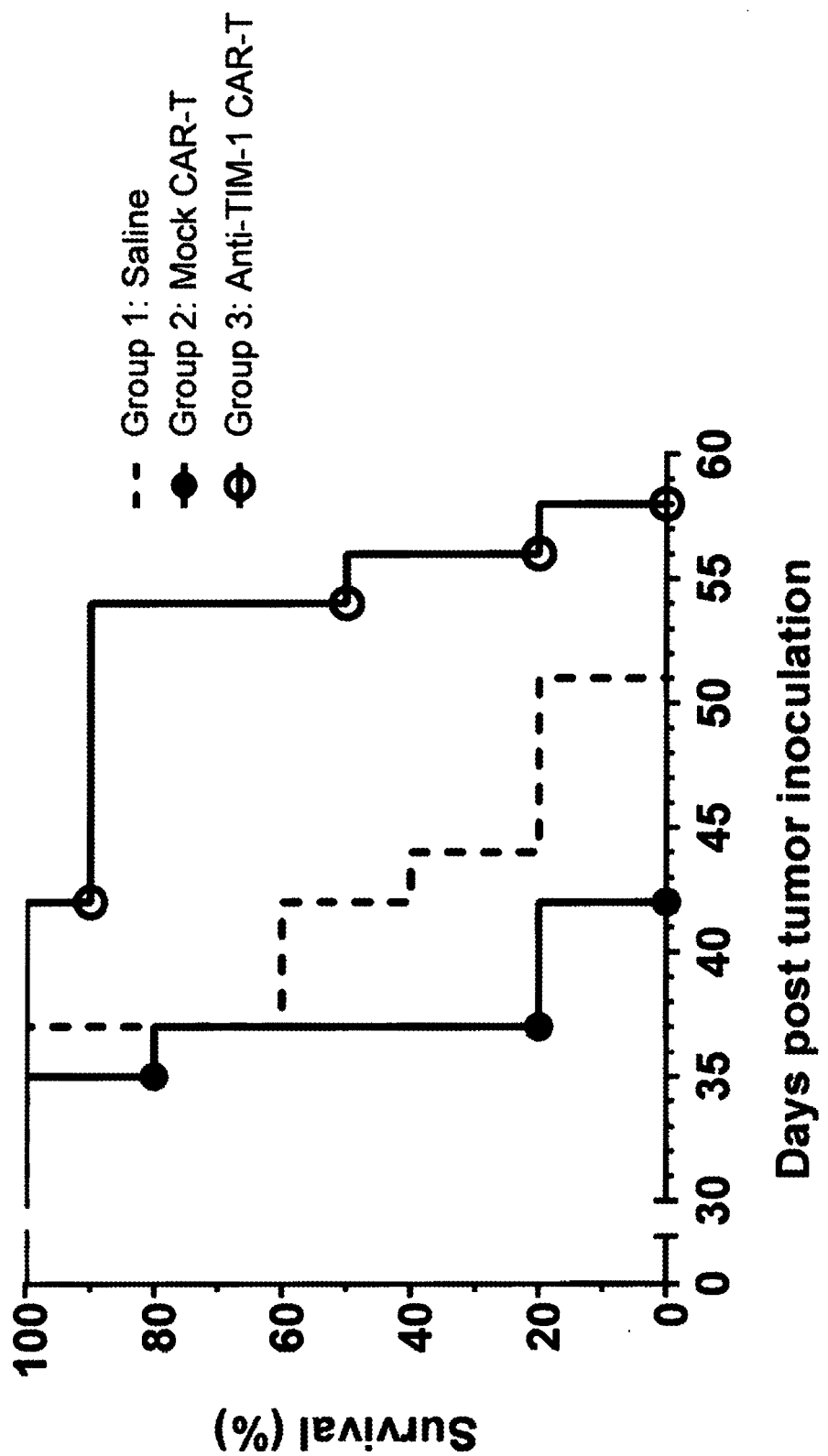

FIG. 21 contains the results of an in vivo survival assay in a murine model of ovarian cancer. SCID-beige mice with established IGROV-1 tumor cells were intraperitoneally injected with saline (Group 1, dotted line), $7.5 \times 10^6$ mock CAR T cells (Group 2, solid line, filled dots), or $7.5 \times 10^6$ anti-TIM-1 CAR T cells (Group 3, solid line, hollow dots). The graph shows the mouse survival results. A Log rank (Mantel-Cox) test shows that mice that received anti-TIM-1 CAR-T cells (Group 3) survived statistically longer than mice that received just saline (Group 1, p=0.0043) or mock CAR-T cells (Group 2, p<0.0001**).

DETAILED DESCRIPTION OF THE INVENTION

An aspect of the invention in general relates to the construction and use of novel TIM-1 binding chimeric antigen receptors (CARs). In particular, the CARs of the present invention comprise an antigen-binding domain that binds to TIM-1, a transmembrane domain, and one or more intracellular signaling domains. The invention also provides polynucleotides encoding these CARs, vectors comprising polynucleotides encoding these CARs, compositions comprising cells expressing these CARs, and methods of making and using these CARs and CAR-expressing cells. The invention also provides methods for treating a condition associated with malignant TIM-1 expression in a subject, such as cancer. These CARs, and particularly isolated cells comprising nucleic acid sequences encoding these CARs, may be used to treat diseases, disorders, or conditions associated with the undesired proliferation of cells expressing TIM-1. In particular embodiments, these cells may be used to treat a cancer.

Car Target: TIM-1

The CAR of the present invention comprises an antigen-binding domain which binds to T-cell immunoglobulin and mucin domain 1 protein (TIM-1), also known as HAVCR1, HAVCR, HAVCR-1, KIM-1, KIM1, TIM, TIM1, TIMD-1, TIMD1, CD365, and hepatitis A virus cellular receptor 1. In general, TIM-1 belongs to the group of type 1 cell-surface glycoproteins, the structure of which include an N-terminal immunoglobulin (Ig)-like domain, a mucin domain with distinct length, a single transmembrane domain, and a C-terminal short cytoplasmic tail. In humans, TIM-1 is encoded by the HAVCR1 gene on chromosome 5, with gene location 5q33.3 (NCBI). Human TIM-1 has an amino acid sequence provided as GenBank Acc. No. AAC39862.1, or the equivalent residues from a non-human species, e.g., mouse, rodent, monkey, ape and the like. In one aspect, TIM-1 is the sequence provided as SEQ ID NO: 315 or the equivalent residues from a non-human species, e.g., mouse, rodent, monkey, ape and the like.

T-cell immunoglobulin mucin I/kidney injury molecule 1 (TIM-1/KIM1) is a protein with limited surface expression in healthy tissues. In the case of ovarian cancer, >93% of OCCC tumors tested positive for TIM-1 expression while other types of ovarian cancer were TIM-1 negative (Lin et al. Am J Surg Pathol. 2007; 31:371-381). The examples below describe chimeric antigen receptors comprising a TIM-1 binding domain that can be used for the treatment of TIM-1 expressing malignancies. It is anticipated that the paucity of TIM-1 expression in healthy tissues will provide a favorable therapeutic window with limited on target, off target effects. To the best of applicant's knowledge this target has never been used in T cell-based interventions.

The historical one therapy fits all approach to cancer therapy has proven largely unsuccessful. Instead, rationally designed therapies that selectively target and exploit the vulnerabilities of a particular cancer type have elicited unprecedented treatment responses and will continue to be the most successful. We have identified potent anti-TIM-1 antibodies that, when formatted into CAR constructs, recognize TIM-1$^+$ target cells and activate CAR T cells. Additionally, anti-TIM-1 CAR T cells prevent the growth of TIM-1$^+$ ovarian tumor cells when administered in vivo. This development of an efficacious CAR T immunotherapy against OCCC represents a significant advance in the treatment of ovarian cancer. Moreover, it is expected that this approach would also be appropriate for the treatment of other TIM-1$^+$ cancers, including renal cell carcinoma.

The examples herein illustrate the potential of targeting TIM-1 as a target selectively expressed in certain cancers such as ovarian clear cell carcinoma through the use of anti-TIM-1 scFvs derived from human full length antibodies.

Antigen-Binding Domain

The present invention provides a chimeric antigen receptor (CAR) comprising an antigen-binding domain, a transmembrane domain, and one or more intracellular signaling domains. The antigen-binding domain comprises a target-specific binding element that binds to TIM-1.

The antigen-binding domain may be derived from a polypeptide that binds to TIM-1. In some embodiments, the polypeptide may be a receptor or a portion of a receptor that binds TIM-1. In another embodiment, the antigen-binding domain may be derived from ligands that bind to TIM-1, including, but not limited to, HAVC, TIM-4, and TIM-1 itself.

In another embodiment, the antigen-binding domain may be derived from an antibody or antigen-binding fragment thereof that binds to TIM-1. Examples of antibody fragments include, but are not limited to, fragment antigen-binding (Fab) fragments, F(ab')$_2$ fragments, Fab' fragments, Fv fragments, recombinant IgG (rIgG) fragments, single chain antibody fragments, single chain variable fragments (scFv), single domain antibodies (e.g., sdAb, sdFv, nanobody) fragments, diabodies, and multi-specific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that may not be produced by enzyme digestion of a naturally-occurring intact antibody. In some aspects, the antibody fragments are scFvs.

In some aspects, the antigen-binding domain may be derived from an antibody or antigen-binding fragment thereof that has one or more specified functional features, such as binding properties, including binding to particular epitopes, such as epitopes that are similar to or overlap with those of other antibodies, the ability to compete for binding with other antibodies, and/or particular binding affinities. In a preferred embodiment, the antibody or antigen-binding fragment thereof binds to TIM-1. In certain aspects, they bind to human TIM-1, such as the human TIM-1 set forth in SEQ ID NO: 315. In another aspect, the antibody or antigen-binding fragment thereof competes for binding to TIM-1 with Ab 1.29, Ab 2.70.2, or Ab 2.59.2. In yet another aspect, the antibody or antigen-binding fragment thereof binds to the same epitope bin as Ab 1.29 and Ab 2.70.2 or Ab 2.59.2 (See U.S. Pat. No. 8,067,544 B2).

In some embodiments, the antigen-binding domain binds to an epitope containing one or more amino acids within (or is entirely within) an extracellular domain of TIM-1 and/or within (or is entirely within) a membrane-proximal region of the extracellular portion of TIM-1. In some embodiments, the antibody binds to an epitope containing one or more amino acids within, or is entirely within, the mucin domain of TIM-1, the IgV-like domain of TIM-1, and/or the membrane-proximal-most 100, 90, 80, 75, 70, 65, 60, 55, 50, 45, 44, 43, 43, 41, or 40 amino acid portion of the extracellular portion of TIM-1. In some embodiments, such a portion or domain is required for binding of the antigen-binding domain to TIM-1. In some embodiments, the epitope contains (or further contains) one or more amino acids that is within, or is entirely within, the mucin domain of TIM-1. In some embodiments, such a portion or domain is required for binding of the antigen-binding domain to TIM-1. In some embodiments, the antigen-binding domain specifically binds to a peptide comprising or consisting of or consisting essentially of the sequence of such a portion, and not containing the entire sequence of full-length TIM-1. For example, the antigen-binding domain may bind in a TCR-like manner, in which it binds to a peptide derived from TIM-1 in the MHC groove without reactivity against MHC.

In some embodiments, the epitope contains one or more amino acids within, is within, or includes a portion of TIM-1 corresponding to residues 192-197 of the human TIM-1 sequence set forth in SEQ ID NO: 315, such as a portion having the sequence set forth in SEQ ID NO: 97. In some embodiments, the epitope may include one or more neighboring residues. In a particular aspect, the epitope may comprise the amino acid sequence PMPLPRQNHEPVAT. In some embodiments, the antigen-binding domain may comprise sequences of anti-TIM-1 antibodies known to bind to such epitopes. In one aspect, the CAR of the invention may comprise an antigen-binding domain comprising sequences of anti-TIM-1 antibodies as disclosed in U.S. Pat. No. 8,067,544, the sequences of which are incorporated herein by reference.

In some embodiments, the epitope includes an amino acid (such as a histidine) at a position of TIM-1 corresponding to the histidine at position 64 of the human TIM-1 sequence set forth in SEQ ID NO: 315; in some embodiments, such amino acid is important for binding of the antigen-binding domain to TIM-1. In some embodiments, the epitope includes an amino acid (such as a glutamate) at a position of TIM-1 corresponding to the glutamate at position 67 of the human TIM-1 sequence set forth in SEQ ID NO: 315; in some embodiments, such amino acid is important for binding of the antigen-binding domain to TIM-1.

In some embodiments, the epitope is the same as, similar to, overlapping with, or contains one or more of the same amino acids as an epitope that is specifically bound to by a reference antibody, such as Ab 1.29, Ab 2.70.2, or Ab 2.59.2. In some embodiments, the same one or more amino acids is important for the binding of the provided antibody and the reference antibody.

In some embodiments, the extent of binding of an anti-TIM-1 antigen-binding domain to an unrelated, non-TIM-1 protein is less than about 40% of the binding of the antigen-binding domain to human TIM-1. In some embodiments, among provided antigen-binding domains are antigen-binding domains in which binding to a non-human TIM-1 or other non-TIM-1 protein is less than or about 30%, less than or about 20% or less than or about 10% of the binding of the antibody to human TIM-1.

In some embodiments, the antigen-binding domain competes for binding with, and/or binds to the same or an overlapping epitope of TIM-1 as Ab 1.29, Ab 2.70.2, or Ab 2.59.2 or an antigen-binding fragment thereof.

In some embodiments, the antigen-binding domain is derived from an antibody or antigen-binding fragment thereof with heavy and light chain CDRs that are distinct from the CDRs present in antibodies such as Ab 1.29, Ab 2.70.2, and Ab 2.59.2. For example, among the provided antibodies and antigen-binding fragments thereof are those that compete for binding with and/or bind to the same or overlapping epitopes of TIM-1 as those bound by an antibody, but nonetheless contain distinct CDRs, e.g., distinct heavy and/or light chain CDR1, CDR2, and CDR3. In some embodiments, the provided antibody contains heavy and light chain CDRs that are distinct from the CDRs present in the antibody designated Ab 1.29, such as present in the VH region set forth in SEQ ID NO: 202 and/or the VL region set forth in SEQ ID NO: 203. In some embodiments, the provided antibody contains heavy and light chain CDRs that are distinct from the CDRs present in the antibody designated Ab 2.70.2, such as present in the VH region set forth in SEQ ID NO:204 and/or the VL region set forth in SEQ ID NO:205. In some embodiments, the provided antibody contains heavy and light chain CDRs that are distinct from the CDRs present in the antibody designated Ab 2.59.2, such as present in the VH region set forth in SEQ ID NO:206 and/or the VL region set forth in SEQ ID NO:207.

In some embodiments, the antigen-binding domain, the CARs comprising such, and the cells comprising such CARs display a binding preference for TIM-1-expressing cells as compared to TIM-1-negative cells, such as particular cells known in the art and/or described herein. In some embodiments, the binding preference is observed where a significantly greater degree of binding is measured to the TIM-1-expressing, as compared to the non-expressing, cells. In some cases, the total degree of observed binding to TIM-1 or to the TIM-1-expressing cells is approximately the same, at least as great, or greater than that observed for non-TIM-1 specific domains, CARs, or cells. In any of the provided embodiments, comparison of binding properties, such as affinities or competition, may be via measurement by the same or similar assay.

In some embodiments, the antigen-binding domain comprises an scFv comprising the CDR sequences of a TIM-1 binding antibody. CDRs may be determined using conventional methods, The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), MacCallum et al., J. Mol. Biol. 262:732-745 (1996), "Antibody-antigen interactions: Contact analysis and binding site topography," J. Mol. Biol. 262, 732-745." ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Pluckthun A, "Yet another numbering scheme for immunoglobulin variable domains: an automatic modeling and analysis tool," J Mol Biol, 2001 Jun. 8; 309(3):657-70, ("Aho" numbering scheme).

In an embodiment, the sequence comprising the antigen-binding domain further comprises a leader sequence or signal sequence. In embodiments where the antigen-binding domain comprises an scFv, the leader sequence may be positioned at the amino terminus of the scFv. In some embodiments, when the heavy chain variable region is N-terminal, the leader sequence may be positioned at the amino terminus of the heavy chain variable region. In some embodiments, when the light chain variable region is N-terminal, the leader sequence may be positioned at the amino terminus of the light chain variable region. The leader sequence may comprise any suitable leader sequence. In embodiments of the invention, the leader sequence may comprise the nucleic acid sequence set forth in SEQ ID NO: 280. In some embodiments, the leader sequence may comprise a nucleic acid sequence encoding the amino acid sequence set forth in SEQ ID NO: 230. In some embodiments, the leader sequence may comprise the amino acid sequence set forth in SEQ ID NO: 230. In the mature form of the isolated cells of the invention, the leader sequence may not be present.

In a preferred embodiment, the antigen-binding domain comprises an scFv comprising the CDR sequences of Ab 1.29, 2.70.2, or 2.59.2.

Preferably, the antigen-binding domain in the CAR of the invention is an anti-TIM-1 scFv, wherein the nucleic acid sequence of the anti-TIM-1 scFv comprises a sequence set forth in SEQ ID NO: 258, 259, 260, 261, 262, or 263. In one embodiment, the anti-TIM-1 scFV comprises a nucleic acid sequence that encodes the amino acid sequence of SEQ ID NO: 208, 209, 210, 211, 212, or 213. In another embodiment, the anti-TIM-1 scFV portion of the CAR of the invention comprises the amino acid sequence set forth in SEQ ID NO: 208, 209, 210, 211, 212, or 213.

In particular, in a preferred embodiment, the antigen-binding domain in the CAR of the invention is derived from the antibody, or antigen-binding fragment thereof, of Ab 2.59.2, Ab 2.70.2, or Ab 1.29. Ab 2.59.2 comprises a VL chain of SEQ ID NO: 207 (encoded by SEQ ID NO: 257) with light chain CDRs of SEQ ID NO: 248, 249, and 250 (encoded by SEQ ID NO: 298, 299, and 300) and a VH chain of SEQ ID NO: 206 (encoded by SEQ ID NO: 256) with heavy chain CDRs of SEQ ID NO: 245, 246, and 247 (encoded by SEQ ID NO: 295, 296, and 297). Ab 2.70.2 comprises a VL chain of SEQ ID NO: 205 (encoded by SEQ ID NO: 255), with light chain CDRs of SEQ ID NO: 242, 243, and 244 (encoded by SEQ ID NO: 292, 293, and 294), and a VH chain of SEQ ID NO: 204 (encoded by SEQ ID NO: 254), with heavy chain CDRs of SEQ ID NO: 239, 240, and 241 (encoded by SEQ ID NO: 289, 290, and 291). Ab 1.29 comprises a VL chain of SEQ ID NO: 203 (encoded by SEQ ID NO: 253), with light chain CDRs of SEQ ID NO: 236, 237, and 238 (encoded by SEQ ID NO: 286, 287, and 288) and a VH chain of SEQ ID NO: 202 (encoded by SEQ ID NO: 252), with heavy chain CDRs of SEQ ID NO: 233, 234, and 235 (encoded by SEQ ID NO: 283, 284, and 285).

Hinge

In some embodiments, the CAR comprises a linker, spacer, or hinge sequence between the antigen-binding domain and the transmembrane domain. One of ordinary skill in the art will appreciate that a hinge sequence is a short sequence of amino acids that facilitates flexibility (see, e.g., Woof et al., Nat. Rev. Immunol., 4(2): 89-99 (2004)). The hinge sequence can be any suitable sequence derived or obtained from any suitable molecule. In some embodiments, the length of the hinge sequence may be optimized based on the distance between the CAR and the TIM-1 binding epitope, e.g., longer hinges may be optimal for membrane proximal TIM-1 epitopes.

In some embodiments, the CAR, such as the antigen-binding portion thereof, further includes a hinge, linker or spacer. The hinge may be derived from or include at least a portion of an immunoglobulin Fc region, for example, an IgG1 Fc region, an IgG2 Fc region, an IgG3 Fc region, an IgG4 Fc region, an IgE Fc region, an IgM Fc region, or an IgA Fc region. In certain embodiments, the spacer domain includes at least a portion of an IgG1, an IgG2, an IgG3, an IgG4, an IgE, an IgM, or an IgA immunoglobulin Fc region that falls within its CH2 and CH3 domains. In some embodiments, the spacer domain may also include at least a portion of a corresponding immunoglobulin hinge region. In some embodiments, the hinge is derived from or includes at least a portion of a modified immunoglobulin Fc region, for example, a modified IgG1 Fc region, a modified IgG2 Fc region, a modified IgG3 Fc region, a modified IgG4 Fc region, a modified IgE Fc region, a modified IgM Fc region, or a modified IgA Fc region. The modified immunoglobulin Fc region may have one or more mutations (e.g., point mutations, insertions, deletions, duplications) resulting in one or more amino acid substitutions, modifications, or deletions that cause impaired binding of the spacer domain to an Fc receptor (FcR). In some aspects, the modified immunoglobulin Fc region may be designed with one or more mutations which result in one or more amino acid substitutions, modifications, or deletions that cause impaired binding of the spacer domain to one or more FcR including, but not limited to, FcγRI, FcγR2A, FcγR2B1, FcγR2B2, FcγR3A, FcγR3B, FcεRI, FcεR2, FcαRI, Fcα/μR, or FcRn.

In some aspects, a portion of the immunoglobulin constant region serves as a spacer region between the antigen-binding domain, e.g., scFv, and transmembrane domain. The spacer can be of a length that provides for increased responsiveness of the cell following antigen-binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include a CD28 hinge, IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153, international patent application publication number WO2014031687, U.S. Pat. No. 8,822,647 or published app. No. US2014/0271635.

In some embodiments, the hinge sequence is derived from the human CD8-alpha molecule or a CD28 molecule. In a preferred embodiment, the hinge sequence is derived from CD28. In one embodiment, the CD28 hinge sequence comprises the nucleic acid sequence encoding CD28H (SEQ ID NO: 264). In one embodiment, the hinge has the amino acid sequence of CD28H (SEQ ID NO: 214). In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 214.

Transmembrane Domain

With respect to the transmembrane domain, the CAR can be designed to comprise a transmembrane domain that is fused to the antigen-binding domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Typically, the transmembrane domain denotes a single transmembrane alpha helix of a transmembrane protein, also known as an integral protein. Transmembrane regions of particular use in this invention may be derived from (i.e. comprise at least the transmembrane region(s) of) CD28, CD3 epsilon, CD4, CD5, CD8, CD9, CD16, CD22, CD33, CD37, CD45, CD64, CD80, CD86, CD134, CD137, CD154, TCR alpha, TCR beta, or CD3 zeta and/or transmembrane regions containing functional variants thereof such as those retaining a substantial portion of the structural, e.g., transmembrane, properties thereof.

Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. A transmembrane domain of the invention is thermodynamically stable in a membrane. It may be a single alpha helix, a transmembrane beta barrel, a beta-helix of gramicidin A, or any other structure. Transmembrane helices are usually about 20 amino acids in length.

Preferably, the transmembrane domain in the CAR of the invention is the CD28 transmembrane domain. In one embodiment, the CD28 transmembrane domain comprises the nucleic acid sequence of CD28TM (SEQ ID NO: 265). In one embodiment, the CD28 transmembrane domain comprises the nucleic acid sequence that encodes the amino acid sequence of CD28TM (SEQ ID NO: 215). In one embodiment, the CD28 transmembrane domain comprises the amino acid sequence of CD28TM (SEQ ID NO: 215).

Optionally, a short oligo- or polypeptide linker, preferably between 2 and 10 amino acids in length may form the linkage between the transmembrane domain and the intracellular signaling domain(s) of the CAR. A glycine-serine doublet may provide a suitable linker.

Intracellular Signaling Domain

The intracellular signaling domain or otherwise the cytoplasmic domain of the CAR of the invention triggers or elicits activation of at least one of the normal effector functions of the immune cell in which the CAR has been placed. The term "effector function" refers to a specialized function of a cell. Effector function of a T cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Signals generated through one intracellular signaling domain alone may be insufficient for full activation of an immune cell, and a secondary or co-stimulatory signal may also be required. For example, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences). Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM-containing primary cytoplasmic signaling sequences that are of particular use in the invention include those derived from an intracellular signaling domain of a lymphocyte receptor chain, a TCR/CD3 complex protein, an Fc receptor subunit, an IL-2 receptor subunit, CD3 ζ, FcR gamma, FcR beta, CD3 gamma, CD3 delta, CD3 epsilon, CD5, CD22, CD79a, CD79b, CD66d, CD278 (ICOS), FcεRI, DAP10, and DAP12. It is particularly preferred that the intracellular signaling domain in the CAR of the invention comprises a cytoplasmic signaling sequence derived from CD3.

In one embodiment, the CD3ζ intracellular signaling domain comprises the nucleic acid sequence of CD3 CYP (SEQ ID NO: 269). In one embodiment, the CD3ζ intracellular signaling domain comprises the nucleic acid sequence that encodes the amino acid sequence of CD3ζCYP (SEQ ID NO: 219). In one embodiment, the CD3ζ intracellular signaling domain comprises the amino acid sequence of CD3ζCYP (SEQ ID NO: 219).

In a preferred embodiment, the cytoplasmic domain of the CAR can be designed to comprise the CD3-ζ (signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen.

Various co-stimulatory domains have been reported to confer differing properties. For example, the 4-1BB co-stimulatory domain showed enhanced persistence in in vivo xenograph models (Milone et al. Mol Ther 2009; 17:1453-1464; Song et al. Cancer Res 2011; 71:4617-4627) whereas CARs that associate with DAP10 are associated with a decreased persistence in vivo (Barber et al. Gene Ther 2011; 18:509-516). Additionally, these different co-stimulatory domains produce different cytokine profiles which, in turn, may produce effects on target cell-mediated cytotoxicity and the tumor microenvironment. Indeed, DAP10 signaling in NK cells has been associated with an increase in Th1 and inhibition of Th2 type cytokine production in CD8$^+$ T cells (Barber et al. Blood 2011; 117:6571-6581).

Examples of co-stimulatory molecules include an MHC class I molecule, TNF receptor proteins, immunoglobulin-like proteins, cytokine receptors, integrins, signaling lymphocytic activation molecules (SLAM proteins), activating NK cell receptors, a Toll ligand receptor, B7-H3, BAFFR, BTLA, BLAME (SLAMF8), CD2, CD4, CD5, CD7, CD8alpha, CD8beta, CD11a, LFA-1 (CD11a/CD18), CD11b, CD11c, CD11d, CD18, CD19, CD19a, CD27, CD28, CD29, CD30, CD40, CD49a, CD49D, CD49f, CD69, CD84, CD96 (Tactile), CD100 (SEMA4D), CD103, CRTAM, OX40 (CD134), 4-1BB (CD137), SLAM (SLAMF1, CD150, IPO-3), CD160 (BY55), SELPLG (CD162), DNAM1 (CD226), Ly9 (CD229), SLAMF4 (CD244, 2B4), ICOS (CD278), CEACAM1, CDS, CRTAM, DAP10, GADS, GITR, HVEM (LIGHTR), IA4, ICAM-1, IL2R beta, IL2R gamma, IL7R alpha, ITGA4, ITGA6, ITGAD, ITGAE, ITGAL, ITGAM, ITGAX, ITGB1, ITGB2, ITGB7, KIRDS2, LAT, LFA-1, LIGHT, LTBR, NKG2C, NKG2D, NKp30, NKp44, NKp46, NKp80 (KLRF1), PAG/Cbp, PD-1, PSGL1, SLAMF6 (NTB-A, Ly108), SLAMF7, SLP-76, TNFR2, TRANCE/RANKL, VLA1, VLA-6, a ligand that specifically binds with CD83, and the like. Thus, while the invention is exemplified primarily with regions of CD28, DAP10, and/or 4-1BB as the co-stimulatory signaling elements, other costimulatory elements are within the scope of the invention.

The cytoplasmic signaling sequences within the intracellular signaling domain of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular signaling domain is designed to comprise the signaling domain of CD3-ζ and a costimulatory domain derived from CD28. In another embodiment, the intracellular signaling domain is designed to comprise the signaling domain of CD3-ζ and a costimulatory domain derived from DAP10. In yet another embodiment, the intracellular signaling domain is designed to comprise the signaling domain of CD3-ζ and a costimulatory domain derived from 4-1BB.

In one embodiment, the intracellular signaling domain in the CAR of the invention is designed to comprise a costimulatory domain derived from CD28 and the signaling domain of CD3-ζ, wherein the costimulatory domain derived from CD28 comprises the nucleic acid sequence set forth in SEQ ID NO: 267 and the signaling domain of CD3-ζ comprises the nucleic acid sequence set forth in SEQ ID NO: 269.

In one embodiment, the intracellular signaling domain in the CAR of the invention is designed to comprise a costimulatory domain derived from CD28 and the signaling domain of CD3-ζ, wherein the costimulatory domain derived from CD28 comprises the nucleic acid sequence that encodes the amino acid sequence of SEQ ID NO: 217 and the signaling domain of CD3-ζ comprises the nucleic acid sequence that encodes the amino acid sequence of SEQ ID NO: 219.

In one embodiment, the intracellular signaling domain in the CAR of the invention is designed to comprise a costimulatory domain derived from CD28 and the signaling domain of CD3-ζ, wherein the costimulatory domain derived from CD28 comprises the amino acid sequence set forth in SEQ ID NO: 217 and the signaling domain of CD3-ζ comprises the amino acid sequence set forth in SEQ ID NO: 219.

In one embodiment, the intracellular signaling domain in the CAR of the invention is designed to comprise a costimulatory domain derived from DAP10 and the signaling domain of CD3-ζ, wherein the costimulatory domain derived from DAP10 comprises the nucleic acid sequence set forth in SEQ ID NO: 268 and the signaling domain of CD3-ζ comprises the nucleic acid sequence set forth in SEQ ID NO: 269.

In one embodiment, the intracellular signaling domain in the CAR of the invention is designed to comprise a costimulatory domain derived from DAP10 and the signaling domain of CD3-ζ wherein the costimulatory domain derived from DAP10 comprises the nucleic acid sequence that encodes the amino acid sequence of SEQ ID NO: 218 and the signaling domain of CD3-ζ comprises the nucleic acid sequence that encodes the amino acid sequence of SEQ ID NO: 219.

In one embodiment, the intracellular signaling domain in the CAR of the invention is designed to comprise a costimulatory domain derived from DAP10 and the signaling domain of CD3-ζ, wherein the costimulatory domain derived from DAP10 comprises the amino acid sequence set forth in SEQ ID NO: 218 and the signaling domain of CD3-ζ comprises the amino acid sequence set forth in SEQ ID NO: 219.

In one embodiment, the intracellular signaling domain in the CAR of the invention is designed to comprise a costimulatory domain derived from 4-1BB and the signaling domain of CD3-ζ, wherein the costimulatory domain derived from 4-1BB comprises the nucleic acid sequence set forth in SEQ ID NO: 266 and the signaling domain of CD3-ζ comprises the nucleic acid sequence set forth in SEQ ID NO: 269.

In one embodiment, the intracellular signaling domain in the CAR of the invention is designed to comprise a costimulatory domain derived from 4-1BB and the signaling domain of CD3-ζ, wherein the costimulatory domain derived from 4-1 BB comprises the nucleic acid sequence that encodes the amino acid sequence of SEQ ID NO: 216 and the signaling domain of CD3-ζ; comprises the nucleic acid sequence that encodes the amino acid sequence of SEQ ID NO: 219.

In one embodiment, the intracellular signaling domain in the CAR of the invention is designed to comprise a costimulatory domain derived from 4-1BB and the signaling domain of CD3-ζ, wherein the costimulatory domain derived from 4-1BB comprises the amino acid sequence set forth in SEQ ID NO: 216 and the signaling domain of CD3-ζ comprises the amino acid sequence set forth in SEQ ID NO: 219.

Exemplary Anti-TIM-1 CAR Constructs

In one embodiment, the CAR of the invention comprises the nucleic acid sequence of 129H-CD28 (SEQ ID NO: 270). In one embodiment, the CAR of the invention comprises the nucleic acid sequence that encodes the amino acid sequence of SEQ ID NO: 220. In one embodiment, the CAR of the invention comprises the amino acid sequence of SEQ ID NO: 220.

In one embodiment, the CAR of the invention comprises the nucleic acid sequence of 129L-CD28 (SEQ ID NO: 271). In one embodiment, the CAR of the invention comprises the nucleic acid sequence that encodes the amino acid sequence of SEQ ID NO: 221. In one embodiment, the CAR of the invention comprises the amino acid sequence of SEQ ID NO: 221.

In one embodiment, the CAR of the invention comprises the nucleic acid sequence of 272H-BB (SEQ ID NO: 272). In one embodiment, the CAR of the invention comprises the nucleic acid sequence that encodes the amino acid sequence of SEQ ID NO: 222. In one embodiment, the CAR of the invention comprises the amino acid sequence of SEQ ID NO: 222.

In one embodiment, the CAR of the invention comprises the nucleic acid sequence of 272H-CD28 (SEQ ID NO: 273). In one embodiment, the CAR of the invention comprises the nucleic acid sequence that encodes the amino acid sequence of SEQ ID NO: 223. In one embodiment, the CAR of the invention comprises the amino acid sequence of SEQ ID NO: 223.

In one embodiment, the CAR of the invention comprises the nucleic acid sequence of 272H-DAP10 (SEQ ID NO: 274). In one embodiment, the CAR of the invention comprises the nucleic acid sequence that encodes the amino acid sequence of SEQ ID NO: 224. In one embodiment, the CAR of the invention comprises the amino acid sequence of SEQ ID NO: 224.

In one embodiment, the CAR of the invention comprises the nucleic acid sequence of 272L-CD28 (SEQ ID NO: 275). In one embodiment, the CAR of the invention comprises the nucleic acid sequence that encodes the amino acid sequence of SEQ ID NO: 225. In one embodiment, the CAR of the invention comprises the amino acid sequence of SEQ ID NO: 225.

In one embodiment, the CAR of the invention comprises the nucleic acid sequence of 2592H-BB (SEQ ID NO: 276). In one embodiment, the CAR of the invention comprises the nucleic acid sequence that encodes the amino acid sequence of SEQ ID NO: 226. In one embodiment, the CAR of the invention comprises the amino acid sequence of SEQ ID NO: 226.

In one embodiment, the CAR of the invention comprises the nucleic acid sequence of 2592H-CD28 (SEQ ID NO: 277). In one embodiment, the CAR of the invention comprises the nucleic acid sequence that encodes the amino acid sequence of SEQ ID NO: 227. In one embodiment, the CAR of the invention comprises the amino acid sequence of SEQ ID NO: 227.

In one embodiment, the CAR of the invention comprises the nucleic acid sequence of 2592H-DAP10 (SEQ ID NO: 278). In one embodiment, the CAR of the invention comprises the nucleic acid sequence that encodes the amino acid sequence of SEQ ID NO: 228. In one embodiment, the CAR of the invention comprises the amino acid sequence of SEQ ID NO: 228.

In one embodiment, the CAR of the invention comprises the nucleic acid sequence of 2592L-CD28 (SEQ ID NO: 279). In one embodiment, the CAR of the invention comprises the nucleic acid sequence that encodes the amino acid sequence of SEQ ID NO: 229. In one embodiment, the CAR of the invention comprises the amino acid sequence of SEQ ID NO: 229.

In some embodiments, the nucleic acid sequences encoding the foregoing exemplary CARs further comprise a T2A ribosomal skip sequence and a sequence encoding tCD19.

In one embodiment, the CAR of the invention comprises the nucleic acid sequence of 272H-BB_tCD19 (SEQ ID NO: 302). In one embodiment, the CAR of the invention comprises the nucleic acid sequence that encodes the amino acid sequence of SEQ ID NO: 301. In one embodiment, the CAR of the invention comprises the amino acid sequence of SEQ ID NO: 301.

In one embodiment, the CAR of the invention comprises the nucleic acid sequence of 272H-CD28_tCD19 (SEQ ID NO: 304). In one embodiment, the CAR of the invention comprises the nucleic acid sequence that encodes the amino acid sequence of SEQ ID NO: 303. In one embodiment, the CAR of the invention comprises the amino acid sequence of SEQ ID NO: 303.

In one embodiment, the CAR of the invention comprises the nucleic acid sequence of 272H-DAP10_tCD19 (SEQ ID NO: 306). In one embodiment, the CAR of the invention comprises the nucleic acid sequence that encodes the amino acid sequence of SEQ ID NO: 305. In one embodiment, the CAR of the invention comprises the amino acid sequence of SEQ ID NO: 305.

In one embodiment, the CAR of the invention comprises the nucleic acid sequence of 2592H-BB_tCD19 (SEQ ID NO: 308). In one embodiment, the CAR of the invention comprises the nucleic acid sequence that encodes the amino acid sequence of SEQ ID NO: 307. In one embodiment, the CAR of the invention comprises the amino acid sequence of SEQ ID NO: 307.

In one embodiment, the CAR of the invention comprises the nucleic acid sequence of 2592H-CD28_tCD19 (SEQ ID NO: 310). In one embodiment, the CAR of the invention comprises the nucleic acid sequence that encodes the amino acid sequence of SEQ ID NO: 309. In one embodiment, the CAR of the invention comprises the amino acid sequence of SEQ ID NO: 309.

In one embodiment, the CAR of the invention comprises the nucleic acid sequence of 2592H-DAP10 tCD19 (SEQ ID NO: 312). In one embodiment, the CAR of the invention comprises the nucleic acid sequence that encodes the amino acid sequence of SEQ ID NO: 311. In one embodiment, the CAR of the invention comprises the amino acid sequence of SEQ ID NO: 311.

In one embodiment, the CAR of the invention comprises the nucleic acid sequence of 2592L-CD28_tCD19 (SEQ ID NO: 314). In one embodiment, the CAR of the invention comprises the nucleic acid sequence that encodes the amino acid sequence of SEQ ID NO: 313. In one embodiment, the CAR of the invention comprises the amino acid sequence of SEQ ID NO: 313.

Further Modifications

The CARs of the present invention, nucleotide sequences encoding the same, vectors encoding the same, and cells comprising nucleotide sequences encoding said CARs may be further modified, engineered, optimized, or appended in order to provide or select for various features. These features may include, but are not limited to, efficacy, persistence, target specificity, reduced immunogenicity, multi-targeting, enhanced immune response, expansion, growth, reduced off-tumor effect, reduced subject toxicity, improved target cytotoxicity, improved tumor infiltration, detection, selection, targeting, and the like. For example, the cells may be engineered to express another CAR, a suicide mechanism, and may be modified to remove or modify expression of an endogenous receptor or molecule such as a TCR and/or MHC molecule.

In some embodiments, the vector or nucleic acid sequence encoding the CAR further encodes other genes. The vector or nucleic acid sequence may be constructed to allow for the co-expression of multiple genes using a multitude of techniques including co-transfection of two or more plasmids, the use of multiple or bidirectional promoters, or the creation of bicistronic or multicistronic vectors. The construction of multicistronic vectors may include the encoding of IRES elements or 2A peptides, such as T2A, P2A, E2A, or F2A. In a particular embodiment, the nucleic acid sequence or vector encoding the CAR further encodes tCD19 with the use of a T2A ribosomal skip sequence. In one embodiment, the T2A ribosomal skip sequence comprises the nucleic acid sequence of SEQ ID NO: 281. In one embodiment, the T2A ribosomal skip sequence comprises the nucleic acid sequence that encodes the amino acid sequence of SEQ ID NO: 231. In one embodiment, the T2A ribosomal skip sequence comprises the amino acid sequence of SEQ ID NO: 231.

In one embodiment, tCD19 comprises the nucleic acid sequence of SEQ ID NO: 282. In one embodiment, tCD19 comprises the nucleic acid sequence that encodes the amino acid sequence of SEQ ID NO: 232. In one embodiment, tCD19 comprises the amino acid sequence of SEQ ID NO: 232.

The CAR expressing cell may further comprise a disruption to one or more endogenous genes. In some embodiments, the endogenous gene encodes TCRα, TCRβ, CD52, glucocorticoid receptor (GR), deoxycytidine kinase (dCK), or an immune checkpoint protein such as, for example, programmed death-1 (PD-1).

Efficacy in Solid Tumors

The CARs of the present invention and cells expressing these CARs may be further modified to improve efficacy against solid tumors. This increased efficacy may be measured by an increase in tumor cytotoxicity, tumor infiltration, and evasion of or resistance to tumor immunosuppressive mediators. In some embodiments, enhanced anti-tumor efficacy may be characterized by increased TCR signaling, increased cytokine release, enhanced killing of tumor cells, increased T cell infiltration of established tumors, improved tumor trafficking, attenuated tumor-induced hypofunction, and improved migration and chemotaxis.

In one aspect, the CAR expressing cells are further modified to evade or neutralize the activity of immunosuppressive mediators, including, but not limited to prostaglandin E2 (PGE2) and adenosine. In some embodiments, this evasion or neutralization is direct. In other embodiments, this evasion or neutralization is mediated via the inhibition of protein kinase A (PKA) with one or more binding partners, for example ezrin. In a specific embodiment, the CAR-expressing cells further express the peptide "regulatory subunit 1 anchoring disruptor" (RIAD). RIAD is thought to inhibit the association of protein kinase A (PKA) with ezrin, which thus prevents PKA-mediated inhibition of TCR activation (Newick et al. Cancer Res 2016 August; 76 (15 Suppl): Abstract nr B27).

In some embodiments, the CAR expressing cells of the invention may induce a broad antitumor immune response consistent with epitope spreading.

In some embodiments, the CAR expressing cells of the invention further comprise a homing mechanism. For example, the cell may transgenically express one or more stimulatory chemokines or cytokines or receptors thereof. In particular embodiments, the cells are genetically modified to express one or more stimulatory cytokines. In certain embodiments, one or more homing mechanisms are used to render the inventive cells resistant to an inhibitory tumor microenvironment. In some embodiments, the CAR expressing cells are further modified to release inducible cytokines upon CAR activation, e.g., to attract or activate innate immune cells to a targeted tumor (so-called fourth generation CARs or TRUCKS). In some embodiments, CARs may co-express homing molecules, e.g., CCR4 or CCR2b, to increase tumor trafficking.

Controlling CAR Expression

In some instances, it may be advantageous to regulate the activity of the CAR or CAR expressing cells CAR. For example, inducing apoptosis using, e.g., a caspase fused to a dimerization domain (see, e.g., Di et al., N Engl. J. Med. 2011 Nov. 3; 365(18):1673-1683), can be used as a safety switch in the CAR therapy of the instant invention. In another example, CAR-expressing cells can also express an inducible Caspase-9 (iCaspase-9) molecule that, upon administration of a dimerizer drug (e.g., rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CAR-expressing cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CAR-expressing cells. See, e.g., Song et al. Cancer Gene Ther. 2008; 15(10):667-75; Clinical Trial Id. No. NCT02107963; and Di Stasi et al. N. Engl. J. Med. 2011; 365:1673-83.

Alternative strategies for regulating the CAR therapy of the instant invention include utilizing small molecules or antibodies that deactivate or turn off CAR activity, e.g., by deleting CAR-expressing cells, e.g., by inducing antibody dependent cell-mediated cytotoxicity (ADCC). For example, CAR-expressing cells described herein may also express an antigen that is recognized by molecules capable of inducing cell death, e.g., ADCC or compliment-induced cell death. For example, CAR expressing cells described herein may also express a receptor capable of being targeted by an antibody or antibody fragment. Examples of such receptors include EpCAM, VEGFR, integrins (e.g., integrins $\alpha v\beta 3$, $\alpha 4$, $\alpha I3/4\beta 3$, $\alpha 4\beta 7$, $\alpha 5\beta 1$, $\alpha v\beta 3$, $\alpha v$), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/lgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain). For example, CAR-expressing cells described herein may also express a truncated epidermal growth factor receptor (EGFR) which lacks signaling capacity but retains the epitope that is recognized by molecules capable of inducing ADCC, e.g., cetuximab (ERBITUX®), such that administration of cetuximab induces ADCC and subsequent depletion of the CAR-expressing cells (see, e.g., WO2011/056894, and Jonnalagadda et al., Gene Ther. 2013; 20(8)853-860).

In some embodiments, the CAR cell comprises a polynucleotide encoding a suicide polypeptide, such as for example RQR8. See, e.g., WO2013153391A, which is hereby incorporated by reference in its entirety. In CAR cells comprising the polynucleotide, the suicide polypeptide may be expressed at the surface of a CAR cell. The suicide polypeptide may also comprise a signal peptide at the amino terminus. Another strategy includes expressing a highly compact marker/suicide gene that combines target epitopes from both CD32 and CD20 antigens in the CAR-expressing cells described herein, which binds rituximab, resulting in selective depletion of the CAR-expressing cells, e.g., by ADCC (see, e.g., Philip et al., Blood. 2014; 124(8)1277-1287). Other methods for depleting CAR-expressing cells described herein include administration of CAMPATH, a monoclonal anti-CD52 antibody that selectively binds and targets mature lymphocytes, e.g., CAR-expressing cells, for destruction, e.g., by inducing ADCC. In other embodiments, the CAR-expressing cell can be selectively targeted using a CAR ligand, e.g., an anti-idiotypic antibody. In some embodiments, the anti-idiotypic antibody can cause effector cell activity, e.g, ADCC or ADC activities, thereby reducing the number of CAR-expressing cells. In other embodiments, the CAR ligand, e.g., the anti-idiotypic antibody, can be coupled to an agent that induces cell killing, e.g., a toxin, thereby reducing the number of CAR-expressing cells. Alternatively, the CAR molecules themselves can be configured such that the activity can be regulated, e.g., turned on and off as described below.

In some embodiments, a regulatable CAR (RCAR) where the CAR activity can be controlled is desirable to optimize the safety and efficacy of a CAR therapy. In some embodiments, a RCAR comprises a set of polypeptides, typically two in the simplest embodiments, in which the components of a standard CAR described herein, e.g., an antigen-binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen-binding domain to an intracellular signaling domain. Additional description and exemplary configurations of such regulatable CARs are provided herein and in International Publication No. WO 2015/090229, hereby incorporated by reference in its entirety.

In an aspect, an RCAR comprises two polypeptides or members: I) an intracellular signaling member comprising an intracellular signaling domain, e.g., a primary intracellular signaling domain described herein, and a first switch domain; 2) an antigen-binding member comprising an antigen-binding domain, e.g., that specifically binds a tumor antigen described herein, as described herein and a second switch domain. Optionally, the RCAR comprises a transmembrane domain described herein. In an embodiment, a transmembrane domain can be disposed on the intracellular signaling member, on the antigen-binding member, or on both. Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to an intracellular signaling domain can be different, e.g., reversed.

In some embodiments, the CAR expressing immune cell may only transiently express a CAR. For example, the cells of the invention may be transduced with mRNA comprising a nucleic acid sequence encoding an inventive CAR. In this vein, the present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequences ("UTRs"), a 5' cap and/or Internal Ribosome Entry Site (IRES), the nucleic acid to be expressed, and a polyA tail, typically 50-2000 bases in length. RNA so produced can efficiently transfect different kinds of cells. In one embodiment, the template includes sequences for the CAR. In an embodiment, an RNA CAR vector is transduced into a cell by electroporation.

Target Specificity

The CAR expressing cells of the present invention may further comprise one or more additional CARs. These additional CARs may or may not be specific for TIM-1. In some embodiments, the one or more additional CARs may act as inhibitory or activating CARs. In some aspects, the TIM-1-targeting CAR is the stimulatory or activating CAR; in other aspects, it is the costimulatory CAR. In some embodiments, the cells further include inhibitory CARs (iCARs, see Fedorov et al., Sci. Transl. Medicine, 2013 December; 5(215): 215ra172), such as a CAR recognizing an antigen other than TIM-1, whereby an activating signal delivered through the TIM-1-targeting CAR is diminished or inhibited by binding of the inhibitory CAR to its ligand, e.g., to reduce off-target effects.

In some embodiments, the CAR expressing cells of the present invention may further comprise one or more additional CARs that may target one or more antigens selected from the group of: BCMA; BCR-Ab1; BST2; CAIX; CD19; CD20; CD22; CD123; CD171; CD30; CD33; CD38; CD44v6; CD44v7/8; CEA; CLL-1; EGFRvIII; EGP-2; EGP-40; ERBB2 (Her2/neu); EPCAM; fetal acetylcholine receptor, FBP; FLT3; Folate receptor alpha; GD2; GD3; Her3 (ErbB3); Her4 (ErbB4); k-light chain; KDR; MAD-CT-1; MAD-CT-2; MAGE-A1; MARTI; ML-IAP; MYCN; Oncofetal antigen (h5T4); NKG2D ligands PDK1; PDL1; PSCA; PSMA; PRSS21; ROR1; SLAMF7; TAG-72; Tn Ag; TSLPR; B7H3 (CD276); KIT (CD17); IL-13Ra2; Mesothelin; IL-11Ra; VEGFR2; LeY; CD24; PDGFR-beta; SSEA-4; CD20; MUC1; EGFR; NCAM; Prostase; PAP; ELF2M; Ephrin B2; FAP; IGF-1 receptor; CAFX; LMP2; gp100; tyrosinase; EphA2; Fucosyl GM1; sLe; ganglioside GM3; TGS5; HMWMAA; OAcGD2; OR51E2; Folate receptor beta; TEM1/CD248; TEM7R; CLDN6; TSHR; GloboH; GPR20; GPRC5D; CXORF61; CD97; CD179a; ADRB3; ALK; Polysialic acid; PANX3; PLAC1; NY-BR-1; NY-ESO-1; UPK2; TIM-1; HAVCR1; LY6K; TARP; WT1; LAGE-1a; ETV6-AML; SPA17; XAGE1; Tie 2; Fos-related antigen 1; p53; p53 mutant; prostein; surviving; telomerase; PCTA-1; Rat sarcoma Ras mutant; hTERT; sarcoma translocation breakpoints; ERG; NA17; PAX3; Androgen receptor; Cyclin B1; RhoC; TRP-2; CYP1B1; BORIS, SART3; PAX5; OY-TES1; LCK; AKAP-4; SSX2; RAGE-1; RU1; RU2; legumain; HPV E6; HPV E7; intestinal carboxyl esterase; mut hsp70-2; CD79a; CD79b; CD72; LAIR1; CD89; LILRA2; CD300LF; CLEC12A; EMR2; FCRL5; GPC3; IGLL1; and LY75.

In some embodiments, the antigen-binding domain of the inventive CAR is affinity tuned. In particular, the affinity of the anti-TIM-1 CAR antigen-binding domain is adjusted to discriminate cells overexpressing TIM-1, e.g. tumor cells, from normal tissues which express TIM-1 at physiological levels. This may be accomplished, e.g., through the use of a CAR-expressing T cell with target antigen affinities varying over three orders of magnitude (Liu et al. Cancer Res 2015 September; 75(17):3596-607). Additionally, in vivo xenograft models may be used to evaluate the toxicity of affinity tuned anti-TIM-1 CARs on normal human tissue (Johnson et al. Sci Transl Med 2015 February; 7(275):275ra22).

In some embodiments, the antigen-binding domain of the CAR is or is part of an immunoconjugate, in which the antigen-binding domain is conjugated to one or more heterologous molecule(s), such as, but not limited to, a cytotoxic agent, an imaging agent, a detectable moiety a multimerization domain or other heterologous molecule. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins. In some embodiments, the antigen-binding domain is conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

Other

In some embodiments, the CAR expressing cells of the invention may be further genetically modified to express the dominant negative form of the transforming growth factor (TGF) beta receptor (DNR).

In another embodiment, the CAR expressing cell may be specific for another antigen, including a tumor antigen in some cases. In some embodiments, the transformed host cells may be selected for specificity for one or more strong viral antigens or may be transformed to exhibit specificity for these antigens. In specific embodiments, the cells are pp65CMV-specific T cells, CMV-specific T cells, EBV-specific T cells, Varicella Virus-specific T cells, Influenza Virus-specific T cells and/or Adenovirus-specific T cells.

To increase persistence, the cells of the invention may be further modified to overexpress pro-survival signals, reverse anti-survival signals, overexpress Bcl-xL, overexpress hTERT, lack Fas, or express a TGFβ dominant negative receptor. Persistence may also be facilitated by the administration of cytokines, e.g., IL-2, IL-7, and IL-15.

Vectors

The present invention also provides vectors in which a DNA of the present invention is inserted. Vectors derived from retroviruses are suitable tools to achieve long-term gene transfer since they allow for genetic stability and high expression, in addition to having a flexible genome. Furthermore, clinical experience with retroviral vectors provides guidance for optimizing efficacy and safety in their use.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration in eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, gammaretroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, retrovirus vectors are used. In some embodiments, the retroviral vector is pFSG or pFB.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

Various promoter sequences may be used, including, but not limited to the immediate early cytomegalovirus (CMV) promoter, Elongation Growth Factor-1α (EF-1α), simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

In a preferred embodiment, the selectable marker gene comprises a nucleic acid sequence encoding truncated CD19 (tCD19).

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Transduction

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vive is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20 degrees Celsius. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Cells of the Invention

Also provided are cells, cell populations, and compositions containing the cells, e.g., cells comprising a nucleic acid sequence encoding an anti-TIM-1 chimeric antigen receptor. Among the compositions are pharmaceutical compositions and formulations for administration, such as for adoptive cell therapy. Also provided are therapeutic methods for administering the cells and compositions to subjects, e.g., patients.

Cell Types

Thus also provided are cells expressing the anti-TIM-1 CARs. The cells generally are eukaryotic cells, such as mammalian cells, and typically are human cells, more typically primary human cells, e.g., allogeneic or autologous donor cells. The cells for introduction of the CAR may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. In some embodiments, the cells are derived from the blood, bone marrow, lymph, or lymphoid organs, are cells of the immune system, such as cells of the innate or adaptive immune systems, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation.

With reference to the subject to be treated, the cells may be allogeneic and/or autologous. Among the methods included are off-the-shelf methods. In some aspects, such as for off-the-shelf technologies, the cells are pluripotent and/or multipotent, such as stem cells, induced pluripotent stem cells (iPSCs), or T cells that either lack or are engineered to be deficient in T cell receptor function. In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of $CD4^+$ and/or of $CD8^+$ T cells are naïve T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells, Natural Killer T (NKT) cells, cytokine-induced killer (CIK) cells, tumor-infiltrating lymphocytes (TIL), lymphokine-activated killer (LAK) cells, or the like. In some embodiments, the cells are monocytes or granulocytes, e.g., myeloid cells, macrophages, neutrophils, dendritic cells, mast cells, eosinophils, and/or basophils.

In some embodiments, the cells are derived from cell lines, e.g., T cell lines. The cells in some embodiments are obtained from a xenogeneic source, for example, from mouse, rat, non-human primate, and pig.

Cell Acquisition

Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, may be used. In some embodiments, cells can be derived from a healthy donor, from a patient diagnosed with cancer, from a patient diagnosed with an autoimmune or inflammatory disorder or from a patient diagnosed with an infection. In some embodiments, cells can be part of a mixed population of cells which present different phenotypic characteristics.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

Also provided herein are cell lines obtained from a transformed cell according to any of the above-described methods. Also provided herein are modified cells resistant to an immunosuppressive treatment. In some embodiments, an isolated cell according to the invention comprises a polynucleotide encoding a CAR.

Cell Purification

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished by a semi-automated "flow-through" centrifuge (for example, the Cobe 2991 cell processor, Baxter) according to the manufacturer's instructions.

In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In a specific embodiment, the surface maker is tCD19. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

In some embodiments, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques. For example, $CD3^+$ T cells can be expanded using CD3 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naïve, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8 population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or subpopulation, such that both the positive and negative fractions from the CD4-based separation are retained and used in subsequent steps of the methods, optionally following one or more further positive or negative selection steps.

In some aspects, the sample or composition of cells to be separated is incubated with small, magnetizable or magnetically responsive material, such as magnetically responsive particles or microparticles, such as paramagnetic beads (e.g., such as Dynabeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)—coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the methods include density-based cell separation methods, such as the preparation of white blood cells from peripheral blood by lysing the red blood cells and centrifugation through a Percoll or Ficoll gradient.

In any of the aforementioned separation steps, the separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

Cell Preparation and Expansion

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation.

In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The cells of the invention can be activated and expanded, either prior to or after genetic modification of the cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874;

6,797,514; 6,867,041; and U.S. Patent Application Publication No. 20060121005. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

T cells can be expanded in vitro or in vivo. Generally, the T cells of the invention can be expanded, for example, by contact with an agent that stimulates a CD3 TCR complex and a co-stimulatory molecule on the surface of the T cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations may be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. In some embodiments, the T cell populations may be stimulated in vitro by contact with Muromonab-CD3 (OKT3). For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, IL-21, TGFp, and TNF, or any other additives for the growth of cells known to the skilled artisan. In a preferred embodiment, T cells are stimulated in vitro by exposure to OKT3 and IL-2. Other additives for the growth of cells include, but are not limited to, surfactant, Plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37 degrees Celsius) and atmosphere (e.g., air plus 5% $CO_2$). T cells that have been exposed to varied stimulation times may exhibit different characteristics.

In some embodiments, the isolated cells of the invention can be expanded by co-culturing with tissue or cells. The cells can also be expanded in vivo, for example in the subject's blood after administrating the cell into the subject.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80 degrees Celsius at a rate of 1 degree per minute and stored in the vapor phase of a liquid nitrogen storage tank.

Therapeutic Applications

Isolated cells obtained by the methods described above, or cell lines derived from such isolated cells, can be used as a medicament in the treatment of a disease, disorder, or condition in a subject. In some embodiments, such a medicament can be used for treating cancer.

Cell Origin

For purposes of the inventive methods, wherein host cells or populations of cells are administered, the cells can be cells that are xenogeneic, allogeneic or autologous to the subject. Generally, the cells are autologous to the subject.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

Subject

The subject referred to herein may be any living subject. In a preferred embodiment, the subject is a mammal. The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes)

In some embodiments, the subject, to whom the cells, cell populations, or compositions are administered is a primate, such as a human. In some embodiments, the primate is a monkey or an ape. The subject can be male or female and can be any suitable age, including infant, juvenile, adolescent, adult, and geriatric subjects. In some examples, the patient or subject is a validated animal model for disease, adoptive cell therapy, and/or for assessing toxic outcomes such as cytokine release syndrome (CRS).

In some embodiments, the subject has persistent or relapsed disease, e.g., following treatment with another immunotherapy and/or other therapy, including chemotherapy, radiation, and/or hematopoietic stem cell transplantation (HSCT), e.g., allogenic HSCT. In some embodiments, the administration effectively treats the subject despite the subject having become resistant to another therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the methods include administration of CAR expressing cells or a composition containing the cells to a subject, tissue, or cell, such as one having, at risk for, or suspected of having a disease, condition or disorder associated with the expression of TIM-1. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition, such as by lessening tumor burden in a TIM-1-expressing cancer.

Functional Activity

In one embodiment, the present invention includes a type of cellular therapy where isolated cells are genetically modified to express an anti-TIM-1 CAR and the CAR cell is infused into a subject in need thereof. Such administration can promote activation of the cells (e.g., T cell activation) in a TIM-1-targeted manner, such that the cells of the disease or disorder are targeted for destruction. In the case where the cell is a T cell, CAR T cells, unlike antibody therapies, are able to replicate in vivo resulting in long-term persistence that may lead to sustained control of TIM-1 related diseases, disorders, or conditions.

In one embodiment, the isolated cells of the invention can undergo in vivo expansion and can persist for an extended amount of time. In another embodiment, where the isolated cell is a T cell, the isolated T cells of the invention evolve into specific memory T cells that can be reactivated to inhibit any additional TIM-1-expressing cell growth. CAR T cells may differentiate in vive into a central memory-like state upon encounter and subsequent elimination of target cells expressing the surrogate antigen.

Without wishing to be bound by any particular theory, the anti-tumor immunity response elicited by the isolated CAR-modified immune cells may be an active or a passive immune response. In addition, the CAR mediated immune response may be part of an adoptive immunotherapy approach in which CAR-modified immune cells induce an immune response specific to the antigen-binding domain in the CAR.

In certain embodiments, CAR expressing cells are modified in any number of ways, such that their therapeutic or prophylactic efficacy is increased. For example, the CAR may be conjugated either directly or indirectly through a linker to a targeting moiety. The practice of conjugating compounds, e.g., the CAR, to targeting moieties is known in the art. See, for instance, Wadhwa et al., J. Drug Targeting 1995; 3(2): 111-127, and U.S. Pat. No. 5,087,616.

Once the cells are administered to a subject (e.g., a human), the biological activity of the engineered cell populations and/or antibodies in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285 (1): 25-40 (2004). In certain embodiments, the biological activity of the cells also can be measured by assaying expression and/or secretion of certain cytokines, such as GM-CSF, IL-6, RANTES (CCL5), TNF-α, IL-4, IL-10, IL-13, IFN-γ, CD 107a, or IL-2.

In some aspects the biological activity is measured by assessing clinical outcome, such as reduction in tumor burden or load, stabilization of tumor, progression free survival, or overall survival.

Target Cells

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Preferably, the CAR expressing cells of the invention are used to treat a cancer the tumorous cells are positive for surface TIM-1 expression. In particular, the cells of the invention may be used to treat TIM-1 positive ovarian carcinoma, renal cell carcinoma, and lung cancer. In general, TIM-1 positive tumor cells may be identified via known methods. For example, TIM-1 expression on tumor cells may be identified via immunofluorescence or flow cytometry using anti-TIM-1 antibodies. Alternatively, TIM-1 expression may be measured functionally through CAR cytotoxicity against target cells.

Methods of testing a CAR for the ability to recognize target cells and for antigen specificity are known in the art. For instance, Clay et al., J. Immunol., 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, CAR function can be evaluated by measurement of cellular cytotoxicity, as described in Zhao et al., J. Immunol., 174: 4415-4423 (2005).

A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer. With respect to detecting the presence of TIM-1 expressing tumor cells in a host, the sample comprising cells of the host can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the host, e.g., the cells of any organ or tissue, including blood cells or endothelial cells.

Other Targets

The CARs of the present invention, and in particular the CAR-expressing immune cells of the invention, may also be used to treat, prevent, or diagnose any other conditions, disorders, or diseases involving the expression of TIM-1 in healthy or diseased cells. For example, the invention also contemplates a method of treating or preventing immune dysfunction, atopic dermatitis, allergy, rheumatoid arthritis, asthma, systemic lupus erythematosus, hepatitis A virus infection, Ebola virus infection, Dengue virus infection, disease of the trachea, or disease of the cornea and conjunctiva in a subject, the method of which comprises administering cells expressing a CAR according to the invention. For example, as a six amino acid insertion in the mucin domain of TIM-1 is associated with protection from atopic diseases, the invention contemplates the administration of cells expressing a CAR targeting the mucin domain of TIM-1 as a method of treating or preventing atopic diseases.

Modes of Administration

The compositions of the present invention may be administered in a number of ways depending upon whether local or systemic treatment is desired.

In the case of adoptive cell therapy, methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10): 577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In general, administration may be topical, parenteral, or enteral.

The compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, intrasynovial injection or infusions; and kidney dialytic infusion techniques. In a preferred embodiment, parenteral administration of the compositions of the present invention comprises subcutaneous or intraperitoneal administration.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The terms "oral", "enteral", "enterally", "orally", "non-parenteral", "non-parenterally", and the like, refer to administration of a compound or composition to an individual by a route or mode along the alimentary canal. Examples of "oral" routes of administration of a composition include, without limitation, swallowing liquid or solid forms of a composition from the mouth, administration of a composition through a nasojejunal or gastrostomy tube, intraduodenal administration of a composition, and rectal administration, e.g., using suppositories for the lower intestinal tract of the alimentary canal.

Preferably, the formulated composition comprising isolated TIM-1 CAR-expressing cells is suitable for administration via injection.

Pharmaceutical compositions and formulations for topical administration may include transdermal patches, ointments, lotions, creams, gels, drops, suppositories, sprays, liquids, semi-solids, monophasic compositions, multiphasic compositions (e.g., oil-in-water, water-in-oil), foams, microsponges, liposomes, nanoemulsions, aerosol foams, polymers, fullerenes, and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal, or intraventricular administration may include sterile aqueous solutions that may also contain buffers, diluents and other suitable additives such as, but not limited to, penetration enhancers, carder compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, aerosols, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Formulations comprising populations of anti-TIM-1-CAR-expressing cells may include pharmaceutically acceptable excipient(s). Excipients included in the formulations will have different purposes depending, for example, on the CAR construct, the subpopulation of cells used, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents. The formulations comprising populations of anti-TIM-1 CAR-expressing cells will typically have been prepared and cultured in the absence of any non-human components, such as animal serum (e.g., bovine serum albumin).

The formulation or composition may also contain more than one active ingredient useful for the particular indication, disease, or condition being treated with the binding molecules or cells, preferably those with activities complementary to the binding molecule or cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the pharmaceutically active agents or drugs may comprise immune checkpoint inhibitors, e.g., drugs that target PD-1, PD-L1, PD-L2, LAG3, CTLA4, KIR, CD244, B7-H3, B7-H4, BTLA, HVEM, GAL9, TIM3, and/or A2aR.

Examples of these inhibitors include, but are not limited to, pidilizumab, nivolumab, pembrolizumab, atezolizumab, MDX-1105, BMS-936559, MED14736, MPDL3280A, MSB0010718C, tremelimumab, and ipilimumab, which may be administered alone or in combination with other agents, e.g., GM-CSF.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

Dosing

The pharmaceutical composition in some embodiments contains the anti-TIM-1 CAR cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, in the context of genetically engineered cells expressing the CARs, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges, and/or such a number of cells per kilogram of body weight of the subject. For example, in some embodiments the administration of the cells or population of cells can comprise administration of about $10^3$ to about $10^9$ cells per kg body weight including all integer values of cell numbers within those ranges.

The cells or population of cells can be administrated in one or more doses. In some embodiments, said effective amount of cells can be administrated as a single dose. In some embodiments, said effective amount of cells can be administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired. In some embodiments, an effective amount of cells or composition comprising those cells are administrated parenterally. In some embodiments, administration can be an intravenous administration. In some embodiments, administration can be directly done by injection within a tumor.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed or IFN-γ is secreted by T cells expressing the inventive CAR, polypeptide, or protein upon administration of a given dose of such T cells to a mammal, among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells or antibodies in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells or antibodies are administered prior to the one or more additional therapeutic agents. In some embodiments, the cells or antibodies are administered after to the one or more additional therapeutic agents.

In embodiments, a lymphodepleting chemotherapy is administered to the subject prior to, concurrently with, or after administration (e.g., infusion) of CAR cells. In an example, the lymphodepleting chemotherapy is administered to the subject prior to administration of the cells. For example, the lymphodepleting chemotherapy ends 1-4 days (e.g., 1, 2, 3, or 4 days) prior to CAR cell infusion. In embodiments, multiple doses of CAR cells are administered, e.g., as described herein. In embodiments, a lymphodepleting chemotherapy is administered to the subject prior to, concurrently with, or after administration (e.g., infusion) of a CAR-expressing cell described herein. Examples of lymphodepletion include, but may not be limited to, nonmyeloablative lymphodepleting chemotherapy, myeloablative lymphodepleting chemotherapy, total body irradiation, etc. Examples of lymphodepleting agents include, but are not limited to, antithymocyte globulin, anti-CD3 antibodies, anti-CD4 antibodies, anti-CD8 antibodies, anti-CD52 antibodies, anti-CD2 antibodies, TCRαβ blockers, anti-CD20 antibodies, anti-CD19 antibodies, Bortezomib, rituximab, anti-CD 154 antibodies, rapamycin, CD3 immunotoxin, fludarabine, cyclophosphamide, busulfan, melphalan, Mabthera, Tacrolimus, alefacept, alemtuzumab, OKT3, OKT4, OKT8, OKT11, fingolimod, anti-CD40 antibodies, anti-BR3 antibodies, Campath-1H, anti-CD25 antibodies, calcineurin inhibitors, mycophenolate, and steroids, which may be used alone or in combination.

Variations

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs described herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, lie, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

Also, amino acids may be added or removed from the sequence based on vector design.

The CAR can consist essentially of the specified amino acid sequence or sequences described herein, such that other components, e.g., other amino acids, do not materially change the biological activity of the functional variant.

The CARs of embodiments of the invention (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs of embodiments of the invention (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the CARs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the inventive CARs can be synthetic, recombinant, isolated, and/or purified.

Definitions

The term "4-1 BB" or "BB" refers to a member of the TNFR superfamily with an amino acid sequence provided as GenBank Acc. No. AAA53133.1, or the equivalent residues from a non-human species, e.g., mouse, rodent, monkey, ape and the like. In one aspect, the "4-1BB costimulatory domain" is the sequence provided as SEQ ID NO: 216 or the equivalent residues from a non-human species, e.g., mouse, rodent, monkey, ape and the like.

As used herein, a "5' cap" (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

The term "allogeneic" or "donor-derived" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "anti-tumor cytotoxicity" generally refers to any cytocidal activity resulting from the exposure of the CARs of the invention or cells comprising the same to target tumor cells. This activity may be measured by known cytotoxicity assays, including IFN-γ production assays.

The term "antibody," as used herein, refers to an immunoglobulin molecule which specifically binds with an antigen. In one aspect, the antigen is TIM-1. Antibodies can be intact immunoglobulins derived from natural sources or from recombinant sources and can be immunoreactive portions of intact immunoglobulins. The term is used in the broadest sense and includes polyclonal and monoclonal antibodies, including intact antibodies and functional (antigen-binding) antibody fragments, including fragment antigen-binding (Fab) fragments, F(ab')$_2$ fragments, Fab' fragments, Fv fragments, recombinant IgG (rIgG) fragments, single chain antibody fragments, including single chain variable fragments (scFv), diabodies, and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD.

The term "antibody fragment" refers to a portion of an intact antibody and refers to the antigenic determining variable regions of an intact antibody. Examples of antibody fragments include, but are not limited to, fragment antigen-binding (Fab) fragments, F(ab')$_2$ fragments, Fab' fragments, Fv fragments, recombinant IgG (rIgG) fragments, single chain antibody fragments, including single chain variable fragments (scFv), single domain antibodies (e.g., sdAb, sdFv, nanobody) fragments, diabodies, and multispecific antibodies formed from antibody fragments. In a specific embodiment, the antibody fragment is an scFv.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. Kappa and lambda light chains refer to the two major antibody light chain isotypes.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated, synthesized, or can be derived from a biological sample, or might be macromolecule besides a polypeptide. Such a biological sample can include, but is not limited to a tissue sample, a tumor sample, a cell or a fluid with other biological components. In one aspect, the antigen is TIM-1.

The term "antigen-binding domain" refers to one or more extracellular domains of the chimeric antigen receptor which have specificity for a particular antigen.

The term "apheresis" as used herein refers to the art-recognized extracorporeal process by which the blood of a donor or patient is removed from the donor or patient and passed through an apparatus that separates out selected particular constituent(s) and returns the remainder to the circulation of the donor or patient, e.g., by retransfusion. Thus, in the context of "an apheresis sample" refers to a sample obtained using apheresis.

The term "autologous" refers to any material derived from the same individual to whom it is later to be re-introduced.

The term "bind" refers to an attractive interaction between two molecules that results in a stable association in which the molecules are in close proximity to each other. The result of molecular binding is sometimes the formation of a molecular complex in which the attractive forces holding the components together are generally non-covalent, and thus are normally energetically weaker than covalent bonds.

The term "cancer" refers to a disease characterized by the uncontrolled growth of aberrant cells. Cancer cells can spread locally or through the bloodstream and lymphatic system to other parts of the body. Examples of various cancers are described herein and include, but are not limited to ovarian cancer, renal cancer, lung cancer, breast cancer, prostate cancer, cervical cancer, skin cancer, pancreatic cancer, colorectal cancer, liver cancer, brain cancer, lymphoma, leukemia, and the like.

The term "CD28" refers to the protein Cluster of Differentiation 28, one of the proteins expressed on T cells that provide co-stimulatory signals required for T cell activation and survival. The protein may have at least 85, 90, 95, 96, 97, 98, 99 or 100% identity to NCBI Reference No: NP_006130 or a fragment thereof that has stimulatory activity.

The term "CD3ζ" or alternatively, "zeta", "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "CD3ζ intracellular signaling domain" or alternatively a "zeta intracellular signaling domain" or a "TCR-zeta intracellular signaling domain" is defined as the amino acid residues from the cytoplasmic domain of the CD3ζ chain, or functional derivatives thereof, that are sufficient to functionally transmit an initial signal necessary for T cell activation. In one aspect, a "CD3ζ intracellular signaling domain" is the sequence provided as SEQ ID NO: 219.

The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen-binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other. In some embodiments, the set of polypeptides include a dimerization switch that, upon the presence of a dimerization molecule, can couple the polypeptides to one another, e.g., can couple an antigen-binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from the costimulatory molecules described herein, e.g., 4-1BB (i.e., CD137), DAP10 and/or CD28. In one aspect, the CAR comprises a chimeric fusion protein comprising an extracellular antigen-binding domain, a transmembrane domain and an intracellular signaling domain comprising a functional signaling domain derived from a stimulatory molecule. In one aspect, the CAR comprises a chimeric fusion protein comprising an extracellular antigen-binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen-binding domain, a transmembrane domain and an intracellular signaling domain comprising two functional signaling domains derived from one or more costimulatory molecule(s) and a functional signaling domain derived from a stimulatory molecule. In one aspect, the CAR comprises a chimeric fusion protein comprising an extracellular antigen-binding domain, a transmembrane domain and an intracellular signaling domain comprising at least two functional signaling domains derived from one or more costimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen-binding domain, wherein the leader sequence is optionally cleaved from the antigen-binding domain (e.g., an scFv) during cellular processing and localization of the CAR to the cellular membrane.

The term "compete", as used herein with regard to an antibody, means that a first antibody, or an antigen-binding fragment (or portion) thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The term "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to a protein selected from the group consisting of an MHC class I molecule, TNF receptor proteins, Immunoglobulin-like proteins, cytokine receptors, integrins, signaling lymphocytic activation molecules (SLAM proteins), activating NK cell receptors, a Toll ligand receptor, B7-H3, BAFFR, BTLA, BLAME (SLAMF8), CD2, CD4, CD5, CD7, CD8alpha, CD8beta, CD11a, LFA-1 (CD11a/CD18), CD11b, CD11c, CD11d, CD18, CD19, CD19a, CD27, CD28, CD29, CD30, CD40, CD49a, CD49D, CD49f, CD69, CD84, CD96 (Tactile), CD100 (SEMA4D), CD103, OX40 (CD134), 4-1BB (CD137), SLAM (SLAMF1, CD150, IPO-3), CD160 (BY55), SELPLG (CD162), DNAM1 (CD226), Ly9 (CD229), SLAMF4 (CD244, 2B4), ICOS (CD278), CEACAM1, CDS, CRTAM, DAP10, GADS, GITR, HVEM (LIGHTR), IA4, ICAM-1, IL2R beta, IL2R gamma, IL7R alpha, ITGA4, ITGA6, ITGAD, ITGAE, ITGAL, ITGAM, ITGAX, ITGB1, ITGB2, ITGB7, KIRDS2, LAT, LFA-1, LIGHT, LTBR, NKG2C, NKG2D, NKp30, NKp44, NKp46, NKp80 (KLRF1), PAG/Cbp, PD-1. PSGL1, SLAMF6 (NTB-A, Ly108), SLAMF7, SLP-76, TNFR2, TRANCE/RANKL, VLA1, VLA-6, and a ligand that specifically binds with CD83. In embodiments, the encoded costimulatory domain comprises 4-1BB, CD28, or DAP10. In one embodiment, the costimulatory domain comprises the amino acid sequence of BBCYP, CD28CYP, or DAP10CYP (SEQ ID NO: 216, 217, or 218), or nucleotide sequence encoding such (SEQ ID NO: 266, 267, or 268).

The term "cytokines" refers to a broad category of small proteins that are involved in cell signaling. Generally, their release has some effect on the behavior of cells around them. Cytokines may be involved in autocrine signalling, paracrine signalling and/or endocrine signalling as immunomodulating agents. Cytokines include chemokines, interferons, interleukins, lymphokines, and tumour necrosis factors. Cytokines are produced by a broad range of cells, including immune cells like macrophages, B lymphocytes, T lymphocytes and mast cells, as well as endothelial cells, fibroblasts, and various stromal cells. "Chemokines" are a family of cytokines generally involved in mediating chemotaxis.

The term "DAP10" refers to a protein, which in humans is encoded by the HSCT gene. It may also be referred to as HCST, KAP10, PIK3AP, or hematopoietic cell signal transducer. In some embodiments, DAP10 may have the sequence provided in Genbank Accession No.: Q9UBK5.1.

The phrase "disease associated with expression of TIM-1" includes, but is not limited to, a disease associated with expression of TIM-1 or condition associated with cells which express TIM-1 including, e.g., proliferative diseases such as a cancer or malignancy or a precancerous condition; or a noncancer related indication associated with cells which express TIM-1. Noncancer-related indications associated with TIM-1 include hepatitis A virus, Ebola virus, Dengue virus, atopic dermatitis, allergy, rheumatoid arthritis, asthma, systemic lupus erythematosus, and immune dysfunction. Examples of various cancers that express TIM-1 include but are not limited to, ovarian cancer, renal cancer, lung cancer, and the like.

An "effective amount" or "an amount effective to treat" refers to a dose that is adequate to prevent or treat a disease, condition, or disorder in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive CAR materials in each or various rounds of administration.

The term "hinge", "spacer", or "linker" refers to an amino acid sequence of variable length typically encoded between two or more domains of a polypeptide construct to confer flexibility, improved spatial organization, proximity, etc.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

An "iCAR" is a chimeric antigen receptor which contains inhibitory receptor signaling domains. These domains may be based, for example, on protectin D1 (PD1) or CTLA-4 (CD152). In some embodiments, the CAR expressing cells of the invention are further transduced to express an iCAR.

In one aspect, this iCAR is added to restrict the CAR expressing cell's functional activity to tumor cells.

As used herein, "immune cell" refers to a cell of hematopoietic origin functionally involved in the initiation and/or execution of innate and/or adaptive immune response.

An "intracellular signaling domain," as the term is used herein, refers to an intracellular portion of a molecule. The intracellular signaling domain generates a signal that promotes an immune effector function of the cell transduced with a nucleic acid sequence comprising a CAR, e.g., a CAR T cell. Examples of immune effector function, e.g., in a CAR T cell, include cytolytic activity and helper activity, including the secretion of cytokines. Intracellular signaling domains include an intracellular signaling domain of a lymphocyte receptor chain, a TCR/CD3 complex protein, an Fc receptor subunit, an IL-2 receptor subunit, CD3ζ, FcR gamma, FcR beta, CD3 gamma, CD3 delta, CD3 epsilon, CD5, CD22, CD79a, CD79b, CD66d, CD278(ICOS), FcεRI, DAP10, and DAP12.

An "isolated" biological component (such as an isolated chimeric antigen receptor or cell or vector or protein or nucleic acid) refers to a component that has been substantially separated or purified away from its environment or other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis. An isolated nucleic acid or protein can exist in substantially purified form, or can exist in a non-native environment such as, for example, a host cell.

The term "linker" as used in the context of an scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises one or more repeats of the amino acid sequence Gly-Gly-Gly-Gly-Ser (SEQ ID NO:200). In one embodiment, the flexible polypeptide linker includes, but is not limited to, (Gly$_4$Ser)$_3$ (SEQ ID NO: 201).

The term "masked CAR" refers to a CAR expressing cell that further comprises a masking peptide. This masking peptide may prevent off-target cell killing. The masking peptide is often N-terminal to the CAR construct and may block the cell's ability to bind to unintended targets. The masking peptide may be cleaved from the CAR expressing cell when it encounters a tumor thereby allowing the CAR expressing cell to attack its target without killing off-target cells.

The term "nucleic acid" and "polynucleotide" refer to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism. The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The term "OKT3" or "Muromonab-CD3" or "Orthoclone OKT3" refers to a monoclonal anti-CD3 antibody.

A "pharmaceutically acceptable carrier" or "excipient" refers to compounds or materials conventionally used in immunogenic compositions during formulation and/or to permit storage.

The term "promoter", as used herein, is defined as a DNA sequence recognized by the synthetic machinery of the cell, or introduced synthetic machinery, required to initiate the specific transcription of a polynucleotide sequence The term "recombinant" means a polynucleotide with semi-synthetic or synthetic origin which either does not occur in nature or is linked to another polynucleotide in an arrangement not found in nature.

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL. The linker may comprise portions of the framework sequences.

A "signal peptide" (also referred to as a signal sequence, targeting signal, localization signal, localization sequence, transit peptide, leader sequence or leader peptide) is a short peptide present at the N-terminus of the majority of newly synthesized proteins that are destined towards the secretory pathway. The core of the signal peptide may contain a long stretch of hydrophobic amino acids. The signal peptide may or may not be cleaved from the mature polypeptide.

The term "signaling domain" refers to the functional portion of a protein which acts by transmitting information within the cell to regulate cellular activity via defined signaling pathways by generating second messengers or functioning as effectors by responding to such messengers.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as an immunoreceptor tyrosine-based activation motif or ITAM. Examples of an ITAM containing cytoplasmic signaling sequence that are of particular use in the invention include, but are not limited to, those derived from CD3ζ, common FcR gamma (FCER1G), Fc gamma RIIa, FcR beta (Fc Epsilon R1b), CD3γ, CD3δ, CD3ε, CD79a, CD79b, DAP10, and DAP12. In a specific CAR of the invention, the intracellular signaling domain in any one or more CARS of the invention comprises an intracellular signaling sequence, e.g., a primary signaling sequence of CD3ζ. In a specific CAR of the invention, the primary signaling sequence of CD3ζ is the amino acid sequence provided as SEQ ID NO: 219, or nucleotide sequence encoding such (SEQ ID NO:269), or the equivalent residues from a non-human species, e.g., mouse, rodent, monkey, ape and the like.

The term "subject" is intended to include living organisms in which an immune response can be elicited (e.g., mammals, human).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The "T2A ribosome skip sequence" refers to an amino acid sequence that, when translated, causes cleavage of a nascent polyprotein on the ribosome, allowing for co-expression of multiple genes. In one aspect, the T2A ribosome skip sequence may comprise the amino acid sequence of SEQ ID NO: 231, or nucleotide sequence encoding such (SEQ ID NO: 281).

The term "tCD19" refers to a truncated version of the CD19 protein, B-lymphocyte antigen CD19, also known as CD19 (Cluster of Differentiation 19), which is a protein that in humans is encoded by the CD19 gene and is found on the surface of B-cells. The tCD19 construct is any truncated version of said protein, such that a nucleic acid sequence encoding this construct may be transduced into a host cell and expressed on the surface of this cell for the purposes of detection, selection, and/or targeting. In one aspect, tCD19 is the amino acid sequence of SEQ ID NO: 232, or nucleotide sequence encoding such (SEQ ID NO: 282).

The term "TIM-1" refers to the T-cell immunoglobulin and mucin domain 1 protein that is encoded in humans by the HAVCR1 gene. TIM-1 is also known as HAVCR1, HAVCR, HAVCR-1, KIM-1, KIM1, TIM, TIM-1, TIM1, TIMD-1, TIMD1, CD365, and hepatitis A virus cellular receptor 1. TIM-1 has an amino acid sequence provided as GenBank Acc. No. AAC39862.1, or the equivalent residues from a non-human species, e.g., mouse, rodent, monkey, ape and the like. In one aspect, TIM-1 is the sequence provided as SEQ ID NO: 315 or the equivalent residues from a non-human species, e.g., mouse, rodent, monkey, ape and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

By the term "transmembrane domain", what is implied is any three-dimensional protein structure which is thermodynamically stable in a membrane. This may be a single alpha helix, a transmembrane beta barrel, a beta-helix of gramicidin A, or any other structure. Transmembrane helices are usually about 20 amino acids in length. Typically, the transmembrane domain denotes a single transmembrane alpha helix of a transmembrane protein, also known as an integral protein.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count. Additionally, the terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

The term "xenogeneic" refers to a graft derived from an animal of a different species.

The experimental details of these experiments are described in more detail in the following examples. These examples are offered to illustrate, but not to limit, the claimed invention.

EXAMPLES

Example 1: Design and Synthesis of Anti-TIM-1 CAR Variants

Anti-TIM-1 CARs were generated according to the general schematic of FIG. 1. For six of the variants, FIG. 2A provides a more detailed schematic of the CAR construct. The CAR structures were based on a second generation CAR format (Gacerez et al. J Cell Physiol, 2016 December; 231(12):2590-8). There were six different TIM-1-reactive single change variable fragments (scFvs) in either Hv-linker-Lv or Lv-linker-Hv orientation from anti-TIM1 hybridoma clones 1.29, 2.70.2 or 2.59.2 (FIG. 2B). These anti-TIM-1 scFvs were formed by fusing the variable region of the heavy chain (VH) and light chain (VL) regions with a 15 amino acid glycine (G)-serine (S) linker: (G4S)3 linker (SEQ ID NO:201), 3 repeats of GGGGS (SEQ ID NO: 200). These were individually cloned in frame with a CAR construct containing the CD28 hinge domain (residues 135-152 of CD28 or SEQ ID NO: 214), the transmembrane domain of CD28 (residues 153-179 of CD28 or SEQ ID NO: 215), the costimulatory region of CD28 (residues 180-220 of CD28 or SEQ ID NO: 217), followed by the CD3ζ signaling domain (residues 52-164 of CD3 or SEQ ID NO: 219). The scFv domain in each of these constructs varied based on order of the light and heavy variable domains, the scFv affinity, and the epitope bin (region on the TIM-1 extracellular domain where the scFv binds). These scFvs were derived from fully human anti-TIM-1 antibodies which minimized potential issues of immunogenicity (specifically murine-based scFvs) used in recent clinical trials (Maus et al. Cancer Immunol Res 2013; 1:26-31; Kershaw et al. Clin Cancer Res 2006; 12:6106-6115; Lamers et al. Blood 2011; 117:72-82). The anti-TIM-1 antibody sequences (1.29 and 2.70.2 vs. 2.59.2) were shown to bind to different epitopes on TIM-1 (U.S. Pat. No. 8,067,544). The full details of the antibodies from which these scFvs were derived may be found in U.S. Pat. No. 8,067,544.

The CAR structures were then further varied based on composition of the intracellular co-stimulatory domain, as depicted in FIG. 2C: CD28 (SEQ ID NO: 217) versus 4-1BB (residues 214-255 of 4-1BB or SEQ ID NO: 216) versus DAP10 (residues 70-93 of DAP10 or SEQ ID NO:218). Briefly, the synthetic CAR construct began with a signal peptide, followed by a variable heavy chain and variable light chain sequence separated by a linker (VH-linker-VL, the scFv) that bound to the extracellular portion of TIM-1. The scFv was in frame with a CD28 hinge and transmembrane domain followed by an intracellular co-stimulatory domain (derived from either CD28, 4-1BB or DAP10) and finally, the CD3ζ signaling domain. In all cases, PCR was performed using a high-fidelity DNA polymerase.

To facilitate the attainment of a high purity of transduced T cells, CAR variant constructs were designed to include a truncated CD19 (tCD19) marker sequence (residues 1-327 of CD19, or SEQ ID NO: 232) separated from the CAR construct by a T2A ribosomal skip element (SEQ ID NO: 231) (FIG. 2C). When translated, tCD19 becomes expressed on the cell surface of the CAR T cells. This allowed for a purification step to enrich the population of transduced, CAR+ cells.

Overall, the CAR variants that were designed and cloned (in frame) into retroviral vectors were as follows. Two variants based on the scFvs derived from Ab 1.29: 129L-CD28 and 129H-CD28. Four variants based on the scFv's derived from Ab 2.70.2: 272L-CD28; 272H-CD28; 272H-BB; and 272H-DAP10. And four variants based on the scFv's derived from Ab 2.59.2: 2592L-CD28; 2592H-CD28; 2592H-BB; and 2592H-DAP10. See Table 1. A number of these constructs were further synthesized with a T2A ribosomal skip sequence and a gene encoding for the expression of tCD19.

TABLE 1

| Name | Antigen-binding domain | Hinge domain | Trans-membrane domain | Co-stimulatory domain | Intracellular signaling domain | Amino acid SEQ ID NO | Nucleic acid SEQ ID NO |
|---|---|---|---|---|---|---|---|
| 129H-CD28 | 129H scFv | CD28 H | CD28 TM | CD28 CYP | CD3ζ CYP | 220 | 270 |
| 129L-CD28 | 129L scFv | CD28 H | CD28 TM | CD28 CYP | CD3ζ CYP | 221 | 271 |
| 272H-BB | 272H scFv | CD28 H | CD28 TM | 4-1BB CYP | CD3ζ CYP | 222 | 272 |
| 272H-CD28 | 272H scFv | CD28 H | CD28 TM | CD28 CYP | CD3ζ CYP | 223 | 273 |
| 272H-DAP10 | 272H scFv | CD28 H | CD28 TM | DAP10 CYP | CD3ζ CYP | 224 | 274 |
| 272L-CD28 | 272L scFv | CD28 H | CD28 TM | CD28 CYP | CD3ζ CYP | 225 | 275 |
| 2592H-BB | 2592H scFv | CD28 H | CD28 TM | 4-1BB CYP | CD3ζ CYP | 226 | 276 |
| 2592H-CD28 | 2592H scFv | CD28 H | CD28 TM | CD28 CYP | CD3ζ CYP | 227 | 277 |
| 2592H-DAP10 | 2592H scFv | CD28 H | CD28 TM | DAP10 CYP | CD3ζ CYP | 228 | 278 |
| 2592L-CD28 | 2592L scFv | CD28 H | CD28 TM | CD28 CYP | CD3ζ CYP | 229 | 279 |

Vectors:

The aforementioned anti-TIM-1 constructs were cloned into either the retroviral vector pFB-neo (Stratagene. Palo Alto. Calif.) or pSFG. pSFG vectors have been used for similar retroviral transduction of T cells in clinical trials (Hollyman et al. J Immunother 2009; 32:169-180; Pule et al. Nat Med 2008; 14:1264-1270). pFB-neo DNA was digested with SaiI and NotI restriction enzymes. Product of digestion was loaded onto agarose gels, and the digested band was cut out and purified using a gel extraction kit (Qiagen).

Example 2: Generation of Anti-TIM-1 CAR T-Cells

Cell Culturing and Retroviral Transduction:

The aforementioned retroviral stocks were used to transduce human T cells from healthy donors, using optimized methods (Cubillos-Ruiz et al. Oncotarget 2010; 1:329-33; Huarte et al. Blood 2008; 112:1259-1268; Stephen et al. Immunity 2014; 41:427-439), protocols, and resources previously developed at Celdara Medical.

For some of the variants, the cell culturing, retroviral transduction and purification scheme is summarized in FIG. 3. The resultant transduced cells were analyzed via flow cytometry (FIG. 4). For the purification of some of the variants, the protocol was as follows. Human PBMCs (HemaCare) from healthy donors were the source of T cells for CAR transduction. Donor PBMCs were thawed, reconstituted in complete medium, and then pelleted by centrifugation. Cells were subsequently resuspended in complete medium and then activated by incubation with IL-2 and anti-CD3 for 48 h. After stimulation, cells were exposed to retrovirus supernatant encoding the anti-TIM-1 CAR variants, placed in retronectin-coated plates in the presence of anti-CD3 and followed by spinoculation. Mock transductions with empty vectors were also performed to act as CAR$^-$ controls in experiments. On day 3, media was changed and spinoculation repeated, followed by T-cell expansion for several days. On day 5, cells were purified. For those cells transduced with constructs featuring the gene for tCD19, this purification was performed using an anti-CD19 antibody to selectively purify all CD19$^+$ cells from the population. CAR T-cells were produced using cells from different donors (e.g., FIG. 4, second column). CD3+CD19$^+$ purities (as determined by flow cytometry) were in excess of 80% after one round of purification using this approach. If necessary, attainment of >90% CD3+CD19$^+$ purity can be achieved through a second round of purification.

For in vivo assays, cells were cultured, transduced, harvested, purified and expanded as in FIG. 14. FIG. 15A and FIG. 15B illustrate the growth and viability, respectively, of the host cells during the manufacturing process, suggesting that anti-TIM-1 CAR expression does not confer deleterious effects to T cells such as toxicity or impaired T cell proliferation in the presence of IL-2. FIG. 17 shows the flow cytometric analysis of the resultant cells.

Example 3: In Vitro Functional Activity of Anti-TIM-1 CAR T-Cells

Anti-TIM-1 CAR T-Cell Production:
anti-TIM-1 CAR T-cells were produced as described in Example 2 and FIG. 3.

IFNγ Induction Assay:
IFNγ induction reports on stimulatory and cytotoxic properties of anti-TIM-1 CAR variants in vitro, i.e., their ability to activate the CAR T-cell upon exposure to TIM-1 target cells. IFNγ is an important effector cytokine, and an increase in its production indicates whether CAR T cells have been stimulated, with it acting as a biomarker of effector cell:target cell engagement. Essentially, the presence of IFNγ only when CAR T cells are incubated with cells expressing the target TIM-1 protein is indicative of selective target engagement.

We co-cultured IGROV-1 cells and CAR T cell variants in triplicate, collected the supernatants at 24 h and measured IFNγ production by ELISA.

Several CAR T cell variants produced with the scFv sequences described in Example 1 were capable of stimulating the production of IFNγ when incubated with the TIM-1 ovarian cancer cell line IGROV-1 (FIG. 5A-E). To demonstrate the specific in vitro targeting of TIM-1-targeted CAR T-cells, the CAR Ts were exposed to other TIM-1+ and TIM-1$^+$ cancer cell lines: TIM-1$^+$ A549 (lung adenocarcinoma) cells; TIM-1$^+$ Caki-1 (renal cell carcinoma) cells; and TIM-1$^-$ EL4 (murine lymphoma) cells. To ensure that IFNγ production was not a non-specific effect of the retrovirus transduction procedure, we mock-transduced T cells and incubated them with TIM-1$^+$ IGROV-1 cells (FIG. 5A-E). To test that the increase in IFNγ production was due to the interaction between the anti-TIM-1 CAR and cell surface TIM-1 on IGROV-1 cells, we also examined the results of co-incubation with a blocking antibody against TIM-1 (FIGS. 5C and 5E), using the full-length antibody from which the scFv sequences were derived.

Similarly, FIG. 18 demonstrates the results of this in vitro functional activity assay for CAR T cells produced as in FIG. 14.

In Vitro Cytokine Production Assay:
Another parameter important for therapeutic effectiveness is the production of effector cytokines that influence the immunoenvironment in vivo. We co-cultured IGROV-1 cells and CAR T cell variants in triplicate, collected the supernatants at 24 h and measured cytokine production via Luminex. CAR T-cells were also co-cultured under the same conditions with A549 cells, Caki-1 cells, (additional TIM-1$^+$ cancer cell lines) and EL-4 cells (TIM-1' control). In addition, to verify that TIM-1 binding was responsible for cytokine production, in one condition, CAR T cells were co-cultured with IGROV-1 cells in the presence of the full length antibody from which the scFv was derived. In each case, mock-transduced cells were used as a control. See results in FIG. 6-12.

In vitro cytotoxicity assay: To determine the specificity of Anti-TIM-1 CAR T cells for TIM-1$^+$ cells, the CAR T cell cytotoxic potential against TIM-1$^+$ (IGROV-1 human ovarian cancer cells) and TIM-1$^-$ cells (EL4 murine lymphoma cells) was determined using a standard cytotoxicity assay based on the release of lactate dehydrogenase. The IGROV-1 ovarian carcinoma cell line serves as a useful initial target population for these experiments (Bernard et al. Cancer Res 1985; 45:4970-4979), as IGROV-1 cells express the TIM-1 target antigen and serve as a model of ovarian clear cell carcinoma (Domcke et al. Nat Commun 2013; 4:2126).

In each well, 10$^4$ IGROV-1 cells were plated and co-cultured with effector T cells expressing the different anti-TIM-1 CAR variants at ratios of 1:1 (effector cells:target cells), 5:1, 10:1 and 20:1. Several control conditions were also carried out, including: media only; CAR T cells only (effector spontaneous release); IGROV-1 cells only (target spontaneous release); and maximum IGROV-1 toxicity (cells treated with Triton-X 100). Twenty-two hours after plating the cells in co-culture, the co-cultures were centrifuged and the supernatants, collected. The assay reagent was added (containing diaphorase and the INT substrate intermediate) and the reaction was allowed to proceed. At the end of the incubation, a stop solution was added and sample absorbance determined. The corrected absorbance values from the experimental samples performed in triplicate were used to calculate a percent cytotoxicity based on the total lysis control, as described above.

FIG. 13A-D shows the results of this assay for T cells transduced with anti-TIM-1 CARs and for mock-transduced cells, in terms of cell lysis in TIM-1$^+$ cells. TIM-1-cell-specific cytotoxicity was also demonstrated, as IGROV-1 cells were killed while TIM-1$^-$ EL4 cells were unaffected (FIG. 13A-D).

For this purpose, OVCAR-5 ovarian carcinoma cells could also be used, as they express the TIM-1 target antigen and have been shown to be responsive to anti-TIM-1 antibodies, as well (U.S. Pat. No. 8,067,544).

Example 4: In Vivo TIM-1 CAR T Antitumor Activity in Murine IGROV-1 Tumor Model Mice:
SCID-beige female, 6 weeks (See Table 2).

TABLE 2

| Group 1: saline | Group 2: Mock CAR-T | Group 3: 2592H_tCD19 | Group 4: 2592L_tCD19 | Group 5: 272H_tCD19 |
| --- | --- | --- | --- | --- |
| sb-118 | sb-123 | sb-133 | sb-143 | sb-153 |
| sb-119 | sb-124 | sb-134 | sb-144 | sb-154 |
| sb-120 | sb-125 | sb-135 | sb-145 | sb-155 |
| sb-121 | sb-126 | sb-136 | sb-146 | sb-156 |
| sb-122 | sb-127 | sb-137 | sb-147 | sb-157 |
|  | sb-128 | sb-138 | sb-148 | sb-158 |
|  | sb-129 | sb-139 | sb-149 | sb-159 |
|  | sb-130 | sb-140 | sb-150 | sb-160 |
|  | sb-131 | sb-141 | sb-151 | sb-161 |
|  | sb-132 | sb-142 | sb-152 | sb-162 |

IGROV-1 Cell Preparation:

IGROV-1 cells were thawed. Cells were passed one day before inoculation. Cells were harvested, washed once with RPMI, and then made into $50 \times 10^6$/ml cell suspensions in RPMI without supplements. IGROV-1 cells were prepared using trypsin.

CAR T Cell Preparation:

Anti-TIM-1 CAR T cells were produced via retroviral transduction of anti-TIM-1 CAR constructs into PBMCs (healthy human volunteer); anti-TIM-1 positive cells were enriched via purification ($CD3^+/CD19t^+$) and further prepared according to FIG. 14.

CAR T cells were thawed, counted and checked for viability instantly. Vials were removed from liquid N2 storage and placed on dry ice. Vials were then warmed in a 37° C. water bath until a small ice crystal remained. At that point, 1 mL of warmed RPMI was added dropwise with swirling. 2 mL of mix was removed from vial and placed into 15 mL conical. 4 mL of warmed RPMI was then added to 15 mL conical. Tubes were centrifuged at 1000 rpm for 5 min at 10° C. Cells were resuspended in 1 mL RPMI and then counted twice and viability analyzed. Tubes were placed on ice when not in use.

CAR T cell suspensions were made at $75 \times 10^6$/ml in RPMI without supplements.

Cell Administration:

On day 0, mice were inoculated in the right flank with $2.5 \times 10^6$ IGROV-1 cells+$7.5 \times 10^6$ CAR T cells in 150 µl RPMI. For each group, 1 volume of IGROV-1 preparation was added to 2 volumes of CAR-T preparation based on CAR-T counts. CAR-T/IGROV mixes were left on ice during injections. Cells injections began immediately after cell preparation and took approximately 1 hr to complete.

1 volume of IGROV-1 cell suspension for group 1 (50 µl injected);

1 volume of IGROV-1 cell suspension+2 volume of Mock CAR-T for group 2;

1 volume of IGROV-1 cell suspension+2 volume of 2592H_tCD19 for group 3;

1 volume of IGROV-1 cell suspension+2 volume of 2592L_tCD19 for group 4;

1 volume of IGROV-1 cell suspension+2 volume of 272H_tCD19 for group 5;

Results:

Tumor size was measured twice a week. A general health check was performed on a daily basis and date of death was recorded for each mouse. Study was terminated on day 56. See FIG. 20A for full results. A tumor size comparison was also performed on day 20, with results in FIG. 20B. Tumor size is reported as the average volume±SEM followed by statistical analysis using a Mann-Whitney test (*, p=0.02; **, p=0.002). Thus, subcutaneous administration of anti-TIM-1 CAR T cells inhibited growth of TIM-1$^+$ IGROV-1 cells.

Example 5: Persistence of CAR T Cells in Tumor-Bearing Mice

An important parameter associated with both safety and potentially long-term protection is the persistence of CAR T cells that can respond on tumor recurrence (Song et al. Cancer Res 2011; 71:4617-4627). To measure persistence in vivo, first establish IGROV-1 cells ($3 \times 10^6$ cells) intraperitoneally in female NSG mice (3 mice/group). On day 10 post implantation, administer $0.5 \times 10^7$ anti-TIM-1 CAR T cells intraperitoneally. Determine the presence of CAR T cells at days 14 and 28 after adoptive transfer using Q-PCR specific to the CAR variant. Tissue compartments to be analyzed will include blood, tumor tissue, bone marrow and spleen. The amount of signal measured by Q-PCR will be used to estimate the relative number of CAR T cells present per tissue analyzed and provide a means to compare the survival and proliferative potential of the two CAR variants.

Example 6: In Vivo TIM-1 CAR T Effect on Survival in Murine IGROV-1 Tumor Model Mice:
SCID-beige female, 6 weeks (See Table 3).

TABLE 3

| Group 1: saline | Group 2: Mock CAR-T | Group 3: 2592H_tCD19 |
| --- | --- | --- |
| sb-383 | sb-388 | sb-398 |
| sb-384 | sb-389 | sb-399 |
| sb-385 | sb-390 | sb-400 |
| sb-386 | sb-391 | sb-401 |
| sb-387 | sb-392 | sb-402 |
|  | sb-393 | sb-403 |
|  | sb-394 | sb-404 |
|  | sb-395 | sb-405 |
|  | sb-396 | sb-406 |
|  | sb-397 | sb-407 |

IGROV-Tumor Establishment:

IGROV-1 cells were thawed and passed one day before inoculation. On day 0, IGROV-1 cells were harvested using trypsin and washed once with RPMI, and each mouse shown in Table 3 was intraperitoneally inoculated with $2.5 \times 10^6$ IGROV-1 cells in 200 µL RPMI without supplements.

CAR T Cell Preparation:

Mock CAR T cells and anti-TIM-1 CAR T cells were produced by transducing PBMCs (from healthy human donor) with retroviruses generated using the mock CAR construct (pSFG._tCD19) or the anti-TIM-1 CAR construct (pSFG.CX272H_tCD19), respectively. Successfully transduced cells were purified, expanded, and frozen until use, according to FIG. 14.

CAR T Cell Administration:

On each of days 2, 9, and 16, mock CAR T cells and anti-TIM-1 CAR T cells were thawed, counted, and checked for viability instantly. Viable cell suspensions were made with $37.5 \times 10^6$ cells/ml in RPMI without supplements and kept on ice until administration into mice were complete (within about 1 h). Each mouse in Group 2 was intraperitoneally administered with 7.5×10⁶ mock CAR-T cells and each mouse in Group 3 was intraperitoneally administered with 7.5×10⁶ anti-TIM-1 CAR-T cells in 200 μL RPMI without supplements. Each mouse in Group 1 was intraperitoneally administered with 200 μL saline.

Results:

Mice were monitored and deaths were recorded on a daily basis. Mice were euthanized when adverse clinical signs, such as severe lethargy, hunched posture, or immobility, were observed. The graph in FIG. 21 shows the mouse survival result. The survival comparison among Groups 1-3 were analyzed using a Log rank (Mantel-Cox) test. Mice that received anti-TIM-1 CAR-T cells (Group 3) survived statistically longer than mice that received just saline (Group 1, p=0.0043) or mock CAR-T cells (Group 2, p<0.0001**). Thus, administration of anti-TIM-1 CAR T cells prolonged survival in an in vivo model of ovarian cancer.

Exemplary Sequences i. 2592 minimal binding epitope 2592 epitope 97 Amino acid sequence of 2592 minimal binding epitope (2592 epitope), SEQ ID NO: 97 LRPQNH ii. Linker region subunit G4S 200 Amino acid sequence of Linker region subunit (G4S), SEQ ID NO: 200 GGGGS iii. Linker region G4S Linker 201 Amino acid sequence of Linker region (G4S Linker), SEQ ID NO: 201 GGGGSGGGGSGGGGS iv. Ab 129 VH 129 VH 202 Amino acid sequence of Ab 129 VH (129 VH), SEQ ID NO: 202 QVQLQESGPGLVKPSETLSLTCTVSGGSVSSGGYYWSWIRQPPGKGLEWIGFIYYT GSTNYNPSLKSRVSISVDTSKNQFSLKLSSVTAADAAVYYCARDYDWSFHFDYWGQGTLVTVSS v. Ab 129 VL 129 VL 203 Amino acid sequence of Ab 129 VL (129 VL), SEQ ID NO: 203 DIQMTQSPSSLSASIGDRVTITCRASQGIRNDLGWYQQKPGKAPKRLIYAASSLQS GVPSRFSGSGSGTEFTLTISSLQPEDFATYYCLQHNSYPLTFGGGTKVEIK vi. Ab 272 VH 272 VH 204 Amino acid sequence of Ab 272 VH (272 VH), SEQ ID NO: 204 QVQLVESGGGVVQPGRSLRLSCAASGFIFSRYGMHWVRQAPGKGLKWVAVIWYDGS NKLYADSVKGRFTISRDNSKNTLYLQMNSLRAEDTAVYYCARDYYDNSRHHWGFDYWGQGLTVTVSS vii. Ab 272 VL 272 VL 205 Amino acid sequence of Ab 272 VL (272 VL), SEQ ID NO: 205 DIVMTQTPLSLPVTPGEPASISCRSSRSLLDSDDGNTYLDWYLQKPGQSPQLLIYT LSYRASGVPDRFSGSGSGTDFTLKISRVEAEDVGVYYCMQRVEFPITFGQGTRLEIK viii. Ab 2592 VH 2592 VH 206 Amino acid sequence of Ab 2592 VH (2592 VH), SEQ ID NO: 206 QVQLQESGPRLVKPSQTLSLTCTVSGGSISSDGYYWSWIRQHPGKGLEWIGYIYYS GSTFYNPSLKSRVAISVDTSKNQFSLKLSSVTAADTAVYYCARESPHSSNWYSGFDCWGQGTLVTVSS ix. Ab 2592 VL 2592 VL 207 Amino acid sequence of Ab 2592 VL (2592 VL), SEQ ID NO: 207 EIVLTQSPDFQSVTPEKEVTITCRASQSIGSRLHWYQQKPDQSPKLLIKYASQSFS GVPSRFSGSGSGTDFTLTINSLEAEDAATYYCHQSSNLPFTFGPGTKVDIK x. 129 hv-linker-lv 129H 208 Amino acid sequence of 129 hv-linker-lv (129H), SEQ ID NO: 208 QVQLQESGPGLVKPSETLSLTCTVSGGSVSSGGYYWSWIRQPPGKGLE WIGFIYYTGSTNYNPSLKSRVSISVDTSKNQFSLKLSSVTAADAAVYYCARDYDWSFHFDYWGQGTLVTVS SGGGGSGGGGSGGGGSDIQMTQSPSSLSASIGDRVTITCRASQGIRNDLGWYQQKPGKAPKRLIYAASSLQ SGVPSRFSGSGSGTEFTLTISSLQPEDFATYYCLQHNSYPLTFGGGTKVEIK xi. 129 lv-linker-hv 129L 209 Amino acid sequence of 129 lv-linker-hv (129L), SEQ ID NO: 209 DIQMTQSPSSLSASIGDRVTITCRASQGIRNDLGWYQQKPGKAPKRLI YAASSLQSGVPSRFSGSGSGTEFTLTISSLQPEDFATYYCLQHNSYPLTFGGGTKVEIKGGGGSGGGGSGG GGSQVQLQESGPGLVKPSETLSLTCTVSGGSVSSGGYYWSWIRQPPGKGLEWIGFIYYTGSTNYNPSLKSR VSISVDTSKNQFSLKLSSVTAADAAVYYCARDYDWSFHFDYWGQGTLVTVSS xii. 272 hv-linker-lv 272H 210 Amino acid sequence of 272 hv-linker-lv (272H), SEQ ID NO: 210 QVQLVESGGGVVQPGRSLRLSCAASGFIFSRYGMHWVRQAPGKGLKWV AVIWYDGSNKLYADSVKGRFTISRDNSKNTLYLQMNSLRAEDTAVYYCARDYYDNSRHHWGFDYWGQGTL VTVSSGGGGSGGGGSGGGGSDIVMTQTPLSLPVTPGEPASISVRSSRSLLDSDDGNTYLDWYLQKPGQSPQ LLIYTLSYRASGVPDRFSGSGSGTDFTLKISRVEAEDVGVYYCMQRVEFPITFGQGTRLEIK xiii. 272 lv-linker-hv 272L 211 Amino acid sequence of 272 lv-linker-hv (272L), SEQ ID NO: 211 DIVMTQTPLSLPVTPGEPASISCRSSRSLLDSDDGNTYLDWYLQKPGQ SPQLLIYTLSYRASGVPDRFSGSGSGTDFLTKISRVEAEDVGVYYCMQRVEFPITFGQGTRLEIKGGGGSG GGGSGGGGSQVQLVESGGGVVQPGRSLRLSCAASGFIFSRYGMHWVRQAPGKGLKWVAVIWYDGSNKLYAD SVKGRFTISRDNSKNTLYLQMNSLRAEDTAVYYCARDYYDNSRHHWGFDYWGQGTLVTVSS xiv. 2529 hv-linker-lv 2592H 212 Amino acid sequence of 2592 hv-linker-lv (2592H), SEQ ID NO: 212 QVQLQESGPRLVKPSQTLSLTCTVSGGSISSDGYYWSWIRQHPGKGL EWIGYIYYSGSTFYNPSLKSRVAISVDTSKNQFSLKLSSVTAADTAVYYCARESPHSSNWYSGFDCWGQGT LVTVSSGGGGSGGGGSGGGGSEIVLTQSPDFQSVTPKEKVTITCRASQSIGSRLHWYQQKPDQSPKLLIKY ASQSFSGVPSRFSGSGSGTDFTLTINSLEAEDAATYYCHQSSNLPFTFGPGTKVDIK xv. 2592 lv-linker-hv 2592L 213 Amino acid sequence of 2592 lv-linker-hv (2592L), SEQ ID NO: 213 EIVLTQSPSFQSVTPKEKVTITCRASQSIGSRLHWYQQKPDQSPLLI KYASQSFSGVPSRFSGSGSGTDFTLTINSLEAEDAATYYCHQSSNLPFTFGPGTKVDIKGGGGSGGGGSGG -continued

```
GGSQVQLQESGPRLVKPSQTLSLTCTVSGGSISSDGYYWSWIRQHPGKGLEWIGYIYYSGSTFYNPSLKSR
VAISVDTSKNQFSLKLSSVTAADTAVYYCARESPHSSNWYSGFDCWGQGTLVTVSS
```

- xvi. CD28 hinge domain CD28H 214 Amino acid sequence of CD28 hinge domain (CD28H), SEQ ID NO: 214 VKGKHLCPSPLFPGPSKP

- xvii. CD28 transmembrane domain CD28TM 215 Amino acid sequence of CD28 transmembrane domain (CD28TM), SEQ ID NO: 215 FWVLVVVGGVLACYSLLVTVAFIIFWV

- xviii. 4-1BB costimulatory domain BBCYP 216 Amino acid sequence of 4-1BB costimulatory domain (BBCYP), SEQ ID NO: 216 KRGRKKLLYIFKQPFMRPVQTTQEEDGCSCRFPEEEEGGCEL

- xix. CD28 costimulatory domain CD28CYP 217 Amino acid sequence of CD28 costimulatory domain (CD28CYP), SEQ ID NO: 217 SKRSRLLHSDYMNMTPRRPGPTRKHYQPYAPPRDFAAYRS

- xx. DAP10 costimulatory domain DAP10CYP 218 Amino acid sequence of DAP10 costimulatory domain (DAP10CYP), SEQ ID NO: 218 LCARPRRSPAQEDGKVYINMPGRG

- xxi. CD3zeat intracellular domain CD3ζCYP 219 Amino acid sequence of CD3zeta intracellular domain (CD3ζCYP), SEQ ID NO: 219 LRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR

- xxii. 129H-CD28H-CD28TM-CD28CYP-CD3ζCYP CAR (includes leader) 129H-CD28 220 Amino acid sequence of 129H-CD28H-CD28TM-CD28CYP-CD3ζCYP CAR (includes leader) (129H-CD28), SEQ ID NO: 220 METPAQLLFLLLLWLPDTTGQVQLQESGPGLVKPSETLSLTCTVSGGSVSSGGYYWSWIRQPPGKGLEWIGFIYYTGSTNYNPSLKSRVSISVDTSKNQFSLKLSSVTAADAAVYYCARDYDWSFHFDYWGQGTLVTVSSGGGGSGGGGSGGGGSDIQMTQSPSSLSASIGDRVTITCRASQGIRNDLGWYQQKPGKAPKRLIYAASSLQSGVPSRFSGSGSGTEFTLTISSLQPEDFATYYCLQHNSYPLTFGGGTKVEIKASVKGKHLCPSPLFPGPSKPFWLVLVVVGGVLACYSLLVTVAFIIFWVRSKRSRLLHSDYMNMTPRRPGPTRKHYQPYAPPRDFAAYRSKLRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR

- xxiii. 129L-CD28H-CD28TM-CD28CYP-CD3ζCYP CAR (includes leader) 129L-CD28 221 Amino acid sequence of 129L-CD28H-CD28TM-CD28CYP-CD3ζCYP CAR (includes leader) (129L-CD28), SEQ ID NO: 221 METPAQLLFLLLLWLPDTTGDIQMTQSPSSLSASIGDRVTITVRASQGIRNDLGWYQQKPGKAPKRLIYAASSLQSGVPSRFSGSGSGTEFTLTISSLQPEDFATYYCLQHNSYPLTFGGGTKVEIKGGGGSGGGGSGGGGSQVQLQESGPGLVKPSETLSLTCTVSGGSVSSGGYYWSWIRQPPGKGLEWIGFIYYTGSTNYNPSLKSRVSISVDTSKNQFSLKLSSVTAADAAVYYCARDYDWSFHFDYWGQGTLVTVSSASVKGKHLCPSPLFPGPSKPFWLVLVVVGGVLACYSLLVTVAFIIFWVRSKRSRLLHSDYMNMTPRRPGPTRKHYQPYAPPRDFAAYRSKLRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR

- xxiv. 272H-CD28H-CD28TM-BBCYP-CD3ζCYP CAR (includes leader) 272H-BB 222 Amino acid sequence of 272H-CD28H-CD28TM-BBCYP-CD3ζCYP CAR (includes leader) (272H-BB), SEQ ID NO: 222 METPAQLLFLLLLWLPDTTGQVQLVESGGGVVQPGRSLRLSCAASGFIFSRYGMHWVRQAPGKGLKWVAVIWYDGSNKLYADSVKGRFTISRDNSKNTLYLQMNSLRAEDTAVYYCARDYDNSRHHWGFDYWGQGTLVTVSSGGGGSGGGGSGGGGSDIVMTQTPLSLPVTPGEPASISVRSSRSLLDSDDGNTYLDWYLQKPGQSPQLLIYTLSYRASGVPDRFSGSGSGTDFTLKISRVEAEDVGVYYCMQRVEFPITFGQGTRLEIKLEVKGKHLCPSPLFPGPSKPFWVLVVVGGVLACYSLLVTVAFIIFWVKRGRKKLLYIFKQPFMRPVQTTQEEDGCSCRFPEEEEGGCELKLRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR

- xxv. 272H-CD28H-CD28TM-CD28CYP-CD3ζCYP CAR (includes leader) 272H-CD28 223 Amino acid sequence of 272H-CD28H-CD28TM-CD28CYP-CD3ζCYP CAR (includes leader) (272H-CD28), SEQ ID NO: 223 METPAQLLFLLLLWLPDTTGQVQLVESGGGVVQPGRSLRLSCAASGFIFSRYGMHWVRQAPGKGLKWVAVIWYDGSNKLYADSVKGRFTISRDNSKNTLYLQMNSLRAEDTAVYYCARDYDNSRHHWGFDYGQGTLVTVSSGGGGSGGGGSGGGGSDIVMTQTPLSLPVTPGEPASISVRSSRSLLDSDDGNTYLDWYLQKPGQSPQLLIYTLSYRASGVPDRFSGSGSGTDFTLKISRVEAEDVYVYYCMQRVEFPITFGQGTRLEIKLEVKGKHLCPSPLFPGPSKPFWVLVVVGGVLACYSLLVTVAFIIFWVRSKRSRLLHSDYMNNTPRRPGPTRKHYQPYAPPRDFAAYRSKLRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR

- xxvi. 272H-CD28H-CD28TM-DAP10CYP-CD3ζCYP CAR (includes leader) 272H-DAP10 224 Amino acid sequence of 272H-CD28H-CD28TM-DAP10CYP-CD3ζCYP CAR (includes leader) (272H-DAP10), SEQ ID NO: 224 METPAQLLFLLLLWLPDTTGQVQLVESGGGVVQPGRSLRLSCAASGFIFSRYGMHWVRQAPGKGLKWVAVIWYDGSNKLYADSVKGRFTISRDNSKNTLYLQMNSLRAEDTAVYYCARDYDNSRHHWGFDYWGQGTLVTVSSGGGGSGGGGSGGGGSDIVMTQTPLSLPVTPGEPASISVRSSRSLLDSDDGNTYLDWYLQKPGQSPQLLIYTLSYRASGVPDRFSGSGSGTDFTLKISRVEAEDVGVYYCMQRVEFPITFGQGTRLEIKLEVKGKHLCPSPLFPGPSKPFWVLVVVGGVLACYSLLVTVAFIIFWVLCARPRRSPAQEDGKVYINMPGRGKLRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR -continued xxvii. 272L-CD28H-CD28TM-CD28CYP-CD3ζCYP CAR (includes leader) 272L-CD28 225
Amino acid sequence of 272L-CD28H-CD28TM-CD28CYP-CD3ζCYP CAR
(includes leader) (272L-CD28), SEQ ID NO: 225 METPQALLFLLLLWLPDTTGDIVMT
QTPLSLPVTPGEPASISCRSSRSLLDSDDGNTYLDWYLQKPGQSPQLLIYTLSYRASGVPDRFSGSGSGTD
FTLKISRVEAEDVGVYYCMQRVEFPITFGQGTRLEIKGGGGSGGGGSGGGGSQVQLVESGGGVVQPGRSLR
LSCAASGFIFSRYGMHWVRQAPGKGLKWVAVIWYDGSNKLYADSVKGRFTISRDNSKNTLYLQMNSLRAED
TAVYYCARDYYDNSRHHWGFDYWGQGTLVTVSSLEVKGKHLCPSPLFPGPSKPFWVLVVVGGVLACYSLLV
TVAFIIFWVRSKRSRLLHSDYMNMTPRRPGPTRKHYQPYAPPRDFAAYRSKLRVKFSRSADAPAYQQGQNQ
LYNELNLGRREEYDVLDKRRGRDPEMGGKPQRRKNPQELGYNELQKDKMAEAYSEIGMKGERRRGKGHDGL
YQGLSTATKDTYDALHMQALPRR xxviii. 2592H-CD28H-CD28TM-BBCYP-CD3ζCYP CAR (includes leader) 2592H-BB28 226
Amino acid sequence of 272H-CD28H-CD28TM-CD28CYP-CD3ζCYP CAR
(includes leader) (2592H-BB), SEQ ID NO: 226 METPAQLLFLLLLWLPDTTGQVQLQE
SGPRLVKPSQTLSLTCTVSGGSISSDGYYWSWIRQHPGKGLEWIGYIYYSGSTFYNPSLKSRVAISVDTSK
NQFSLKLSSVTAADTAVYYCARESPHSSNWYSGFDCWGQGTLVTVSSGGGGSGGGGSGGGGSEIVLTQSPD
FQSVTPKEKVTITCRASQSIGSRLHWYQQKPDQSKPKLLIHYASQSFSGVPSRFSGSGSGTDFTLTINSLE
AEDAATYYCHQSSNLPFTFGPGTKVDIKASVKGKHLCPSPLFPGPSKPFWVLVVVGGVLACYSLLVTVAFI
IFWVKRGRKKLLYIFKQPFMRPVQTTQEEDGCSCRFPEEEEGGCELKLRVKFSRSADAPAYQQGQNQLYNE
LNLGRREEYDVLDKRRGRDPEMGGKPQRRKNPQEGLYNELQKDKMAEAYSEIGMKGERRRGKGHDGLYQGL
STATKDTYDALHMQALPPR xxix. 2592H-CD28H-CD28TM-CD28CYP-CD3ζCYP CAR (includes leader) 2592H-CD28
227 Amino acid sequence of 2592H-CD28H-CD28TM-CD28CYP-CD3ζCYP CAR
(includes leader) (2592H-CD28), SEQ ID NO: 227 METPAQLLFLLLLWLPDTTGQVQL
QESGPRLVKPSQTLSLTCTVSGGSISSDGYYWSWIRQHPGKGLEWIGYIYYSGSTFYNPSLKSRVAISVDT
SKNQFSLKLSSVTAADTAVYYCARESPHSSNWYSGFDCWGQGTLVTVSSGGGGSGGGGSGGGGSEIVLTQS
PDFQSVTPKEKVTITCRASQSIGSRLHWYQQKPDQSPKLLIKYASQSFSGVPSRFSGSGSGTDFTLTINSL
EAEDAATYYCHQSSNLPFTFGPGTKVDIKASVKGKHLCPSPLFPGPSKPFWVLVVVGGVLACYSLLVTVAF
IIFWVRSKRSRLLHSDYMNMTPRRPGPTRKHYQPYAPPRDFAAYRSKLRVKFSRSADAPAYQQGQNQLYNE
LNLGRREEYDVLDKRRGRDPEMGGKPQRRKNPQEGLYNELQKDKMAEAYSEIGMKGERRRGKGHDGLYQGL
STATKDTYDALHMQALPPR xxx. 2592H-CD28H-CD28TM-DAP10CYP-CD3ζCYP CAR (includes leader) 2592H-DAP10
228 Amino acid sequence of 2592H-CD28H-CD28TM-DAP10CYP-CD3ζCYP CAR
(includes leader) (2592H-DAP10), SEQ ID NO: 228 METPAQLLFLLLLWLPDTTGQVQ
LQESGPRLVKPSQTLSLTCTVSGGSISSDGYYWSWIRQHPGKGLEWIGYIYYSGSTFYNPSLKSRVAISVD
TSKNQFSLSGGGGSEIVLTQSPDFQSVTPKEKVTITCRASQSIGSRLHWYQQKPDQSPKLLIKYASQSFSG
VPSRFSGSGSGTDFTLTINSLEAEDAATYYCHQSSNLPFTFGPGTKVDIKASVKGKHLCPSPLFPGPSKPF
WVLVVVGGVLACYSLLVTVAFIIFWVLCARPRRSPAQEDGKVYINMPGRGKLRVKFSRSADAPAYQQGQNQ
LYNELNLGRREEYDVLDKRRGRDPEMGGKPQRRKNPQEGLYNELQKDKMAEAYSEIGMKGERRRGKGHDGL
YQGLSTATKDTYDALHMQALPPR xxxi. 2592L-CD28H-CD28TM-CD28CYP-CD3ζCYP CAR (includes leader) 2592L-CD28
229 Amino acid sequence of 2592H-CD28H-CD28TM-CD28CYP-CD3ζCYP CAR
(includes leader) (2592L-CD28), SEQ ID NO: 229 METPAQLLFLLLLWLPDTTGEIVL
TQSPDFQSVTPKEKVTITCRASQSIGSRLHWYQQKPDQSPKLLIKYASQSFSGVPSRFSGSGSGTDFTLTI
NSLEAEDAATYYCHQSSNLPFTFGPGTKVDIKGGGGSGGGGSGGGGSQVQLQESGPRLVKPSQTLSLTCTV
SGGSISSDGYYWSWIRQHPGKGLEWIGYIYYSGSTFYNPSLKSRVAISVDTSKNQFSLKLSSVTAADTAVY
YCARESPHSSNWYSGFDCWGQGTLVTVSSASVKGKHLCPSPLFPGPSKPFWVLVVVGGVLACYSLLVTVAF
IIFWVRSKRSRLLHSDYMNMTPRRPGPTRKHYQPYAPPRDFAAYRSKLRVKFSRSADAPAYQQGQNQLYNE
LNLGRREEYDVLDKRRGRDPEMGGKPQRRKNPQEGLYNELQKDKMAEAYSEIGMKGERRRGKGHDGLYQGL
STATKDTYDALHMQALPPR xxxii. signal peptide signal 230 Amino acid sequence of signal peptide
(signal), SEQ ID NO: 230 METPAQLLFLLLLWLPDTTG xxxiii. T2A ribosomal skip sequence T2A 231 Amino acid sequence of T2A
ribosomal skip sequence (T2A), SEQ ID NO: 231 GSGEGRGSLLTCGDVEENPGP xxxiv. Truncated CD19 tCD19 232 Amino acid sequence of Truncated CD19 (tCD19),
SEQ ID NO: 232 MPPPRLLFFLLFLTPMEVRPEEPLVVKVEEGDVANLQCLKGTSDGPTQQLTWSRES
PLKPFLKLSLGLPGLGIHMRPLAIWLFIFNVWQQMGGYFLCQPGPGPSEKAWGPGWTVNVEGSGELFRWNVS
DLGGLGCGLKNRSSEGPSSPSGKLMSPKLYVWAKDRPEIWEGEPPCLPPRDSLNQSLSQDLTMAPGSTLWL
SCGVPPDSVSRGPLSWTHVHPKGPKSLLSLELKDDRPARDMWVMETGLLLPRATAQDAGKYYCHRGNLTMS
FHLEITARPVLWHWLLRTGGWKVSAVTLAYLIFCLCSLVGILHLQRALVLRRKRKRMT xxxv. Ab 129 CDR H1 Ab129 CDR 1 233 Amino acid sequence of Ab 129 CDR H1
(Ab129 CDR 1), SEQ ID NO: 233 GGSVSSGGYY xxxvi. Ab 129 CDR H2 Ab129 CDR 2 234 Amino acid sequence of Ab 129 CDR H2
(Ab129 CDR 2), SEQ ID NO: 234 IYYTGST xxxvii. Ab 129 CDR H3 Ab129 CDR 3 235 Amino acid sequence of Ab 129 CDR H3
(Ab129 CDR 3, SEQ ID NO: 235 DYDWSFHFDY xxxviii. Ab 129 CDR L1 Ab129 CDR 4 236 Amino acid sequence of Ab 129 CDR L1
(Ab129 CDR 4), SEQ ID NO: 236 QGIRND -continued xxxix. Ab 129 CDR L2 Ab129 CDR 5 237 Amino acid sequence of Ab 129 CDR L2 (Ab129 CDR 5), SEQ ID NO: 237 AAS xl. Ab 129 CDR L3 Ab129 CDR 6 238 Amino acid sequence of Ab 129 CDR L3 (Ab129 CDR 6), SEQ ID NO: 238 LQHNSYP xli. Ab 272 CDR H1 Ab272 CDR 1 239 Amino acid sequence of Ab 272 CDR H1 (Ab272 CDR 1), SEQ ID NO: 239 GFIFSRYG xlii. Ab 272 CDR H2 Ab272 CDR 2 240 Amino acid sequence of Ab 272 CDR H2 (Ab272 CDR 2), SEQ ID NO: 240 IWYDGSNK xliii. Ab 272 CDR H3 Ab272 CDR 3 241 Amino acid sequence of Ab 272 CDR H3 (Ab272 CDR 3), SEQ ID NO: 241 DYYDNSRHHWGFDY xliv. Ab 272 CDR L1 Ab272 CDR 4 242 Amino acid sequence of Ab 272 CDR L1 (Ab272 CDR 4), SEQ ID NO: 242 RSSRSLLDSDDGNTYLD xlv. Ab 272 CDR L2 Ab272 CDR 5 243 Amino acid sequence of Ab 272 CDR L2 (Ab272 CDR 5), SEQ ID NO: 243 TLSYRAS xlvi. Ab 272 CDR L3 Ab272 CDR 6 244 Amino acid sequence of Ab 272 CDR L3 (Ab272 CDR 6), SEQ ID NO: 244 MQRVEFPIT xlvii. Ab 2592 CDR H1 Ab2592 CDR 1 245 Amino acid sequence of Ab 2592 CDR H1 (Ab2592 CDR 1), SEQ ID NO: 245 GGSISSDGY xlviii. Ab 2592 CDR H2 Ab2592 CDR 2 246 Amino acid sequence of Ab 2592 CDR H2 (Ab2592 CDR 2), SEQ ID NO: 246 IYYSGST xlix. Ab 2592 CDR H3 Ab2592 CDR 3 247 Amino acid sequence of Ab 2592 CDR H3 (Ab2592 CDR 3), SEQ ID NO: 247 ESPHSSNWYSGFDC l. Ab 2592 CDR L1 Ab2592 CDR 4 248 Amino acid sequence of Ab 2592 CDR L1 (Ab2592 CDR 4), SEQ ID NO: 248 QSIGSR li. Ab 2592 CDR L2 Ab2592 CDR 5 249 Amino acid sequence of Ab 2592 CDR L2 (Ab2592 CDR 5), SEQ ID NO: 249 YAS lii. Ab 2592 CDR L3 Ab2592 CDR 6 250 Amino acid sequence of Ab 2592 CDR L3 (Ab2592 CDR 6), SEQ ID NO: 250 HQSSNLPFT liii. Linker region subunit G4S 316 Nucleic acid sequence of Linker region subunit (G4S), SEQ ID NO: 316 GGTGGTGGTGGTTCT liv. Linker region G4S Linker 251 Nucleic acid sequence of Linker regino (G4S Linker), SEQ ID NO: 251 GGTGGTGGTGGTTCTGGCGGCGGCGGCTCCGGTGGTGGTGGT TCC lv. Ab 129 VH 129 VH 252 Nucleic acid sequence of Ab 129 VH (129 VH), SEQ ID NO: 252 CAGGTGCAGCTGCAGGAGTCGGGCCCAGGACTGGTGAAGACCCTGTC CCTCACCTGCACTGTCTCTGGTGGCTCCGTCAGCAGTGGTGGTTACTACTGGAGCTGGATCCGGACGGGGG CAGGGAAGGGACTGGAGTGGATTGGGTTTATCTATTACACTGGGAGCACCAACTACAACCCCTCCCTCAAG AGTCGAGTCTCCATATCAGTAGACACGTCCAAGAACCAGTTCTCCCTGAAGCTGAGCTCTGTGACCGCTGC GGACGCGGCCGTGTATTACTGTGCGAGAGATTATGACTGGAGCTTCCACTTTGACTACTGGGGCCAGGGAA CCCTGGTCACCGTCTCCTCA lvi. Ab 129 VL 129 VL 253 Nucleic acid sequence of Ab 129 VL (129 VL), SEQ ID NO: 253 GACATCCAGATGACCCAGTCTCCATCCTCCCTGTCTGCATCTATAGGAGACAGAGT CACCATCACTTGCCGGGCAAGTCAGGGCATTAGAAATGATTTAGGCTGGTATCAGCAGAAACCAGGGAAAG CCCCTAAGCGCCTGATCTATGCTGCATCCAGTTTGCAAAGTGGGGTCCCATCAAGGTTCAGCGGCAGTGGA TCTGGGACAGAATTCACTCTCACAATCAGCAGCCTGCAGCCTGAAGATTTTGCAACTTATTACTGTCTACA GCATAATAGTTACCCTCTCACTTTCGGCGGAGGGACCAAGGTGGAGATCAAA lvii. Ab 272 VH 272 VH 254 Nucleic acid sequence of Ab 272 VH (272 VH), SEQ ID NO: 254 CAGGTGCAGCTGGTGGAGTCTGGGGGAGGCGTGGTCCAGCCTGGGAGGTCCCTGAG ACTCTCCTGTGCAGCGTCTGGATTCATCTTCAGTCGCTATGGCATGCACTGGGTCCGCCAGGCTCCAGGCA AGGGGCTGAAATGGGTGGCAGTTATATGGTATGATGGAAGTAATAAACTCTATGCAGACTCCGTGAAGGGC CGATTCACCATCTCCAGAGACAATTCCAAGAACACGCTGTATCTGCAAATGAACAGCCTGAGAGCCGAGGA CACGGCTGTGTATTACTGTGCGAGAGATTACTATGATAATAGTAGACATCACTGGGGGTTTGACTACTGGG GCCAGGGAACCCTGGTCACCGTCTCCTCA lviii. Ab 272 VL 272 VL 255 Nucleic acid sequence of Ab 272 VL (272 VL), SEQ ID NO: 255 GATATTGTGATGACCCAGACTCCACTCTCCCTGCCCGTCACCCCTG-
GAGAGCCGGC
CTCCATCTCCTGCAGGTCTAGTCGGAGCCTCTTGGATAGTGATGATGGAAACACCTATTTGGACTGGTACC TGCAGAAGCCAGGGCAGTCTCCACAGCTCCTGATCTACACGCTTTCCTATCGGGCCTCTGGAGTCCCAGAC AGGTTCAGTGGCAGTGGGTCAGGCACTGATTTCACACTGAAAATCAGCAGGGTGGAGGCTGAGGATGTTGG AGTTTATTACTGCATGCAACGTGTAGAGTTTCCTATCACCTTCGGCCAAGGGACACGACTGGAGATTAAA -continued lix. Ab 2592 VH 2592 VH 256 Nucleic acid sequence of Ab 2592 VH (2592 VH),
SEQ ID NO: 256 CAGGTGCAGCTGCAGGAGTCGGGCCCAAGACTGGTGAAGCCTTCACAGACCCTGTC
CCTCACCTGCACTGTCTCTGGTGGCTCCATCAGTAGTGATGGTTACTACTGGAGCTGGATCCGCCAGCACC
CAGGGAAGGGCCTGGAGTGGATTGGGTACATCTATTACAGTGGGAGCACCTTCTACAACCCGTCCCTCAAG
AGTCGAGTTGCCATATCAGTGGACACGTCTAAGAACCAGTTCTCCCTGAAGCTGAGCTCTGTGACTGCCGC
GGACACGGCCGTGTATTACTGTGCGAGAGAATCCCCTCATAGCAGCAACTGGTACTCGGGCTTTGACTGCT
GGGGCCAGGGAACCCTGGTCACCGTCTCCTCA lx. Ab 2592 VL 2592 VH 257 Nucleic acid sequence of Ab 2592 VL (2592 VL),
SEQ ID NO: 257 GAAATTGTGCTGACTCAGTCTCCAGACTTTCAGTCTGTGACTC-
CAAAGGAGAAAGT
CACCATCACCTGCCGGGCCAGTCAGAGCATTGGTAGTAGGTTACACTGGTACCAGCAGAAACCAGATCAGT
CTCCAAAGCTCCTCATCAAGTATGCTTCCCAGTCCTTCTCAGGGGTCCCCTCGAGGTTCAGTGGCAGTGGA
TCTGGGACAGATTTCACCCTCACCATCAATAGCCTGGAAGCTGAAGATGCTGCAACGTATTACTGTCATCA
GAGTAGTAATTTACCATTCACTTTCGGCCCTGGGACCAAAGTGGATATCAAA lxi. 129 hv-linker-lv 129H 258 Nucleic acid sequence of 129 hv-linker-lv
(129H), SEQ ID NO: 258 CAGGTGCAGCTGCAGAGTCGGGCCCAGGACTGGTGAAGCCTTCGGAGA
CCCTGTCCCTCACCTGCACTGTCTCTGGTGGCTCCGTCAGCAGTGGTGGTTACTACTGGAGCTGGATCCGG
CAGCCCCCAGGGAAGGGACTGGAGTGGATTGGGTTTATCTATTACACTGGGAGCACCAACTACAACCCCTC
CCTCAAGAGTCGAGTCTCCATATCAGTAGACACGTCCAAGAACCAGTTCTCCCTGAAGCTGAGCTCTGTGA
CCGCTGCGGACGCGGCCGTGTATTACTGTGCGAGAGATTATGACTGGAGCTTCCACTTTGACTACTGGGGC
CAGGGAACCCTGGTCACCGTCTCCTCAGGTGGTGGTGGTTCGGCGGCGGCGGCTCCGGTGGTGGTGGTTC
CGACATCCAGATGACCCAGTCTCCATCCTCCCTGTCTGCATCTATAGGAGACAGAGTCACCATCACTTGCC
GGGCAAGTCAGGGCATTAGAAATGATTTAGGCTGGTATCAGCAGAAACCAGGGAAAGCCCCTAAGCGCCTG
ATCTATGCTGCATCCAGTTTGCAAAGTGGGGTCCCATCAAGGTTCAGCGGCAGTGGATCTGGGACAGAATT
CACTCTCACAATCAGCAGCCTGCAGCCTGAAGATTTTGCAACTTATTACTGTCTACAGCATAATAGTTACC
CTCTCACTTTCGGCGGAGGGACCAAGGTGGAGATCAAA lxii. 129 lv-linker-hv 129L 259 Nucleic acid sequence of 129 lv-linker-hv
(129L), SEQ ID NO: 259 GACATCCAGATGACCCAGTCTCCATCCTCCCTGTCTGCATCTATAGGA
GACAGAGTCACCATCACTTGCCGGGCAAGTCAGGGCATTAGAAATGATTTAGGCTGGTATCAGCAGAAACC
AGGGAAAGCCCCTAAGCGCCTGATCTATGCTGCATCCAGTTTGCAAAGTGGGGTCCCATCAAGGTTCAGCG
GCAGTGGATCTGGGACAGAATTCACTCTCACAATCAGCAGCCTGCAGCCTGAAGATTTTGCAACTTATTAC
TGTCTACAGCATAATAGTTACCCTCTCACTTTCGGCGGAGGGACCAAGGTGGAGATCAAAGGTGGTGGTGG
TTCTGGCGGCGGCGGCTCCGGTGGTGGTGGTTCCCAGGTGCAGCTGCAGGAGTCGGGCCCAGGACTGGTGA
AGCCTTCGGAGACCCTGTCCCTCACCTGCACTGTCTCTGGTGGCTCCGTCAGCAGTGGTGGTTACTACTGG
AGCTGGATCCGGCAGCCCCCAGGGAAGGGACTGGAGTGGATTGGGTTTATCTATTACACTGGGAGCACCAA
CTACAACCCCTCCCTCAAGAGTCGAGTCTCCATATCAGTAGACACGTCCAAGAACCAGTTCTCCCTGAAGC
TCTGTGACCGCTGCGGACGCGGCCGTGTATTACTGTGCGAGAGATTATGACTGGAGCTTCCACTTTGACTA
CTGGGGCCAGGGAACCCTGGTCACCGTCTCCTCA lxiii. 272 hv-linker-lv 272H 260 Nucleic acid sequence of 272 hv-linker-lv
(272H), SEQ ID NO: 260 CAGGTGCAGCTGGTGGAGTCTGGGGGAGGCGTGGTCCAGCCTGGGAGG
TCCCTGAGACTCTCCTGTGCAGCGTCTGGATTCATCTTCAGTCGCTATGGCATGCACTGGGTCCGCCAGGC
TCCAGGCAAGGGCTGAAATGGGTGGCAGTTATATGTATGATGGAAGTAATAAACTCTATGCAGACTCCGT
GAAGGGCCGATTCACCATCTCCAGAGACAATTCCAAGAACACGCTGTATCTGCAAATGAACAGCCTGAGAG
CCGAGGACACGGCTGTGTATTACTGTGCGAGAGATTACTATGATAATAGTAGACATCACTGGGGGTTTGAC
TACTGGGGCCAGGGAACCCTGGTCACCGTCTCCTCAGGTGGTGGTGGTTCTGGCGGCGGCGGCTCCGGTGG
TGGTGGTTCCGATATTGTGATGACCCAGACTCCACTCTCCCTGCCCGTCACCCCTGGAGAGCCGGCCTCCA
TCTCCTGCAGGTCTAGTCGGAGCCTCTTGGATAGTGATGATGGAAACACCTATTTGGACTGGTACCTGCAG
AAGCCAGGGCAGTCTCCACAGCTCCTGATCTACACGCTTTCCTATCGGGCCTCTGGAGTCCCAGACAGGTT
CAGTGGCAGTGGGTCAGGCACTGATTTCACACTGAAAATCAGCAGGGTGGAGGCTGAGAGGATGTTGGAGT
TTATTACTGCATGCAACGTGTAGAGTTTCCTATCACCTTCGGCCAAGGGACACGACTGGAGATTAAA lxiv. 272 lv-linker-hv 272L 261 Nucleic acid sequence of 272 lv-linker-hv
(272L), SEQ ID NO: 261 GATATTGTGATGACCCAGACTCCACTCTCCCTGCCCGTCACCCCTGGA
GAGCCGGCCTCCATCTCCTGCAGGTCTAGTCGGAGCCTCTTGGATAGTGATGATGGAAACACCTATTTGGA
CTGGTACCTGCAGAAGCCAGGGCAGTCTCCACAGCTCCTGATCTACACGCTTTCCTATCGGGCCTCTGGAG
TCCCAGACAGGTTCAGTGGCAGTGGGTCAGGCACTGATTTCACACTGAAAATCAGCACAGGTTCAGTGGC
AGTGGGTCAGGCACTGATTTCACACTGAAAATCAGCAGGGTGGAGGCTGAGGATGTTGGAGTTTATTACTG
CATGCAACGTGTAGAGTTTCCTATCACCTTCGGCCAAGGGACACGACTGGAGATTAAAGGTGGTGGTGGTT
CTGGCGGCGGCGGCTCCGGTGGTGGTGGTTCCCAGGTGCAGCTGGTGGAGTCTGGGGGAGGCGTGGTCCAG
CCTGGGAGGTCCCTGAGACTCTCCTGTGCAGCGTCTGGATTCATCTTCAGTCGCTATGGCATGCACTGGGT
CCGCCAGGCTCCAGGCAAGGGGCTGAAATGGGTGGCAGTTATATGTATGATGGAAGTAATAAACTCTATG
CAGACTCCGTGAAGGGCCGATTCACCATCTCCAGAGACAATTCCAAGAACACGCTGTATCTGCAAATGAAC
AGCCTGAGAGCCGAGGACACGGCTGTGTATTACTGTGCGAGAGATTACTATGATAATAGTAGACATCACTG
GGGGTTTGACTACTGGGGCCAGGGAACCCTGGTCACCGTCTCCTCA lxv. 2592 hv-linker-lv 259H 262 Nucleic acid sequence of 2592 hv-linker-lv
(2592H), SEQ ID NO: 262 CAGGTGCAGCTGCAGGAGTCGGGCCCAAGACTGGTGAAGCCTTCACA
GACCCTGTCCCTCACCTGCACTGTCTCTGGTGGCTCCATCAGTAGTGATGGTTACTACTGGAGCTGGATCC
GCCAGCACCCAGGGAAGGGCCTGGAGTGGATTGGGTACATCTATTACAGTGGGAGCACCTTCTACAACCCG
TCCCTCAAGAGTCGAGTTGCCATATCAGTGGACACGTCTAAGAACCAGTTCTCCCTGAAGCTGAGCTCTGT
GACTGCCGCGGACACGGCCGTGTATTACTGTGCGAGAGAATCCCTCATAGCAGCAACTGGTACTCGGGCT
TTGACTGCTGGGGCCAGGGAACCCTGGTCACCGTCTCCTCAGGTGGTGGTGGTTCTGGCGGCGGCGGCTCC
GGTGGTGGTGGTTCCGAAATTGTGCTGACTCAGTCTCCAGACTTTCAGTCTGTGACTCCAAAGGAGAAAGT
CACCATCACCTGCCGGGCCAGTCAGAGCATTGGTAGTAGGTTACACTGGTACCAGCAGAAACCAGATCAGT
CTCCAAAGCTCCTCATCAAGTATGCTTCCCAGTCCTTCTCAGGGGTCCCCTCGAGGTTCAGTGGCAGTGGA
TCTGGGACAGATTTCACCCTCACCATCAATAGCCTGGAAGCTGAAGATGCTGCAACGTATTACTGTCATCA
GAGTAGTAATTTACCATTCACTTTCGGCCCTGGGACCAAAGTGGATATCAAA -continued lxvi. 2592 lv-linker-hv 259L 263 Nucleic acid sequence of 2592 lv-linker-hv
(2592L), SEQ ID NO: 263 GAAATTGTGCTGACTCAGTCTCCAGACTTTCAGTCTGTGACTCCAAA
GGAGAAAGTCACCATCACCTGCCGGGCCAGTCAGAGCATTGGTAGTAGGTTACACTGGTACCAGCAGAAAC
CAGATCAGTCTCCAAAGCTCCTCATCAAGTATGCTTCCCAGTCCTTCTCAGGGGTCCCCTCGAGGTTCAGT
GGCAGTGGATCTGGGACAGATTTCACCCTCACCATCAATAGCCTGGAAGCTGAAGATGCTGCAACGTATTA
CTGTCATCAGAGTAGTAATTTACCATTCACTTTCGGCCCTGGGACCAAAGTGGATATCAAAGGTGGTGGTG
GTTCTGGCGGCGGCGGCTCCGGTGGTGGTGGTTCCCAGGTGCAGCTGCAGGAGTCGGGCCCAAGACTGGTG
AAGCCTTCACAGACCCTGTCCCTCACCTGCACTGTCTCTGGTGGCTCCATCAGTAGTGATGGTTACTACTG
GAGCTGGATCCGCCAGCACCCAGGGAAGGGCCTGGAGTGGATTGGGTACATCTATTACAGTGGGAGCACCT
TCTACAACCCGTCCCTCAAGAGTCGAGTTGCCATATCAGTGGACACGTCTAAGAACCAGTTCTCCCTGAAG
CTGAGCTCTGTGACTGCCGCGGACACGGCCGTGTATTACTGTGCGAGAGAATCCCCTCATAGCAGCAACTG
GTACTCGGGCTTTGACTGCTGGGGCCAGGGAACCCTGGTCACCGTCTCCTCA lxvii. CD28 hinge domain CD28H 264 Nucleic acid sequence of CD28 hinge domain
(CD28H), SEQ ID NO: 264 GTGAAAGGGAAACACCTTTGTCCAAGTCCCCTATTTCCCGGACCTTC
TAAGCCC lxviii. CD28 transmembrane domain CD28TM 265 Nucleic acid sequence of CD28
transmembrane domain (CD28TM), SEQ ID NO: 265 TTTTGGGTGCTGGTGGTGGTTGGTG
GAGTCCTGGCTTGCTATAGCTTGCTAGTAACAGTGGCCTTTATTATTTTCTGGGTG lxix. 4-1BB costimulatorydomain BBCYP 266 Nucleic acid sequence of 4-1BB
costimulatorydomain (BBCYP), SEQ ID NO: 266 AAACGGGGCAGAAAGAAACTCCTGTAT
ATATTCAAACAACCATTTATGAGACCAGTACAAACTACTCAAGAGGAAGATGGCTGTAGCTGCCGATTTCC
AGAAGAAGAAGAAGGAGGATGTGAACTG lxx. CD28 costimulatorydomain CD28CYP 267 Nucleic acid sequence of CD28
costim domain (CD28CYP), SEQ ID NO: 267 AGGAGTAAGAGGAGCAGGCTCCTGCACAGTG
ACTACATGAACATGACTCCCCGCCGCCCGGGCCCACCCGCAAGCATTACCAGCCCTATGCCCCACCACGC
GACTTCGCAGCCTATCGCTCC lxxi. DAP10 costimulatory domainDAP10CYP 268 Nucleic acid sequence of DAP10
costimulatory domain (DAP10CYP), SEQ ID NO: 268 CTGTGCGCACGCCCACGCCGCAG
CCCCGCCCAAGAAGATGGCAAAGTCTACATCAACATGCCAGGCAGGGGC lxxii. CD3zeta intracellular domain CD3ζCYP 269 Nucleic acid sequence of
CD3zeta intracellular domein (CD3ζCYP), SEQ ID NO: 269 CTTAGAGTGAAGTTCA
GCAGGAGCGCAGACGCCCCCGCGTACCAGCAGGGCCAGAACCAGCTCTATAACGAGCTCAATCTAGGACGA
AGAGAGGAGTACGATGTTTTGGACAAGAGACGTGGCCGGGACCCTGAGATGGGGGGAAAGCCGCAGAGAAG
GAAGAACCCTCAGGAAGGCCTGTACAATGAACTGCAGAAAGATAAGATGGCGGAGGCCTACAGTGAGATTG
GGATGAAAGGCGAGCGCCGGAGGGGCAAGGGGCACGATGGCCTTTACCAGGGTCTCAGTACAGCCACCAAG
GACACCTACGACGCCCTTCACATGCAGGCCCTGCCCCCTCGC lxxiii. 129H-CD28H-CD28TM-CD28CYP-CD3ζCYP CAR (includes leader) 129H-CD28 270
Nucleic acid sequence of 129H-CD28H-CD28TM-CD28CYP-CD3ζCYP CAR
(includes leader) (129H-CD28), SEQ ID NO: 270 ATGGAAACCCCAGCGCAGCTTCTCT
TCCTCCTGCTACTCTGGCTCCCAGATACCACCGGACAGGTGCAGCTGCAGGAGTCGGGCCCAGGACTGGTG
AAGCCTTCGGAGACCCTGTCCCTCACCTGCACTGTCTCTGGTGGCTCCGTCAGCAGTGGTGGTTACTACTG
GAGCTGGATCCGGCAGCCCCCAGGGAAGGGACTGGAGTGGATTGGGTTTATCTATTACACTGGGAGCACCA
ACTACAACCCCTCCCTCAAGAGTCGAGTCTCCATATCAGTAGACACGTCCAAGAACCAGTTCTCCCTGAAG
CTGAGCTCTGTGACCGCTGCGGACGCGGCCGTGTATTACTGTGCGAGAGATTATGACTGGAGCTTCCACTT
TGACTACTGGGGCCAGGGAACCCTGGTCACCGTCTCCTCAGGTGGTGGTGGTTCTGGCGGCGGCGGCTCCG
GTGGTGGTGGTTCCGACATCCAGATGACCCAGTCTCCATCCTCCCTGTCTGCATCTATAGGAGACAGAGTC
ACCATCACTTGCCGGGCAAGTCAGGGCATTAGAAATGATTTAGGCTGGTATCAGCAGAAACCAGGGAAAGC
CCCTAAGCGCCTGATCTATGCTGCATCCAGTTTGCAAAGTGGGGTCCCATCAAGGTTCAGCGGCAGTGGAT
CTGGGACAGAATTCACTCTCACAATCAGCAGCCTGCAGCCTGAAGATTTTGCAACTTATTACTGTCTACAG
CATAATAGTTACCCTCTCACTTTCGGCGAGGGACCAAGGTGGAGATCAAAGCTAGCGTGAAAGGGAAACA
CCTTTGTCCAAGTCCCCTATTTCCCGGACCTTCTAAGCCCTTTGGGTGCTGGTGGTGGTTGGTGGAGTCC
TGGCTTGCTATAGCTTGCTAGTAACAGTGGCCTTTATTATTTTCTGGGTGAGGAGTAAGAGGAGCAGGCTC
CTGCACAGTGACTACATGAACATGACTCCCCGCCGCCCGGGCCCACCCGCAAGCATTACCAGCCCTATGC
CCCACCACGCGACTTCGCAGCCTATCGCTCCAAGCTTAGAGTGAAGTTCAGCAGGAGCGCAGACGCCCCCG
CGTACCAGCAGGGCCAGAACCAGCTCTATAACGAGCTCAATCTAGGACGAAGAGAGGAGTACGATGTTTTG
GACAAGAGACGTGGCCGGGACCCTGAGATGGGGGGAAAGCCGCAGAGAAGGAAGAACCCTCAGGAAGGCCT
GTACAATGAACTGCAGAAAGATAAGATGGCGGAGGCCTACAGTGAGATTGGGATGAAAGGCGAGCGCCGGA
GGGGCAAGGGGCACGATGGCCTTTACCAGGGTCTCAGTACAGCCACCAAGGACACCTACGACGCCCTTCAC
ATGCAGGCCCTGCCCCCTCGCTAA lxxiv. 129L-CD28H-CD28TM-CD28CYP-CD3ζCYP CAR (includes leader) 129L-CD28 271
Nucleic acid sequence of 129L-CD28H-CD28TM-CD28CYP-CD3ζCYP CAR
(includes leader) (129L-CD28), SEQ ID NO: 271 ATGGAAACCCCAGCGCAGCTTCTCT
TCCTCCTGCTACTCTGGCTCCCAGATACCACCGGAGACATCCAGATGACCCAGTCTCCATCCTCCCTGTCT
GCATCTATAGGAGACAGAGTCACCATCACTTGCCGGGCAAGTCAGGGCATTAGAAATGATTTAGGCTGGTA
TCAGCAGAAACCAGGGAAAGCCCCTAAGCGCCTGATCTATGCTGCATCCAGTTTGCAAAGTGGGGTCCCAT
CAAGGTTCAGCGGCAGTGGATCTGGGACAGAATTCACTCTCACAATCAGCAGCCTGCAGCCTGAAGATTTT
GCAACTTATTACTGTCTACAGCATAATAGTTACCCTCTCACTTTCGGCGAGGGACCAAGGTGGAGATCAA
AGGTGGTGGTGGTTCTGGCGGCGGCGGCTCCGGTGGTGGTGGTTCCCAGGTGCAGCTGCAGGAGTCGGGCC
CAGGACTGGTGAAGCCTTCGGAGACCCTGTCCCTCACCTGCACTGTCTCTGGTGGCTCCGTCAGCAGTGGT
GGTTACTACTGGAGCTGGATCCGGCAGCCCCCAGGGAAGGGACTGGAGTGGATTGGGTTTATCTATTACAC
TGGGAGCACCAACTACAACCCCTCCCTCAAGAGTCGAGTCTCCATATCAGTAGACACGTCCAAGAACCAGT
TCTCCCTGAAGCTGAGCTCTGTGACCGCTGCGGACGCGGCCGTGTATTACTGTGCGAGAGATTATGACTGG -continued
AGCTTCCACTTTGACTACTGGGGCCAGGGAACCCTGGTCACCGTCTCCTCAGCTAGCGTGAAAGGGAAACA
CCTTTGTCCAAGTCCCCTATTTCCCGGACCTTCTAAGCCCTTTTGGGTGCTGGTGGTGGTTGGTGGAGTCC
TGGCTTGCTATAGCTTGCTAGTAACAGTGGCCTTTATTATTTTCTGGGTGAGGAGTAAGAGGAGCAGGCTC
CTGCACAGTGACTACATGAACATGACTCCCCGCCGCCCCGGGCCCACCCGCAAGCATTACCAGCCCTATGC
CCCACCACGCGACTTCGCAGCCTATCGCTCCAAGCTTAGAGTGAAGTTCAGCAGGAGCGCAGACGCCCCCG
CGTACCAGCAGGGCCAGAACCAGCTCTATAACGAGCTCAATCTAGGACGAAGAGAGGAGTACGATGTTTTG
GACAAGAGACGTGGCCGGGACCCTGAGATGGGGGAAAGCCGCAGAGAAGGAAGAACCCTCAGGAAGGCCT
GTACAATGAACTGCAGAAAGATAAGATGGCGGAGGCCTACAGTGAGATTGGGATGAAAGGCGAGCGCCGGA
GGGCAAGGGGCACGATGGCCTTTACCAGGGTCTCAGTACAGCCACCAAGGACACCTACGACGCCCTTCACA
TGCAGGCCCTGCCCCCTCGCTAA lxxv. 272H-CD28H-CD28TM-BBCYP-CD3ζCYP CAR (includes leader) 272H-BB 272
Nucleic acid sequence of 272H-CD28H-CD28TM-BBCYP-CD3ζCYP CAR
(includes leader) (272H-BB), SEQ ID NO: 272 ATGGAAACCCCAGCGCAGCTTCTCTTC
CTCCTGCTACTCTGGCTCCCAGATACCACCGGACAGGTGCAGCTGGTGGAGTCTGGGGGAGGCGTGGTCCA
GCCTGGGAGGTCCCTGAGACTCTCCTGTGCAGCGTCTGGATTCATCTTCAGTCGCTATGGCATGCACTGGG
TCCGCCAGGCTCCAGGCAAGGGGCTGAAATGGGTGGCAGTTATATGGTATGATGGAAGTAATAAACTCTAT
GCAGACTCCGTGAAGGGCCGATTCACCATCTCCAGAGACAATTCCAAGAACACGCTGTATCTGCAAATGAA
CAGCCTGAGAGCCGAGGACACGGCTGTGTATTACTGTGCGAGAGATTACTATGATAATAGTAGACATCACT
GGGGGTTTGACTACTGGGGCCAGGGAACCCTGGCTCACCGTCTCCTCAGGTGGTGGTGGTTCTGGCGGCGG
CGGCTCCGGTGGTGGTGGTTCCGATATTGTGATGACCCAGACTCCACTCTCCCTGCCCGTCACCCCTGGAG
AGCCGGCCTCCATCTCCTGCAGGTCTAGTCGGAGCCTCTTGGATAGTGATGATGGAAACACCTATTTGGAC
TGGTACCTGCAGAAGCCAGGGCAGTCTCCACAGCTCCTGATCTACACGCTTTCCTATCGGGCCTCTGGAGT
CCCAGACAGGTTCAGTGGCAGTGGGTCAGGCACTGATTTCACACTGAAAATCAGCAGGGTGGAGGCTGAGG
ATGTTGGAGTTTATTACTGCATGCAACGTGTAGAGTTTCCTATCACCTTCGGCCAAGGGACACGACTGGAG
ATTAAACTCGAGGTGAAAGGGAAACACCTTTGTCCAAGTCCCCTATTTCCCGGACCTTCTAAGCCCTTTTG
GGTGCTGGTGGTGGTTGGTGGAGTCCTGGCTTGCTATAGCTTGCTAGTAACAGTGGCCTTTATTATTTTCT
GGGTGAAACGGGGCAGAAAGAAACTCCTGTATATATTCAAACAACCATTTATGAGACCAGTACAAACTACT
CAAGAGGAAGATGGCTGTAGCTGCCGATTTCCAGAAGAAGAAGAAGGAGGATGTGAACTGAAGCTTAGAGT
GAAGTTCAGCAGGAGCGCAGACGCCCCCGCGTACCAGCAGGGCCAGAACCAGCTCTATAACGAGCTCAATC
TAGGACGAAGAGAGGAGTACGATGTTTTGGACAAGAGACGTGGCCGGGACCCTGAGATGGGGGAAAGCCG
CAGAGAAGGAAGAACCCTCAGGAAGGCCTGTACAATGAACTGCAGAAAGATAAGATGGCGGAGGCCTACAG
TGAGATTGGGATGAAAGGCGAGCGCCGGAGGGGCAAGGGGCACGATGGCCTTTACCAGGGTCTCAGTACAG
CCACCAAGGACACCTACGACGCCCTTCACATGCAGGCCCTGCCCCCTCGC lxxvi. 272H-CD28H-CD28TM-CD28CYP-CD3ζCYP CAR (includes leader) 272H-CD28 273
Nucleic acid sequence of 272H-CD28H-CD28TM-CD28CYP-CD3ζCYP CAR
(includes leader) (272H-CD28), SEQ ID NO: 273 ATGGAAACCCCAGCGCAGCTTCTCT
TCCTCCTGCTACTCTGGCTCCCAGATACCACCGGACAGGTGCAGCTGGTGGAGTCTGGGGGAGGCGTGGTC
CAGCCTGGGAGGTCCCTGAGACTCTCCTGTGCAGCGTCTGGATTCATCTTCAGTCGCTATGGCATGCACTG
GGTCCGCCAGGCTCCAGGCAAGGGGCTGAAATGGGTGGCAGTTATATGGTATGATGGAAGTAATAAACTCT
ATGCAGACTCCGTGAAGGGCCGATTCACCATCTCCAGAGACAATTCCAAGAACACGCTGTATCTGCAAATG
AACAGCCTGAGAGCCGAGGACACGGCTGTGTATTACTGTGCGAGAGATTACTATGATAATAGTAGACATCA
CTGGGGGTTTGACTACTGGGGCCAGGGAACCCTGGTCACCGTCTCCTCAGGTGGTGGTGGTTCTGGCGGCG
GCGGCTCCGGTGGTGGTGGTTCCGATATTGTGATGACCCAGACTCCACTCTCCCTGCCCGTCACCCCTGGA
GAGCCGGCCTCCATCTCCTGCAGGTCTAGTCGGAGCCTCTTGGATAGTGATGATGGAAACACCTATTTGGA
CTGGTACCTGCAGAAGCCAGGGCAGTCTCCACAGCTCCTGATCTACACGCTTTCCTATCGGGCCTCTGGAG
TCCCAGACAGGTTCAGTGGCAGTGGGTCAGGCACTGATTTCACACTGAAAATCAGCAGGGTGGAGGCTGAG
GATGTTGGAGTTTATTACTGCATGCAACGTGTAGAGTTTCCTATCACCTTCGGCCAAGGGACACGACTGGA
GATTAAACTCGAGGTGAAAGGGAAACACCTTTGTCCAAGTCCCCTATTTCCCGGACCTTCTAAGCCCTTTT
GGGTGCTGGTGGTGGTTGGTGGAGTCCTGGCTTGCTATAGCTTGCTAGTAACAGTGGCCTTTATTATTTTCT
GGGTGAGGAGTAAGAGGAGCAGGCTCCTGCACAGTGACTACATGAACATGACTCCCCGCCGCCCCGGGCC
CACCCGCAAGCATTACCAGCCCTATGCCCCACCACGCGACTTCGCAGCCTATCGCTCCAAGCTTAGAGTGA
AGTTCAGCAGGAGCGCAGACGCCCCCGCGTACCAGCAGGGCCAGAACCAGCTCTATAACGAGCTCAATCTA
GGACGAAGAGAGGAGTACGATGTTTTGGACAAGAGACGTGGCCGGGACCCTGAGATGGGGGAAAGCCGCA
GAGAAGGAAGAACCCTCAGGAAGGCCTGTACAATGAACTGCAGAAAGATAAGATGGCGGAGGCCTACAGTG
AGATTGGGATGAAAGGCGAGCGCCGGAGGGGCAAGGGGCACGATGGCCTTTACCAGGGTCTCAGTACAGCC
ACCAAGGACACCTACGACGCCCTTCACATGCAGGCCCTGCCCCCTCGC lxxvii. 272H-CD28H-CD28TM-DAP10CYP-CD3ζCYP CAR (includes leader) 272H-DAP10
274 Nucleic acid sequence of 272H-CD28H-CD28TM-DAP10CYP-CD3ζCYP CAR
(includes leader) (272H-DAP10), SEQ ID NO: 274 ATGGAAACCCCAGCGCAGCTTCTC
TTCCTCCTGCTACTCTGGC TCCCAGATACCACCGGACAGGTGCAGCTGGTGGAGTCTGGGGGAGGCGTGG
TCCAGCCTGGGAGGTCCCTGAGACTCTCCTGTGCAGCGTCTGGATTCATCTTCAGTCGCTATGGCATGCAC
TGGGTCCGCCAGGCTCCAGGCAAGGGGCTGAAATGGGTGGCAGTTATATGGTATGATGGAAGTAATAAACT
CTATGCAGACTCCGTGAAGGGCCGATTCACCATCTCCAGAGACAATTCCAAGAACACGCTGTATCTGCAAA
TGAACAGCCTGAGAGCCGAGGACACGGCTGTGTATTACTGTGCGAGAGATTACTATGATAATAGTAGACAT
CACTGGGGGTTTGACTACTGGGGCCAGGGAACCCTGGTCACCGTCTCCTCAGGTGGTGGTGGTTCTGGCGG
CGGCGGCTCCGGTGGTGGTGGTTCCGATATTGTGATGACCCAGACTCCACTCTCCCTGCCCGTCACCCCTG
GAGAGCCGGCCTCCATCTCCTGCAGGTCTAGTCGGAGCCTCTTGGATAGTGATGATGGAAACACCTATTTG
GACTGGTACCTGCAGAAGCCAGGGCAGTCTCCACAGCTCCTGATCTACACGCTTTCCTATCGGGCCTCTGG
AGTCCCAGACAGGTTCAGTGGCAGTGGGTCAGGCACTGATTTCACACTGAAAATCAGCAGGGTGGAGGCTG
AGGATGTTGGAGTTTATTACTGCATGCAACGTGTAGAGTTTCCTATCACCTTCGGCCAAGGGACACGACTG
GAGATTAAACTCGAGGTGAAAGGGAAACACCTTTGTCCAAGTCCCCTATTTCCCGGACCTTCTAAGCCCTT
TTGGGTGCTGGTGGTGGTTGGTGGAGTCCTGGCTTGCTATAGCTTGCTAGTAACAGTGGCCTTTATTATTT
TCTGGGTAGCTGTCGCACGCCCACGCCGCAGCCCCGCCAAGAAGATGGCAAAGTCTACATCAACATGCCA
GGCAGGGGCAAGCTTAGAGTGAAGTTCAGCAGGAGCGCAGACGCCCCCGCGTACCAGCAGGGCCAGAACCA
GCTCTATAACGAGCTCAATCTAGGACGAAGAGAGGAGTACGATGTTTTGGACAAGAGACGTGGCCGGGACC
CTGAGATGGGGGAAAGCCGCAGAGAAGGAAGAACCCTCAGGAAGGCCTGTACAATGAACTGCAGAAAGAT
AAGATGGCGGAGGCCTACAGTGAGATTGGGATGAAAGGCGAGCGCCGGAGGGGCAAGGGGCACGATGGCCT
TTACCAGGGTCTCAGTACAGCCACCAAGGACACCTACGACGCCCTTCACATGCAGGCCCTGCCCCCTCGC -continued lxxviii. 272L-CD28H-CD28TM-CD28CYP-CD3ζCYP CAR (includes leader) 272L-CD28
275 Nucleic acid sequence of 272L-CD28H-CD28TM-CD28CYP-CD3ζCYP CAR
(includes leader) (272L-CD28), SEQ ID NO: 275 ATGGAAACCCCAGCGCAGCTTCTCT
TCCTCCTGCTACTCTGGCTCCCAGATACCACCGGAGATATTGTGATGACCCAGACTCCACTCTCCCTGCCC
GTCACCCCTGGAGAGCCGGCCTCCATCTCCTGCAGGTCTAGTCGGAGCCTCTTGGATAGTGATGATGGAAA
CACCTATTTGGACTGGTACCTGCAGAAGCCAGGGCAGTCTCCACAGCTCCTGATCTACACGCTTTCCTATC
GGGCCTCTGGAGTCCCAGACAGGTTCAGTGGCAGTGGGTCAGGCACTGATTTCACACTGAAAATCAGCAGG
GTGGAGGCTGAGGATGTTGGAGTTTATTACTGCATGCAACGTGTAGAGTTTCCTATCACCTTCGGCCAAGG
GACACGACTGGAGATTAAAGGTGGTGGTGGTTCTGGCGGCGGCGGCTCCGGTGGTGGTGGTTCCCAGGTGC
AGCTGGTGGAGTCTGGGGGAGGCGTGGTCCAGCCTGGGAGGTCCCTGAGACTCTCCTGTGCAGCGTCTGGA
TTCATCTTCAGTCGCTATGGCATGCACTGGGTCCGCCAGGCTCCAGGCAAGGGGCTGAAATGGGTGGCAGT
TATATGGTATGATGGAAGTAATAAACTCTATGCAGACTCCGTGAAGGGCCGATTCACCATCTCCAGAGACA
ATTCCAAGAACACGCTGTATCTGCAAATGAACAGCCTGAGAGCCGAGGACACGGCTGTGTATTACTGTGCG
AGAGATTACTATGATAATAGTAGACATCACTGGGGGTTTGACTACTGGGGCCAGGGAACCCTGGTCACCGT
CTCCTCACTCGAGGTGAAAGGGAAACACCTTTGTCCAAGTCCCCTATTTCCCGGACCTTCTAAGCCCTTTT
GGGTGCTGGTGGTGGTTGGTGGAGTCCTGGCTTGCTATAGCTTGCTAGTAACAGTGGCCTTTATTATTTTC
TGGGTGAGGAGTAAGAGGAGCAGGCTCCTGCACAGTGACTACATGAACATGACTCCCCGCCGCCCCGGGCC
CACCCGCAAGCATTACCAGCCCTATGCCCCACCACGCGACTTCGCAGCCTATCGCTCCAAGCTTAGAGTGA
AGTTCAGCAGGAGCGCAGACGCCCCCGCGTACCAGCAGGGCCAGAACCAGCTCTATAACGAGCTCAATCTA
GGACGAAGAGAGGAGTACGATGTTTTGGACAAGAGACGTGGCCGGGACCCTGAGATGGGGGGAAAGCCGCA
GAGAAGGAAGAACCCTCAGGAAGGCCTGTACAATGAACTGCAGAAAGATAAGATGGCGGAGGCCTACAGTG
AGATTGGGATGAAAGGCGAGCGCCGGAGGGGCAAGGGGCACGATGGCCTTTACCAGGGTCTCAGTACAGCC
ACCAAGGACACCTACGACGCCCTTCACATGCAGGCCCTGCCCCCTCGC lxxix. 2592H-CD28H-CD28TM-BBCYP-CD3ζCYP CAR (includes leader) 2592H-BB
276 Nucleic acid sequence of 2592H-CD28H-CD28TM-BBCYP-CD3ζCYP CAR
(includes leader) (2592H-BB), SEQ ID NO: 276 ATGGAAACCCCAGCGCAGCTTCTCTT
CCTCCTGCTACTCTGGCTCCCAGATACCACCGGACAGGTGCAGCTGCAGGAGTCGGGCCCAAGACTGGTGA
AGCCTTCACAGACCCTGTCCCTCACCTGCACTGTCTCTGGTGGCTCCATCAGTAGTGATGGTTACTACTGG
AGCTGGATCCGCCAGCACCCAGGGAAGGGCCTGGAGTGGATTGGGTACATCTATTACAGTGGGAGCACCTT
CTACAACCCGTCCCTCAAGAGTCGAGTTGCCATATCAGTGGACACGTCTAAGAACCAGTTCTCCCTGAAGC
TGAGCTCTGTGACTGCCGCGGACACGGCCGTGTATTACTGTGCGAGAGAATCCCCTCATAGCAGCAACTGG
TACTCGGGCTTTGACTGCTGGGGCCAGGGAACCCTGGTCACCGTCTCCTCAGGTGGTGGTGGTTCTGGCGG
CGGCGGCTCCGGTGGTGGTGGTTCCGAAATTGTGCTGACTCAGTCTCCAGACTTTCAGTCTGTGACTCCAA
AGGAGAAAGTCACCATCACCTGCCGGGCCAGTCAGAGCATTGGTAGTAGGTTACACTGGTACCAGCAGAAA
CCAGATCAGTCTCCAAAGCTCCTCATCAAGTATGCTTCCCAGTCCTTCTCAGGGGTCCCCTCGAGGTTCAG
TGGCAGTGGATCTGGGACAGATTTCACCCTCACCATCAATAGCCTGGAAGCTGAAGATGCTGCAACGTATT
ACTGTCATCAGAGTAGTAATTTACCATTCACTTTCGGCCCTGGGACCAAAGTGGATATCAAAGCTAGCGTG
AAAGGGAAACACCTTTGTCCAAGTCCCCTATTTCCCGGACCTTCTAAGCCCTTTTGGGTGCTGGTGGTGGT
TGGTGGAGTCCTGGCTTGCTATAGCTTGCTAGTAACAGTGGCCTTTATTATTTTCTGGGTGAAACGGGGCA
GAAAGAAACTCCTGTATATATTCAAACAACCATTTATGAGACCAGTACAAACTACTCAAGAGGAAGATGGC
TGTAGCTGCCGATTTCCAGAAGAAGAAGAAGGAGGATGTGAACTGAAGCTTAGAGTGAAGTTCAGCAGGAG
CGCAGACGCCCCCGCGTACCAGCAGGGCCAGAACCAGCTCTATAACGAGCTCAATCTAGGACGAAGAGAGG
AGTACGATGTTTTGGACAAGAGACGTGGCCGGGACCCTGAGATGGGGGAAAGCCGCAGAGAAGGAAGAAC
CCTCAGGAAGGCCTGTACAATGAACTGCAGAAAGATAAGATGGCGGAGGCCTACAGTGAGATTGGGATGAA
AGGCGAGCGCCGGAGGGGCAAGGGCACGATGGCCTTTACCAGGGTCTCAGTACAGCCACCAAGGACACCTA
CGACGCCCTTCACATGCAGGCCCTGCCCCCTCGC lxxx. 2592H-CD28H-CD28TM-CD28CYP-CD3ζCYP CAR (includes leader) 2592H-CD28
277 Nucleic acid sequence of 2592H-CD28H-CD28TM-CD28CYP-CD3ζCYP CAR
(includes leader) (2592H-CD28), SEQ ID NO: 277 ATGGAAACCCCAGCGCAGCTTCTC
TTCCTCCTGCTACTCTGGCTCCCAGATACCACCGGACAGGTGCAGCTGCAGGAGTCGGGCCCAAGACTGGT
GAAGCCTTCACAGACCCTGTCCCTCACCTGCACTGTCTCTGGTGGCTCCATCAGTAGTGATGGTTACTACT
GGAGCTGGATCCGCCAGCACCCAGGGAAGGGCCTGGAGTGGATTGGGTACATCTATTACAGTGGGAGCACC
TTCTACAACCCGTCCCTCAAGAGTCGAGTTGCCATATCAGTGGACACGTCTAAGAACCAGTTCTCCCTGAA
GCTGAGCTCTGTGACTGCCGCGGACACGGCCGTGTATTACTGTGCGAGAGAATCCCCTCATAGCAGCAACT
GGTACTCGGGCTTTGACTGCTGGGGCCAGGGAACCCTGGTCACCGTCTCCTCAGGTGGTGGTGGTTCTGGC
GGCGGCGGCTCCGGTGGTGGTGGTTCCGAAATTGTGCTGACTCAGTCTCCAGACTTTCAGTCTGTGACTCC
AAAGGAGAAAGTCACCATCACCTGCCGGGCCAGTCAGAGCATTGGTAGTAGGTTACACTGGTACCAGCAGA
AACCAGATCAGTCTCCAAAGCTCCTCATCAAGTATGCTTCCCAGTCCTTCTCAGGGGTCCCCTCGAGGTTC
AGTGGCAGTGGATCTGGGACAGATTTCACCCTCACCATCAATAGCCTGGAAGCTGAAGATGCTGCAACGTA
TTACTGTCATCAGAGTAGTAATTTACCATTCACTTTCGGCCCTGGGACCAAAGTGGATATCAAAGCTAGCG
TGAAAGGGAAACACCTTTGTCCAAGTCCCCTATTTCCCGGACCTTCTAAGCCCTTTTGGGTGCTGGTGGTG
GTTGGTGGAGTCCTGGCTTGCTATAGCTTGCTAGTAACAGTGGCCTTTATTATTTTCTGGGTGAGGAGTAA
GAGGAGCAGGCTCCTGCACAGTGACTACATGAACATGACTCCCCGCCGCCCCGGGCCCACCCGCAAGCATT
ACCAGCCCTATGCCCCACCACGCGACTTCGCAGCCTATCGCTCCAAGCTTAGAGTGAAGTTCAGCAGGAGC
GCAGACGCCCCCGCGTACCAGCAGGGCCAGAACCAGCTCTATAACGAGCTCAATCTAGGACGAAGAGAGGA
GTACGATGTTTTGGACAAGAGACGTGGCCGGGACCCTGAGATGGGGGAAAGCCGCAGAGAAGGAAGAACC
CTCAGGAAGGCCTGTACAATGAACTGCAGAAAGATAAGATGGCGGAGGCCTACAGTGAGATTGGGATGAAA
GGCGAGCGCCGGAGGGGCAAGGGCACGATGGCCTTTACCAGGGTCTCAGTACAGCCACCAAGGACACCTA
CGACGCCCTTCACATGCAGGCCCTGCCCCCTCGC lxxxi. 2592H-CD28H-CD28TM-DAP10CYP-CD3ζCYP CAR (includes leader) 2592H-DAP10
278 Nucleic acid sequence of 2592H-CD28H-CD28TM-DAP10CYP-CD3ζCYP CAR
(includes leader) (2592H-DAP10), SEQ ID NO: 278 ATGGAAACCCCAGCGCAGCTTCT
CTTCCTCCTGCTACTCTGGCTCCCAGATACCACCGGACAGGTGCAGCTGCAGGAGTCGGGCCCAAGACTGG
TGAAGCCTTCACAGACCCTGTCCCTCACCTGCACTGTCTCTGGTGGCTCCATCAGTAGTGATGGTTACTAC
TGGAGCTGGATCCGCCAGCACCCAGGGAAGGGCCTGGAGTGGATTGGGTACATCTATTACAGTGGGAGCAC
CTTCTACAACCCGTCCCTCAAGAGTCGAGTTGCCATATCAGTGGACACGTCTAAGAACCAGTTCTCCCTGA
AGCTGAGCTCTGTGACTGCCGCGGACACGGCCGTGTATTACTGTGCGAGAGAATCCCCTCATAGCAGCAAC -continued
TGGTACTCGGGCTTTGACTGCTGGGGCCAGGGAACCCTGGTCACCGTCTCCTCAGGTGGTGGTGGTTCTGG
CGGCGGCGGCTCCGGTGGTGGTGGTTCCGAAATTGTGCTGACTCAGTCTCCAGACTTTCAGTCTGTGACTC
CAAAGGAGAAAGTCACCATCACCTGCCGGGCCAGTCAGAGCATTGGTAGTAGGTTACACTGGTACCAGCAG
AAACCAGATCAGTCTCCAAAGCTCCTCATCAAGTATGCTTCCCAGTCCTTCTCAGGGGTCCCCTCGAGGTT
CAGTGGCAGTGGATCTGGGACAGATTTCACCCTCACCATCAATAGCCTGGAAGCTGAAGATGCTGCAACGT
ATTACTGTCATCAGAGTAGTAATTTACCATTCACTTTCGGCCCTGGGACCAAAGTGGATATCAAAGCTAGC
GTGAAAGGGAAACACCTTTGTCCAAGTCCCCTATTTCCCGGACCTTCTAAGCCCTTTTGGGTGCTGGTGGT
GGTTGGTGGAGTCCTGGCTTGCTATAGCTTGCTAGTAACAGTGGCCTTTATTATTTTCTGGGTGCTGTGCG
CACGCCCACGCCGCAGCCCCGCCCAAGAAGATGGCAAAGTCTACATCAACATGCCAGGCAGGGCAAGCTT
AGAGTGAAGTTCAGCAGGAGCGCAGACGCCCCCGCGTACCAGCAGGGCCAGAACCAGCTCTATAACGAGCT
CAATCTAGGACGAAGAGAGGAGTACGATGTTTTGGACAAGAGACGTGGCCGGGACCCTGAGATGGGGGGAA
AGCCGCAGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCAG
TACAGCCACCAAGGACACCTACGACGCCCTTCACATGCAGGCCCTGCCCCCTCGC lxxxii. 2592L-CD28H-CD28TM-CD28CYP-CD3ζCYP CAR (includes leader) 2592L-CD28
279 Nucleic acid sequence of 2592L-CD28H-CD28TM-CD28CYP-CD3ζCYP CAR
(includes leader) (2592L-CD28), SEQ ID NO: 279 ATGGAAACCCCAGCGCAGCTTCTC
TTCCTCCTGCTACTCTGGCTCCCAGATACCACCGGAGAAATTGTGCTGACTCAGTCTCCAGACTTTCAGTC
TGTGACTCCAAAGGAGAAAGTCACCATCACCTGCCGGGCCAGTCAGAGCATTGGTAGTAGGTTACACTGGT
ACCAGCAGAAACCAGATCAGTCTCCAAAGCTCCTCATCAAGTATGCTTCCCAGTCCTTCTCAGGGGTCCCC
TCGAGGTTCAGTGGCAGTGGATCTGGGACAGATTTCACCCTCACCATCAATAGCCTGGAAGCTGAAGATGC
TGCAACGTATTACTGTCATCAGAGTAGTAATTTACCATTCACTTTCGGCCCTGGGACCAAAGTGGATATCA
AAGGTGGTGGTGGTTCTGGCGGCGGCGGCTCCGGTGGTGGTGGTTCCCAGGTGCAGCTGCAGGAGTCGGGC
CCAAGACTGGTGAAGCCTTCACAGACCCTGTCCCTCACCTGCACTGTCTCTGGTGGCTCCATCAGTAGTGA
TGGTTACTACTGGAGCTGGATCCGCCAGCACCCAGGGAAGGGCCTGGAGTGGATTGGGTACATCTATTACA
GTGGGAGCACCTTCTACAACCCGTCCCTCAAGAGTCGAGTTGCCATATCAGTGGACACGTCTAAGAACCAG
TTCTCCCTGAAGCTGAGCTCTGTGACTGCCGCGGACACGGCCGTGTATTACTGTGCGAGAGAATCCCCTCA
TAGCAGCAACTGGTACTCGGGCTTTGACTGCTGGGGCCAGGGAACCCTGGTCACCGTCTCCTCAGCTAGCG
TGAAAGGGAAACACCTTTGTCCAAGTCCCCTATTTCCCGGACCTTCTAAGCCCTTTTGGGTGCTGGTGGTG
GTTGGTGGAGTCCTGGCTTGCTATAGCTTGCTAGTAACAGTGGCCTTTATTATTTTCTGGGTGAGGAGTAA
GAGGAGCAGGCTCCTGCACAGTGACTACATGAACATGACTCCCCGCCGCCCCGGGCCCACCCGCAAGCATT
ACCAGCCCTATGCCCCACCACGCGACTTCGCAGCCTATCGCTCCAAGCTTAGAGTGAAGTTCAGCAGGAGC
GCAGACGCCCCCGCGTACCAGCAGGGCCAGAACCAGCTCTATAACGAGCTCAATCTAGGACGAAGAGAGGA
GTACGATGTTTTGGACAAGAGACGTGGCCGGGACCCTGAGATGGGGGGAAAGCCGCAGAGAAGGAAGAACC
CTCAGGAAGGCCTGTACAATGAACTGCAGAAAGATAAGATGGCGGAGGCCTACAGTGAGATTGGGATGAAA
GGCGAGCGCCGGAGGGGCAAGGGGCACGATGGCCTTTACCAGGGTCTCAGTACAGCCACCAAGGACACCTA
CGACGCCCTTCACATGCAGGCCCTGCCCCCTCGC lxxxiii. signal peptide signal 280 Nucleid acid sequence of signal peptide
(signal), SEQ ID NO: 280 ATGGAAACCCCAGCGCAGCTTCTCTTCCTCCTGCTACTCTGGCTCC
CAGATACCACCGGA lxxxiv. T2A ribosomal skip sequence T2A 281 Nucleic acid sequence of T2A
ribosomal skip sequence (T2A), SEQ ID NO: 281 GGCTCCGGTGAGGGCAGAGGAAGTC
TTCTAACATGCGGTGACGTGGAGGAGAATCCCGGCCCT lxxxv. Truncated CD19 tCD19 282 Nucleic acid sequence of Truncated CD19
(tCD19), SEQ ID NO: 282 ATGCCACCTCCTCGCCTCCTCTTCTTCCTCCTCTTCCTCACCCCCAT
GGAAGTCAGGCCCGAGGAACCTCTAGTGGTGAAGGTGGAAGAGGGAGATAACGCTGTGCTGCAGTGCCTCA
AGGGGACCTCAGATGGCCCCACTCAGCAGCTGACCTGGTCTCGGGAGTCCCCGCTTAAACCCTTCTTAAAA
CTCAGCCTGGGGCTGCCAGGCCTGGGAATCCACATGAGGCCCCTGGCCATCTGGCTTTTCATCTTCAACGT
CTCTCAACAGATGGGGGGCTTCTACCTGTGCCAGCCGGGGCCCCCTCTGAGAAGGCCTGGCAGCCTGGCT
GGACAGTCAATGTGGAGGGCAGCGGGGAGCTGTTCCGGTGGAATGTTTCGGACCTAGGTGGCCTGGGCTGT
GGCCTGAAGAACAGGTCCTCAGAGGGCCCCAGCTCCCCTTCCGGAACTCATGAGCCCCAAGCTGTATGT
GTGGGCCAAAGACCGCCCTGAGATCTGGGAGGGAGAGCCTCCGTGTCTCCCACCGAGGGACAGCCTGAACC
AGAGCCTCAGCCAGGACCTCACCATGGCCCCTGCCTCCACACTCTGGCTGTCCTGTGGGGTACCCCCTGAC
TCTGTGTCCAGGGGCCCCCTCTCCTGGACCCATGTGCACCCCAAGGGGCCTAAGTCATTGCTGAGCCTAGA
GCTGAAGGACGATCGCCGGCCAGAGATATGTGGGTAATGGAGACGGGTCTGTTGTTGCCCCAGGCCACAG
CTCAAGACGCTGGAAAGTATTATTGTCACCGTGGCAACCTGACCATGTCATTCCACCTGGAGATCACTGCT
CGGCCAGTACTATGGCACTGGCTGCTGAGGACTGTGGCTGGAAGGTCTCAGCTGTGACTTTGGCTTATCT
GATCTTCTGCCTGTGTTCCCTTGTGGGCATTCTTCATCTTCAAAGAGCCCTGGTCCTGAGGAGGAAAAGAA
AGCGAATGACTTAA lxxxvi. Ab 129 CDR H1 Ab129 CDR 1 283 Nucleic acid sequence of Ab 129 CDR H1
(Ab129 CDR 1), SEQ ID NO: 283 GGTGGCTCCGTCAGCAGTGGTGGTTACTAC lxxxvii. Ab 129 CDR H2 Ab129 CDR 2 284 Nucleic acid sequence of Ab 129 CDR H2
(Ab129 CDR 2), SEQ ID NO: 284 ATCTATTACACTGGGAGCACC lxxxviii. Ab 129 CDR H3 Ab129 CDR 3 285 Nucleic acid sequence of Ab 129 CDR H3
(Ab129 CDR 3), SEQ ID NO: 285 GATTATGACTGGAGCTTCCACTTTGACTAC lxxxix. Ab 129 CDR L1 Ab129 CDR 4 286 Nucleic acid sequence of Ab 129 CDR L1
(Ab129 CDR 4), SEQ ID NO: 286 CAGGGCATTAGAAATGAT xc. Ab 129 CDR L2 Ab129 CDR 5 287 Nucleic acid sequence of Ab 129 CDR L2
(Ab129 CDR 5), SEQ ID NO: 287 GCTGCATCC xci. Ab 129 CDR L3 Ab129 CDR 6 288 Nucleic acid sequence of Ab 129 CDR L3
(Ab129 CDR 6), SEQ ID NO: 288 CTACAGCATAATAGTTACCCT -continued xcii. Ab 272 CDR H1 Ab272 CDR 1 289 Nucleic acid sequence of Ab 272 CDR H1
(Ab272 CDR 1), SEQ ID NO: 289 GGATTCATCTTCAGTCGCTATGGC xciii. Ab 272 CDR H2 Ab272 CDR 2 290 Nucleic acid sequence of Ab 272 CDR H2
(Ab272 CDR 2), SEQ ID NO: 290 ATATGGTATGATGGAAGTAATAAA xciv. Ab 272 CDR H3 Ab272 CDR 3 291 Nucleic acid sequence of Ab 272 CDR H3
(Ab272 CDR 3), SEQ ID NO: 291 GATTACTATGATAATAGTAGACATCACTGGGGGTTTGACTA
C xcv. Ab 272 CDR L1 Ab272 CDR 4 292 Nucleic acid sequence of Ab 272 CDR L1
(Ab272 CDR 4), SEQ ID NO: 292 AGGTCTAGTCGGAGCCTCTTGGATAGTGATGATGGAAACAC
CTATTTGGAC xcvi. Ab 272 CDR L2 Ab272 CDR 5 293 Nucleic acid sequence of Ab 272 CDR L2
(Ab272 CDR 5), SEQ ID NO: 293 ACGCTTTCCTATCGGGCCTCT xcvii. Ab 272 CDR L3 Ab272 CDR 6 294 Nucleic acid sequence of Ab 272 CDR L3
(Ab272 CDR 6), SEQ ID NO: 294 ATGCAACGTGTAGAGTTTCCTATCACC xcviii. Ab 2592 CDR H1 Ab2592 CDR 1 295 Nucleic acid sequence of Ab 2592 CDR H1
(Ab2592 CDR 1), SEQ ID NO: 295 GGTGGCTCCATCAGTAGTGATGGTTAC xcix. Ab 2592 CDR H2 Ab2592 CDR 2 296 Nucleic acid sequence of Ab 2592 CDR H2
(Ab2592 CDR 2), SEQ ID NO: 296 ATCTATTACAGTGGGAGCACC c. Ab 2592 CDR H3 Ab2592 CDR 3 297 Nucleic acid sequence of Ab 2592 CDR H3
(Ab2592 CDR 3), SEQ ID NO: 297 GAATCCCCTCATAGCAGCAACTGGTACTCGGGCTTTGACT
GC ci. Ab 2592 CDR L1 Ab2592 CDR 4 298 Nucleic acid sequence of Ab 2592 CDR L1
(Ab2592 CDR 4), SEQ ID NO: 298 CAGAGCATTGGTAGTAGG cii. Ab 2592 CDR L2 Ab2592 CDR 5 299 Nucleic acid sequence of Ab 2592 CDR L2
(Ab2592 CDR 5), SEQ ID NO: 299 TATGCTTCC ciii. Ab 2592 CDR L3 Ab2592 CDR 6 300 Nucleic acid sequence of Ab 2592 CDR L3
(Ab2592 CDR 6), SEQ ID NO: 300 CATCAGAGTAGTAATTTACCATTCACT civ. leader_272H-CD28H-CD28TM-BBCYP-CD3ζCYP_T2A-tCD19 272H-BB_tCD19 301
Amino acid sequence of leader_272H-CD28H-CD28TM-BBCYP-CD3ζCYP_T2A-
tCD19 (272H-BB_tCD19), SEQ ID NO: 301 METPAQLLFLLLLWLPDTTG2QVQLVESGGGVV
QPGRSLRLSCAASGFIFSRYGMHWVRQAPGKGLKWVAVIWYDGSNKLYADSVKGRFTISRDNSKNTLYLQM
NSLRAEDTAVYYCARDYYDNSRHHWGFDYWGQGTLVTVSSGGGGSGGGGSGGGGSDIVMTQTPLSLPVTPG
EPASISCRSSRSLLDSDDGNTYLDWYLQKPGQSPQLLIYTLSYRASGVPDRFSGSGSGTDFTLKISRVEAE
DVGVYYCMQRVEFPITFGQGTRLEIKLEVKGKHLCPSPLFPGPSKPFWVLVVVGGVLACYSLLVTVAFIIF
WVKRGRKKLLYIFKQPFMRPVQTTQEEDGCSCRFPEEEEGGCELKLRVFKSRSADAPAYQQGQNQLYNELN
LGRREEYDVLDKRRGRDPEMGGKPQRRKNPQEGLYNELQKDKMAEAYSEIGMKGERRRGKGHDGLYQGLST
ATKDTYDALHMQALPPRAGAKRSGSGEGRGSLLTCGDVEENPGPMPPPRLLFFLLFLTPMEVRPEEPLVVK
VEEGDNAVLQCLKGTSDGPTQQLTWSRESPLKPFLKLSLGLPGLGIHMRPLAIWLFIFNVSQQMGGFYLCQ
PGPPSEKAWQPGWTVNVEGSGELFRWNVSDLGGLGCGLKNRSSEGPSSPSGKLMSPKLYVWAKDRPEIWEG
EPPCLPPRDSLNQSLSQDLTMAPGSTLWLSCGVPPDSVSRGPLSWTHVHPKGPKSLLSLELKDDRPARDMW
VMETGLLLPRATAQDAGKYYCHRGNLTMSFHLEITARPVLWHWLLRTGGWKVSAVTLAYLIFCLCSLVGIL
HLQRALVLRRKRKRMT cv. leader_272H-CD28H-CD28TM-BBCYP-CD3ζCYP_T2A-tCD19 272H-BB_tCD19 302
Nucleic acid sequence of leader_272H-CD28H-CD28TM-BBCYP-CD3ζCYP_T2A-
tCD19 (272H-BB_tCD19), SEQ ID NO: 302 ATGGAAACCCCAGCGCAGCTTCTCTTCCTCCTG
CTACTCTGGCTCCCAGATACCACCGGACAGGTGCAGCTGGTGGAGTCTGGGGGAGGCGTGGTCCAGCCTGG
GAGGTCCCTGAGACTCTCCTGTGCAGCGTCTGGATTCATCTTCAGTCGCTATGGCATGCACTGGGTCCGCC
AGGCTCCAGGCAAGGGGCTGAAATGGGTGGCAGTTATATGGTATGATGGAAGTAATAAAACTCTATGCAGAC
TCCGTGAAGGGCCGATTCACCATCTCCAGAGACAATTCCAAGAACACGCTGTATCTGCAAATGAACAGCCT
GAGAGCCGAGGACACGGCTGTGTATTACTGTGCGAGAGATTACTATGATAATAGTAGACATCACTGGGGGT
TTGACTACTGGGGCCAGGGAACCCTGGTCACCGTCTCCTCAGGTGGTGGTGGTTCTGGCGGCGGCGGCTCC
GGTGGTGGTGGTTCCGATATTGTGATGACCCAGACTCCACTCTCCCTGCCCGTCACCCCTGGAGAGCCGGC
CTCCATCTCCTGCAGGTCTAGTCGGAGCCTCTTGGATAGTGATGATGGAAACACCTATTTGGACTGGTACC
TGCAGAAGCCAGGGCAGTCTCCACAGCTCCTGATCTACACGCTTTCCTATCGGGCCTCTGGAGTCCCAGAC
AGGTTCAGTGGCAGTGGGTCAGGCACTGATTTCACACTGAAAATCAGCAGGGTGGAGGCTGAGGATGTTGG
AGTTTATTACTGCATGCAACGTGTAGAGTTTCCTATCACCTTCGGCCAAGGGACACGACTGGAGATTAAAC
TCGAGGTGAAAGGGAAACACCTTTGTCCAAGTCCCCTATTTCCCGGACCTTCTAAGCCCTTTTGGGTGCTG
GTGGTGGTTGGTGGAGTCCTGGCTTGCTATAGCTTGCTAGTAACAGTGGCCTTTATTATTTTCTGGGTGAA
ACGGGGCAGAAAGAAACTCCTGTATATATTCAAACAACCATTTATGAGACCAGTACAAACTACTCAAGAGG
AAGATGGCTGTAGCTGCCGATTTCCAGAAGAAGAAGAAGGAGGATGTGAACTGAAGCTTAGAGTGAAGTTC
AGCAGGAGCGCAGACGCCCCCGCGTACCAGCAGGGCCAGAACCAGCTCTATAACGAGCTCAATCTAGGACG
AAGAGAGGAGTACGATGTTTTGGACAAGAGACGTGGCCGGGACCCTGAGATGGGGGGAAAGCCGCAGAGAA
GGAAGAACCCTCAGGAAGGCCTGTACAATGAACTGCAGAAAGATAAGATGGCGGAGGCCTACAGTGAGATT
GGGATGAAAGGCGAGCGCCGGAGGGGCAAGGGGCACGATGGCCTTTACCAGGGTCTCAGTACAGCCACCAA
GGACACCTACGACGCCCTTCACATGCAGGCCCTGCCCCCTCGCGCCGGCGCCAAAAGGTCTGGCTCCGGTG
AGGGCAGAGGAAGTCTTCTAACATGCGGTGACGTGGAGGAGAATCCCGGCCCTATGCCACCTCCTCGCCTC
CTCTTCTTCCTCCTCTTCCTCACCCCCATGGAAGTCAGGCCCGAGGAACCTCTAGTGGTGAAGGTGGAAGA

```
GGGAGATAACGCTGTGCTGCAGTGCCTCAAGGGGACCTCAGATGGCCCCACTCAGCAGCTGACCTGGTCTC
GGGAGTCCCCGCTTAAACCCTTCTTAAAACTCAGCCTGGGGCTGCCAGGCCTGGGAATCCACATGAGGCCC
CTGGCCATCTGGCTTTTCATCTTCAACGTCTCTCAACAGATGGGGGGCTTCTACCTGTGCCAGCCGGGGCC
CCCCTCTGAGAAGGCCTGGCAGCCTGGCTGGACAGTCAATGTGGAGGGCAGCGGGGAGCTGTTCCGGTGGA
ATGTTTCGGACCTAGGTGGCCTGGGCTGTGGCCTGAAGAACAGGTCCTCAGAGGGCCCCAGCTCCCCTTCC
GGGAAGCTCATGAGCCCCAAGCTGTATGTGTGGGCCAAAGACCGCCCTGAGATCTGGGAGGGAGAGCCTCC
GTGTCTCCCACCGAGGGACAGCCTGAACCAGAGCCTCAGCCAGGACCTCACCATGGCCCCTGGCTCCACAC
TCTGGCTGTCCTGTGGGGTACCCCCTGACTCTGTGTCCAGGGGCCCCCTCTCCTGGACCCATGTGCACCCC
AAGGGGCCTAAGTCATTGCTGAGCCTAGAGCTGAAGGACGATCGCCCGGCCAGAGATATGTGGGTAATGGA
GACGGGTCTGTTGTTGCCCCGGGCCACAGCTCAAGACGCTGGAAAGTATTATTGTCACCGTGGCAACCTGA
CCATGTCATTCCACCTGGAGATCACTGCTCGGCCAGTACTATGGCACTGGCTGCTGAGGACTGGTGGCTGG
AAGGTCTCAGCTGTGACTTTGGCTTATCTGATCTTCTGCCTGTGTTCCCTTGTGGGCATTCTTCATCTTCA
AAGAGCCCTGGTCCTGAGGAGGAAAAGAAAGCGAATGACTTAA
``` cvi. leader_272H-CD28H-CD28TM-CD28CYP-CD3ζCYP_T2A-tCD19 272H-CD28_tCD19 303
Amino acid sequence of leader_272H-CD28H-CD28TM-CD28CYP-CD3ζCYP_T2A-
tCD19 (272H-CD28_tCD19), SEQ ID NO: 303 METPAQLLFLLLLWLPDTTGQVQLVESGGGV
VQPGRSLRLSCAASGFIFSRYGMHWVRQAPGKGLKWVAVIWYDGSNKLYADSVKGRFTISRDNSKNTLYLQ
MNSLRAEDTAVYYCARDYYDNSRHHWGFDYWGQGTLVTVSSGGGGSGGGGSGGGGSDIVMTQTPLSLPVTP
GEPASISCRSSRSLLDSDDGNTYLDWYLQKPGQSPQLLIYTLSYRASGVPDRFSGSGSGTDFTLKISRVEA
EDVGVYYCMQRVEFPITFGQGTRLEIKLEVGKHLCPSPLFPGPSKPFWVLVVVGGVLACYSLLVTVAFII
FWVRSKRSRLLHSDYMNMTPRRPGPTRKHYQPYAPPRDFAAYRSKLRVKFSRSADAPAYQQGQNQLYNELN
LGRREEYDVLDKRRGRDPEMGGKPQRRKNPQEGLYNELQKDKMAEAYSEIGMKGERRRGKGHDGLYQGLST
ATKDTYDALHMQALPPRAGAKRSGSGEGRGSLLTCGDVEENPGPRMPPPRLLFFLLFLTPMEVRPEEPLVV
KVEEGDNAVLQCLKGTSDGPTQQLTWSRESPLKPFLGLSLGPLGIHMRPLAIWLFIFNVSQQMGGFYLC
QPGPPSEKAWQPGWTVNVEGSGELFRWNVSDLGGLGCGLKNRSSEGPSSPSGKLMSPKLYVWAKDRPEIWE
GEPPCLPPRDSLNQSLSQDLTMAPGSTLWLSCGVPPDSVSRGPSWTHVHPKGPKSLLSLELKDDRPARDMW
VMETGLLLPRATAQDAGKYYCHRGNLTMSFHLEITARPVLWHWLLRTGGWKVSAVTLAYLIFCLCSLVGIL
HLQRALVLRRKRKRMT cvii. leader_272H-CD28H-CD28TM-CD28CYP-CD3ζCYP_T2A-tCD19 272H-CD28_tCD19 304
Nucleic acid sequence of leader_272H-CD28H-CD28TM-CD28CYP-CD3ζCYP_T2A-
tCD19 (272H-CD28_tCD19), SEQ ID NO: 304 ATGGAAACCCCAGCGCAGCTTCTCTTCCTCC
TGCTACTCTGGCTCCCAGATACCACCGGACAGGTGCAGTTGGTGGAGTCTGGGGGAGGCGTGGTCCAGCCT
GGGAGGTCCCTGAGACTCTCCTGTGCAGCGTCTGGATTCATCTTCAGTCGCTATGGCATGCACTGGGTCCG
CCAGGCTCCAGGCAAGGGGCTGGAAATGGGTGGCAGTTATATGGTATGATGAAGTAATAAACTCTATGCAG
ACTCCGTGAAGGGCCGATTCACCATCTCCAGAGACAATTCCAAGAACACGCTGTATCTGCAAATGAACAGC
CTGAGAGCCGAGGACACGGCTGTGTATTACTGTGCGAGAGATTACTATGATAATAGTAGACATCACTGGGG
GTTTGACTACTGGGGCCAGGGAACCCTGGTCACCGTCTCCTCAGGTGGTGGTGGTTCTGGCGGCGGCGGCT
CCGGTGGTGGTGGTTCCGATATTGTGATGACCCAGACTCCACTCTCCCTGCCCGTCACCCCTGGAGAGCCG
GCCTCCATCTCCTGCAGGTCTAGTCGGAGCCTCTTGGATAGTGATGATGGAAACACCTATTTGGACTGGTA
CCTGCAGAAGCCAGGGCAGTCTCCACAGCTCCTGATCTACACGCTTTCCTATCGGGCCTCTGGAGTCCCAG
ACAGGTTCAGTGGCAGTGGGTCAGGCACTGATTTCACACTGAAAATCAGCAGGGTGGAGGCTGAGGATGTT
GGAGTTTATTACTGCATGCAACGTGTAGAGTTTCCTATCACCTTCGGCCAAGGGACACGACTGGAGATTAA
ACTCGAGGTGAAAGGGAAACACCTTTGTCCAAGTCCCCTATTTCCCGGACCTTCTAAGCCCTTTTGGGTGC
TGGTGGTGGTTGGTGGAGTCCTGGCTTGCTATAGCTTGCTAGTAACAGTGGCCTTTATTATTTTCTGGGTG
AGGAGTAAGAGGAGCAGGCTCCTGCACAGTGACTACATGAACATGACTCCCCGCCGCCCCGGCCCACCCG
CAAGCATTACCAGCCCTATGCCCCACCACGCGACTTCGCAGCCTATCGCTCCAAGCTTAGAGTGAAGTTCA
GCAGGAGCGCAGACGCCCCCGCGTACCAGCAGGGCCAGAACCAGCTCTATAACGAGCTCAATCTAGGACGA
AGAGAGGAGTACGATGTTTTGGACAAGAGACGTGGCCGGGACCCTGAGATGGGGGAAAGCCGCAGAGAAG
GAAGAACCCTCAGGAAGGCCTGTACAATGAACTGCAGAAAGATAAGATGGCGGAGGCCTACAGTGAGATTG
GGATGAAAGGCGAGCGCCGGAGGGGCAAGGGGCACGATGGCCTTTACCAGGGTCTCAGTACAGCCACCAAG
GACACCTACGACGCCCTTCACATGCAGGCCCTGCCCCCTCGCGCCGGCGCCAAAAGGTCTGGCTCCGGTGA
GGGCAGAGGAAGTCTTCTAACATGCGGTGACGTGGAGGAGAATCCCGGCCCTAGAATGCCACCTCCTCGCC
TCCTCTTCTTCCTCCTCTTCCTCACCCCCATGGAAGTCAGGCCCGAGAACCTCTAGTGGTGAAGGTGGAA
GAGGGAGATAACGCTGTGCTGCAGTGCCTCAAGGGGACCTCAGATGGCCCCACTCAGCAGCTGACCTGGTC
TCGGGAGTCCCCGCTTAAACCCTTCTTAAAACTCAGCCTGGGGCTGCCAGGCCTGGGAATCCACATGAGGC
CCCTGGCCATCTGGCTTTTCATCTTCAACGTCTCTCAACAGATGGGGGCTTCTACCTGTGCCAGCCGGGG
CCCCCTCTGAGAAGGCCTGGCAGCCTGGCTGGACAGTCAATGTGGAGGGCAGCGGGGAGCTGTTCCGGTG
GAATGTTTCGGACCTAGGTGGCCTGGGCTGTGGCCTGAAGAACAGGTCCTCAGAGGGCCCCAGCTCCCCTT
CCGGGAAGCTCATGAGCCCCAAGCTGTATGTGTGGGCCAAAGACCGCCCTGAGATCTGGGAGGGAGAGCCT
CCGTGTCTCCCACCGAGGGACAGCCTGAACCAGAGCCTCAGCCAGGACCTCACCATGGCCCCTGGCTCCAC
ACTCTGGCTGTCCTGTGGGGTACCCCCTGACTCTGTGTCCAGGGGCCCCCTCTCCTGGACCCATGTGCACC
CCAAGGGGCCTAAGTCATTGCTGAGCCTAGAGCTGAAGGACGATCGCCCGGCCAGAGATATGTGGGTAATG
GAGACGGGTCTGTTGTTGCCCCGGGCCACAGCTCAAGACGCTGGAAAGTATTATTGTCACCGTGGCAACCT
GACCATGTCATTCCACCTGGAGATCACTGCTCGGCCAGTACTATGGCACTGGCTGCTGAGGACTGGTGGCT
GGAAGGTCTCAGCTGTGACTTTGGCTTATCTGATCTTCTGCCTGTGTTCCCTTGTGGGCATTCTTCATCTT
CAAAGAGCCCTGGTCCTGAGGAGGAAAAGAAAGCGAATGACTTAA cviii. leader_272H-CD28H-CD28TM-DAP10CYP-CD3ζCYP_T2A-tCD19 272H-DAP10_tCD19
305 Amino acid sequence of leader_272H-CD28H-CD28TM-DAP10CYP-CD3ζCYP_
T2A-tCD19 (272H-DAP10_tCD19), SEQ ID NO: 305 METPAQLLFLLLLWLPDTTGQVQLVE
SGGGVVQPGRSLRLSCAASGFIFSRYGMHWVRQAPGKGLKWVAVIWYDGSNKLYADSVKGRFTISRDNSKN
TLYLQMNSLRAEDTAVYYCARDYYDNSRHHWGFDYWGQGTLVTVSSGGGGSGGGGSGGGGSDIVMTQTPLS
LPVTPGEPASISCRSSRSLLDSDDGNTYLDWYLQKPGQSPQLLIYTLSYRASGVPDRFSGSGSGTDFTLKI
SRVEAEDVGVYYCMQRVEFPITFGQGTRLEIKLEVGKHLCPSPLFPGPSKPFWVLVVVGGVLACYSLLVT
VAFIIFWVLCARPRRSPAQEDGKVYINMPGRGKLRVKFSRSADAPAYQQGQNQLYNELNLGRREEYDVLDK
RRGRDPEMGGKPQRRKNPQEGLYNELQKDKMAEAYSEIGMKGERRRGKGHDGLYQGLSTATKDTYDALHMQ
ALPPRAGAKRSGSGEGRGSLLTCGDVEENPGPMPPRLLFFLLFLTPMEVRPEEPLVVKVEEGDNAVLQCLK
GTSDGPTQQLTWSRESPLKPFLKLSLGPLGIHMRPLAIWLFIFNVSQQMGGFYLCQPGPPSEKAWQPGW
TVNVEGSGELFRWNVSDLGGLGCGLKNRSSEGPSSPSGKLMSPKLYVWAKDRPEIWEGEPPCLPPRDSLNQ -continued SLSQDLTMAPGSTLWLSCGVPPDSVSRGPLSWTHVHPKGPKSLLSLELKDDRPARDMWVMETGLLLPRATA
QDAGKYYCHRGNLTMSFHLEITARPVLWHWLLRTGGWKVSAVTLAYLIFCLSLVGILHLQRALVLRRKRK
RMT cix. leader_272H-CD28H-CD28TM-DAP10CYP-CD3ζCYP_T2A-tCD19 272H-DAP10_tCD19
306 Nucleic acid sequence of leader_272H-CD28H-CD28TM-DAP10CYP-CD3ζCYP_
T2A-tCD19 (272H-DAP10_tCD19), SEQ ID NO: 306 ATGGAAACCCCAGCGCAGCTTCTCTT
CCTCCTGCTACTCTGGCTCCCAGATACCACCGGACAGGTGCAGCTGGTGGAGTCTGGGGGAGGCGTGGTCC
AGCCTGGGAGGTCCCTGAGACTCTCCTGTGCAGCGTCTGGATTCATCTTCAGTCGCTATGGCATGCACTGG
GTCCGCCAGGCTCCAGGCAAGGGGCTGAAATGGGTGGCAGTTATATGGTATGATGGAAGTAATAAACTCTA
TGCAGACTCCGTGAAGGGCCGATTCACCATCTCCAGAGACAATTCCAAGAACACGCTGTATCTGCAAATGA
ACAGCCTGAGAGCCGAGGACACGGCTGTGTATTACTGTGCGAGAGATTACTATGATAATAGTAGACATCAC
TGGGGGTTTGACTACTGGGGCCAGGGAACCCTGGTCACCGTCTCCTCAGGTGGTGGTGGTTCTGGCGGCGG
CGGCTCCGGTGGTGGTGGTTCCGATATTGTGATGACCCAGACTCCACTCTCCCTGCCCGTCACCCCTGGAG
AGCCGGCCTCCATCTCCTGCAGGTCTAGTCGGAGCCTCTTGGATAGTGATGATGGAAACACCTATTTGGAC
TGGTACCTGCAGAAGCCAGGGCAGTCTCCACAGCCTCCTGATCTACACGCTTTCCTATCGGGCCTCTGGAGT
CCCAGACAGGTTCAGTGGCAGTGGGTCAGGCACTGATTTCACACTGAAAATCAGCAGGGTGGAGGCTGAGG
ATGTTGGAGTTTATTACTGCATGCAACGTGTAGAGTTTCCTATCACCTTCGGCCAAGGGACACGACTGGAG
ATTAAACTCGAGGTGAAAGGGAAACACCTTTGTCCAAGTCCCCTATTTCCCGGACCTTCTAAGCCCTTTTG
GGTGCTGGTGGTGGTTGGTGGAGTCCTGGCTTGCTATAGCTTGCTAGTAACAGTGGCCTTTATTATTTTCT
GGGTGCTGTGCGCACGCCCACGCCGCAGCCCCGCCCAAGAAGATGGCAAAGTCTACATCAACATGCCAGGC
AGGGGCAAGCTTAGAGTGAAGTTCAGCAGGAGCGCAGACGCCCCCGCGTACCAGCAGGGCCAGAACCAGCT
CTATAACGAGCTCAATCTAGGACGAAGAGAGGAGTACGATGTTTTGGACAAGAGACGTGGCCGGGACCCTG
AGATGGGGGGAAAGCCGCAGAGAAGGAAGAACCCTCAGGAAGGCCTGTACAATGAACTGCAGAAAGATAAG
ATGGCGGAGGCCTACAGTGAGATTGGGATGAAAGGCGAGCGCCGGAGGGGCAAGGGGCACGATGGCCTTTA
CCAGGGTCTCAGTACAGCCACCAAGGACACCTACGACGCCCTTCACATGCAGGCCCTGCCCCCTCGCGCCG
GCGCCAAAAGGTCTGGCTCCGGTGAGGGCAGAGGAAGTCTTCTAACATGCGGTGACGTGGAGGAGAATCCC
GGCCCTATGCCACCTCCTCGCCTCCTCTTCTTCCTCCTCTTCCTCACCCCCATGGAAGTCAGGCCCGAGGA
ACCTCTAGTGGTGAAGGTGGAAGAGGGAGATAACGCTGTGCTGCAGTGCCTCAAGGGGACCTCAGATGGCC
CCACTCAGCAGCTGACCTGGTCTCGGGAGTCCCCGCTTAAACCCTTCTTAAAACTCAGCCTGGGGCTGCCA
GGCCTGGGAATCCACATGAGGCCCCTGGCCATCTGGCTTTTTCATCTTCAACGTCTCTCAACAGATGGGGGG
CTTCTACCTGTGCCAGCCGGGGCCCCCCTCTGAGAAGGCCTGGCAGCCTGGCTGGACAGTCAATGTGGAGG
GCAGCGGGGAGCTGTTCCGGTGGAATGTTTCGGACCTAGGTGGCCTGGGCTGTGGCCTGAAGAACAGGTCC
TCAGAGGGCCCCAGCTCCCCTTCCGGGAAGCTCATGAGCCCCAAGCTGTATGTGTGGGCCAAAGACCGCCC
TGAGATCTGGGAGGGAGAGCCTCCGTGTCTCCCACCGAGGGACAGCCTGAACCAGAGCCTCAGCCAGGACC
TCACCATGGCCCCTGGCTCCACACTCTGGCTGTCCTGTGGGGTACCCCCTGACTCTGTGTCCAGGGGCCCC
CTCTCCTGGACCCATGTGCACCCCAAGGGGCCTAAGTCATTGCTGAGCCTAGAGCTGAAGGACGATCGCCC
GGCCAGAGATATGTGGGTAATGGAGACGGGTCTGTTGTTGCCCCGGGCCACAGCTCAAGACGCTGGAAAGT
ATTATTGTCACCGTGGCAACCTGACCATGTCATTCCACCTGGAGATCACTGCTCGGCCAGTACTATGGCAC
TGGCTGCTGAGGACTGGTGGCTGGAAGGTCTCAGCTGTGACTTTGGCTTATCTGATCTTCTGCCTGTGTTC
CCTTGTGGGCATTCTTCATCTTCAAAGAGCCCTGGTCCTGAGGAGGAAAAGAAAGCGAATGACTTAA cx. leader_2592H-CD28H-CD28TM-BBCYP-CD3ζCYP_T2A-tCD19 2592H-BB_tCD19
307 Amino acid sequence of leader_2592H-CD28H-CD28TM-BBCYP-
CD3ζCYP_T2A-tCD19 (272H-BB_tCD19), SEQ ID NO: 307 METPAQLLFLLLLWLPDTTGQ
VQLQESGPRLVKPSQTLSLTCTVSGGSISSDGYYWSWIRQHPGKGLEWIGYIYYSGSTFYNPSLKSRVAIS
VDTSKNQFSLKLSSVTAADTAVYYCARESPHSSNWYSGFDCWGQGTLVTVSSGGGGSGGGGSGGGGSEIVL
TQSPDFQSVTPKEKVTITCRASQSIGSRLHWYQQKPDQSPKLLIKYASQSFSGVPSRFSGSGSGTDFTLTI
NSLEAEDAATYYCHQSSNLPFTFGPGTKVDIKASVKGKHLCPSPLFPGPSKPFWVLVVVGGVLACYSLLVT
VAFIIFWVKRGRKKLLYIFKQPFMRPVQTTQEEDGCSCRFPEEEEGGCELKLRVKFSRSADAPAYQQGQNQ
LYNELNLGRREEYDVLDKRRGRDPEMGGKPQRRKNPQEGLYNELQKDKMAEAYSEIGMKGERRRGKGHDGL
YQGLSTATKDTYDALHMQALPPRAGAKRSGSGEGRGSLLTCGEVEENPGPMPPPRLLFFLLFLTPMEVRPE
EPLVVKVEEGDNAVLQCLKGTSDGPTQQLTWSRESPLKPFKLSLGLPGLGIHMRPLAIWLFIFNVSQQMG
GFYLCQPGPPSEKAWQPGWTVNVEGSGELFRWNVSDLGGLGCGLKNRSSEGPSSPSGKLMSPKLYVWAKDR
PEIWEGEPPCLPPRDSLNQSLSQDLTMAPGSTLWLSCGVPPDSVSRGPLSWTHVHPKGPKSLLSLELKDDR
PARDMWVMETGLLLPRATAQDAGKYYCHRGNLTMSFHLEITARPVLWHWLLRTGGWKVSAVTLAYLIFCLC
SLVGILHLQRALVLRRKRKRMT cxi. leader_2592H-CD28H-CD28TM-BBCYP-CD3ζCYP_T2A-tCD19 2592H-BB_tCD19
308 Nucleic acid sequence of leader_2592H-CD28H-CD28TM-BBCYP-
CD3ζCYP_T2A-tCD19 (2592H-BB_tCD19), SEQ ID NO: 308 ATGGAAACCCCAGCGCAGCT
TCTCTTCCTCCTGCTACTCTGGCTCCCAGATACCACCGGACAGGTGCAGCTGCAGGAGTCGGGCCCAAGAC
TGGTGAAGCCTTCACAGACCCTGTCCCTCACCTGCACTGTCTCTGGTGGCTCCATCAGTAGTGATGGTTAC
TACTGGAGCTGGATCCGCCAGCACCCAGGGAAGGGCCTGGAGTGGATTGGGTACATCTATTACAGTGGGAG
CACCTTCTACAACCCGTCCCTCAAGAGTCGAGTTGCCATATCAGTGGACACGTCTAAGAACCAGTTCTCCC
TGAAGCTGAGCTCTGTGACTGCCGCGGACACGGCCGTGTATTACTGTGCGAGAGAATCCCCTCATAGCAGC
AACTGGTACTCGGGCTTTGACTGCTGGGGCCAGGGAACCCTGGTCACCGTCTCCTCAGGTGGTGGTGGTTC
TGGCGGCGGCGGCTCCGGTGGTGGTGGTTCCGAAATTGTGCTGACTCAGTCTCCAGACTTTCAGTCTGTGA
CTCCAAAGGAGAAAGTCACCATCACCTGCCGGGCCAGTCAGAGCATTGGTAGTAGGTTACACTGGTACCAG
CAGAAACCAGATCAGTCTCCAAAGCTCCTCATCAAGTATGCTTCCCAGTCCTTCTCAGGGGTCCCCTCGAG
GTTCAGTGGCAGTGGATCTGGGACAGATTTCACCCTCACCATCAATAGCCTGGAAGCTGAAGATGCTGCAA
CGTATTACTGTCATCAGAGTAGTAATTTACCATTCACTTTCGGCCCTGGGACCAAAGTGGATATCAAAGCT
AGCGTGAAAGGGAAACACCTTTGTCCAAGTCCCCTATTTCCCGGACCTTCTAAGCCCTTTTGGGTGCTGGT
GGTGGTTGGTGGAGTCCTGGCTTGCTATAGCTTGCTAGTAACAGTGGCCTTTATTATTTTCTGGGTGAAAC
GGGGCAGAAAGAAACTCCTGTATATATTCAAACAACCATTTATGAGACCAGTACAAACTACTCAAGAGGAA
GATGGCTGTAGCTGCCGATTTCCAGAAGAAGAAGAGGAGGTGTGAACTGAAGCTTAGAGTGAAGTTCAG
CAGGAGCGCAGACGCCCCCGCGTACCAGCAGGGCCAGAACCAGCTCTATAACGAGCTCAATCTAGGACGAA
GAGAGGAGTACGATGTTTTGGACAAGAGACGTGGCCGGGACCCTGAGATGGGGGGAAAGCCGCAGAGAAGG
AAGAACCCTCAGGAAGGCCTGTACAATGAACTGCAGAAAGATAAGATGGCGGAGGCCTACAGTGAGATTGG
GATGAAAGGCGAGCGCCGGAGGGGCAAGGGGCACGATGGCCTTTACCACGGTCTCAGTACAGCCACCAAGG
ACACCTACGACGCCCTTCACATGCAGGCCCTGCCCCCTCGCGCCGGCGCCAAAAGGTCTGGCTCCGGTGAG -continued GGCAGAGGAAGTCTTCTAACATGCGGTGACGTGGAGGAGAATCCCGGCCCTATGCCACCTCCTCGCCTCCT
CTTCTTCCTCCTCTTCCTCACCCCCATGGAAGTCAGGCCCGAGGAACCTCTAGTGGTGAAGGTGGAAGAGG
GAGATAACGCTGTGCTGCAGTGCCTCAAGGGGACCTCAGATGGCCCCACTCAGCAGCTGACCTGGTCTCGG
GAGTCCCCGCTTAAACCCTTCTTAAAACTCAGCCTGGGGCTGCCAGGCCTGGGAATCCACATGAGGCCCCT
GGCCATCTGGCTTTTCATCTTCAACGTCTCTCAACAGATGGGGGGCTTCTACCTGTGCCAGCCGGGGCCCC
CCTCTGAGAAGGCCTGGCAGCCTGGCTGGACAGTCAATGTGGAGGGCAGCGGGGAGCTGTTCCGGTGGAAT
GTTTCGGACCTAGGTGGCCTGGGCTGTGGCCTGAAGAACAGGTCCTCAGAGGGCCCCAGCTCCCCTTCCGG
GAAGCTCATGAGCCCCAAGCTGTATGTGTGGGCCAAAGACCGCCCTGAGATCTGGGAGGGAGAGCCTCCGT
GTCTCCCACCGAGGGACAGCCTGAACCAGAGCCTCAGCCAGGACCTCACCATGGCCCCTGGCTCCACACTC
TGGCTGTCCTGTGGGGTACCCCCTGACTCTGTGTCCAGGGGCCCCCTCTCCTGGACCCATGTGCACCCCAA
GGGGCCTAAGTCATTGCTGAGCCTAGAGCTGAAGGACGATCGCCCGGCCAGAGATATGTGGGTAATGGAGA
CGGGTCTGTTGTTGCCCCGGGCCACAGCTCAAGACGCTGGAAAGTATTATTGTCACCGTGGCAACCTGACC
ATGTCATTCCACCTGGAGATCACTGCTCGGCCAGTACTATGGCACTGGCTGCTGAGGACTGGTGGCTGGAA
GTCTCAGCTGTGACTTTGGCTTATCTGATCTTCTGCCTGTGTTCCCTTGTGGGCATTCTTCATCTTCAAA
GAGCCCTGGTCCTGAGGAGGAAAAGAAAGCGAATGACTTAA cxii. leader_2592H-CD28H-CD28TM-CD28CYP-CD3ζCYP_T2A-tCD19 2592H-CD28_tCD19
309 Amino acid sequence of leader_2592H-CD28H-CD28TM-CD28CYP-
CD3ζCYP_T2A-tCD19 (2592H-CD28_tCD19), SEQ ID NO: 309 METPAQLLFLLLLWLPDT
TGQVQLQESGPRLVKPSQTLSLTCTVSGGSISSDGYYWSWIRQHPGKGLEWIGYIYYSGSTFYNPSLKSRV
AISVDTSKNQFSLKLSSVTAADTAVYYCARESPHSSNWYSGFDCWGQGTLVTVSSGGGGSGGGGSGGGGSE
IVLTQSPDFQSVTPKEKVTITCRASQSIGSRLHWYQQKPDQSPKLLIKYASQSFSGVPSRFSGSGSGTDFT
LTINSLEAEDAATYYCHQSSNLPFTFGPGTKVDIKASVKGKHLCPSPLFPGPSKPFWVLVVGGVLACYSLL
VTVAFIIFWVRSKRSRLLHSDYMNMTPRRPGPTRKHYQPYAPPRDFAAYRSKLRVKFSRSADAPAYQQGQN
QLYNELNLGRREEYDVLDKRRGRDPEMGGKPQRRKNPQEGLYNELQKDKMAEAYSEIGMKGERRRGKGHDG
LYQGLSTATKDTYDALHMQALPPRAGAKRSGSGEFRGSLLTCGDVEENPGPMPPPRLLFFLLFLTPMEVRP
EEPLVKVVEEGDNAVLQCLKGTSDGPTQQLTWSRESPLKPFLKLSLGLPGLGIHMRPLAIWLFIFNVSQQM
GGFYLCQPGPPSEKAWQPGWTVNVEGSGELFRWNVSDLGGLGCGLKNRSSEGPSSPSGKLMSPKLYVWAKD
RPEIWEGEPPCLPPRDSLNQSLSQDLTMAPGSTLWLSCGVPPDSVSRGPLSWTHVHPKGPKSLLSLELKDD
RPARDMWVMETGLLLPRATAQDAGKYYCHRGNLTMSFHLEITARPVLWHWLLRTGGWKVSAVTLAYLIFCL
CSLVGILHLQRALVLRRKRKRMT cxiii. leader_2592H-CD28H-CD28TM-CD28CYP-CD3ζCYP_T2A-tCD19 2592H-CD28_tCD19
310 Nucleic acid sequence of leader_2592H-CD28H-CD28TM-CD28CYP-
CD3ζCYP_T2A-tCD19 (2592H-CD28_tCD19), SEQ ID NO: 310 ATGGAAACCCCAGCGCAG
CTTCTCTTCCTCCTGCTACTCTGGCTCCCAGATACCACCGGACAGGTGCAGCTGCAGGAGTCGGGCCCAAG
ACTGGTGAAGCCTTCACAGACCCTGTCCCTCACCTGCACTGTCTCTGGTGGCTCCATCAGTAGTGATGGTT
ACTACTGGAGCTGGATCCGCCAGCACCCAGGGAAGGGCCTGGAGTGGATTGGGTACATCTATTACAGTGGG
AGCACCTTCTACAACCCGTCCCTCAAGAGTCGAGTTGCCATATCAGTGGACACGTCTAAGAACCAGTTCTC
CCTGAAGCTGAGCTCTGTGACTGCCGCGGACACGGCCGTGTATTACTGTGCGAGAGAATCCCCTCATAGCA
GCAACTGGTACTCGGGCTTTGACTGCTGGGGCCAGGGAACCCTGGTCACCGTCTCCTCAGGTGGTGGTGGT
TCTGGCGGCGGCGGCTCCGGTGGTGGTGGTTCCGAAATTGTGCTGACTCAGTCTCCAGACTTTCAGTCTGT
GACTCCAAAGGAGAAAGTCACCATCACCTGCCGGGCCAGTCAGAGCATTGGTAGTAGGTTACACTGGTACC
AGCAGAAACCAGATCAGTCTCCAAAGCTCCTCATCAAGTATGCTTCCCAGTCCTTCTCAGGGGTCCCCTCG
AGGTTCAGTGGCAGTGGATCTGGGACAGATTTCACCCTCACCATCAATAGCCTGGAAGCTGAAGATGCTGC
AACGTATTACTGTCATCAGAGTAGTAATTTACCATTCACTTTCGGCCCTGGGACCAAAGTGGATATCAAAG
CTAGCGTGAAAGGGAAACACCTTTGTCCAAGTCCCCTATTTCCCGGACCTTCTAAGCCCTTTTGGGTGCTG
GTGGTGGTTGGTGGAGTCCTGGCTTGCTATAGCTTGCTAGTAACAGTGGCCTTTATTATTTTCTGGGTGAG
GAGTAAGAGGAGCAGGCTCCTGCACAGTGACTACATGAACATGACTCCCCGCCGCCCCGGGCCCACCCGCA
AGCATTACCAGCCCTATGCCCCACCACGCGACTTCGCAGCCTATCGCTCCAAGCTTAGAGTGAAGTTCAGC
AGGAGCGCAGACGCCCCCGCGTACCAGCAGGGCCAGAACCAGCTCTATAACGAGCTCAATCTAGGACGAAG
AGAGGAGTACGATGTTTTGGACAAGAGACGTGGCCGGGACCCTGAGATGGGGGGAAAGCCGCAGAAGAAGG
AGAACCCTCAGGAAGGCCTGTACAATGAACTGCAGAAAGATAAGATGGCGGAGGCCTACAGTGAGATTGGG
ATGAAAGGCGAGCGCCGGAGGGGCAAGGGGCACGATGGCCTTTACCAGGGTCTCAGTACAGCCACCAAGGA
CACCTACGACGCCCTTCACATGCAGGCCCTGCCCCCTCGCGCCGGCCAAAAGGTCTGGCTCCGGTGAGG
GCAGAGGAAGTCTTCTAACATGCGGTGACGTGGAGGAGAATCCCGCCCTATGCCACCTCCTCGCCTCCTC
TTCTTCCTCCTCTTCCTCACCCCCATGGAAGTCAGGCCCGAGGAACCTCTAGTGGTGAAGGTGGAAGAGGG
AGATAACGCTGTGCTGCAGTGCCTCAAGGGGACCTCAGATGGCCCCACTCAGCAGCTGACCTGGTCTCGGG
AGTCCCCGCTTAAACCCTTCTTAAAACTCAGCCTGGGGCTGCCAGGCCTGGGAATCCACATGAGGCCCCTG
GCCATCTGGCTTTTCATCTTCAACGTCTCTCAACAGATGGGGGGCTTCTACCTGTGCCAGCCGGGGCCCCC
CTCTGAGAAGGCCTGGCAGCCTGGCTGGACAGTCAATGTGGAGGGCAGCGGGGAGCTGTTCCGGTGGAATG
TTTCGGACCTAGGTGGCCTGGGCTGTGGCCTGAAGAACAGGTCCTCAGAGGGCCCCAGCTCCCCTTCCGGG
AAGCTCATGAGCCCCAAGCTGTATGTGTGGGCCAAAGACCGCCCTGAGATCTGGGAGGGAGAGCCTCCGTG
TCTCCCACCGAGGGACAGCCTGAACCAGAGCCTCAGCCAGGACCTCACCATGGCCCCTGGCTCCACACTCT
GGCTGTCCTGTGGGGTACCCCCTGACTCTGTGTCCAGGGGCCCCCTCTCCTGGACCCATGTGCACCCCAAG
GGGCCTAAGTCATTGCTGAGCCTAGAGCTGAAGGACGATCGCCCGGCCAGAGATATGTGGGTAATGGAGAC
GGGTCTGTTGTTGCCCCGGGCCACAGCTCAAGACGCTGGAAAGTATTATTGTCACCGTGGCAACCTGACCA
TGTCATTCCACCTGGAGATCACTGCTCGGCCAGTACTATGGCACTGGCTGCTGAGGACTGGTGGCTGGAAG
GTCTCAGCTGTGACTTTGGCTTATCTGATCTTCTGCCTGTGTTCCCTTGTGGGCATTCTTCATCTTCAAAG
AGCCCTGGTCCTGAGGAGGAAAAGAAAGCGAATGACTTAA cxiv. leader_2592H-CD28H-CD28TM-DAP10CYP-CD3ζCYP_T2A-tCD19 2592H-DAP10_tCD19
311 Amino acid sequence of leader_2592H-CD28H-CD28TM-DAP10CYP-
CD3ζCYP_T2A-tCD19 (2592H-DAP10_tCD19), SEQ ID NO: 311 METPAQLLFLLLLWLPD
TTGQVQLQESGPRLVKPSQTLSLTCTVSGGSISSDGYYWSWIRQHPGKGLEWIGYIYYSGSTFYNPSLKSR
VAISVDTSKNQFSLKLSSVTAADTAVYYCARESPHSSNWYSGFDCWGQGTLVTVSSGGGGSGGGGSGGGGS
EIVLTQSPDFQSVTPKEKVTITCRASQSIGSRLHWYQQKPDQSPKLLIKYASQSFSGVPSRFSGSGSGTDF
TLTINSLEAEDAATYYCHQSSNLPFTFGPGTKVDIKASVKGKHLCPSPLFPGPSKPFWVLVVGGVLACYS
LLVTVAFIIFWVLCARPRRSPAQEDGKVYINMPGRGKLRVKFSRSADAPAYQQGQNQLYNELNLGRREEYD
VLDKRRGRDPEMGGKPQRRKNPQEGLYNELQKDKMAEAYSEIGMKGERRRGKGHDGLYQGLSTATKDTYDA
LHMQALPPRAGAKRSGSGEGRGSLLTCGVEENPGPMPPPRLLFFLLFLTPMEVRPEEPLVKVVEEGDNAVL cxv. leader_2592H-CD28H-CD28TM-DAP10CYP-CD3ζCYP_T2A-tCD19 2592H-DAP10_tCD19
312 Nucleic acid sequence of leader_2592H-CD28H-CD28TM-DAP10CYP-
CD3ζCYP_T2A-tCD19 (2592H-DAP10_tCD19), SEQ ID NO: 312ATGGAAACCCCAGCGCAG
CTTCTCTTCCTCCTGCTACTCTGGCTCCCAGATACCACCGGACAGGTGCAGCTGCAGGAGTCGGGCCCAAG
ACTGGTGAAGCCTTCACAGACCCTGTCCCTCACCTGCACTGTCTCTGGTGGCTCCATCAGTAGTGATGGTT
ACTACTGGAGCTGGATCCGCCAGCACCCAGGGAAGGGCCTGGAGTGGATTGGGTACATCTATTACAGTGGG
AGCACCTTCTACAACCCGTCCCTCAAGAGTCGAGTTGCCATATCAGTGGACACGTCTAAGAACCAGTTCTC
CCTGAAGCTGAGCTCTGTGACTGCCGCGGACACGGCCGTGTATTACTGTGCGAGAGAATCCCCTCATAGCA
GCAACTGGTACTCGGGCTTTGACTGCTGGGGCCAGGGAACCCTGGTCACCGTCTCCTCAGGTGGTGGTGGT
TCTGGCGGCGGCGGCTCCGGTGGTGGTGGTTCCGAATTGTGCTGACTCAGTCTCCAGACTTTCAGTCTGT
GACTCCAAAGGAGAAAGTCACCATCACCTGCCGGGCCAGTCAGAGCATTGGTAGTAGGTTACACTGGTACC
AGCAGAAACCAGATCAGTCTCCAAAGCTCCTCATCAAGTATGCTTCCCAGTCCTTCTCAGGGGTCCCCTCG
AGGTTCAGTGGCAGTGGATCTGGGACAGATTTCACCCTCACCATCAATAGCCTGGAAGCTGAAGATGCTGC
AACGTATTACTGTCATCAGAGTAGTAATTTACCATTCACTTTCGGCCCTGGGACCAAAGTGGATATCAAAG
CTAGCGTGAAAGGGAAACACCTTTGTCCAAGTCCCCTATTTCCCGGACCTTCTAAGCCCTTTTGGGTGCTG
GTGGTGGTTGGTGGAGTCCTGGCTTGCTATAGCTTGCTAGTAACAGTGGCCTTTATTATTTTCTGGGTGCT
GTGCGCACGCCCACGCCGCAGCCCCGCCCAAGAAGATGGCAAAGTCTACATCAACATGCCAGGCAGGGCA
AGCTTAGAGTGAAGTTCAGCAGGAGCGCAGACGCCCCCGCGTACCAGCAGGGCCAGAACCAGCTCTATAAC
GAGCTCAATCTAGGACGAAGAGAGGGAGTACGATGTTTTGGACAAGAGACGTGGCCGGGACCCTGAGATGGG
GGGAAAGCCGCAGAGAAGGAAGCACCCTCAGGAAGGCCTGTACAATGAACTGCAGAAAGATAAGATGGCGG
AGGCCTACAGTGAGATTGGGATGAAAGGCGAGCGCCGGAGGGGCAAGGGGCACGATGGCCTTTACCAGGGT
CTCAGTACAGCCACCAAGGACACCTACGACGCCCTTCACATGCAGGCCCTGCCCCCTCGCGCCGGCGCCAA
AAGGTCTGGCTCCGGTGAGGGCAGAGGAAGTCTTCTAACATGCGGTGACGTGGAGGAGAATCCCGGCCCTA
TGCCACCTCCTGCCTCCTCTTCTTCCTCCTCTTCCTCACCCCCATGGAAGTCAGGCCCGAGGAACCTCTA
GTGGTGAAGGTGGAAGAGGGAGATAACGCTGTGCTGCAGTGCCTCAAGGGGACCTCAGATGGCCCCACTCA
GCAGCTGACCTGGTCTCGGGAGTCCCCGCTTAAACCCTTCTTAAAACTCAGCCTGGGGCTGCCAGGCCTGG
GAATCCACATGAGGCCCCTGGCCATCTGGCTTTTCATCTTCAACGTCTCTCAACAGATGGGGGCTTCTAC
CTGTGCCAGCCGGGGCCCCCCTCTGAGAAGGCCTGGCAGCCTGGCTGGACAGTCAATGTGGAGGGCAGCGG
GGAGCTGTTCCGGTGGAATGTTTCGGACCTAGGTGGCCTGGGCTGTGGCCTGAAGAACAGGTCCTCAGAGG
GCCCCAGCTCCCCTTCCGGGAAGCTCATGAGCCCCAAGCTGTATGTGTGGGCCAAAGACCGCCCTGAGATC
TGGGAGGGAGAGCCTCCGTGTCTCCCACCGAGGGACAGCCTGAACCAGAGCCTCAGCCAGGACCTCACCAT
GGCCCCTGGCTCCACACTCTGGCTGTCCTGTGGGGTACCCCCTGACTCTGTGTCCAGGGGCCCCCTCTCCT
GGACCCATGTGCACCCCAAGGGGCCTAAGTCATTGCTGAGCCTAGAGCTGAAGGACGATCGCCCGGCCAGA
GATATGTGGGTAATGGAGACGGGTCTGTTGTTGCCCCGGGCCACAGCTCAAGACGCTGGAAAGTATTATTG
TCACCGTGGCAACCTGACCATGTCATTCCACCTGGAGATCACTGCTCGGCCAGTACTATGGCACTGGCTGC
TGAGGACTGGTGGCTGGAAGGTCTCAGCTGTGACTTTGGCTTATCTGATCTTCTGCCTGTGTTCCCTTGTG
GGCATTCTTCATCTTCAAAGAGCCCTGGTCCTGAGGAGGAAAAGAAAGCGAATGACTTAA cxvi. leader_2592L-CD28H-CD28TM-CD28CYP-CD3ζCYP_T2A-tCD19 2592L-CD28_tCD19
313 Amino acid sequence of leader_2592L-CD28H-CD28TM-CD28CYP-
CD3ζCYP_T2A-tCD19 (2592L-CD28_tCD19), SEQ ID NO: 313 METPAQLLFLLLLWLPDT
TGEIVLTQSPDFQSVTPKEKVTITCRASQSIGSRLHWYQQKPDQSPKLLIKYASQSFSGVPSRFSGSGSGT
DFTLTINSLEAEDAATYYCHQSSNLPFTFGPGTKVDIKGGGGSGGGGSGGGGSQVQLQESGPRLVKPSQTL
SLTCTVSGGSISSDGYYWSWIRQHPGKGLEWIGYIYYSGSTFYNPSLKSRVAISVDTSKNQFSLKLSSVTA
ADTAVYYCARESPHSSNWYSGFDCWGQGTLVTVSSASVKGKHLCPSPLFPGPSKPFWVLVVVGVLACYSLL
VTVAFIIFWVRSKRSRLLHSDYMNMTPRRPGPTRKHYQPYAPPRDFAAYRSKLRVKFSRSADAPAYQQGQN
QLYNELNLGRREEYDVLDKRRGRDPEMGGKPQRRKNPQEGLYNELQKDKMAEAYSEIGMKGERRRGKGHDG
LYQGLSTATKDTYDALHMQALPPRAGAKRSGSGEGRGSLLTCGDVEENPGPMPPPRLLFFLLFLTPMEVRP
EEPLVVKVEEGDNAVLQCLKGTSDGPTQQLTWSRESPLKPFLKLSLGLPGLGIHMRPLAIWLFIFNVSQQM
GGFYLCQPGPPSEKAWQPGWTVNVEGSGELFRWNVSDLGGLGCGLKNRSSEGPSSPSGKLMSPKLYVWAKD
RPEIWEGEPPCLPPRDSLNQSLSQDLTMAPGSTLWLSCGVPPDSVSRGPLSWTHVHPKGPKSLLSLELKDD
RPARDMWVMETGLLLPRATAQDAGKYYCHRGNLTMSFHLEITARPVLWHWLLRTGGWKVSAVTLAYLIFCL
CSLVGILHLQRALVLRRKRKRMT cxvii. leader_2592L-CD28H-CD28TM-CD28CYP-CD3ζCYP_T2A-tCD19 2592L-CD28_tCD19
314 Nucleic acid sequence of leader_2592L-CD28H-CD28TM-CD28CYP-
CD3ζCYP_T2A-tCD19 (2592L-CD28_tCD19), SEQ ID NO: 314 ATGGAAACCCCAGCGCAG
CTTCTCTTCCTCCTGCTACTCTGGCTCCCAGATACCACCGGAGAAATTGTGCTGACTCAGTCTCCAGACTT
TCAGTCTGTGACTCCAAAGGAGAAAGTCACCATCACCTGCCGGGCCAGTCAGAGCATTGGTAGTAGGTTAC
ACTGGTACCAGCAGAAACCAGATCAGTCTCCAAAGCTCCTCATCAAGTATGCTTCCCAGTCCTTCTCAGGG
GTCCCCTCGAGGTTCAGTGGCAGTGGATCTGGGACAGATTTCACCCTCACCATCAATAGCCTGGAAGCTGA
AGATGCTGCAACGTATTACTGTCATCAGAGTAGTAATTTACCATTCACTTTCGGCCCTGGGACCAAAGTGG
ATATCAAAGGTGGTGGTGGTTCTGGCGGCGGCGGCTCCGGTGGTGGTGGTTCCCAGGTGCAGCTGCAGGAG
TCGGGCCCAAGACTGGTGAAGCCTTCACAGACCCTGTCCCTCACCTGCACTGTCTCTGGTGGCTCCATCAG
TAGTGATGGTTACTACTGGAGCTGGATCCGCCAGCACCCAGGGAAGGGCCTGGAGTGGATTGGGTACATCT
ATTACAGTGGGAGCACCTTCTACAACCCGTCCCTCAAGAGTCGAGTTGCCATATCAGTGGACACGTCTAAG
AACCAGTTCTCCCTGAAGCTGAGCTCTGTGACTGCCGCGGACACGGCCGTGTATTACTGTGCGAGAGAATC
CCCTCATAGCAGCAACTGGTACTCGGGCTTTGACTGCTGGGGCCAGGGAACCCTGGTCACCGTCTCCTCAG
CTAGCGTGAAAGGGAAACACCTTTGTCCAAGTCCCCTATTTCCCGGACCTTCTAAGCCCTTTTGGGTGCTG
GTGGTGGTTGGTGGAGTCCTGGCTTGCTATAGCTTGCTAGTAACAGTGGCCTTTATTATTTTCTGGGTAGG
GAGTAAGAGGAGCAGGCTCCTGCACAGTGACTACATGAACATGACTCCCCGCCGCCCCGGGCCCACCCGCA
AGCATTACCAGCCCTATGCCCCACCACGCGACTTCGCAGCCTATCGCTCCAAGCTTAGAGTGAAGTTCAGC
AGGAGCGCAGACGCCCCCGCGTACCAGCAGGGCCAGAACCAGCTCTATAACGAGCTCAATCTAGGACGAAG
AGAGGAGTACGATGTTTTGGACAAGAGACGTGGCCGGGACCCTGAGATGGGGGGAAAGCCGCAGAGAAGGA
AGAACCCTCAGGAAGGCCTGTACAATGAACTGCAGAAAGATAAGATGGCGGAGGCCTACAGTGAGATTGGG

```
                        -continued
           ATGAAAGGCGAGCGCCGGAGGGGCAAGGGGCACGATGGCCTTTACCAGGGTCTCAGTACAGCCACCAAGGA
           CACCTACGACGCCCTTCACATGCAGGCCCTGCCCCCTCGCGCCGGCGCCAAAAGGTCTGGCTCCGGTGAGG
           GCAGAGGAAGTCTTCTAACATGCGGTGACGTGGAGGAGAATCCCGGCCCTATGCCACCTCCTCGCCTCCTC
           TTCTTCCTCCTCTTCCTCACCCCCATGGAAGTCAGGCCCGAGGAACCTCTAGTGGTGAAGGTGGAAGAGGG
           AGATAACGCTGTGCTGCAGTGCCTCAAGGGGACCTCAGATGGCCCCACTCAGCAGCTGACCTGGTCTCGGG
           AGTCCCCGCTTAAACCCTTCTTAAAACTCAGCCTGGGGCTGCCAGGCCTGGGAATCCACATGAGGCCCCTG
           GCCATCTGGCTTTTCATCTTCAACGTCTCTCAACAGATGGGGGCTTCTACCTGTGCCAGCCGGGGCCCCC
           CTCTGAGAAGGCCTGGCAGCCTGGCTGGACAGTCAATGTGGAGGGCAGCGGGGAGCTGTTCCGGTGGAATG
           TTTCGGACCTAGGTGGCCTGGGCTGTGGCCTGAAGAACAGGTCCTCAGAGGGCCCCAGCTCCCCTTCCGGG
           AAGCTCATGAGCCCCAAGCTGTATGTGTGGGCCAAAGACCGCCCTGAGATCTGGGAGGGAGAGCCTCCGTG
           TCTCCCACCGAGGGACAGCCTGAACCAGAGCCTCAGCCAGGACCTCACCATGGCCCCTGGCTCCACACTCT
           GGCTGTCCTGTGGGGTACCCCCTGACTCTGTGTCCAGGGGCCCCCTCTCCTGGACCCATGTGCACCCCAAG
           GGGCCTAAGTCATTGCTGAGCCTAGAGCTGAAGGACGATCGCCCGGCCAGAGATATGTGGGTAATGGAGAC
           GGGTCTGTTGTTGCCCCGGGCCACAGCTCAAGACGCTGGAAAGTATTATTGTCACCGTGGCAACCTGACCA
           TGTCATTCCACCTGGAGATCACTGCTCGGCCAGTACTATGGCACTGGCTGCTGAGGACTGGTGGCTGGAAG
           GTCTCAGCTGTGACTTTGGCTTATCTGATCTTCTGCCTGTGTTCCCTTGTGGGCATTCTTCATCTTCAAAG
           AGCCCTGGTCCTGAGGAGGAAAAGAAAGCGAATGACTTAA
    cxviii. human TIM-1 TIM-1 315 Amino acid sequence of TIM-1 (TIM-1),
           SEQ ID NO: 315 MHPQVVILSLILHLADSVAGSVKVGGEAGPSVTLPCHYSGAVTSMCWNRGSCSLFT
           CQNGIVWTNGTHVTYRKDTRYKLLGDLSRRDVSLTIENTAVSDSGVYCCRVEHRGWFNDMKITVSLEIVPP
           KVTTTPIVTTVPTVTTVRTSTTVPTTTTVPTTTVPTTMSIPTTTTVPTTMTVSTTTSVPTTTSIPTTTTSVP
           VTTTVSTFVPPMPLPRQNHEPVATSPSSPQPAETHPTTLQGAIRREPTSSPLYSYTTDGNDTVTESSDGLW
           NNNQTQLFLEHSLLTANTTKGIYAGVCISVLVLLALLGVIIAKKYFFKKEVQQLSVSFSSLQIKALQNAVE
           KEVQAEDNIYIENSLYATD
```

REFERENCES

References in this list are cited by number above and incorporated by reference in their entirety herein.

1. Zhang, L. et al. Intratumoral T cells, recurrence, and survival in epithelial ovarian cancer. N Engl J Med 348, 203-213, doi:10.1056/NEJMoa020177 (2003).
2. Coukos, G., Conejo-Garcia, J. R., Roden, R. B. & Wu, T. C. Immunotherapy for gynaecological malignancies. Expert Opin Biol Ther 5, 1193-1210, doi:10.1517/14712598.5.9.1193 (2005).
3. Hamanishi, J. et al. Programmed cell death 1 ligand 1 and tumor-infiltrating CD8⁻T lymphocytes are prognostic factors of human ovarian cancer. Proc Natl Acad Sci USA 104, 3360-3365, doi: 10.1073/pnas.0611533104 (2007).
4. Kandalaft, L. E., Powell, D. J., Jr., Singh, N. & Coukos, G. Immunotherapy for ovarian cancer: what's next? J Clin Oncol 29, 925-933, doi: 10.1200/JCO.2009.27.2369 (2011).
5. Urba, W. J. & Longo, D. L. Redirecting T cells. N Engl J Med 365, 754-757, doi:10.1056/NEJMe1106965 (2011).
6. Maude, S. L. et al. Chimeric antigen receptor T cells for sustained remissions in leukemia. N Engl J Med 371, 1507-1517, doi:10.1056/NEJMoa1407222 (2014).
7. Khademi, M. et al. T Cell Ig⁻ and mucin-domain-containing molecule-3 (TIM-3) and TIM-1 molecules are differentially expressed on human Th1 and Th2 cells and in cerebrospinal fluid-derived mononuclear cells in multiple sclerosis. J Immunol 172, 7169-7176 (2004).
8. Mesri, M. et al. Inhibition of in vitro and in vive T cell responses by recombinant human Tim-1 extracellular domain proteins. Int Immunol 18, 473-484, doi: 10.1093/intimm/dxh388 (2006).
9. Kondratowicz, A. S. et al. T-cell immunoglobulin and mucin domain 1 (TIM-1) is a receptor for Zaire Ebolavirus and Lake Victoria Marburgvirus. Proc Natl Acad Sci USA 108, 8426-8431, doi:10.1073/pnas.1019030108 (2011).
10. Benard, J. et al. Characterization of a human ovarian adenocarcinoma line, IGROV1, in tissue culture and in nude mice. Cancer Res 45, 4970-4979 (1985).
11. Lengyel, E. et al. Epithelial ovarian cancer experimental models. Oncogene 33, 3619-3633, doi:10.1038/onc.2013.321 (2014).
12. Volk, A. et al. Comparison of three humanized mouse models for adoptive T cell transfer. J Gene Med 14, 540-548, doi:10.1002/jgm.2652 (2012).
13. von Bonin, M. et al. In vivo expansion of co-transplanted T cells impacts on tumor re-initiating activity of human acute myeloid leukemia in NSG mice. PLoS One 8, e60680, doi: 10.1371/journal.pone.0060680 (2013).
14. Ritchie, D. S. et al. Persistence and efficacy of second generation CAR T cell against the LeY antigen in acute myeloid leukemia. Mol Ther 21, 2122-2129, doi:10.1038/mt.2013.154 (2013).
15. Scholler, J. et al. Decade-long safety and function of retroviral-modified chimeric antigen receptor T cells. Sci Transl Med 4, 132ra153, doi: 10.1126/scitranslmed.3003761 (2012).

What is claimed is:

1. An isolated nucleic acid encoding a chimeric antigen receptor (CAR), wherein the CAR comprises:
   (I) an antigen-binding domain that binds to T-cell immunoglobulin and mucin domain 1 (TIM-1);
   (II) a transmembrane domain; and
   (III) at least one intracellular signaling domain, wherein the antigen-binding domain comprises an antibody or an antigen-binding fragment thereof comprising:
   (a) a heavy chain variable region (VH) comprising the CDR-H1 of SEQ ID NO: 239, the CDR-H2 of SEQ ID NO: 240, and the HDR-H3 of SEQ ID NO: 241; and
   (b) a light chain variable region (VL) comprising the CDR-L1 of SEQ ID NO: 242, the CDR-L2 of SEQ ID NO: 243, and the HDR-L3 of SEQ ID NO: 244
   optionally wherein:
   (a) the CDR-H1 is encoded by SEQ ID NO: 289, the CDR-H2 is encoded by SEQ ID NO: 290, and/or the HDR-H3 is encoded by SEQ ID NO: 291; and/or
   (b) the CDR-L1 is encoded by SEQ ID NO: 292, the CDR-L2 is encoded by SEQ ID NO: 293, and/or the HDR-L3 is encoded by SEQ ID NO: 294.

2. The isolated nucleic acid of claim 1, wherein:
   (a) the VH has at least 90%, at least 95%, at least 98%, at least 99%, or 100% identity to the amino acid sequence of SEQ ID NO: 204, optionally wherein the VH is encoded by SEQ ID NO: 254; and
   (b) the VL has at least 90%, at least 95%, at least 98%, at least 99%, or 100% identity to the amino acid sequence of SEQ ID NO: 205, optionally wherein the VL is encoded by SEQ ID NO: 255.

3. The isolated nucleic acid of claim 1, wherein the an antibody or an antigen-binding fragment thereof is selected from the group consisting of: a humanized antibody; a tetravalent antibody; a single chain antibody; a chimeric antibody; a CDR-grafted antibody; an antibody fragment comprising an Fab; an F(ab')2 fragment; an Fab' fragment; an Fv fragment; a single-chain Fv (scFv) fragment; a diabody; a minibody, and an IgG antibody or antigen-binding fragment thereof, optionally wherein the antigen-binding domain is conjugated to a cytotoxic agent.

4. The isolated nucleic acid of claim 1, wherein the antigen-binding domain comprises a scFv fragment comprising said VH and VL,
   wherein:
   (i) the VL is optionally positioned N-terminal to the VH in the CAR; or
   (ii) the VH is optionally positioned N-terminal to the VL in the CAR, optionally wherein the VL is linked to the VH by a linker, further optionally wherein the linker comprises at least 90%, at least 95%, at least 98%, at least 99%, or 100% identity to the amino acid sequence of SEQ ID NO: 201, further optionally wherein the linker is encoded by SEQ ID NO: 251.

5. The isolated nucleic acid of claim 4, wherein the scFv fragment has at least 90%, at least 95%, at least 98%, at least 99%, or 100% identity to the amino acid sequence of SEQ ID NO: 210 or 211, optionally wherein the scFv is encoded by SEQ ID NO: 260 or 261.

6. The isolated nucleic acid of claim 1, wherein the CAR comprises one or more of the following features:
   (I) said antigen-binding domain is joined to said transmembrane domain by a linker, a spacer, or a hinge, optionally wherein the linker, the spacer, or the hinge is derived from
      (i) one or more selected from the group consisting of CD28, CD8α, an immunoglobulin constant region or variant thereof, an immunoglobulin hinge region, an IgG4 hinge region, an immunoglobulin CH1/CL region, an Fc region, an immunoglobulin CH2 domain, an immunoglobulin CH3 domain, and any combination thereof, or
      (ii) CD28, optionally having at least 90%, at least 95%, at least 98%, at least 99%, or 100% identity to the amino acid sequence of SEQ ID NO: 214, further optionally encoded by SEQ ID NO: 264;
   (II) the transmembrane domain is derived from a transmembrane domain of
      (II-i) a protein selected from the group consisting of CD28, CD3 epsilon, CD4, CD5, CD8, CD9, CD16, CD22, CD33, CD37, CD45, CD64, CD80, CD86, CD134, CD137, CD154, TCR alpha, TCR beta, and CD3 zeta, or (II-ii) CD28, optionally having at least 90%, at least 95%, at least 98%, at least 99%, or 100% identity to the amino acid sequence of SEQ ID NO: 215, further optionally encoded by SEQ ID NO: 265;

(III) the intracellular signaling domain is derived from (III-i) an intracellular signaling domain of a protein selected from the group consisting of a lymphocyte receptor chain, a TCR/CD3 complex protein, an Fc receptor subunit, an IL-2 receptor subunit, CD3ζ, FcR gamma, FcR beta, CD3 gamma, CD3 delta, CD3 epsilon, CD5, CD22, CD79a, CD79b, CD66d, CD278 (ICOS), FcεRI, DAP10, and DAP12, or (III-ii) CD3ζ, optionally having at least 90%, at least 95%, at least 98%, at least 99%, or 100% identity to the amino acid sequence of SEQ ID NO: 219, further optionally encoded by SEQ ID NO: 269; and/or (IV) the CAR further comprises one or more costimulatory domains optionally derived from a protein selected from:

(IV-i) the group consisting of an MHC class I molecule, TNF receptor proteins, Immunoglobulin-like proteins, cytokine receptors, integrins, signaling lymphocytic activation molecules (SLAM proteins), activating NK cell receptors, a Toll ligand receptor, B7-H3, BAFFR, BTLA, BLAME (SLAMF8), CD2, CD4, CD5, CD7, CD8alpha, CD8beta, CD11a, LFA-1 (CD11a/CD18), CD11b, CD11c, CD11d, CD18, CD19, CD19a, CD27, CD28, CD29, CD30, CD40, CD49a, CD49D, CD49f, CD69, CD84, CD96 (Tactile), CD100 (SEMA4D), CD103, OX40 (CD134), 4-1BB (CD137), SLAM (SLAMF1, CD150, IPO-3), CD160 (BY55), SELPLG (CD162), DNAM1 (CD226), Ly9 (CD229), SLAMF4 (CD244, 2B4), ICOS (CD278), CEACAM1, CD S, CRTAM, DAP10, GADS, GITR, HVEM (LIGHTR), IA4, ICAM-1, IL2R beta, IL2R gamma, IL7R alpha, ITGA4, ITGA6, ITGAD, ITGAE, ITGAL, ITGAM, ITGAX, ITGB1, ITGB2, ITGB7, KIRDS2, LAT, LFA-1, LIGHT, LTBR, NKG2C, NKG2D, NKp30, NKp44, NKp46, NKp80 (KLRF1), PAG/Cbp, PD-1, PSGL1, SLAMF6 (NTB-A, Ly108), SLAMF7, SLP-76, TNFR2, TRANCE/RANKL, VLA1, VLA-6, and a ligand that specifically binds with CD83; or (IV-ii) the group consisting of CD28, 4-1BB (CD137), and DAP10, optionally having at least 90%, at least 95%, at least 98%, at least 99%, or 100% identity to the amino acid sequence of SEQ ID NO: 217, 216, or 218, further optionally encoded by encoded by SEQ ID NO: 267, 266, or 268.

7. The isolated nucleic acid of claim 1, wherein:

(I) the transmembrane domain is derived from a transmembrane domain of CD28, optionally having at least 90%, at least 95%, at least 98%, at least 99%, or 100% identity to the amino acid sequence of SEQ ID NO: 215, further optionally encoded by SEQ ID NO: 265; and (II) the intracellular signaling domain is derived from CD3ζ, optionally having at least 90%, at least 95%, at least 98%, at least 99%, or 100% identity to the amino acid sequence of SEQ ID NO: 219, further optionally encoded by SEQ ID NO: 269.

8. The isolated nucleic acid of claim 7, wherein the CAR further comprises one or more costimulatory domains derived from the group consisting of CD28, 4-1BB (CD137), and DAP10, optionally having at least 90%, at least 95%, at least 98%, at least 99%, or 100% identity to the amino acid sequence of SEQ ID NO: 217, 216, or 218, respectively, further optionally encoded by SEQ ID NO: 267, 266, or 268, respectively, optionally wherein the antigen-binding domain is joined to the transmembrane domain via a CD28 hinge, said CD28 hinge optionally having at least 90%, at least 95%, at least 98%, at least 99%, or 100% identity to the amino acid sequence of SEQ ID NO: 214, further optionally encoded by SEQ ID NO: 264.

9. The isolated nucleic acid of claim 4, wherein:

(I) the transmembrane domain is derived from a transmembrane domain of CD28, optionally having at least 90%, at least 95%, at least 98%, at least 99%, or 100% identity to the amino acid sequence of SEQ ID NO: 215, further optionally encoded by SEQ ID NO: 265; and (II) the intracellular signaling domain is derived from CD3ζ, optionally having at least 90%, at least 95%, at least 98%, at least 99%, or 100% identity to the amino acid sequence of SEQ ID NO: 219, further optionally encoded by SEQ ID NO: 269, optionally wherein the CAR comprises one or more of the following features:

(i) the antigen-binding domain is joined to the transmembrane domain via a CD28 hinge, said CD28 hinge optionally having at least 90%, at least 95%, at least 98%, at least 99%, or 100% identity to the amino acid sequence of SEQ ID NO: 214, further optionally encoded by SEQ ID NO: 264; and/or (ii) the CAR further comprises one or more costimulatory domains derived from CD28, 4-1BB, or DAP10, optionally having at least 90%, at least 95%, at least 98%, at least 99%, or 100% identity to the amino acid sequence of SEQ ID NO: 217, 216, or 218, further optionally encoded by SEQ ID NO: 267, 266, or 268.

10. The isolated nucleic acid of claim 1, wherein:

(I) the antigen-binding domain comprises the amino acid sequence of SEQ ID NO: 210 or 211 and optionally is encoded by SEQ ID NO: 260 or 261, respectively;

(II) the transmembrane domain comprises a CD28 transmembrane domain comprising the amino acid sequence of SEQ ID NO: 215 and optionally is encoded by SEQ ID NO: 265;

(III) the intracellular signaling domain comprises a CD3ζ intracellular signaling domain comprising the amino acid sequence of SEQ ID NO: 219 and optionally is encoded by SEQ ID NO: 269;

(IV) the CAR further comprises one or more costimulatory domains comprising the amino acid sequence of SEQ ID NO: 217, 216, or 218, optionally encoded by SEQ ID NO: 267, 266, or 268, respectively; and (V) the antigen-binding domain is joined to the transmembrane domain via a CD28 hinge comprising the amino acid sequence of SEQ ID NO: 214, optionally encoded by SEQ ID NO: 264.

11. The isolated nucleic acid of claim 10, which encodes an amino acid sequence having at least 90%, at least 95%, at least 98%, at least 99%, or 100% identity to the amino acid sequence of SEQ ID NO: 223, 222, or 224, optionally wherein the nucleic acid comprises the nucleic acid sequence of SEQ ID NO: 273, 272, 274, 304, 302, or 306.

12. The isolated nucleic acid of claim 1, which further encodes:

(i) a signal peptide, optionally having at least 90%, at least 95%, at least 98%, at least 99%, or 100% identity to the amino acid sequence of SEQ ID NO: 230, further optionally encoded by SEQ ID NO: 280;

(ii) a T2A ribosome skip sequence, optionally having at least 90%, at least 95%, at least 98%, at least 99%, or 100% identity to the amino acid sequence of SEQ ID NO: 231, further optionally encoded by SEQ ID NO: 281;

(iii) a selectable marker, optionally wherein the selectable marker is truncated CD19 (tCD19), optionally having at least 90%, at least 95%, at least 98%, at least 99%, or 100% identity to the amino acid sequence of SEQ ID NO: 232, further optionally encoded by SEQ ID NO: 282;

(iv) a promoter;

(v) a poly(A) tail;

(vi) a 3'UTR;

(vii) a suicide mechanism;

(viii) one or more signaling domains of a co-inhibitory receptor, such as CTLA-4 or PD-1 ("iCAR");

(ix) a substrate peptide cleaved in the presence of matrix metalloproteinases enriched within the tumor microenvironment ("masked CAR"); or (x) any combination thereof, optionally wherein the isolated nucleic acid:

(I) encodes the amino acid sequence of: SEQ ID NO: 303, 301, or 305; or (II) comprises the nucleic acid sequence of SEQ ID NO: 304, 302, or 306.

13. The isolated nucleic acid of claim 1, which encodes an amino acid sequence of SEQ ID NO: 223, optionally wherein the isolated nucleic acid comprises the nucleic acid sequence of SEQ ID NO: 273.

14. A vector comprising the nucleic acid of claim 1, optionally wherein the vector is selected from the group consisting of a DNA, an RNA, a plasmid, a lentivirus vector, adenoviral vector, a retrovirus vector, and an in vitro transcribed vector.

15. A vector comprising the nucleic acid of claim 9, optionally wherein the vector is selected from the group consisting of a DNA, an RNA, a plasmid, a lentivirus vector, adenoviral vector, a retrovirus vector, and an in vitro transcribed vector.

16. A vector comprising the nucleic acid of claim 13, optionally wherein the vector is a plasmid or a viral vector, further optionally a lentivirus vector, adenoviral vector, or a retrovirus vector.

17. A recombinant or isolated cell comprising the nucleic acid of claim 1 or a vector comprising the nucleic acid, optionally wherein the cell comprises one or more of the following features:

(I) the cell is a primary human cell or other mammalian cell or a cell derived therefrom;

(II) the cell is an immune cell, optionally selected from the group consisting of a T lymphocyte, a B lymphocyte, a natural killer cell, an eosinophil, an NK/T cells, a macrophage, and a monocyte;

(III) the cell is selected from the group consisting of a T cell, a T cell progenitor cell, a CD4+ T cell, a CD8+ T cell, a naive T (TN) cell, an effector T (TEFF) cell, a memory T cell, a stem cell memory T (TSCM) cell, a central memory T (TCM) cell, an effector memory T (TEM) cell, a terminally differentiated effector memory T cell, a tumor-infiltrating lymphocyte (TIL), an immature T cell, a mature T cell, a helper T cell, a cytotoxic T cell, a mucosa-associated invariant T (MAIT) cell, a regulatory T (Treg) cell, a helper T cell, a TH1 cell, a TH2 cell, a TH3 cell, a TH17 cell, a TH9 cell, a TH22 cell, a follicular helper T cell, an alpha/beta T cell, a delta/gamma T cell, a Natural Killer (NK) cell, a Natural Killer T (NKT) cell, a cytokine-induced killer (CIK) cell, and a lymphokine-activated killer (LAK) cell;

(IV) the cell is further modified or selected to incorporate one or more of the following features:

(IV-1) to express another CAR, optionally an activating or inhibitory CAR;

(IV-2) to comprise a suicide gene;

(IV-3) to be specific for another antigen, optionally a tumor antigen;

(IV-4) to be a pp65CMV-specific T cell, a CMV-specific T cell, an EBV-specific T cell, a Varicella Virus-specific T cell, an Influenza Virus-specific T cell or an Adenovirus-specific T cell;

(IV-5) to overexpress pro-survival signals;

(IV-6) to reverse anti-survival signals; (IV-7) to overexpress Bcl-xL or BCL-2;

(IV-8) to suppress the expression or inhibit the function of cell death genes, optionally Bak or Bax;

(IV-9) to overexpress hTERT;

(IV-10) to eliminate Fas expression;

(IV-11) to express a TGFβ dominant negative receptor;

(IV-12) to reduce or eliminate expression of its endogenous TCR compared to a wildtype T cell;

(IV-13) to evade immunosuppressive mediators; or (IV-14) to comprise a homing mechanism;

(V) the cell exhibits anti-tumor cytotoxicity when the CAR binds to TIM-1;

(VI) the cell increases production of cytokines and/or chemokines upon exposure to TIM-1-expressing cells, optionally one or more of GM-CSF, IL-6, RANTES (CCL5), TNF-α, IL-4, IL-10, IL-13, and IFN-γ;

(VII) the cell exhibits cytotoxic activity upon exposure to TIM-1-expressing cells, optionally measured via lactate dehydrogenase production; or (VIII) the cell is activated or stimulated to proliferate when the CAR binds to TIM-1.

18. The recombinant or isolated cell of claim 17, wherein the nucleic acid is according to claim 9.

19. The recombinant or isolated cell of claim 17, which is a T cell, wherein the nucleic acid is according to claim 13.

20. The recombinant or isolated cell of claim 17, which is a T cell, wherein the nucleic acid:

(I) encodes the amino acid sequence of: SEQ ID NO: 303, 301, or 305; or (II) comprises the nucleic acid sequence of SEQ ID NO: 304, 302, or 306.

* * * * *